(12) United States Patent
Masui et al.

(10) Patent No.: US 9,290,466 B2
(45) Date of Patent: Mar. 22, 2016

(54) OXAZINE DERIVATIVES

(71) Applicant: Shionogi & Co., Ltd., Osaka-shi, Osaka (JP)

(72) Inventors: Moriyasu Masui, Osaka (JP); Akihiro Hori, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 14/627,700

(22) Filed: Feb. 20, 2015

(65) Prior Publication Data

US 2015/0166491 A1 Jun. 18, 2015

Related U.S. Application Data

(63) Continuation of application No. 13/513,839, filed as application No. PCT/JP2010/072193 on Dec. 10, 2010, now Pat. No. 8,999,980.

(30) Foreign Application Priority Data

Dec. 11, 2009 (JP) ................................ 2009-282184
Oct. 22, 2010 (JP) ................................ 2010-237030

(51) Int. Cl.
| | |
|---|---|
| *C07D 265/08* | (2006.01) |
| *C07D 413/12* | (2006.01) |
| *C07D 498/04* | (2006.01) |
| *A61K 31/535* | (2006.01) |
| *A61K 31/5355* | (2006.01) |
| *C07D 265/06* | (2006.01) |
| *C07D 413/14* | (2006.01) |

(52) U.S. Cl.
CPC ............ *C07D 265/08* (2013.01); *C07D 265/06* (2013.01); *C07D 413/12* (2013.01); *C07D 413/14* (2013.01); *C07D 498/04* (2013.01)

(58) Field of Classification Search
CPC .. C07D 265/08; C07D 413/12; C07D 498/04; A61K 31/535; A61K 31/5355
USPC ............. 544/88, 90, 91, 96; 514/228.8, 230.5
See application file for complete search history.

(56) References Cited

U.S. PATENT DOCUMENTS

| | | |
|---|---|---|
| 2,899,426 A | 8/1959 | Bloom et al. |
| 3,115,494 A | 12/1963 | Joseph et al. |
| 3,227,713 A | 1/1966 | Behner et al. |
| 3,235,551 A | 2/1966 | Schubert et al. |
| 3,577,428 A | 5/1971 | Suh et al. |
| 3,636,116 A | 1/1972 | Trepanier |
| 3,719,674 A | 3/1973 | Trepanier |
| 3,775,409 A | 11/1973 | Harsanyi et al. |
| 4,049,807 A | 9/1977 | Paulus et al. |
| 4,311,840 A | 1/1982 | Condon |
| 4,895,841 A | 1/1990 | Sugimoto et al. |
| 4,906,626 A | 3/1990 | Amrein et al. |
| 5,100,901 A | 3/1992 | Sugimoto et al. |
| 5,236,942 A | 8/1993 | Miller |
| 5,328,915 A | 7/1994 | Long et al. |
| 5,880,147 A | 3/1999 | Yoshida et al. |
| 5,952,374 A | 9/1999 | Clarkson, Jr. et al. |
| 6,096,753 A | 8/2000 | Spohr et al. |
| 6,590,123 B2 | 7/2003 | Bekesi et al. |
| 6,713,276 B2 | 3/2004 | Cordell et al. |
| 7,183,070 B2 | 2/2007 | Cordell et al. |
| 7,309,706 B2 | 12/2007 | Rupp et al. |
| 7,326,792 B2 | 2/2008 | Shum et al. |
| 7,414,050 B2 | 8/2008 | Illig et al. |
| 7,763,609 B2 | 7/2010 | Zhu et al. |
| 7,902,238 B2 | 3/2011 | Galley et al. |

(Continued)

FOREIGN PATENT DOCUMENTS

| | | |
|---|---|---|
| CA | 2163724 | 5/1996 |
| CA | 2165386 | 6/1996 |

(Continued)

OTHER PUBLICATIONS

Cohen et al. "Synthesis of 2-Amino-5, +-dihydro-4*H*-1, 3-thiazines and Related Compounds by Acid Catalyzed Cyclization of Allylic Isothiuronium Salts." Journal of Heterocyclic Chemistry 14(5), 1977, p. 717-723.
Kuo et al. "A Synthesis of Estrone via Novel Intermediates. Mechanism of Coupling Reaction of a Vinyl Carbinol with a β Diketone." Journal of Organic Chemistry 33(8), Aug. 1968, p. 3126-3132.
Liebscher et al. "2-Arylimino-3-Thiazolines—Formation of Unusual Tautomers of 2-Acylamino-Thiazolines—A Revision." Tetrahedron Letters, 26(35), 1985, p. 4179-4180.
Fernández et al. "Syntheses and Spectral Properties of β-Iodoureas ans 2-Amino-4, 4-diphenyl-2-oxazolines." Journal of Heterocyclic Chemistry, 28(3), Apr.-May 1991, p. 777-780.
Schaumann et al. "Stickstoffhaltige Fünfring-Heterocyclen aus Carbodiimiden orderKeteniminen mit 3-Dimethylamino-2*H*-azirinen." Liebigs Annalen der Chemie, 1981, p. 290-305.

(Continued)

*Primary Examiner* — Kahsay Habte
(74) *Attorney, Agent, or Firm* — Hamre, Schumann, Mueller & Larson, P.C.

(57) ABSTRACT

The present invention provides, for example, a compound mentioned below as a medicament for treating or preventing the diseases induced by production, secretion or deposition of amyloid-β proteins.
A compound of the formula (I):

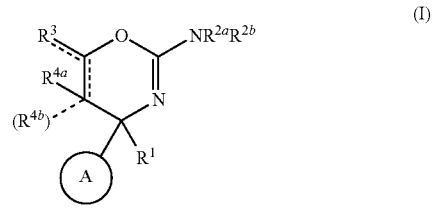

wherein $R^1$, $R^{2a}$, $R^{2b}$, $R^3$, $R^{4a}$, $R^{4b}$, ring A and the dashed lines are defined in the specification,
its pharmaceutically acceptable salt or a solvate thereof.

12 Claims, No Drawings

(56) References Cited

U.S. PATENT DOCUMENTS

| | | |
|---|---|---|
| 8,173,642 B2 | 5/2012 | Kobayashi et al. |
| 8,338,413 B1 | 12/2012 | Rueeger |
| 2002/0019427 A1 | 2/2002 | Carry et al. |
| 2005/0165080 A1 | 7/2005 | Rupp et al. |
| 2006/0173006 A1 | 8/2006 | Sun et al. |
| 2006/0183790 A1 | 8/2006 | Cole et al. |
| 2006/0183792 A1 | 8/2006 | Fobare et al. |
| 2006/0183943 A1 | 8/2006 | Hu et al. |
| 2007/0004730 A1 | 1/2007 | Zhou et al. |
| 2007/0004786 A1 | 1/2007 | Malamas et al. |
| 2007/0027199 A1 | 2/2007 | Malamas et al. |
| 2007/0224656 A1 | 9/2007 | Cordell et al. |
| 2008/0200445 A1 | 8/2008 | Zhu et al. |
| 2009/0023729 A1 | 1/2009 | Nakamura et al. |
| 2009/0082560 A1 | 3/2009 | Kobayashi et al. |
| 2010/0075957 A1 | 3/2010 | Tamura et al. |
| 2010/0093999 A1 | 4/2010 | Motoki et al. |
| 2010/0125087 A1 | 5/2010 | Holenz et al. |
| 2010/0160290 A1 | 6/2010 | Kobayashi et al. |
| 2010/0234365 A1 | 9/2010 | Liu et al. |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2011/0237576 A1 | 9/2011 | Yonezawa et al. |
| 2012/0015961 A1 | 1/2012 | Tamura et al. |
| 2012/0016116 A1 | 1/2012 | Kobayashi et al. |
| 2012/0022249 A1 | 1/2012 | Kobayashi et al. |
| 2012/0172355 A1 | 7/2012 | Tamura et al. |
| 2012/0202828 A1 | 8/2012 | Castro Pineiro et al. |
| 2012/0238548 A1 | 9/2012 | Gabellieri et al. |
| 2012/0238557 A1 | 9/2012 | Masui et al. |
| 2012/0245154 A1 | 9/2012 | Anan et al. |
| 2012/0245155 A1 | 9/2012 | Yoshida et al. |
| 2012/0245157 A1 | 9/2012 | Masui et al. |
| 2012/0253035 A1 | 10/2012 | Narquizian et al. |
| 2012/0258961 A1 | 10/2012 | Suzuki et al. |
| 2012/0258962 A1 | 10/2012 | Hilpert et al. |
| 2012/0295900 A1 | 11/2012 | Hilpert et al. |
| 2013/0158260 A1 | 6/2013 | Kobayashi et al. |
| 2013/0210839 A1 | 8/2013 | Masui et al. |
| 2013/0217705 A1 | 8/2013 | Mitsuoka et al. |
| 2013/0303755 A1 | 11/2013 | Kobayashi et al. |
| 2014/0051691 A1 | 2/2014 | Masui et al. |
| 2014/0058097 A1 | 2/2014 | Kobayashi et al. |
| 2014/0235626 A1 | 8/2014 | Tada et al. |

FOREIGN PATENT DOCUMENTS

| | | |
|---|---|---|
| DE | 140144 | 2/1980 |
| EP | 0798 292 | 10/1995 |
| EP | 0713704 | 5/1996 |
| EP | 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1 942 105 | 7/2008 |
| EP | 1942105 | 7/2008 |
| EP | 2147914 | 1/2010 |
| EP | 2151435 | 2/2010 |
| EP | 2 233 474 | 9/2010 |
| EP | 2305672 | 4/2011 |
| EP | 2332943 | 6/2011 |
| EP | 2 360 155 | 8/2011 |
| EP | 2360155 | 8/2011 |
| EP | 2415756 | 2/2012 |
| EP | 2500344 | 9/2012 |
| EP | 2511268 | 10/2012 |
| EP | 2511269 | 10/2012 |
| EP | 2514747 | 10/2012 |
| EP | 2518059 | 10/2012 |
| EP | 2634186 | 9/2013 |
| EP | 2634188 | 9/2013 |
| EP | 2689780 | 1/2014 |
| EP | 2703399 | 3/2014 |
| EP | 2703401 | 3/2014 |
| GB | 1001093 | 8/1965 |
| JP | 62-120374 | 6/1987 |
| JP | 8-231521 | 9/1996 |
| JP | 9-67355 | 3/1997 |
| JP | 10-505862 | 12/1999 |
| JP | 11-349572 | 12/1999 |
| JP | 2005-509651 | 4/2004 |
| JP | 2004-149429 | 5/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-051828 | 3/2009 |
| JP | 2009-520685 | 5/2009 |
| JP | 2012250933 | 12/2012 |
| JP | 2014101354 | 6/2014 |
| WO | 94/12165 | 6/1994 |
| WO | 95/09619 | 4/1995 |
| WO | 96/09286 | 3/1996 |
| WO | 96/14842 | 5/1996 |
| WO | 96/18608 | 6/1996 |
| WO | 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | 01/19788 | 3/2001 |
| WO | 01/78709 | 10/2001 |
| WO | 01/87293 | 11/2001 |
| WO | 02/062766 | 8/2002 |
| WO | 02/088101 | 11/2002 |
| WO | 02/096897 | 12/2002 |
| WO | 03/039446 | 5/2003 |
| WO | 03/040096 | 5/2003 |
| WO | 03/040115 | 5/2003 |
| WO | 03/040142 | 5/2003 |
| WO | 03/082191 | 10/2003 |
| WO | 2004/009549 | 1/2004 |
| WO | 2004/014843 | 2/2004 |
| WO | 2004/031154 | 4/2004 |
| WO | 2004/039404 | 5/2004 |
| WO | 2004/043916 | 5/2004 |
| WO | 2004/096795 | 11/2004 |
| WO | 2005/014555 | 2/2005 |
| WO | 2005/032493 | 4/2005 |
| WO | 2005/058311 | 6/2005 |
| WO | 2005/097767 | 10/2005 |
| WO | 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | 2006/041404 | 4/2006 |
| WO | 2006/041405 | 4/2006 |
| WO | 2006/065204 | 6/2006 |
| WO | 2006/065277 | 6/2006 |
| WO | 2006/076284 | 7/2006 |
| WO | 2006/099379 | 9/2006 |
| WO | 2006/138192 | 12/2006 |
| WO | 2006/138217 | 12/2006 |
| WO | 2006/138265 | 12/2006 |
| WO | 2006/138304 | 12/2006 |
| WO | 2007/002220 | 1/2007 |
| WO | 2007/005366 | 1/2007 |
| WO | 2007/005404 | 1/2007 |
| WO | 2007/016012 | 2/2007 |
| WO | 2007/038271 | 4/2007 |
| WO | 2007/049532 | 5/2007 |
| WO | 2007/058580 | 5/2007 |
| WO | 2007/058582 | 5/2007 |
| WO | 2007/058583 | 5/2007 |
| WO | 2007/058601 | 5/2007 |
| WO | 2007/058602 | 5/2007 |
| WO | 2007/073284 | 6/2007 |
| WO | 2007/078813 | 7/2007 |

(56) References Cited

FOREIGN PATENT DOCUMENTS

| | | |
|---|---|---|
| WO | 2007/092846 | 8/2007 |
| WO | 2007/092854 | 8/2007 |
| WO | 2007/114771 | 10/2007 |
| WO | 2007/120096 | 10/2007 |
| WO | 2007/146225 | 12/2007 |
| WO | 2008/011560 | 1/2008 |
| WO | 2008/022024 | 2/2008 |
| WO | 2008/073365 | 6/2008 |
| WO | 2008/073370 | 6/2008 |
| WO | 2008/103351 | 8/2008 |
| WO | 2008/133273 | 11/2008 |
| WO | 2008/133274 | 11/2008 |
| WO | 2009/010454 | 1/2009 |
| WO | 2009/064418 | 5/2009 |
| WO | 2009/091016 | 7/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | 2009/134617 | 11/2009 |
| WO | 2009/151098 | 12/2009 |
| WO | 2010/013302 | 2/2010 |
| WO | 2010/013794 | 2/2010 |
| WO | 2010/019392 | 2/2010 |
| WO | 2010/019393 | 2/2010 |
| WO | 2010/038686 | 4/2010 |
| WO | 2010/047372 | 4/2010 |
| WO | 2010/056194 | 5/2010 |
| WO | 2010/056195 | 5/2010 |
| WO | 2010/056196 | 5/2010 |
| WO | 2010/113848 | 10/2010 |
| WO | 2010/128058 | 11/2010 |
| WO | 2010/129864 | 11/2010 |
| WO | 2011/005738 | 1/2011 |
| WO | 2011/009897 | 1/2011 |
| WO | 2011/009898 | 1/2011 |
| WO | 2011/009943 | 1/2011 |
| WO | 2011/020806 | 2/2011 |
| WO | 2011/029803 | 3/2011 |
| WO | 2011/044181 | 4/2011 |
| WO | 2011/044184 | 4/2011 |
| WO | 2011/044185 | 4/2011 |
| WO | 2011/044187 | 4/2011 |
| WO | 2011/058763 | 5/2011 |
| WO | 2011/060207 | 5/2011 |
| WO | 2011057973 | 5/2011 |
| WO | 2011/069934 | 6/2011 |
| WO | 2011/070029 | 6/2011 |
| WO | 2011/070781 | 6/2011 |
| WO | 2011/071057 | 6/2011 |
| WO | 2011/071109 | 6/2011 |
| WO | 2011/071135 | 6/2011 |
| WO | 2011/077726 | 6/2011 |
| WO | 2011/080176 | 7/2011 |
| WO | 2011/138293 | 11/2011 |
| WO | 2011/154374 | 12/2011 |
| WO | 2011/154431 | 12/2011 |
| WO | 2012/000933 | 1/2012 |
| WO | 2012/006953 | 1/2012 |
| WO | 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/095469 | 7/2012 |
| WO | 2012/095521 | 7/2012 |
| WO | 2012/098064 | 7/2012 |
| WO | 2012/098213 | 7/2012 |
| WO | 2012/098461 | 7/2012 |
| WO | 2012095451 | 7/2012 |
| WO | 2012095463 | 7/2012 |
| WO | 2012095469 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/119883 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |
| WO | 2013027188 | 2/2013 |
| WO | 2013041499 | 3/2013 |
| WO | 2013083556 | 6/2013 |
| WO | 2013083557 | 6/2013 |
| WO | 2013110622 | 8/2013 |
| WO | 2013142613 | 9/2013 |

OTHER PUBLICATIONS

Fernández et al. "Syntheses of β-iodourea derivatives of carbohydrates and glycosylamino-ozazolines." Carbohydrate Research, 216, 1991, p. 21-32.

Cambie et al. "*vic*-Iodothiocyanates and Iodoisothiocyanates. Part 2. New Syntheses of Thiazolidin-2-ones and 2-Amino-thiazolines." Journal of the Chemical Society, Perkin Transactions I, 3, 1979, p. 765-770.

Kondrat'eva et al. "Noncyclic dimer of 4-methyl-2-(dimenthylamino)oxazole." Akademii Nauk SSSR, Seriya Khimicheskaya, 7, 1977, p. 1680-1682.

Hünig et al. "Azo dyes by oxidative coupling, XVIII. Synthesis of 3-substituted 2-thiazolone hydrazones and 2-thiazolone benzenesulfonylhydrazones." Ann. 647, 1961, p. 66-76.

Edwards et al., "Application of fragment-based lead generation to the discovery of novel, cyclic amidine β-secretase inhibitors with nanomolar potency, cellular activity, and high ligand efficiency", Journal of Medicinal Chemistry., vol. 50, No. 24, 2007, pp. 5912-5925.

Koriyama et al., "Reversal of diastereofacial selectivity in the nucleophilic addition reaction to chiral *N*-sulfmimine and application to the synthesis of indrizidine 223AB," Tetrahedron, vol. 58, 2002, pp. 9621-9628.

Fujisawa et al., "Switchover of diastereofacial selectivity in the condensation reaction of optically active *N*-sulfmimine with ester enolate," Tetrahedron Letters, vol. 37, No. 22, 1996, pp. 3881-3884.

Vilaivan et al., "Recent Advances in Catalytic Asymmetric Addition to Imines and Related C=N Systems," Current Organic Chemistry, vol. 9, 2005, pp. 1315-1392.

Hua et al., "*N*-Alkylidenesulfmamides," Sulfur Reports, vol. 21, 1999, pp. 211-239.

Savoca et al., "1,5-Diazabicyclo[4.3.0]non-5-ene[1]," Encyclopedia of Reagents for Organic Synthesis, 2006, 10 pages total.

Creeke et al., "Synthesis and elaboration of heterocycles via iodocyclisation of unsaturated thioureas," Tetrahedron Letters, 1989, vol. 30, No. 33, pp. 4435-4438.

Mellor et al., A general route to spirocycles by radical additions to exocyclic unsaturated sulphides and related compounds, Tetrahedron Letters, 1991, vol. 32, No. 48, pp. 7111-7114.

Murai et al., "Iodo-cyclization of *N*-homoallyl thioamides leading to 2,4-diary1-5,6-dihydro-4*H*-1,3-thiazines," Chemistry Letters, 2004, vol. 33, No. 5, pp. 508-509.

Singh et al., "Synthesis of heterocyclic compounds via enamines. Part 8.τ Acid-catalysed transformations in a 4,4,6-trimethy1-1,4-dihydropyrimidine-2(3*H*)-thione derivatives and related compounds," J. Chem. Soc., Perkin Trans. 1, 1980, pp. 1013-1018.

Vippagunta et al. "Crystalline Solids". Advanced Drug Delivery Reviews, vol. 48, 2001, pp. 3-26.

(56) References Cited

OTHER PUBLICATIONS

Gavezzotti. "Are Crystal Structures Predictable". Accounts of Chemical Research, vol. 27, 1994, pp. 309-314.

Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).

Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-yl)-1,3-dihydro-", XP002646872, Database accession No. 935998-84-8.

Schubert et al., "Neue synthesen von 2-Amino-5,6-dihydro-4H-1,3-thiazinen," Archiv der Pharmazie, 1968, vol. 301, No. 10, pp. 750-762.

Huang et al., "Pharmacophore model construction of β-secretase inhibitors," 2008, Acta Chimica Sinica, vol. 66, No. 16, pp. 1889-1897 (English language abstract provided).

Clark, et al., "Antitumor Imidazotetrazines. 32.[1] Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.

Congreve, et al., "Application of Fragment Screening by X-ray Crystallography to the Discovery of Aminopyridines as Inhibitors of β-Secretase", J. Med. Chem., vol. 50, 2007, pp. 1124-1132.

Huang, et al., "Progress in the Development of Nonpeptidomimetic BACE 1 Inhibitors for Alzheimer's Disease", Current Medicinal Chemistry, vol. 16, 2009, pp. 1806-1820.

Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.

Siddiqui et al., "Some extensions of Von Bruan (BrCN) reaction on organic bases," Proc. Pakistan Acad Sci., 1988, vol. 25, No. 3, pp. 231-240.

Ozawa et al., Pharmacological actions of 2-Aminoethylisothiuronium (AET) derivatives. I[1)], Yakugaku Zasshi, 1968, vol. 88, No. 2, pp. 156-162 (with English language abstract).

Curtis et al., The byozynsethis of Phenols. Part VIII. The synthesis of (2-carboxy-3,5-dihydroxyphynyl)propan-2-one (C-acetyl-o-orsellinic acid). Journal of the Chemical Society, 1964, pp. 5382-5385.

Burton et al., "Addition reactions of quinones. Part I. The reaction of cysteine and thiourea and its derivatives with some quinones," Journal of the Chemical Society, 1952, pp. 2193-2196.

Matsui, "Yomo bochuzai no kenkyu (the 6th report) Kagaku kozo to yomo shokugai boshi koka tono kankei (III)," Journal of Synthetic Organic Chemistry, Japan, 1950, vol. 8, No. 10, pp. Ho61-Ho65 (and International Search Report issued in PCT/JP2010/055528, which corresponds to co-pending U.S. Appl. No. 13/260,103).

Desai et al., "The condensation of thiocarbamides with monochloroacetic acide and the conversion of arylformamidinethiolacetic acids into pseudothiohydantoin derivatives," Recuil des Travaux Chimiques des Pays-Bas et de la Belgique, 1935, pp. 118-121.

Cole et al., "Acylguanidines as small-molecule beta-secretase inhibitors," J. Med. Chem., 2006, pp. 6158-6161.

Bol'but et al., Heterocyclizations of Functionalized Heterocumulenes with C,N- and C,O-Dinucleophiles: III.* Cyclization of N-(1-Aryl-1-chloro-2,2,2-trifluoroethyl)-N'-arylcarbodiimides with 3-Substituted 1-Phenylpyrazol-5-ones, Russian Journal of Organic Chemistry, 2003, vol. 29, No. 2, pp. 1789-1791.

Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.

Sayed et al., "α-Enones in heterocyclic synthesis of indazole, thiazine, chromene and quinolone derivatives with their antimicrobial activities," Journal of Chemical Research, 2009, vol. 12, pp. 726-728.

Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 *abstract* Accessed Jul. 13, 2012.

Bol'but et al., "Synthesis of 4-imino-2-trifluoromethyl-3,4-dihydro-2h-Benzo-[1,3]Thiazines," Chemistry of Heterocyclic Compounds, 2001, vol. 37, No. 4, pp. 522-523.

Vovk et al., "Intramolecular thermal cyclization of N-(1-Aryl-1-aryloxy-2,2,2-trifluoroethyl)-N'-arylcarbodiimides," Russian Journal of Organic Chemistry, 2000, vol. 36, No. 12, pp. 1739-1742.

Vovk et al., "Regio selective cyclization of 1-chloroalkylcarbodiimides with 1,1- and 1,2-bifunctional nucleophilic reagents," Russian Journal of Organic Chemistry, 1997, vol. 22, No. 1, pp. 96-102.

Potts et al., "N-Acyl-β-enamino Ketones: Versatile Heterocyclic Synthons," J. Org. Chem., 1983, 48, pp. 625-626.

Rivkin et al., "Piperazinyl pyrimidine derivatives as potent γ-secretase modulators," Bioorganic & Medicinal Chemistry Letters, 2010, 20, pp. 1269-1271.

Rivkin et al., "Purine derivatives as potent γ-secretase modulators," Bioorganic & Medicinal Chemistry Letters, 2010, 20, pp. 2279-2282.

STN a the Web, RN 79005-45-1, 1964.

Zhu et al., Two novel Diastereoselective Three-Component Reactions of Alkenes or 3,4-Dihydro-(2H)-pyran with Urea/Thiourea-Aldehyde Mixtures: [4 +2] Cycloaddition vs Biginelli-Type Reaction, Organic Letters, 2006, vol. 8, No. 12, pp. 2599-2602.

Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).

Kavya et al. "Nitric oxide synthase regulation and diversity: Implications in Parkinson's Disease". Nitric Oxide: Biology and Chemistry, vol. 15, No. 4, pp. 280-294 (2006).

Chiou et al. "Review: Effects of Nitric Oxide on Eye Diseases and Their Treatment". Journal of Ocular Pharmacology and Therapeutics, vol. 17, No. 2, pp. 189-198 (2001).

Ishii et al. "Subacute NO generation induced by Alzheimer's β-amyloid in the living brain: reversal by inhibition of the inducible NO synthase". The Federation of American Societies for Experimental Biology Journal, vol. 14, pp. 1485-1489 (2000).

Pak et al. "Morphine via nitric oxide modulates β-amyloid metabolism: a novel protective mechanism for Alzheimer's disease". Medical Science Monitor, vol. 11, No. 10, pp. BR357-BR366 (2005).

Kiselyov et al., "Design and chemical synthesis of [1,2,4]triazol[1,5-c]pyrimidin-5-yl amines, a novel class of VEGFR-2 kinase inhibitors," 2009, Tetrahedron Letters, vol. 50, pp. 3809-3812.

Mulcahy et al., "A stereoselective synthesis of (+)-Gonyautoxin 3," Journal of the American Chemical Society, 2008, vol. 130, pp. 12630-12631.

"Diphenyl Cyanocarbonimidate," e-EROS Encyclopedia of Reagents for Organic Synthesis, 2001, 2 pages total.

Shafik et al., "Synthesis of novel 2-[2-(substituted amino)phenethyl]-1H-benzimidazoles; 3,4-dihydro and 1,2,3,4-tetrahydropyrimido[1,6-a]-benzimidazoles as potential antiulcer agents," 2004, Pharmazie, vol. 59, No. 12, pp. 899-905.

Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.

Buschauer et al., "Isohistamine and Homologe als Bausteine von H$_2$-Antagonisten,"Arzneimittel-Forschung, 1985, vol. 35, pp. 1025-1029 (English language abstract provided).

Buschauer et al., "7,8-Dihydroimidazo[1,2-c]pyrimidin-5(6H)-one, -5(6H)-thione and -5(6H)-ylidencyanamide," Chemische Berichte, 1984, vol. 117, pp. 2597-2614.

Borchers et al., "H$_2$-Antihystaminika, 19. Mitt.[1)] Syntheses and H$_2$-antihistaminische Wirkung N$^α$-substituierter Histamine," Archiv der Pharmazie (Weinheim, Germany), 1984, vol. 317, pp. 455-459.

Cheong et al., "Pharmacophore elucidation for a new series of 2-aryl-pyrazolo-triazolo-pyrimidines as potent human A$_3$ adenosine receptor antagonists," Bioorganic & Medicinal Chemistry Letters, 2011, vol. 21, pp. 2898-2905.

(56) References Cited

OTHER PUBLICATIONS

Xu et al., "Copper-catalyzed cascade synthesis of benzimidazoquinazoline derivatives under mild condition," Chemical Communications, 2011, vol. 47, pp. 5596-5598.

Kishore et al., "QSAR of adenosine receptor antagonists: exploring physicochemical requirements for binding of pyrazolo[4,3-e]-1,2,4-triazolo[1,5-c]pyrimidine derivatives with human adenosine $A_3$ receptor subtype," Bioorganic & Medicinal Chemistry Letters, 2011, vol. 21, No. 2, pp. 818-823.

Dolzhenko et al., "8-methyl-2-[4-(trifluoromethyl)phenyl]-8H-pyrazolo[4,3-e][1,2,4]triazolo[1,5-c]pyrimidin-5-amine methanol disolvate," Acta Crystallographica, Section E: Structure Reports Online, 2010, E66(7), 12 pages total.

Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.

Beaton et al., "The synthesis of 1-aminodihydroisoquinolines by an imine addition cyclisation reaction," 1998, Tetrahedron Letters, vol. 39, pp. 1227-1230.

Tian et al., "Radiosynthesis of 8-Fluoro-3-(4-[$^{18}$F]Fluorophenyl)-3,4-Dihydro-1-Isoquinolinamine ([$^{18}$F]FFDI), a potential PET radiotracer for the inducible nitric oxide synthase," 2008, Current Radiopharmaceuticals, vol. 1, pp. 49-53.

Weinhardt et al. "Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No. 6, 1985, pp. 694-698.

Meschino et al., "2-Amino-5,6-dihydro-1,3-oxazines. The reduction of carboxylic esters with sodium borohydride," J. Org. Chem., vol. 28, 1963, pp. 3129-3134.

Poos et al., "2-amino-5-aryl-2-oxazolines. Potent new anorectic agent," J. Med. Chem., vol. 6, 1963, pp. 266-272.

Sandin et al., "A fast and parallel route to cyclic isothioureas and guanidines with use of microwave-assisted chemistry," J. Org. Chem., vol. 69, 2004, pp. 1571-1580.

Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.

Woodgate et al., "A new synthesis of 2-amino-2-thiazolines," Heterocycles, vol. 7, No. 1, 1977, pp. 109-112.

Dörwald, "Side reactions in organic synthesis: a guide to successful synthesis design" 2005 Wiley-VCH Verlag GmbH & Co., KGaA, Wienheim, chapter 1, 32 pages total.

Wermuth; Practice of Medicinal Chemistry, Third Ed., 2008, Elsevier, chapter 15.

Emilio Testa et al.: "Auf das Zentralnervensystem wirkende Substanzen, XXXVI. Weitere Untersuchungen über die 2-substituierten Azetidine"; Justus Liebigs Annalen Der Chemie, vol. 673, No. 1., May 4, 1964, pp. 60-70 XP055091964.

Portnyagin et al.: Russian Journal of Organic Chemistry, Consultants Bureau, US, vol. 10, Jan. 1, 1974, pp. 95-98, XP009174887.

Database Caplus [Online]; Chemical Abstracts Service, Columbus, OH, US; 2006, Bathich, Yaser: "Synthesis of Branched Amino Polyoly and Aminohydroxy Acids: Stereoselective Additiom of C-Nucleophiles ti Isoxazolines and Isoxazolinium Salts and Assignment of Configurations", XP002717806.

Database Registry [Online]; Chemical Abstracts Service, Columbus, OH, US; 3-Pyridinepropanol, .beta., .gamma.-diamino-6-fluoro-.gamma.-(4-fluorophenyl)-, (.beta.-R,.gamma.S)-, Apr. 29, 2004, XP002717807.

Church J et al.: "Anticonvulsant actions of phencyclidine receptor ligands: Correlation with N-Methylaspartate Antagonism in vivo"; General Phamacology, Pergamon Press, Oxford, GB, vol. 21, No. 2, Jan. 1, 1990, pp. 165-170, XP023834032.

Bathich, "Synthesis of branched amino polyols and amino hydroxy acids: stereoselective addition of C-Nucleophiles to isoxazoline and isoxazolinium salts and assignment of configurations," 2006, pp. 148.

Co-pending U.S. Appl. No. 13/952,073, entitled Sulfur-Containing Heterocyclic Derivative Having Beta Secretase Inhibitory Activity, filed Jul. 26, 2013.

Hilpert et al., "Beta-secretase (BACE1) inhibitors with high in vivo efficacy suitable for clinical evaluation in Alzheimer's disease," Journal of Medicinal Chemistry, 2013, 56, pp. 3980-3995.

Delgado et al., "A practical entry to beta-aryl-beta-alkyl amino alcohols: application to the synthesis of a potent BACE1 inhibitor," Organic & Biomolecular Chemistry 2012, 10, pp. 6758-6766.

Woltering et al., "BACE1 inhibitors: a head group scan on a series of amides," Bioorganic & Medicinal Chemistry Letters, 2013, vol. 23, issue14, pp. 4239-4243.

Co-pending U.S. Appl. No. 14/434,013, entitled "Dihydrooxazine or Oxazepine Derivatives Having BACE1 Inhibitory Activity", filed Apr. 7, 2015 (271 pages total).

Medicinal Chemistry, Nozaki et al., Kagaku-Dojin, Jul. 1, 1995, pp. 98-99 and English translation thereof, 4 pages total.

OXAZINE DERIVATIVES

TECHNICAL FIELD

The present invention relates to a compound which has amyloid β production inhibitory activity, and is useful as an agent for treating or preventing disease induced by production, secretion and/or deposition of amyloid β proteins.

BACKGROUND ART

In the brain of Alzheimer's patient, the peptide composed of about 40 amino acids residue as is called amyloid β protein, that accumulates to form insoluble specks (senile specks) outside nerve cells is widely observed. It is concerned that these senile specks kill nerve cells to cause Alzheimer's disease, so the therapeutic agents for Alzheimer's disease, such as decomposition agents of amyloid β protein and amyloid vaccine, are under investigation.

Secretase is an enzyme which cleaves a protein called amyloid β precursor protein (APP) in cell and produces amyloid β protein. The enzyme which controls the production of N terminus of amyloid β protein is called as β-secretase (beta-site APP-cleaving enzyme 1, BACE1). It is thought that inhibition of this enzyme leads to reduction of producing amyloid β protein and that the therapeutic or prophylactic agent for Alzheimer's disease will be created due to the inhibition.

Patent Documents 1 to 11 disclose compounds having a structure similar to those of the compounds of the present invention. Each of these document discloses each of these compound is useful as a therapeutic agent for Alzheimer's disease or Alzheimer's relating symptoms, but each of these substantially disclosed compounds has a structure different from those of the compounds of the present invention. Non Patent Document 1 disclose compounds having a structure similar to those of the compounds of the present invention but does not suggest any pharmacological activities.

PRIOR ART

Patent Document

[Patent Document 1] WO2007/058583 pamphlet
[Patent Document 2] WO2007/049532 pamphlet
[Patent Document 3] WO2008/133273 pamphlet
[Patent Document 4] WO2008/133274 pamphlet
[Patent Document 5] WO20. 09/151098 pamphlet
[Patent Document 6] WO2009/091016 pamphlet
[Patent Document 7] WO2009/103626 pamphlet
[Patent Document 8] WO2009/134617 pamphlet
[Patent Document 9] WO2006/065277 pamphlet
[Patent Document 10] WO2005/58311 pamphlet
[Patent Document 11] WO2008/103351 pamphlet

Non-Patent Document

[Non-patent Document 1] Russian Journal of Organic Chemistry (2003), 39 (12), 1789-1791

SUMMARY OF THE INVENTION

Problems to be Solved by the Invention

The present invention provides compounds which have reducing effects to produce amyloid β protein, especially BACE1 inhibitory activity, and are useful as an agent for treating disease induced by production, secretion and/or deposition of amyloid β protein.

Means for Solving the Problem

The present invention, for example, provides the inventions described in the following items.

(1) A compound of formula (I):

[Chemical Formula 1]

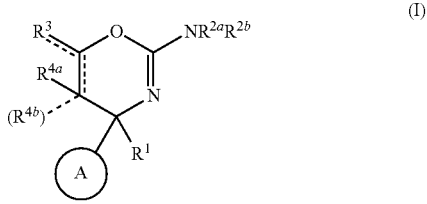

wherein
ring A is a substituted carbocycle or a substituted or unsubstituted heterocycle, $R^1$ is substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, a substituted or unsubstituted carbocyclic group or a substituted or unsubstituted heterocyclic group, $R^{2a}$ and $R^{2b}$ are each independently hydrogen, substituted or unsubstituted alkyl, substituted or unsubstituted acyl, substituted or unsubstituted alkoxycarbonyl or substituted or unsubstituted carbamoyl,

[Chemical Formula 2]

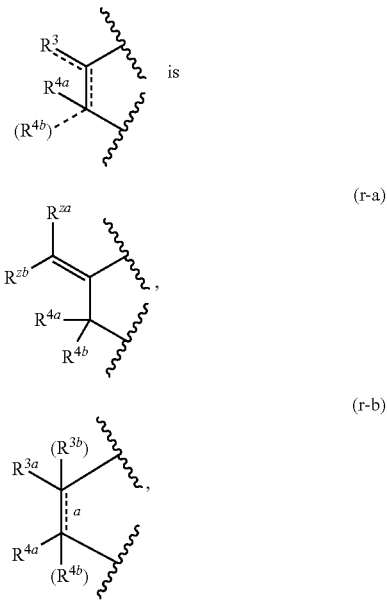

-continued

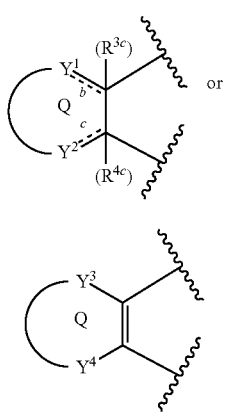

wherein $R^{2a}$ and $R^{2b}$ are each independently hydrogen, halogen, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, a substituted or unsubstituted carbocyclic group, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, a substituted or unsubstituted heterocyclic group, substituted or unsubstituted heterocyclyloxy, substituted or unsubstituted heterocyclylthio, substituted or unsubstituted heterocyclylalkyl, substituted or unsubstituted heterocyclylalkoxy or substituted or unsubstituted heterocyclyloxycarbonyl, or $R^{za}$ and $R^{zb}$ together with the carbon atom to which they are attached may form a substituted or unsubstituted non-aromatic carbocycle or a substituted or unsubstituted non-aromatic heterocycle, $R^{3a}$, $R^{3b}$, $R^{3c}$, $R^{4a}$, $R^{4b}$ and $R^{4c}$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, $R^{3a}$ and $R^{3b}$ together with the carbon atom to which they are attached may form a substituted or unsubstituted carbocycle or a substituted or unsubstituted heterocycle, $R^{4a}$ and $R^{4b}$ together with the carbon atom to which they are attached may form a substituted or unsubstituted carbocycle or a substituted or unsubstituted heterocycle, ring Q is a substituted or unsubstituted carbocycle or a substituted or unsubstituted heterocycle, dashed line a, dashed line b and dashed line c each independently mean the presence or absence of a bond, when dashed line a means the presence of a bond, then $R^{3b}$ and $R^{4b}$ are absent, when dashed line b means the presence of a bond, then $R^{3c}$ is absent, when dashed line c means the presence of a bond, then $R^{4c}$ is absent, $Y^1$ and $Y^2$ are each independently —C($R^5$)($R^6$)—, —C($R^5$)=, —N($R^7$)—, —S—, —SO—, —SO$_2$— or —O—, $Y^3$ and $Y^4$ are each independently —C($R^5$)($R^6$)—, —N($R^7$)—, —S—, —SO—, —SO$_2$— or —O—, $R^5$ and $R^6$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, and $R^7$ is hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted thiocarbamoyl, substituted or unsubstituted sulfamoyl, substituted or unsubstituted amino, a substituted or unsubstituted carbocyclic group, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, excluding the compounds wherein

[Chemical Formula 3]

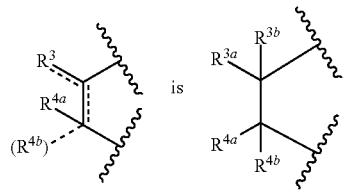

ring A is

[Chemical Formula 4]

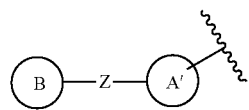

wherein ring A' and ring B are each independently a substituted or unsubstituted carbocycle or a substituted or unsubstituted heterocycle, Z is $-L^{1'}-N(R^8)-L^{2'}-$, $L^{1'}$ and $L^{2'}$ are each independently a bond;

substituted or unsubstituted alkylene wherein the substituent is one or more selected from halogen, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkyl carbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group, each of which carbocycle and heterocycle is optionally substituted by one or more substituent selected from halogen, alkyl, hydroxy and alkoxy;

substituted or unsubstituted alkenylene wherein the substituent is one or more selected from halogen, alkoxy, halogenoalkoxy, hydroxyalkoxy, alkoxyalkoxy, acyl, acyloxy, carboxy, alkoxycarbonyl, amino, acylamino, alkylamino, imino, hydroxy imino, alkoxyimino, alkylthio, carbamoyl, alkylcarbamoyl, hydroxy alkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group, each of which carbocycle and heterocycle is optionally substituted by one or more substituent selected from halogen, alkyl, hydroxy and alkoxy; or substituted or unsubstituted alkynylene wherein the substituent is one or more selected from halogen, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group, each of which carbocycle and heterocycle is optionally substituted by one or more substituent selected from halogen, alkyl, hydroxy and alkoxy; and $R^8$ is hydrogen, substituted or unsubstituted alkyl, substituted or unsubstituted alkenyl, substituted or unsubstituted alkynyl or substituted or unsubstituted acyl, its pharmaceutically acceptable salt or a solvate thereof.

When Z is "$-L^{1'}-N(R^8)-L^{2'}-$", then "$L^{1'}$" bonds to ring B and "$L^{2'}$" bonds to ring A', respectively.

(1-1) A compound of the formula (Iα)

[Chemical Formula 5]

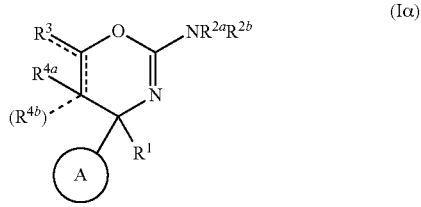

wherein ring A is a substituted carbocycle or a substituted or unsubstituted heterocycle, $R^1$ is substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, a substituted or unsubstituted carbocyclic group or a substituted or unsubstituted heterocyclic group, $R^{2a}$ and $R^{2b}$ are each independently hydrogen, substituted or unsubstituted alkyl, substituted or unsubstituted acyl, substituted or unsubstituted alkoxycarbonyl or substituted or unsubstituted carbamoyl,

[Chemical Formula 6]

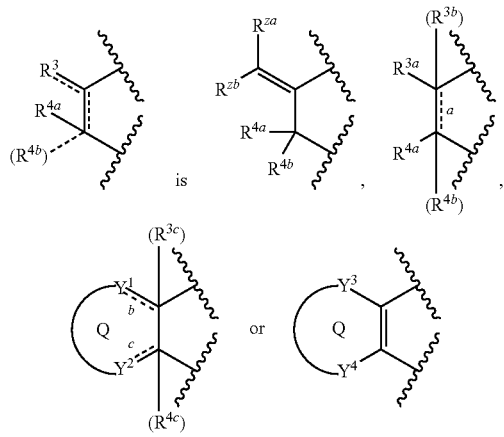

wherein $R^{za}$ and $R^{zb}$ are each independently hydrogen, halogen, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, a substituted or unsubstituted carbocyclic group, substituted or unsubstituted carbocyclyloxy, substituted or unsubstituted carbocyclylthio, substituted or unsubstituted carbocyclyloxycarbonyl; a substituted or unsubstituted heterocyclic group, substituted or unsubstituted heterocyclyloxy, substituted or unsubstituted heterocyclylthio, or substituted or unsubstituted heterocyclyloxycarbonyl, or $R^{za}$ and $R^{zb}$ together with the carbon atom to which they are attached may form a substituted or unsubstituted non-aromatic carbocycle or a substituted or unsubstituted non-aromatic heterocycle, $R^{3a}$, $R^{3b}$, $R^{1c}$, $R^{4a}$, $R^{4b}$ and $R^{4c}$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl, $R^{3a}$ and $R^{3b}$ together with the carbon atom to which they are attached may form a substituted or unsubstituted carbocycle or a substituted or unsubstituted heterocycle, $R^{4a}$ and $R^{4b}$ together with the carbon atom to which they are attached may form a substituted or unsubstituted carbocycle or a substituted or unsubstituted heterocycle, ring Q is a substituted or unsubstituted carbocycle or a substituted or unsubstituted heterocycle, dashed line a, dashed line b and dashed line c each independently mean the presence or absence of a bond, when dashed line a means the presence of a bond, then $R^{3b}$ and $R^{4b}$ are absent, when dashed line b means the presence of a bond, then $R^{3c}$ is absent, when dashed line c means the presence of a bond, then $R^{4c}$ is absent, $Y^1$ and $Y^2$ are each independently —C($R^5$)($R^6$)—, —C($R^5$)=, —N($R^7$)—, —N=, —S—, —SO—, —SO$_2$— or —O—, $Y^3$ and $Y^4$ are each independently —C($R^5$)($R^6$)—, —N($R^7$)—, —S—, —SO—, —SO$_2$— or —O—, $R^5$ and $R^6$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl, and $R^7$ is hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted thiocarbamoyl, substituted or unsubstituted sulfamoyl, substituted or unsubstituted amino, a substituted or unsubstituted carbocyclic group, substituted or unsubstituted carbocycyloxy, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclyloxycarbonyl, substituted or unsubstituted heterocyclylsulfinyl or substituted or unsubstituted heterocyclylsulfonyl, excluding the compounds wherein

[Chemical Formula 7]

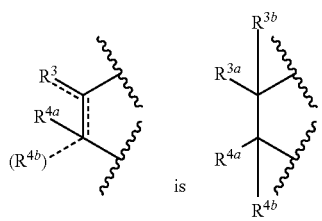

ring A is

[Chemical formula 8]

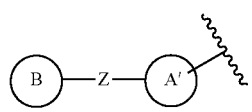

wherein ring A' and ring B are each independently a substituted or unsubstituted carbocycle or a substituted or unsubstituted heterocycle, Z is $-L^{1'}-N(R^8)-L^{2'}-$, $L^{1'}$ and $L^{2'}$ are each independently a bond;

substituted or unsubstituted alkylene wherein the substituent is one or more selected from halogen, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group, each of which carbocycle and heterocycle is optionally substituted by one or more substituent selected from halogen, alkyl, hydroxy and alkoxy;

substituted or unsubstituted alkenylene wherein the substituent is one or more selected from halogen, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group, each of which carbocycle and heterocycle is optionally substituted by one or more substituent selected from halogen, alkyl, hydroxy and alkoxy; or substituted or unsubstituted alkynylene wherein the substituent is one or more selected from halogen, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group, each of which carbocycle and heterocycle is optionally substituted by one or more substituent selected from halogen, alkyl, hydroxy and alkoxy; and $R^8$ is hydrogen, substituted or unsubstituted alkyl, substituted or unsubstituted alkenyl, substituted or unsubstituted alkynyl or substituted or unsubstituted acyl, its pharmaceutically acceptable salt or a solvate thereof.

When Z is "$-L^1-N(R^8)-L^2-$", then "$L^1$" bonds to ring B and "$L^2$" bonds to ring A', respectively.

(1-2) A compound of the type (Ia)

[Chemical Formula 9]

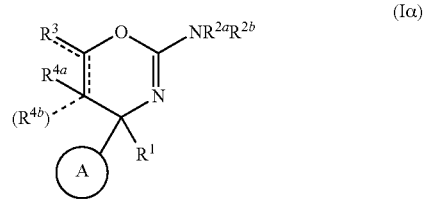

wherein ring A is a substituted carbocycle or a substituted or unsubstituted heterocycle, $R^1$ is substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, a substituted or unsubstituted carbocyclic group or a substituted or unsubstituted heterocyclic group, $R^{2a}$ and $R^{2b}$ are each independently hydrogen, substituted or unsubstituted alkyl, substituted or unsubstituted acyl, substituted or unsubstituted alkoxycarbonyl or substituted or unsubstituted carbamoyl,

[Chemical Formula 10]

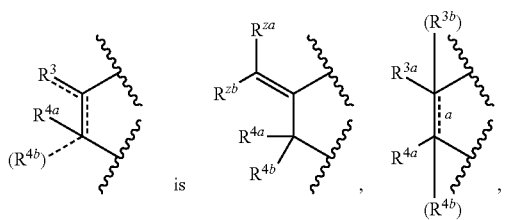

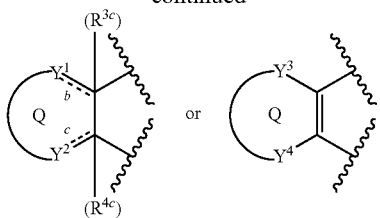

wherein $R^{za}$ and $R^{zb}$ are each independently hydrogen, halogen, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, a substituted or unsubstituted carbocyclic group, substituted or unsubstituted carbocyclyloxy, substituted or unsubstituted carbocyclylthio, substituted or unsubstituted carbocyclyloxycarbonyl, a substituted or unsubstituted heterocyclic group, substituted or unsubstituted heterocyclyloxy, substituted or unsubstituted heterocyclylthio, or substituted or unsubstituted heterocyclyloxycarbonyl, or $R^{za}$ and $R^{zb}$ together with the carbon atom to which they are attached may form a substituted or unsubstituted carbocycle or a substituted or unsubstituted heterocycle, $R^{3a}$, $R^{3b}$, $R^{3c}$, $R^{4a}$, $R^{4b}$ and $R^{4c}$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl, $R^{3a}$ and $R^{3b}$ together with the carbon atom to which they are attached may form a substituted or unsubstituted carbocycle or a substituted or unsubstituted heterocycle, $R^{4a}$ and $R^{4b}$ together with the carbon atom to which they are attached may form a substituted or unsubstituted carbocycle or a substituted or unsubstituted heterocycle, ring Q is a substituted or unsubstituted carbocycle or a substituted or unsubstituted heterocycle, dashed line a, dashed line b and dashed line c each independently mean the presence or absence of a bond, when dashed line a means the presence of a bond, then $R^{3b}$ and $R^{4b}$ are absent, when dashed line b means the presence of a bond, then $R^{3c}$ is absent, when dashed line c means the presence of a bond, then $R^{4c}$ is absent, $Y^1$ and $Y^2$ are each independently $-C(R^5)(R^6)-$, $-C(R^5)=$, $-N(R^7)-$, $-N=$, $-S-$, $-SO-$, $-SO_2-$ or $-O-$, $Y^3$ and $Y^4$ are each independently $-C(R^5)(R^6)-$, $-N(R^7)-$, $-S-$, $-SO-$, $-SO_2-$ or $-O-$, $R^5$ and $R^6$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl, and $R^7$ is hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted thiocarbamoyl, substituted or unsubstituted sulfamoyl, substituted or unsubstituted amino, a substituted or unsubstituted carbocyclic group, substituted or unsubstituted carbocyclyloxy, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclyloxycarbonyl, substituted or unsubstituted heterocyclylsulfinyl or substituted or unsubstituted heterocyclylsulfonyl, excluding the compounds wherein

[Chemical Formula 11]

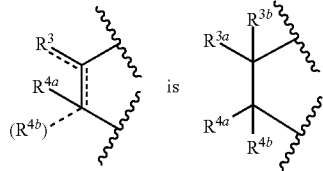

ring A is

[Chemical Formula 12]

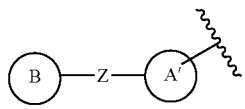

wherein ring A' and ring B are each independently a substituted or unsubstituted carbocycle or a substituted or unsubstituted heterocycle, Z is $-L^1-N(R^8)-L^2-$, $L^1$ and $L^2$ are each independently a bond, substituted or unsubstituted alkylene or substituted or unsubstituted alkynylene; and $R^8$ is hydrogen, substituted or unsubstituted alkyl, substituted or unsubstituted alkenyl, substituted or unsubstituted alkynyl or substituted or unsubstituted acyl, its pharmaceutically acceptable salt or a solvate thereof.

When Z is "$-L^1-N(R^8)-L^2-$", then "$L^1$" bonds to ring B and "$L^2$" bonds to ring A', respectively.

(2) The compound according to any one of items (1), (1-1), and (1-2) wherein ring A is

[Chemical Formula 13]

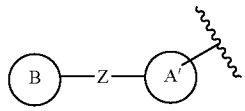

wherein ring A' and ring B are each independently a substituted or unsubstituted carbocycle or a substituted or unsubstituted heterocycle, Z is $-L^1-C(\!=\!O)N(R^8)-L^2-$, $-L^1-N(R^8)C(\!=\!O)-L^2-$ or $-L^1-N(R^8)-L^2-$, $L^1$ and $L^2$ are each independently a bond, substituted or unsubstituted alkylene, substituted or unsubstituted alkenylene or substituted or unsubstituted alkynylene and $R^8$ is hydrogen, substituted or unsubstituted alkyl, substituted or unsubstituted alkenyl, substituted or unsubstituted alkynyl or substituted or unsubstituted acyl, its pharmaceutically acceptable salt or a solvate thereof.

When Z is "$-L^1-C(\!=\!O) N(R^8)-L^2-$, $-L^1-N(R^8) C(\!=\!O)-L^2-$, or $-L^1-N(R^8)-L^2-$", "$L^1$" bonds to ring B and "$L^2$" bonds to ring A', respectively.

(3)
The compound according to any one of items (1), (1-1), (1-2), and (2) wherein

[Chemical Formula 14]

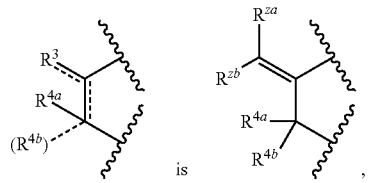

wherein $R^{za}$ and $R^{zb}$ are each independently hydrogen, halogen or substituted or unsubstituted alkyl, and $R^{4a}$ and $R^{4b}$ are each independently hydrogen or substituted or unsubstituted alkyl, its pharmaceutically acceptable salt or a solvate thereof.

(4)
The compound according to any one of items (1), (1-1), (1-2) and (2) wherein

[Chemical Formula 15]

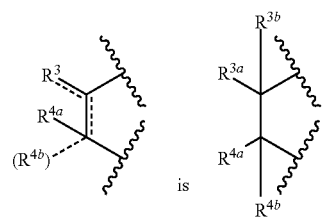

wherein $R^{3a}$, $R^{3b}$, $R^{4a}$ and $R^{4b}$ are the same as defined in item (1), its pharmaceutically acceptable salt or a solvate thereof.

(5-1)
The compound according to any one of items (1), (1-1), (1-2) and (2) wherein

[Chemical Formula 16]

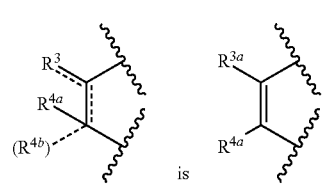

wherein $R^{3a}$ and $R^{4a}$ are the same as defined in item (1), its pharmaceutically acceptable salt or a solvate thereof.

(5-2)

The compound according to any one of items (1), (1-1), (1-2) and (2) wherein

[Chemical Formula 17]

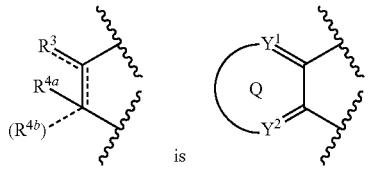

is wherein $Y^1$ and $Y^2$ are each independently —$C(R^5)$= or —N=, and Q is the same as defined in item (1), its pharmaceutically acceptable salt, or solvate thereof.

(5-3)

The compound according to any one of items (1), (1-1), (1-2) and (2) wherein

[Chemical Formula 18]

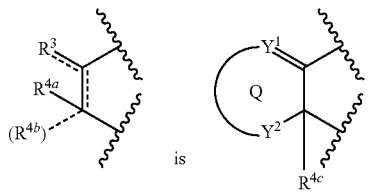

is wherein $Y^1$ is —$C(R^5)$= or —N=, $Y^2$ is —$C(R^5)(R^6)$—, —$N(R^7)$—, —S—, —SO—, —$SO_2$— or —O—, and Q and $R^{4c}$ are the same as defined in item (1), its pharmaceutically acceptable salt, or solvate thereof.

(5-4)

The compound according to any one of items (1), (1-1), (1.2) and (2) wherein

[Chemical Formula 19]

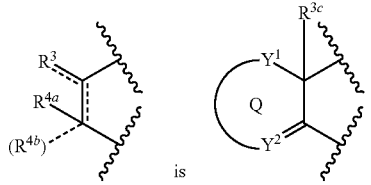

is wherein $Y^1$—$C(R^5)(R^6)$—, —$N(R^7)$—, —S—, —SO—, —$SO_2$—, or —O—, $Y^2$ is —$C(R^5)$= or —N=, and Q and $R^{3c}$ are the same as defined in item (1), its pharmaceutically acceptable salt, or solvate thereof.

(5-5)

The compound according to any one of items (1), (1-1), (1-2) and (2) wherein

[Chemical Formula 20]

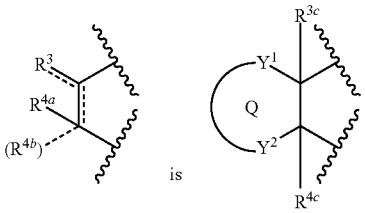

is wherein Q, $Y^1$ and $Y^2$ are each independently —$C(R^5)(R^6)$—, —$N(R^7)$—, —S—, —SO—, —$SO_2$—, or —O—, $R^{3c}$ and $R^{4c}$ are the same as defined in item (1), its pharmaceutically acceptable salt, or solvate thereof.

(5-6)

The compound according to any one of items (1), (1-1), (1-2) and (2) wherein

[Chemical Formula 21]

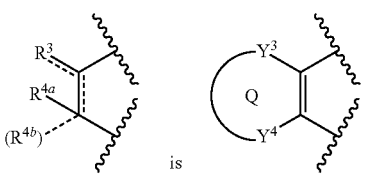

is wherein Q, $Y^3$ and $Y^4$ are the same as defined in item (1), its pharmaceutically acceptable salt, or solvate thereof.

(6) The compound according to any one of items (2) to (4) and (5-1) to (5-6) wherein —Z— is —C(=O)N($R^8$)—, its pharmaceutically acceptable salt or a solvate thereof.

(7) The compound according to any one of items (2) to (4), (5-1) to (5-6) and (6) wherein ring A' is substituted or unsubstituted benzene, and ring B is substituted or unsubstituted pyridine, substituted or unsubstituted pyrimidine or substituted or unsubstituted pyrazine, its pharmaceutically acceptable salt or a solvate thereof.

(8) The compound according to any one of items (1), (1-1), (1-2), (2) to (4), (6) and (7) wherein $R^{4a}$ and $R^{4b}$ are both hydrogen, its pharmaceutically acceptable salt or a solvate thereof.

(9) The compound according to any one of items (1), (1-1), (1-2), (2) to (4), (5-1) to (5-6) and (6) to (8) wherein $R^1$ is C1 to C3 unsubstituted alkyl, its pharmaceutically acceptable salt or a solvate thereof.

(10) The compound according to any one of items (1), (1-1), (1-2), (2) to (4), (5-1) to (5-6) and (6) to (9) wherein $R^{2a}$ and $R^{2b}$ are both hydrogen, its pharmaceutically acceptable salt or a solvate thereof.

(11) A pharmaceutical composition comprising the compound according to any one of items (1), (1-1), (1-2), (2) to (4), (5-1) to (5-6) and (6) to (10), its pharmaceutically acceptable salt or a solvate thereof as an active ingredient.

(12) A pharmaceutical composition having BACE1 inhibitory activity comprising the compound according to any one of items (1), (1-1), (1-2), (2) to (4), (5-1) to (5-6) and (6) to (10), its pharmaceutically acceptable salt or a solvate thereof as an active ingredient.

(13) A method for inhibiting BACE1 activity comprising administering the compound according to any one of items (1), (1-1), (1-2), (2) to (4), (5-1) to (5-6) and (6) to (10), its pharmaceutically acceptable salt or a solvate thereof.

(14) The compound according to any one of items (1), (1-1), (1-2), (2) to (4), (5-1) to (5-6) and (6) to (10), its pharmaceutically acceptable salt or a solvate thereof for use in a method for inhibiting BACE1 activity.

(15) Use of a compound according to any one of items (1), (1-1), (1-2), (2) to (4), (5-1) to (5-6) and (6) to (10), its pharmaceutically acceptable salt, or solvate thereof for manufacturing a medicament for inhibiting BACE1 activity.

(16) A method for treating or preventing diseases induced by production, secretion or deposition of amyloid β proteins comprising administering the compound according to any one of items (1), (1-1), (1-2), (2) to (4), (5-1) to (5-6) and (6) to (10), its pharmaceutically acceptable salt or a solvate thereof.

(17) Use of a compound according to any one of items (1), (1-1), (1-2), (2) to (4), (5-1) to (5-6) and (6) to (10), its pharmaceutically acceptable salt, or solvate thereof for manufacturing a medicament for treating or preventing diseases induced by production, secretion or deposition of amyloid β proteins.

(18) A compound according to any one of items (1), (1-1), (1-2), (2) to (4), (5-1) to (5-6) and (6) to (10), its pharmaceutically acceptable salt, or solvate thereof for use in treating or preventing diseases induced by production, secretion or deposition of amyloid β proteins.

(19) A method for treating or preventing Alzheimer's disease comprising administering the compound according to any one of items (1), (1-1), (1-2), (2) to (4), (5-1) to (5-6) and (6) to (10), its pharmaceutically acceptable salt, or solvate thereof.

(20) Use of a compound according to any one of items (1), (1-1), (1.2), (2) to (4), (5-1) to (5-6) and (6) to (10), its pharmaceutically acceptable salt or solvate thereof for manufacturing a medicament for treating or preventing Alzheimer's disease.

(21) A compound according to any one of items (1), (1-1), (1-2), (2) to (4), (5-1) to (5-6) and (6) to (10), its pharmaceutically acceptable salt or solvate thereof for use in treating or preventing Alzheimer's disease.

(22) A method, a system, an apparatus, a kit or the like for manufacturing the compound according to any one of items (1), (1-1), (1-2), (2) to (4), (5-1) to (5-6) and (6) to (10), its pharmaceutically acceptable salt or a solvate thereof.

(23) A method, a system, an apparatus, a kit or the like for preparing a pharmaceutical composition comprising the compound according to any one of items (1), (1-1), (1-2), (2) to (4), (5-1) to (5-6) and (6) to (10), its pharmaceutically acceptable salt or a solvate thereof.

(24) A method, a system, an apparatus, a kit or the like for use the compound according to any one of items (1), (1-1), (1-2), (2) to (4), (5-1) to (5-6) and (6) to (10), its pharmaceutically acceptable salt or a solvate thereof.

(25) A pharmaceutical composition according to item (11) or (12) for treating or preventing a disease induced by production, secretion or deposition of amyloid β proteins.

(26) A pharmaceutical composition according to item (11) or (12) for treating or preventing Alzheimer's disease.

Effect of the Invention

The compound of the present invention is useful as an agent for treating or preventing disease induced by production, secretion or deposition of amyloid β proteins such as Alzheimer's disease.

MODE FOR CARRYING OUT THE INVENTION

In the specification, the "halogen" includes fluorine, chlorine, bromine, and iodine.

In the specification, the "alkyl" includes linear or branched alkyl of a carbon number of 1 to 15, for example, a carbon number of 1 to 10, for example, a carbon number of 1 to 6, and for example, a carbon number of 1 to 3. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl.

The alkyl portions in "alkoxy", "halogenoalkyl", "hydroxyalkyl", "halogenoalkoxy", "hydroxy alkoxy", "alkoxycarbonyl", "halogenoalkoxycarbonyl", "alkylamino", "aminoalkyl", "alkoxyalkoxy", "alkoxyalkenyloxy", "alkoxyalkynyl", "alkylcarbonyl", "alkylcarbamoyl", "hydroxyalkylcarbamoyl", "alkoxyimino", "alkylthio", "alkylsulfonyl", "alkylsulfonylamino", "alkylsulfonylalkylamino", "alkylsulfonylimino", "alkylsulfinylamino", "alkylsulfinylalkylamino", "alkylsulfinylimino", "alkylsulfamoyl", "alkylsulfinyl", "carbocyclylalkyl", "carbocyclylalkoxy", "carbocyclylalkoxycarbonyl", "carbocyclylalkylamino", "carbocyclylalkylcarbamoyl", "cycloalkylalkyl", "cycloalkylalkoxy", "cycloalkylalkylamino", "cycloalkylalkoxycarbonyl", "cycloalkylalkylcarbamoyl", "arylalkyl", "arylalkoxy", "arylalkylamino", "arylalkoxycarbonyl", "arylalkylcarbamoyl", "heterocyclylalkyl", "heterocyclylalkoxy", "heterocyclylalkylamino", "heterocyclylalkoxycarbonyl" and "heterocyclylalkylcarbamoyl" are the same as the above "alkyl."

"Substituted or unsubstituted alkyl" may be substituted with one or more substituents selected from a substituent group α.

As used herein, the substituent group α is a group consisting of halogen, hydroxy, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group, each of which carbocycle and heterocycle is optionally substituted with one or more substituent selected from halogen, alkyl, hydroxy, and alkoxy.

Examples of the substituents of "substituted or unsubstituted alkoxy", "substituted or unsubstituted alkoxycarbonyl", "substituted or unsubstituted alkylthio", "substituted or unsubstituted alkylsulfonyl" and "substituted or unsubstituted alkylsulfinyl" are one or more selected from the above-mentioned substituent group α.

Examples of "halogenoalkyl" are trifluoromethyl, fluoromethyl and trichloromethyl.

Examples of "halogenoalkoxy" are trifluoromethoxy, fluoromethoxy, trichloromethoxy.

The term "alkylidene" includes a divalent group of the above "alkyl" and examples are methylidene, ethylidene, propylidene, isopropylidene, butylidene, pentylidene and hexylidene.

The term "alkenyl" includes linear or branched alkenyl of a carbon number or 2 to 15, for example, a carbon number of 2 to 10, for example, a carbon number of 2 to 6, and for example, a carbon number of 2 to 4, having one or more double bonds at any available positions. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

The alkenyl portions in "alkenyloxy", "alkenyloxycarbonyl", "alkenylcarbonyl", "alkoxyalkenyloxy", "alkenylthio", "alkenylamino", "alkenylsulfonyl" and "alkenylsulfinyl" are the same as the above "alkenyl."

The term "alkynyl" includes a linear or branched alkynyl of a carbon number of 2 to 10, preferably a carbon number of 2 to 8, further preferably a carbon number of 3 to 6 having one or more triple bonds at optionally positions. Examples include ethynyl, propynyl, butynyl, pentynyl, hexynyl, heptynyl, octynyl, nonynyl and decynyl. These may have further a double bond at any available position.

Alkynyl portions in "alkoxyalkynyl", "alkynyloxy", "alkynyloxycarbonyl", "alkynylcarbonyl", "alkoxyalkynyloxy", "alkynylthio", "alkynylsulfinyl", "alkynylsulfonyl" and "alkynylamino" are the same as the above "alkynyl."

Examples of the substituent of "substituted or unsubstituted alkenyl", "substituted or unsubstituted alkenyloxy", "substituted or unsubstituted alkenyloxycarbonyl", "substituted or unsubstituted alkenylthio", "substituted or unsubstituted alkenylsulfinyl", "substituted or unsubstituted alkenylsulfonyl", "substituted or unsubstituted alkynyl", "substituted or unsubstituted alkynyloxy", "substituted or unsubstituted alkynylthio", "substituted or unsubstituted alkynyloxycarbony", "substituted or unsubstituted alkynylsulfinyl" and "substituted or unsubstituted alkynylsulfonyl" are one or more substituent selected from the above-mentioned substituent group α.

Examples of the substituent in "substituted or unsubstituted amino", "substituted or unsubstituted carbamoyl", "substituted or unsubstituted thiocarbamoyl" and "substituted or unsubstituted sulfamoyl" are one or two substituents selected from alkyl, acyl, hydroxy, alkoxy, alkoxycarbonyl, carbocyclic group and heterocyclic group.

The term "acyl" includes formyl, alkylcarbonyl of a carbon number of 1 to 10, alkenylcarbonyl of a carbon number of 2 to 10, alkynylcarbonyl of a carbon number of 2 to 10, carbocyclylcarbonyl and heterocyclylcarbonyl. Examples are formyl, acetyl, propionyl, butyryl, isobutyryl, valeryl, pivaloyl, hexanoyl, acryloyl, propioloyl, methacryloyl, crotonoyl, benzoyl, cyclohexanecarbonyl, pyridinecarbonyl, furancarbonyl, thiophenecarbonyl, benzothiazolecarbonyl, pyrazinecarbonyl, piperidinecarbonyl and thiomorpholino.

The acyl portions in "acyloxy" and "acylamino" are the same as the above "acyl."

Examples of the substituents of "substituted or unsubstituted acyl" and "substituted or unsubstituted acyloxy" are one or more substituents selected from the substituent group α. The ring portions of carbocyclylcarbonyl and heterocyclylcarbonyl may be substituted with one or more substituents selected from alkyl, substituent group α, and alkyl substituted with one or more substituents selected from substituent group α.

The term "carbocyclic group" includes cycloalkyl, cycloalkenyl, aryl and non-aromatic fused carbocyclyl.

The term "cycloalkyl" includes a carbocyclic group of a carbon number of 3 to 10, for example, a carbon number of 3 to 8, and for example, a carbon number 4 to 8. Examples are cyclopropyl, cyclobutyl, cyclopentyl, cyclohexyl, cycloheptyl, cyclooctyl, cyclononyl and cyclodecyl.

The cycloalkyl portions in "cycloalkylalkyl", "cycloalkyloxy", "cycloalkylalkoxy", "cycloalkylthio", "cycloalkylamino", "cycloalkylalkylamino", "cycloalkylsulfamoyl", "cycloalkylsulfonyl", "cycloalkylcarbamoyl", "cycloalkylalkylcarbamoyl", "cycloalkylalkoxycarbonyl" and "cycloalkyloxycarbonyl" are the same as the above "cycloalkyl."

The term "cycloalkenyl" includes a group having one or more double bonds at optionally positions in the ring of the above "cycloalkyl". Examples are cyclopropenyl, cyclobutenyl, cyclopentenyl, cyclohexenyl, cycloheptenyl, cyclooctenyl and cyclohexadienyl.

The term "aryl" includes phenyl, naphthyl, anthryl and phenanthryl. Specific example is phenyl.

The term "non-aromatic fused carbocyclic group" includes non-aromatic groups wherein two or more cyclic groups selected from the above "cycloalkyl", "cycloalkenyl" and "aryl" are fused. Examples are indanyl, indenyl, tetrahydronaphthyl and fluorenyl.

The carbocycle portions in "non-aromatic carbocycle" are the same as "cycloalkyl", "cycloalkenyl" and "non-aromatic fused carbocyclic group." Examples are cyclopropane, cyclobutane, cyclopentane, cyclohexane, cycloheptane, cyclooctane, cyclononane, cyclodecane, cyclopropene, cyclobutene, cyclopentene, cyclohexene, cycloheptene and cyclooctene.

The carbocycle portions in "carbocycle", "carbocyclyloxy", "carbocyclylalkyl", "carbocyclylalkoxy", "carbocyclylalkoxycarbonyl", "carbocyclylthio", "carbocyclylamino", "carbocyclylalkylamino", "carbocyclylcarbonyl", "carbocyclylsulfamoyl", "carbocyclylsulfonyl", "carbocyclylcarbamoyl", "carbocyclylalkylcarbamoyl", "carbocyclyloxycarbonyl", "carbocyclylsulfinyl" and "carbocyclylsulfonyl" are the same as that of the above "carbocyclic group."

The aryl portions in "arylalkyl", "aryloxy", "aryloxycarbonyl", "arylalkoxycarbonyl", "arylthio", "arylamino", "arylalkoxy", "arylalkylamino", "arylsulfonyl", "arylsulfamoyl", "arylcarbamoyl" and "arylalkylcarbamoyl" are the same as the above "aryl."

The term "heterocyclic group" includes a heterocyclic group having one or more hetero atoms optionally selected from O, S and N in a ring, and examples include 5- to 6-membered heteroaryl such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl and thiadiazolyl; non-aromatic heterocyclyl such as dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl and tetrahydropyridazinyl; fused bicyclic heterocyclyl such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisooxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, furopyridyl, thienothienyl, imidazopyridyl, imidazopyrazolyl, pyrazolopyridyl, pyrazolopyrazinyl, thiazolopyridyl, pyrazolopyrimidinyl, pyrazolotriazinyl, pyridazolopyridyl, triazolopyridyl, imidazothiazolyl, pyrazinopyridazinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxinyl, dihydrobenzoxezinyl, dihydrobenzodioxepinyl, and dihydrothienodioxinyl; fused tricyclic heterocyclyl such as carbazolyl, acridinyl, xanthenyl, phenothiazinyl, phenoxathiinyl, phenoxazinyl, dibenzofuryl, imidazoquinolyl, and tetrahydrocarbazolyl. Specific examples are 5- or 6-membered heteroaryl and non-aromatic heterocyclyl.

The heterocycle portions in "heterocycle", "heterocyclylalkyl", "heterocyclyloxy", "heterocyclylthio", "heterocyclylcarbonyl", "heterocyclylalkoxy", "heterocyclylamino", "heterocyclylsulfamoyl", "heterocyclylsulfonyl", "heterocyclylcarbamoyl", "heterocyclyloxycarbonyl", "heterocyclylalkylamino", "heterocyclylalkoxycarbonyl", "heterocyclylalkylcarbamoyl" and "heterocyclylsulfinyl" are the same as that of the above "heterocyclyl."

The heterocycle portions of "non-aromatic heterocycle" are the same as the heterocycle portion of the above "non-aromatic heterocyclyl." Specific examples are dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazole, tetrahydrothiazole, tetrahydroisothiazole, dihydrooxazine, hexahydroazepine, tetrahydrodiazepine, and tetrahydropyridazine.

A bond of the above "heterocyclic group" may be situated on any ring.

The term "heteroaryl" includes an aromatic cyclic group among the "heterocyclic group".

In the specification, examples of ring A are as follows:

[Chemical Formula 22]

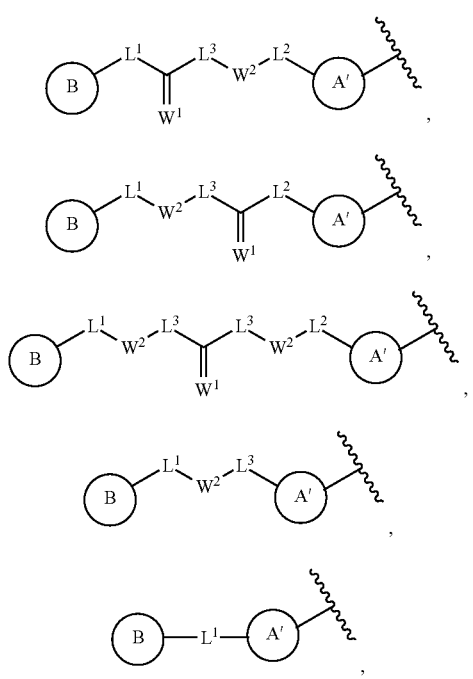

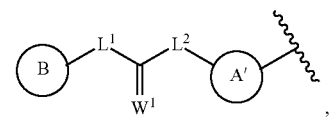

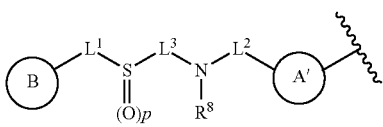

or

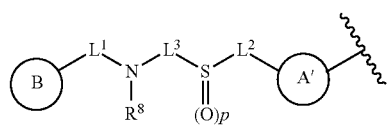

wherein ring A' and ring B are each independently substituted or unsubstituted carbocycle or substituted or unsubstituted heterocycle, $L^1$, $L^2$, and $L^3$ are each independently a bond, substituted or unsubstituted alkynylene, substituted or unsubstituted alkenylene or substituted or unsubstituted alkynylene, $=W^1$ is $=O$, $=S$, or $=NR^9$, $W^2$ is O, S, or $N(R^8)$, $R^8$ is hydrogen, substituted or unsubstituted alkyl, substituted or unsubstituted alkenyl, substituted or unsubstituted alkynyl or substituted or unsubstituted acyl, $R^9$ is hydrogen, hydroxy, substituted or unsubstituted alkyl, substituted or unsubstituted alkenyl, substituted or unsubstituted alkynyl or substituted or unsubstituted acyl, when ring A is (i), then the constituent carbon atom of $L^1$ and the constituent carbon atom of $L^2$, or the constituent carbon atom of $L^1$ and the nitrogen atom of $W^2$ may be connected with substituted or unsubstituted alkylene to form a ring, when ring A is (ii), then the constituent carbon atom of $L^1$ and the constituent carbon atom of $L^2$, or the nitrogen atom of $W^2$ and the constituent carbon atom of $L^2$ may be connected with substituted or unsubstituted alkylene to form a ring, when ring A is (iii), then two nitrogen atoms of $W^2$ may be connected with substituted or unsubstituted alkylene to form a ring, when ring A is (vi), then the constituent carbon atom of $L^1$ and the constituent carbon atom of $L^2$ may be connected by substituted or unsubstituted alkylene to form a ring, p is 1 or 2, and when multiple $L^3$, multiple $W^2$, or multiple $R^9$ are present, each of them may be independently different.

Specific examples are as follows:

[Chemical Formula 23]

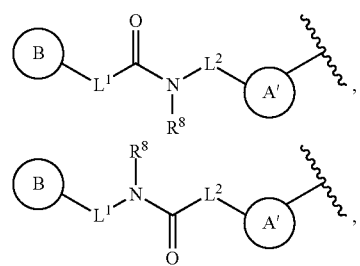

-continued

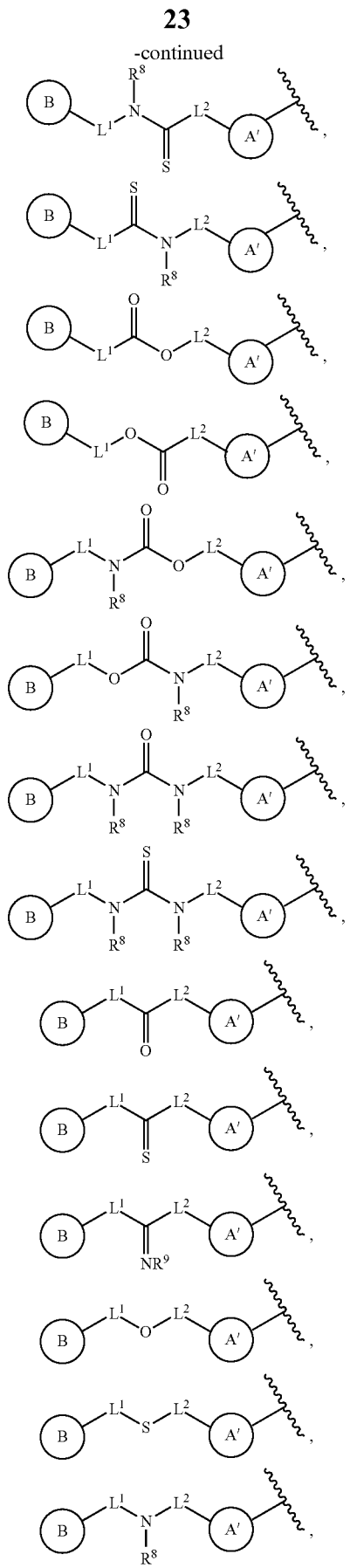

-continued

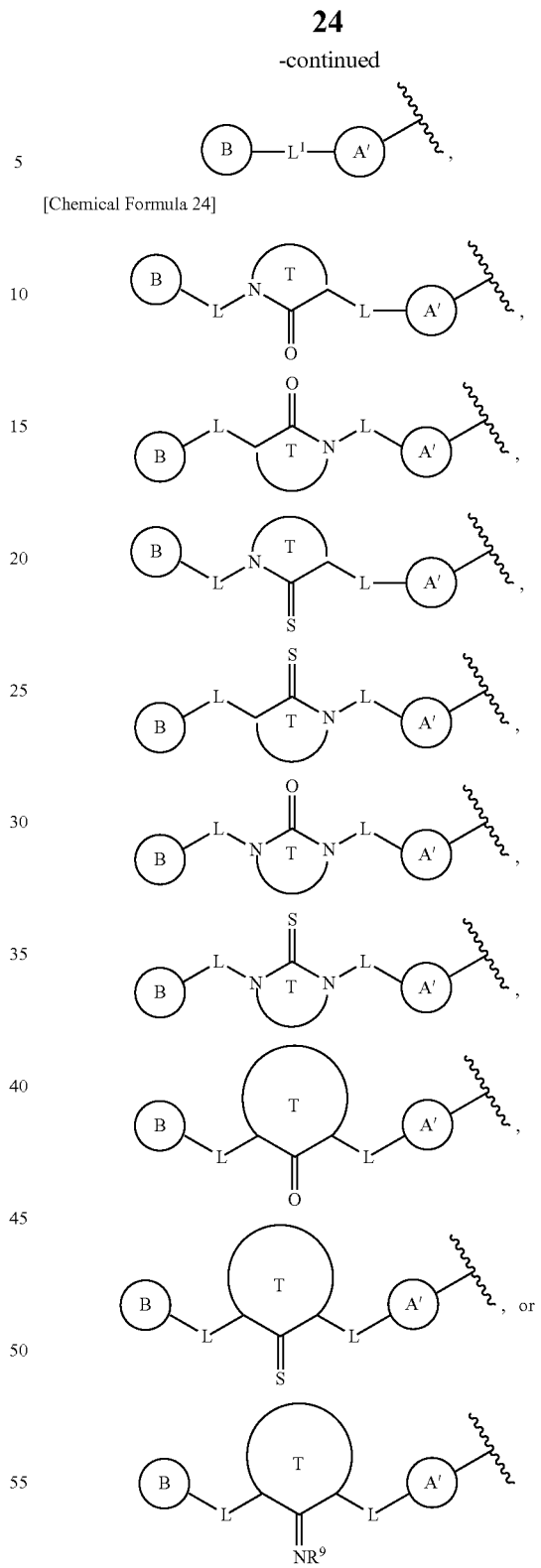

wherein L is each independently a bond, substituted or unsubstituted alkylene, substituted or unsubstituted alkenylene or substituted or unsubstituted alkynylene, ring T is a carbocycle optionally substituted with a group(s) selected from the substituent group α, or a heterocycle optionally substituted with a group(s) selected from the group α, and that and other symbols are the same as defined above.

More specific examples are as follows:
[Chemical Formula 25]
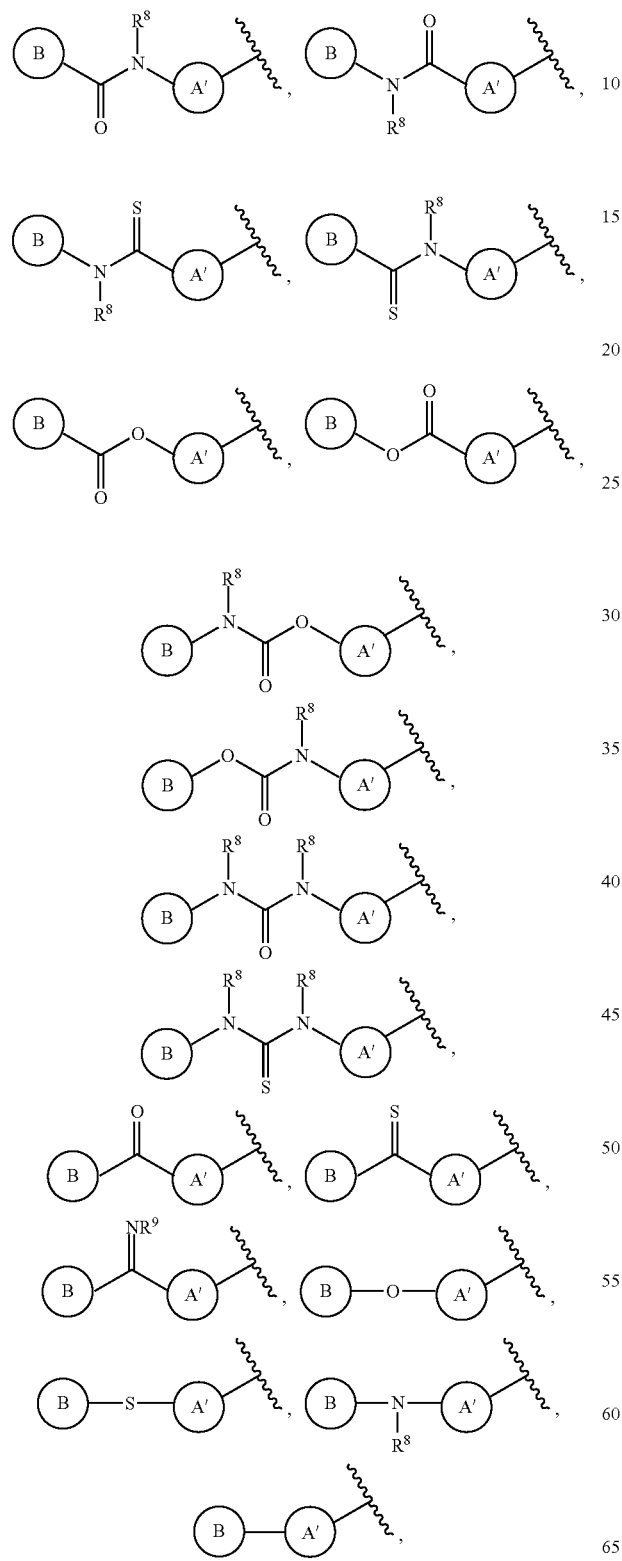
[Chemical Formula 26]
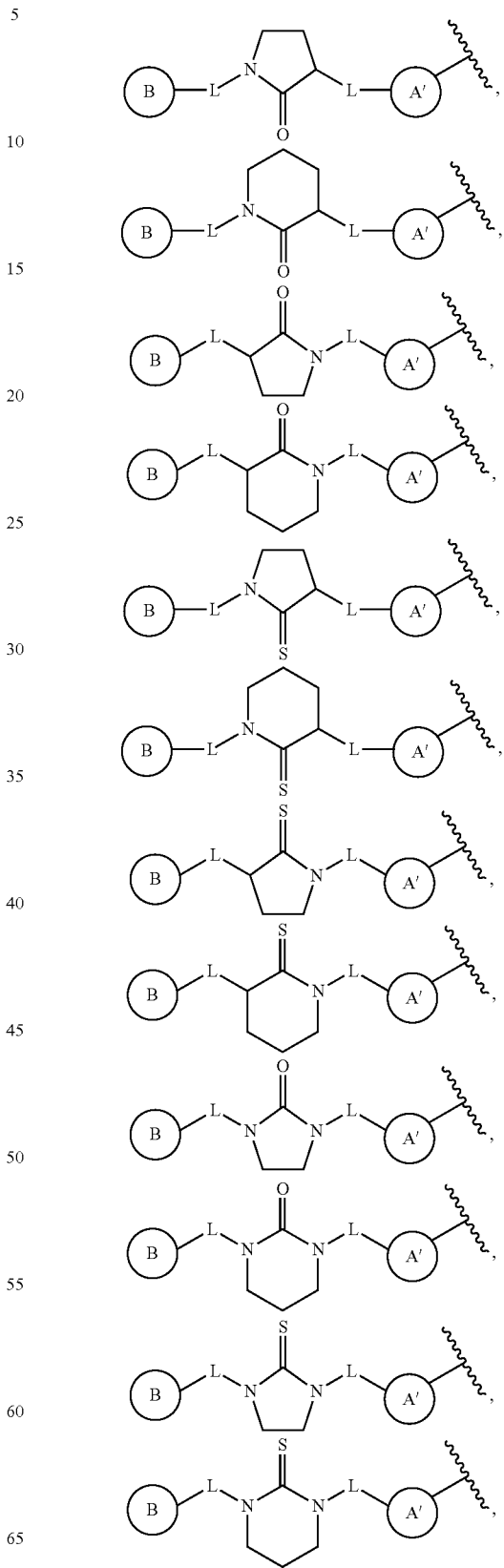
wherein each symbol is the same as defined above.

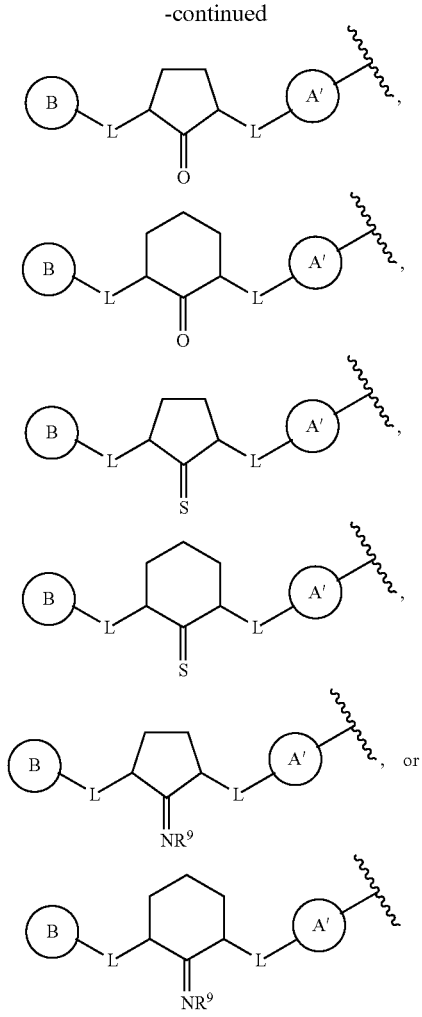

wherein each symbol is the same as defined above.

Other examples of the substituent of "substituted carbocycle", "substituted or unsubstituted carbocycle", "substituted or unsubstituted heterocycle", "substituted or unsubstituted benzene", "substituted or unsubstituted pyridine", "substituted or unsubstituted pyrimidine", and "substituted or unsubstituted pyrazine" in ring A, ring A', and ring B include:

a group selected from the substituent group α such as halogen, hydroxy, alkoxy, acyl, acyloxy, carboxy, alkoxycarbonyl, carbamoyl, amino, cyano, alkylamino and/or alkylthio; alkyl substituted with one or more groups selected from the substituent group α, hydroxyimino and alkoxyimino, wherein the substituent is, for example, halogen, hydroxy, alkoxy and/or alkoxycarbonyl, or unsubstituted alkyl;

aminoalkyl substituted with one or more groups selected from the substituent group α;

wherein the substituent is, for example, acyl, alkyl and/or alkoxy;

alkenyl substituted with one or more substituents selected from the substituent group α, wherein the substituent is, for example, alkoxycarbonyl, halogen, and/or halogenoalkoxycarbonyl, or unsubstituted alkenyl;

alkynyl substituted with one or more substituents selected from the substituent group α, wherein the substituent is, for example, alkoxycarbonyl, or unsubstituted alkynyl;

alkoxy substituted with one or more substituents selected from the substituent group α, wherein the substituent is, for example, halogen, carbamoyl, alkylcarbamoyl and/or hydroxyalkylcarbamoyl;

alkoxyalkoxy substituted with one or more substituents selected from the substituent group α;

alkenyloxy substituted with one or more substituents selected from the substituent group α, wherein the substituent is, for example, halogen, hydroxy, amino and/or alkylamino, or unsubstituted alkenyloxy; alkoxyalkenyloxy substituted with one or more substituents selected from the substituent group α;

alkynyloxy substituted with one or more substituents selected from the substituent group α, wherein the substituent is, for example, halogen and/or hydroxy, or unsubstituted alkynyloxy;

alkoxyalkynyloxy substituted with one or more groups selected from the substituent group α;

alkylthio substituted with one or more substituents selected from the substituent group α, or unsubstituted alkylthio;

alkenylthio substituted with one or more substituents selected from the substituent group α, or unsubstituted alkenylthio;

alkynylthio substituted with one or more substituents selected from the substituent group α, or unsubstituted alkynylthio;

alkylamino substituted with one or more substituents selected from the substituent group α;

alkenylamino substituted with one or more substituents selected from the substituent group α;

alkynylamino substituted with one or more substituents selected from the substituent group α;

aminooxy substituted with one or more substituents selected from the substituent group α and alkylidene, or unsubstituted aminooxy;

acyl substituted with one or more substituents selected from the substituent group α; alkylsulfonyl substituted with one or more substituents selected from the substituent group α, or unsubstituted alkylsulfonyl;

alkylsulfinyl substituted with one or more substituents selected from the substituent group α, or unsubstituted alkylsulfinyl;

alkylsulfamoyl substituted with one or more substituents selected from the substituent group α;

a carbocyclic group such as cycloalkyl and aryl, substituted with one or more substituents selected from the substituent group α, azide, alkyl and halogenoalkyl; a heterocyclic group substituted with one or more substituents selected from the substituent group α, azide, alkyl and halogenoalkyl;

carbocyclylalkyl such as cycloalkylalkyl and arylalkyl, substituted with one or more substituents selected from the substituent group α, azide, alkyl and halogenoalkyl, or unsubstituted carbocyclylalkyl;

heterocyclylalkyl substituted with one or more substituents selected from the substituent group α, azide, alkyl and halogenoalkyl, or unsubstituted heterocyclylalkyl; carbocyclyloxy such as cycloalkyloxy and aryloxy, substituted with one or more substituents selected from the substituent group α, azide, alkyl and halogenoalkyl, or unsubstituted carbocyclyloxy;

heterocyclyloxy substituted with one or more substituents selected from the substituent group α, azide, alkyl and halogenoalkyl, or unsubstituted heterocyclyloxy;

carbocyclylalkoxy such as cycloalkylalkoxy and arylalkoxy, substituted with one or more substituents selected from the substituent group α, azide, alkyl and halogenoalkyl, or unsubstituted carbocyclylalkoxy;

heterocyclylalkoxy substituted with one or more substituents selected from the substituent group α, azide, alkyl and halogenoalkyl, or unsubstituted heterocyclylalkoxy;

carbocyclylalkoxycarbonyl such as cycloalkylalkoxycarbonyl and arylalkoxycarbonyl, substituted with one or more substituents selected from the substituent group α, azide, alkyl and halogenoalkyl, or unsubstituted carbocyclylalkoxycarbonyl such as cycloalkylalkoxycarbonyl and arylalkoxycarbonyl;

heterocyclylalkoxycarbonyl substituted with one or more substituents selected from the substituent group α, azide, alkyl and halogenoalkyl, or unsubstituted heterocyclylalkoxycarbonyl;

carbocyclylthio such as cycloalkylthio and arylthio, substituted with one or more substituents selected from the substituent group α, azide, alkyl and halogenoalkyl, or unsubstituted carbocyclylthio such as cycloalkylthio and arylthio;

heterocyclylthio substituted with one or more substituents selected from the substituent group α, azide, alkyl and halogenoalkyl, or unsubstituted heterocyclylthio;

carbocyclylamino such as cycloalkylamino and arylamino, substituted with one or more substituents selected from the substituent group α, azide, alkyl and halogenoalkyl, or unsubstituted carbocyclylamino such as cycloalkylamino and arylamino;

heterocyclylamino substituted with one or more substituents selected from the substituent group α, azide, alkyl and halogenoalkyl, or unsubstituted heterocyclylamino;

carbocyclylalkylamino such as cycloalkylalkylamino and arylalkylamino, substituted with one or more substituents selected from the substituent group α, azide, alkyl and halogenoalkyl or unsubstituted carbocyclylalkylamino such as cycloalkylalkylamino and arylalkylamino;

heterocyclylalkylamino substituted with one or more substituents selected from the substituent group α, azide, alkyl and halogenoalkyl, or unsubstituted heterocyclylalkylamino;

carbocyclylsulfamoyl such as cycloalkylsulfamoyl and arylsulfamoyl, substituted with one or more substituents selected from the substituent group α, azide, alkyl and halogenoalkyl, or unsubstituted carbocyclylsulfamoyl;

heterocyclylsulfamoyl substituted with one or more substituents selected from the substituent group α, azide, alkyl and halogenoalkyl, or unsubstituted heterocyclylsulfamoyl;

carbocyclylsulfonyl such as cycloalkylsulfonyl and arylsulfonyl, substituted with one or more substituents selected from the substituent group α, azide, alkyl and halogenoalkyl, or unsubstituted carbocyclylsulfonyl such as cycloalkylsulfonyl and arylsulfonyl; heterocyclylsulfonyl substituted with one or more substituents selected from the substituent group α, azide, alkyl and halogenoalkyl, or unsubstituted heterocyclylsulfonyl;

carbocyclylcarbamoyl such as cycloalkylcarbamoyl and arylcarbamoyl, substituted with one or more substituents selected from the substituent group α, azide, alkyl and halogenoalkyl, or unsubstituted carbocyclylcarbamoyl such as cycloalkylcarbamoyl and arylcarbamoyl;

heterocyclylcarbamoyl substituted with one or more substituents selected from the substituent group α, azide, alkyl and halogenoalkyl, or unsubstituted heterocyclylcarbamoyl;

carbocyclylalkylcarbamoyl such as cycloalkylalkylcarbamoyl and arylalkylcarbamoyl, substituted with one or more substituents selected from the substituent group α, azide, alkyl and halogenoalkyl, or unsubstituted carbocyclylalkylcarbamoyl such as cycloalkylalkylcarbamoyl and arylalkylcarbamoyl;

heterocyclylalkylcarbamoyl substituted with one or more substituents selected from the substituent group α, azide, alkyl and halogenoalkyl, or unsubstituted heterocyclylalkylcarbamoyl;

carbocyclyloxycarbonyl such as cycloalkyloxycarbonyl and aryloxycarbonyl, substituted with one or more substituents selected from the substituent group α, azide, alkyl and halogenoalkyl, or unsubstituted carbocyclyloxycarbonyl such as cycloalkyloxycarbonyl and aryloxycarbonyl;

heterocyclyloxycarbonyl substituted with one or more substituents selected from the substituent group α, azide, alkyl and halogenoalkyl, or unsubstituted heterocyclyloxycarbonyl;

alkylenedioxy substituted with halogen, or unsubstituted alkylenedioxy;

oxo; and azide.

The aforementioned ring of ring A and ring B each may be substituted with one or more substituents selected from them.

In the specification, examples of the substituent of "substituted or unsubstituted carbocycle", "substituted or unsubstituted benzene", "substituted or unsubstituted heterocycle", "substituted or unsubstituted pyridine", "substituted or unsubstituted pyrimidine" and "substituted or unsubstituted pyrazine" in ring A' and ring B include halogen, cyano, hydroxy, nitro, carboxy, alkyl substituted with one or more substituents selected from the substituent group α, unsubstituted alkyl, alkoxy substituted with one or more substituents selected from the substituent group α, unsubstituted alkoxy, amino substituted with one or more substituents selected from the substituent group α, unsubstituted amino, carbamoyl substituted with one or more substituents selected from the substituent group α, unsubstituted carbamoyl, alkoxycarbonyl substituted with one or more substituents selected from the substituent group α, and unsubstituted alkoxycarbonyl.

Examples of the substituents other than "-Z-ring B" of "substituted or unsubstituted carbocycle" or "substituted or unsubstituted heterocycle" in ring A include halogen, alkyl, alkenyl, alkynyl, alkoxy, alkenyloxy, alkynyloxy, or cyano.

Examples of the substituents of "substituted or unsubstituted carbocycle", "substituted or unsubstituted benzene" or "substituted or unsubstituted heterocycle" in ring A' include halogen.

Examples of the substituents of "substituted or unsubstituted carbocycle", "substituted or unsubstituted heterocycle", "substituted or unsubstituted pyridine", "substituted or unsubstituted pyrimidine", or "substituted or unsubstituted pyrazine" in ring B include halogen, alkyl, alkenyl, alkynyl, alkoxy, alkenyloxy, alkynyloxy, or cyano.

Examples of the substituents of "substituted or unsubstituted carbocyclic group", "substituted or unsubstituted carbocyclylthio", "substituted or unsubstituted carbocyclyloxycarbonyl", "substituted or unsubstituted heterocyclyl", "substituted or unsubstituted carbocyclyloxy", "substituted or unsubstituted carbocyclylsulfinyl", "substituted or unsubstituted carbocyclylsulfonyl", "substituted or unsubstituted carbocycle", "substituted or unsubstituted heterocyclyl", "substituted or unsubstituted heterocyclyloxy", "substituted or unsubstituted heterocyclylthio", "substituted or unsubstituted heterocyclyloxycarbonyl", "substituted or unsubstituted heterocycylsulfinyl", "substituted or unsubstituted heterocyclylsulfonyl", "substituted or unsubstituted heterocycle", "substituted or unsubstituted cyclopentane", "substituted or unsubstituted cyclopentene", "substituted or unsubstituted cyclohexane" and "substituted or unsubstituted cyclohexene" in other than the above ring A, ring A' and ring B include one or more substituents selected from the substituent group α, unsubstituted alkyl, and alkyl substituted with one or more substituents selected from the substituent group α.

The term "alkylene" include a linear or branched divalent carbon chain of a carbon number of 1 to 10, for example, a carbon number of 1 to 6, or a carbon number of 1 to 3. Examples include methylene, dimethylene, trimethylene, tetramethylene, and methyltrimethylene.

The alkylene portion in "alkylenedioxy" s the same as the above "alkylene."

The term "alkenylene" includes a linear or branched divalent carbon chain of a carbon number of 2 to 10, for example, a carbon number of 2 to 6, or a carbon number of 2 to 4, having a double bond at any available position. Examples include vinylene, propenylene, butenylene, butadienylene, methylpropenylene, pentenylene and hexenylene.

The term "alkynylene", includes a linear or branched divalent carbon chain of a carbon number of 2 to 10, for example, a carbon number of 2 to 6, or a carbon number of 2 to 4, having a triple bond at any available position and, further, optionally having a double bond. Examples include ethynylene, propynylene, butynylene, pentynylene and hexynylene.

Examples of the substituents of "substituted or unsubstituted alkylene", "substituted or unsubstituted alkenylene", and "substituted or unsubstituted alkynylene" include a group(s) selected from the substituent group α, and specific examples are halogen and hydroxy.

In formula (I), examples of groups wherein

[Chemical Formula 27]

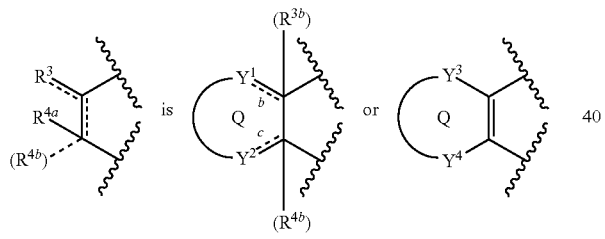

wherein each symbol is the same as defined in the item (1), include,

[Chemical Formula 28]

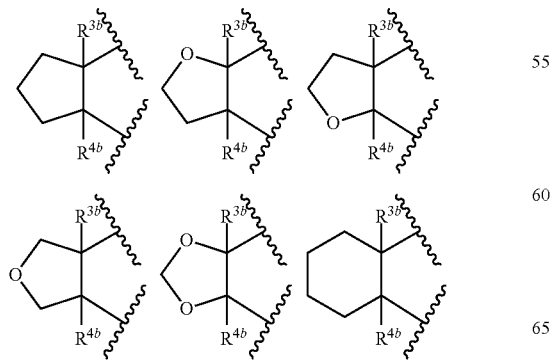

-continued

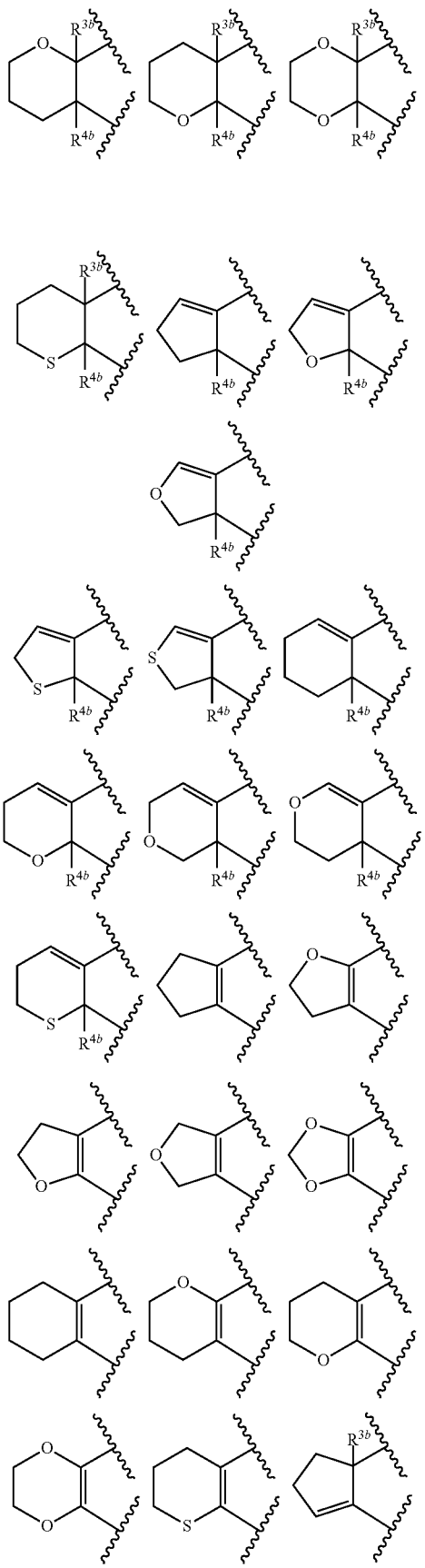

33
-continued
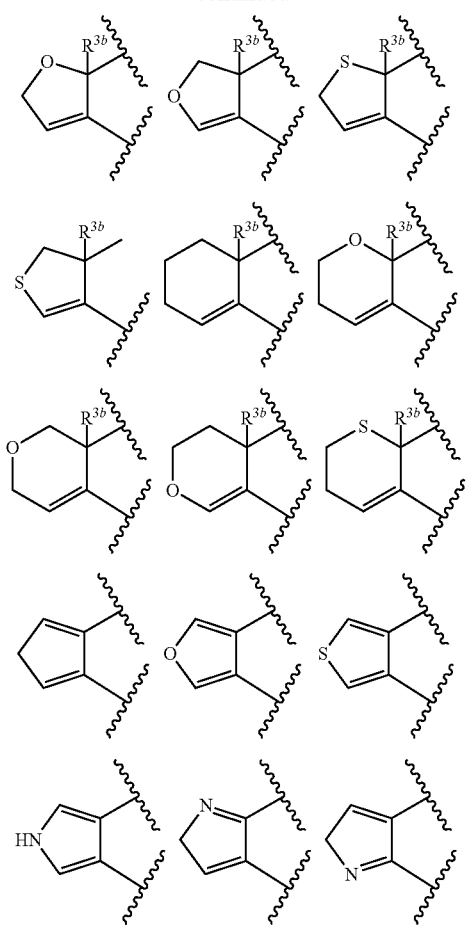
[Chemical Formula 29]
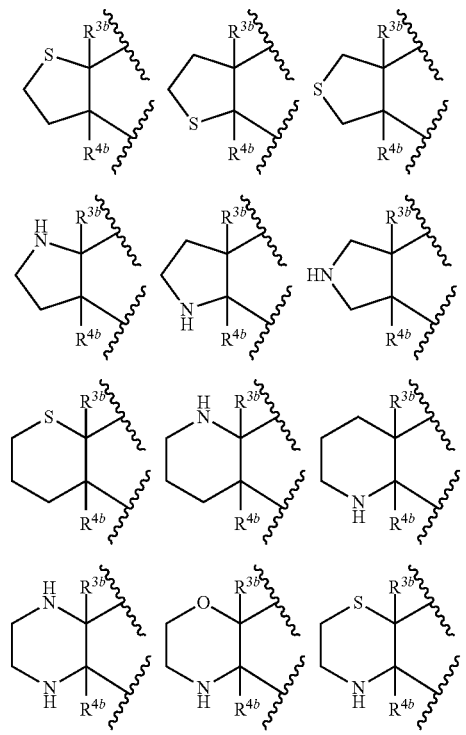
34
-continued
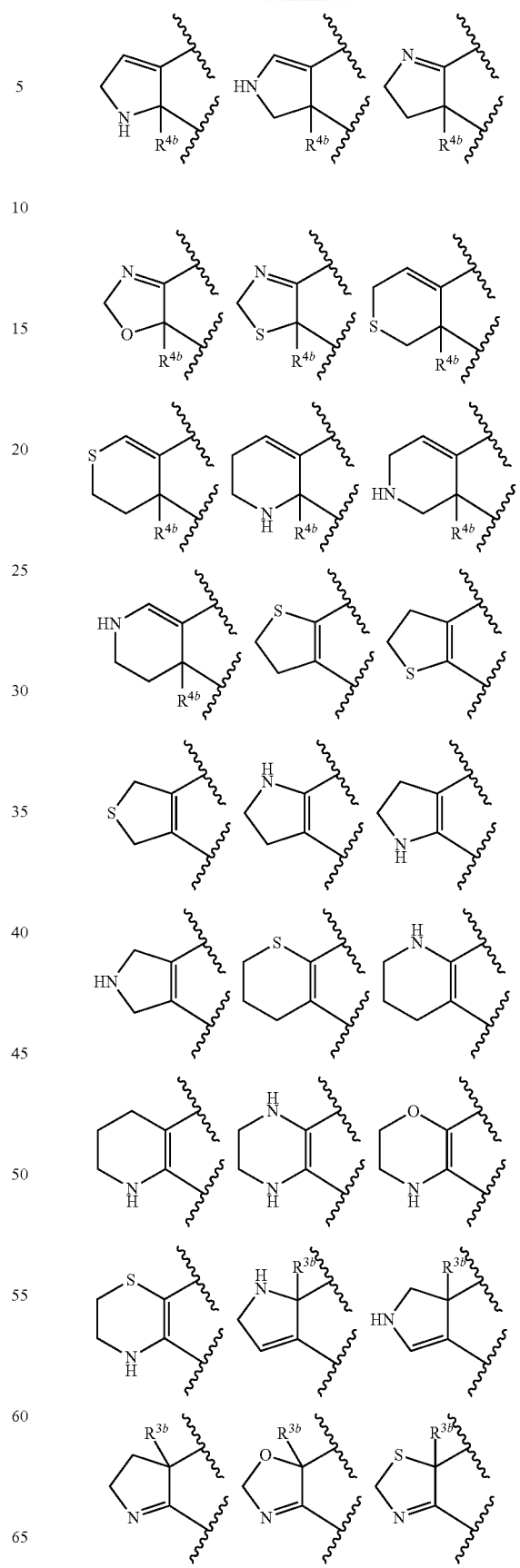

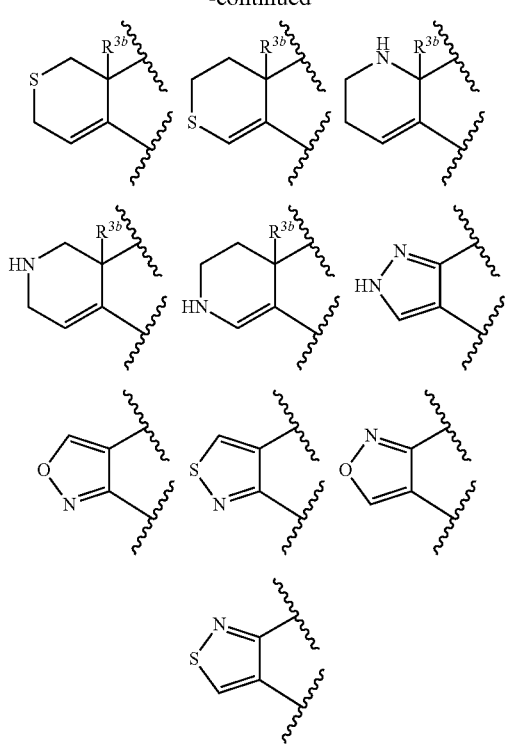
[Chemical Formula 30]
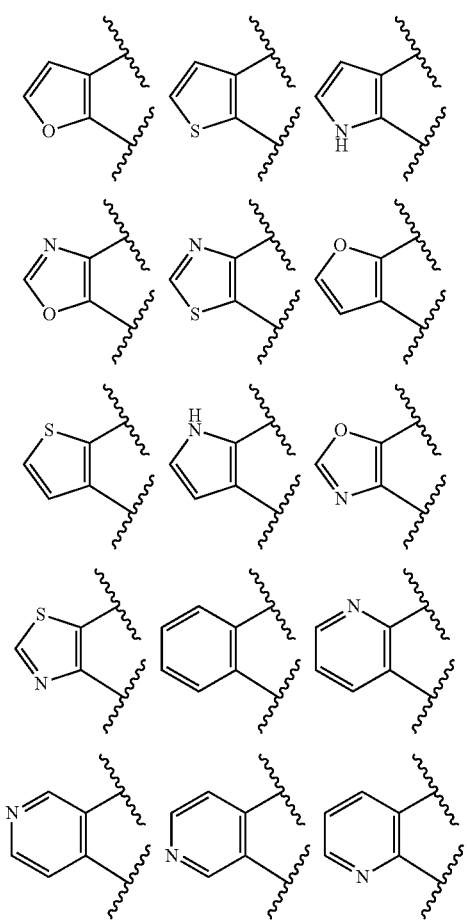
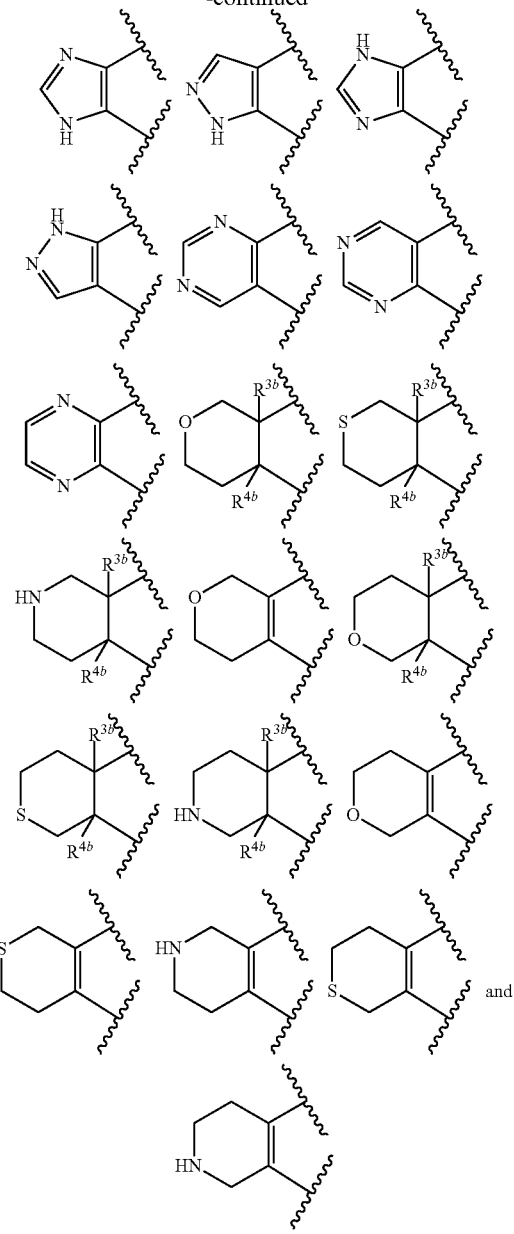
These groups may be substituted with one or more selected from alkyl substituted with one or more selected from the substituent group α, unsubstituted alkyl and alkyl substituted with one or more substituents selected from the substituent group α at any available position.
Examples of groups wherein
[Chemical Formula 31]
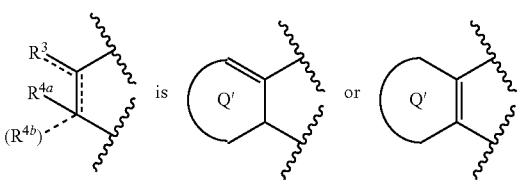

wherein each symbol is the same as defined in the item (1), and Q' is substituted or unsubstituted carbocycle, include

[Chemical Formula 32]

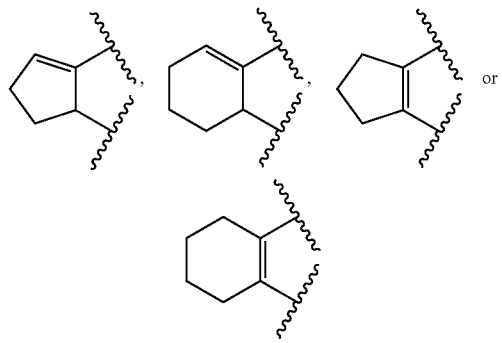

These groups may be substituted with one or more selected from alkyl substituted with one or more selected from the substituent group α, unsubstituted alkyl and alkyl substituted with one or more substituents selected from the substituent group α at any available position.

The phrase "$R^{za}$ and $R^{zb}$ together with the carbon atom to which they are attached may form a substituted or unsubstituted non-aromatic carbocycle or a substituted or unsubstituted non-aromatic heterocycle" include the following examples.

[Chemical Formula 33]

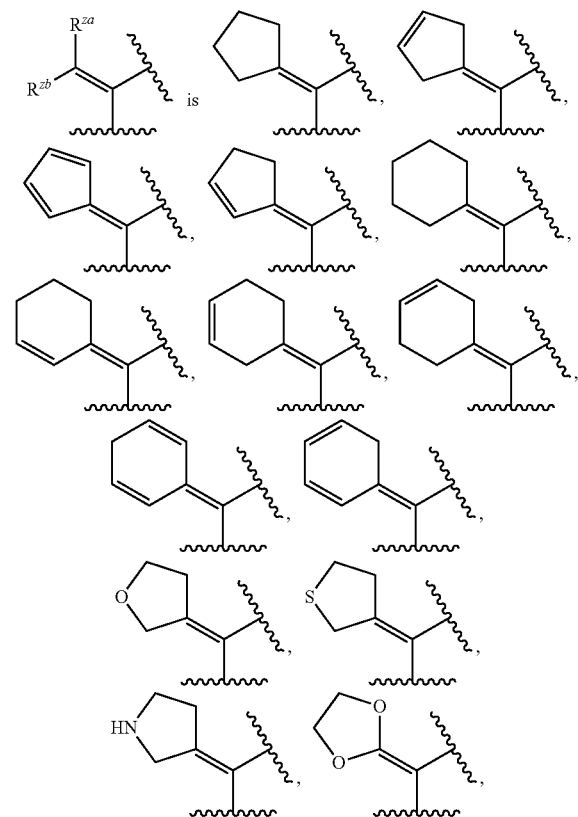

These groups may be substituted with one or more selected from alkyl substituted with one or more selected from the substituent group α, unsubstituted alkyl and alkyl substituted with one or more substituents selected from the substituent group α at any available position.

The phrases "$R^{3a}$ and $R^{3b}$ together with the carbon atom to which they are attached may form a substituted or unsubstituted carbocycle or a substituted or unsubstituted heterocycle" and "$R^{4a}$ and $R^{4b}$ together with the carbon atom to which they are attached may form a substituted or unsubstituted carbocycle or a substituted or unsubstituted heterocycle" include the following examples.

[Chemical Formula 34]

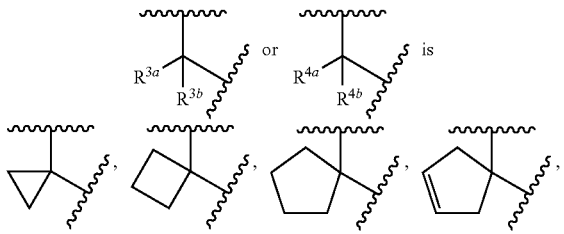

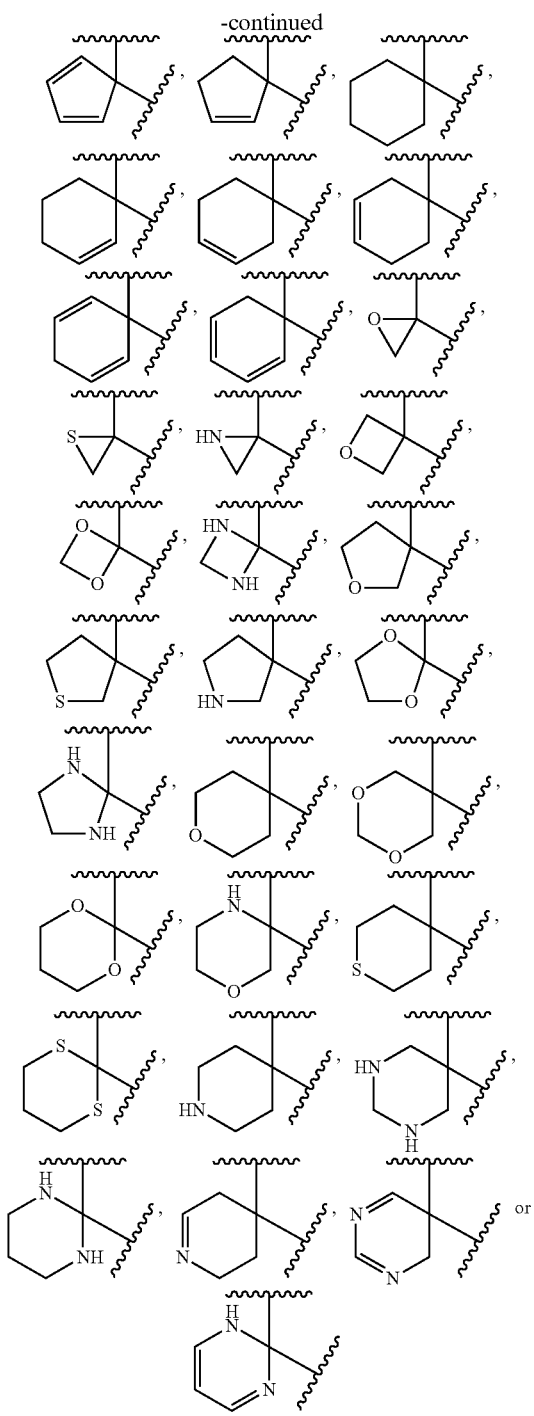

These groups may be substituted with one or more selected from alkyl substituted with one or more selected from the substituent group α, unsubstituted alkyl and alkyl substituted with one or more substituents selected from the substituent group α at any available position.

In the specification, the term "solvate" includes, for example, solvates with organic solvents and hydrates. It can be prepared in accordance with the known methods. Examples of solvate include a solvate with acetone, 2-butanol, 2-propanol, ethanol, ethyl acetate, tetrahydrofuran or diethyl ether. For example, it includes a non-toxic and water-soluble hydrate or solvate such as a solvate with ethanol. In the case that a hydrate or solvate is formed, the compound or salt may be coordinated with any number of solvate molecules or water molecules.

The compound of the formula (I) includes a pharmaceutically acceptable salt. Examples include salts with alkali metals such as lithium, sodium or potassium; alkaline earth metals such as calcium; magnesium; transition metals such as zinc or iron; ammonium; organic bases; and amino acids; or salts with inorganic acids such as hydrochloric acid, sulfuric, nitric acid, hydrobromic acid, phosphoric acid or hydroiodic acid; and organic acids such as acetic acid, trifluoroacetic acid, citric acid, lactic acid, tartaric acid, oxalic acid, maleic acid, fumaric acid, mandelic acid, glutaric acid, malic acid, benzoic acid, phthalic acid, benzenesulfonic acid, p-toluenesulfonic acid, methanesulfonic acid or ethanesulfonic acid. Specific examples are hydrochloric acid, phosphoric acid, tartaric acid and methanesulfonic acid. These salts can be formed by ordinary methods.

In addition, the compound of the formula (I) is not limited to a specific isomer, but includes all possible isomers, such as keto-enol isomers, imine-enamine isomers, diastereoisomers, optical isomers and rotation isomers; and racemate. For example, the compound of the formula (I) wherein $R^{2a}$ is hydrogen includes the following tautomers.

[Chemical Formula 35]

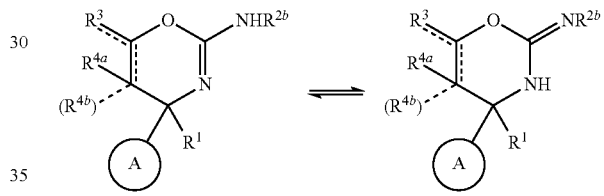

The compounds of the formulas (Ia) to (If) mentioned below also include similar tautomers.

The compound of the formula (I) has an asymmetric carbon atom and the compound includes the following optical isomers.

[Chemical Formula 36]

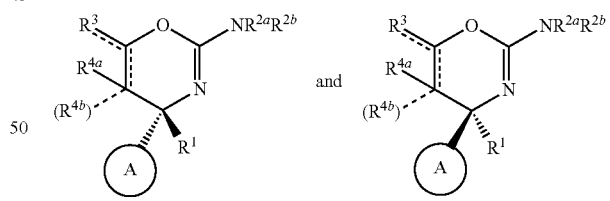

Preferable example is as follows:

[Chemical Formula 37]

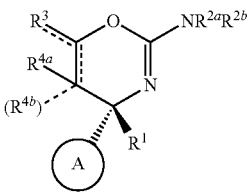

The optical isomer of the compound of the formula (I) can be obtained with known methods such as chiral chromatography or diastereomer salt formation using an optical active acid or base.

In addition, one or more hydrogen, carbon or other atoms of the compound of the formula (I) can be replaced by an isotope of the hydrogen, carbon or other atoms. Compounds of the formula (I) include all radiolabeled forms of compounds of the formula (I). The "radiolabeled," "radiolabeled form" and the like of the compound of the formula (I) are encompassed by the present invention and useful as a research and/or diagnostic tool in metabolism pharmacokinetic studies and in binding assays. It is also useful for a medicament.

Examples of isotopes that can be incorporated into the compound of the formula (I) of the invention include isotopes of hydrogen, carbon, nitrogen, oxygen, phosphorous, sulfur, fluorine, iodine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I and $^{36}$Cl, respectively. Radiolabeled compounds of the invention can be prepared by methods known in the art. For example, tritiated compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in *Isotopes in the Physical and Biomedical Sciences, Vol. 1, Labeled Compounds (Part A)* Chapter 6, (1987). $^{14}$C-labeled compounds can be prepared by employing starting materials having a $^{14}$C carbon.

(General Procedures)

The compounds of the formulas (I) and (Ia) to (If) of the present invention can be prepared by the methods described below. In the following steps, when a substituent which interferes with the reaction, e.g. hydroxy, mercapto, amino, formyl, carbonyl, carboxy, is possessed, the substituent is protected by the method such as those described in Protective Groups in organic Synthesis, and Theodora W Greene (John Wiley & Sons) in advance, and the protective group may be removed at a desirable step.

1) Synthesis of Compound (Ia)

[Chemical Formula 38]

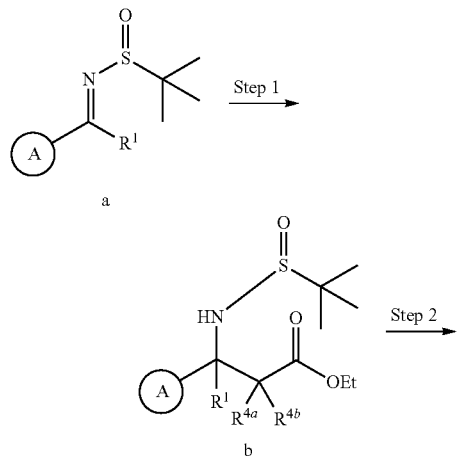
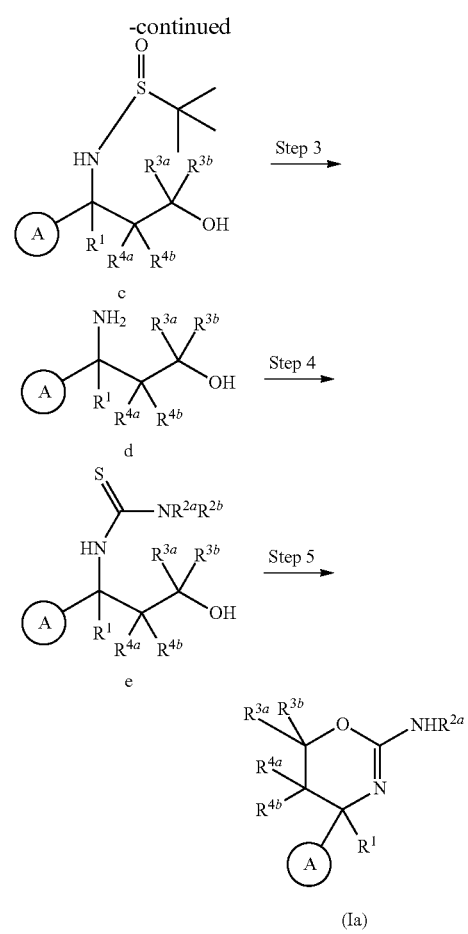

wherein each symbol is the same as defined above.

Step 1

Compound b can be prepared by adding a titanium reagent such as chlorotitanium triisopropoxide to enolate, which is obtained by reacting an objective ester such as ethyl propionate in the presence of a base such as lithium diisopropylamide in a solvent such as toluene, dichloromethane and tetrahydrofuran, or a mixed solvent thereof, adding Compound a which can be prepared by the known methods, and reacting them at −80° C. to 30° C., preferably −80° C. to 0° C., for 0.1 to 24 hours, preferably 0.1 to 12 hours.

Step 2

Compound c can be prepared by adding a Grignard reagent such as methylmagnesium bromide which is commercially available or can be prepared by the known methods or a reductant such as borane, sodium borohydride and lithium aluminium hydride to Compound b in a solvent such as dioxane, tetrahydrofuran, ether and toluene, or a mixed solvent thereof, and reacting at −80° C. to 80° C., preferably −20° C. to 30° C., for 0.5 to 48 hours, preferably 1 to 12 hours.

Step 3

Compound d can be prepared by reacting Compound c in the presence of an acid such as hydrochloric acid, hydrobromic acid, sulfuric acid and trifluoroacetic acid in a solvent such as dioxane, methanol and dichloromethane, or a mixed solvent thereof at 0° C. to 80° C., preferably 0° C. to 30° C. for 0.5 to 48 hours, preferably 1 to 24 hours.

Step 4

Compound e can be prepared by adding isothiocyanate having a protective group such as benzoyl isothiocyanate which is commercially available or is prepared by the known methods to Compound d in a solvent such as dioxane, tetrahydrofuran, toluene, and acetone, or a mixed solvent thereof and reacting at −30 to 50° C., preferably −10 to 25° C. for 0.1 to 12 hours, preferably 0.1 to 3 hours.

Step 5

Compound (Ia) can be prepared by adding an alkylating agent such as methyl iodide, diethyl sulfate and benzyl bromide to Compound e in the presence or absence of a base such as diisopropyl ethyl amine, triethylamine, pyridine and sodium hydroxide in a solvent such as methanol, ethanol, dimethylformamide and tetrahydrofuran and reacting at 0 to 200° C., preferably 40 to 150° C. for 1 to 48 hours, preferably 0.5 to 24 hours.

2) Synthesis of Compound (Ib)

[Chemical Formula 39]

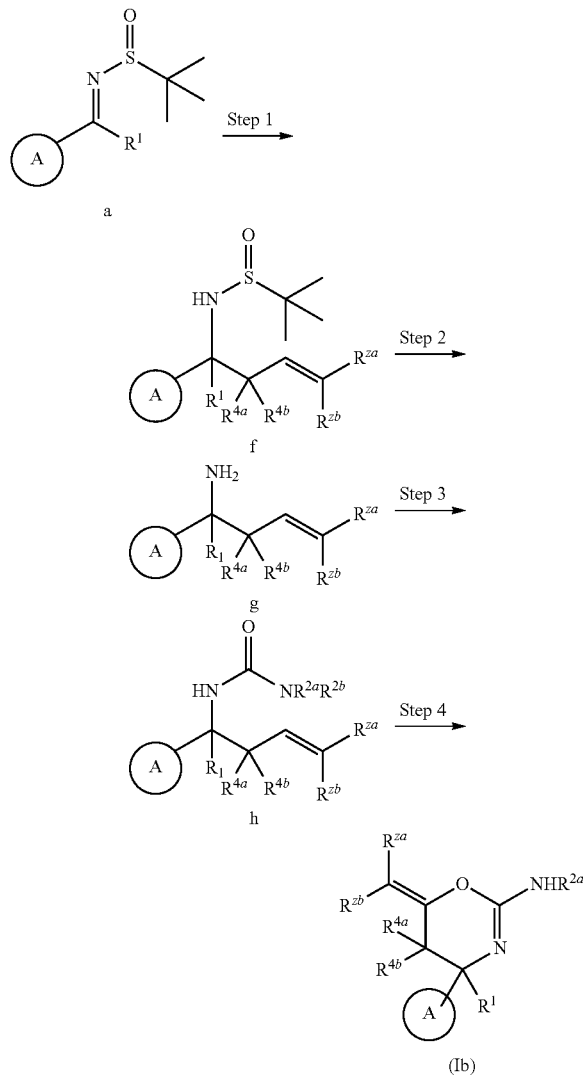

wherein each symbol is the same as defined above.

Step 1

Compound f can be prepared by adding Compound a which can be prepared by the known methods to a Grignard reagent such as allylmagnesium bromide in a solvent such as toluene, dichloromethane and tetrahydrofuran, or a mixed solvent thereof and reacting at −80 to 30° C., preferably −80 to 0° C. for 0.1 to 24 hours, preferably 0.1 to 12 hours.

Step 2

Compound g can be prepared by reacting Compound f which is prepared in Step 1 in the presence of an acid such as hydrochloric acid, hydrobromic acid, sulfuric acid and trifluoroacetic acid in a solvent such as dioxane, methanol and dichloromethane, or a mixed solvent thereof at 0 to 80° C., preferably 0 to 30° C. for 0.5 to 48 hours, preferably 1 to 24 hours.

Step 3

Compound h can be prepared by adding isocyanate having a protective group such as benzoyl isocyanate which is commercially available or is prepared by the known methods to Compound g in a solvent such as dichloromethane, dioxane, tetrahydrofuran, toluene, and acetone, or a mixed solvent thereof and reacting at −30 to 50° C., preferably −10 to 25° C. for 0.1 to 12 hours, preferably 0.1 to 3 hours.

Step 4

Compound (Ib) can be prepared by adding a halogenium cation source such as iodine, bromine, N-bromosuccinimide (NBS) to Compound h in a solvent such as dichloromethane and reacting at −20 to 40° C., preferably 0 to 20° C. for 0.1 to 12 hours, preferably 0.1 to 6 hours, followed by adding a base such as pyrrolidine, piperidine, piperazine and morpholine and reacting at 20 to 100° C., preferably 40 to 80° C. for 0.1 to 24 hours, preferably 1 to 12 hours.

3) Synthesis of Compound (Ic)

[Chemical Formula 40]

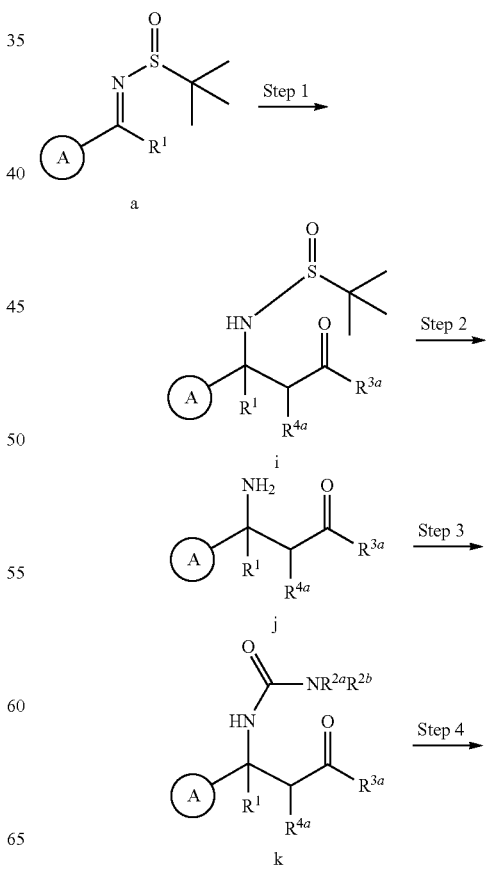

45
-continued

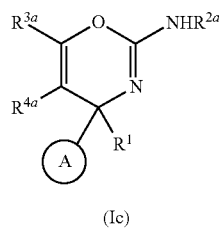

(Ic)

wherein each symbol is the same as defined above.

Step 1

Compound i can be prepared by adding a titanium reagent such as chlorotitanium triisopropoxide to enolate which can be prepared from an objective carbonyl compound such as diethyl ketone in the presence of a base such as lithium diisopropylamide in a solvent such as toluene, dichloromethane, tetrahydrofuran, or a mixed solvent thereof, adding Compound a which can be prepared by the known methods and reacting them at −80° C. to 30° C., preferably −80° C. to 0° C., for 0.1 to 24 hours, preferably 0.1 to 12 hours.

Step 2

Compound j can be prepared by reacting Compound i in the presence of an acid such as hydrochloric acid, hydrobromic acid, sulfuric acid and trifluoroacetic acid in a solvent such as dioxane, methanol, and dichloromethane, or a mixed solvent thereof at 0 to 80° C., preferably 0 to 30° C., for 0.5 to 48 hours, preferably 1 to 24 hours.

Step 3

Compound k can be prepared by adding isocyanate having a protective group such as benzoyl isocyanate which is commercially available or prepared by the known methods to Compound j in a solvent such as dioxane, tetrahydrofuran, toluene and acetone, or a mixed solvent thereof and reacting at −30 to 50° C., preferably −10 to 15° C. for 0.1 to 12 hours, preferably 0.1 to 3 hours.

Step 4

Compound (Ic) can be prepared by adding concentrated sulfuric acid, concentrated nitric acid or the like and reacting them at 0 to 100° C., preferably 0 to 60° C. for 0.5 to 24 hours, preferably 1 to 12 hours.

Compounds (Id) to (If), i.e., compounds of the formula (I) wherein

[Chemical Formula 41]

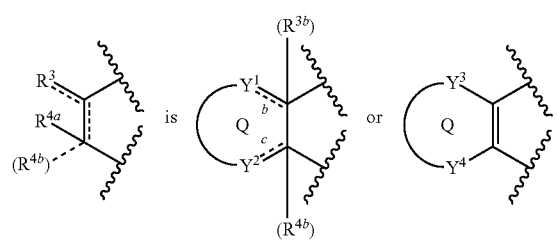

can be prepared, for example, by the procedures mentioned below.

46

4) Synthesis of Compound (Id)

[Chemical Formula 42]

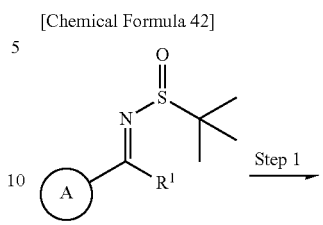

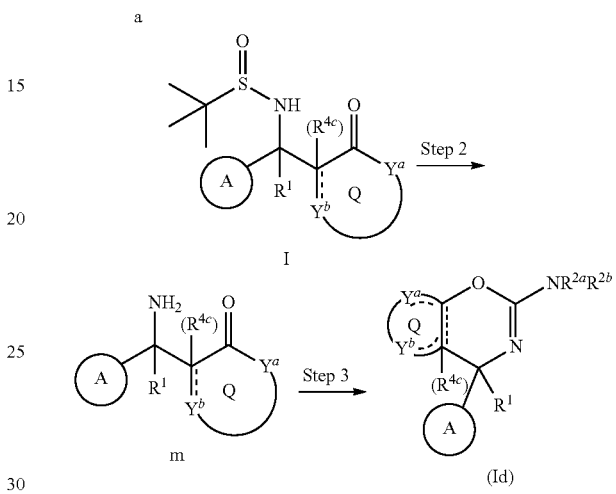

wherein $Y^a$ is $Y^1$ or $Y^3$, $Y^b$ is $Y^2$ or $Y^4$, a dashed line indicates the presence or absence of a bond, and other each symbol is the same as defined above.

Step 1

Compound 1 can be prepared by adding Compound a which can be prepared by the known methods to enolate which is prepared by reacting an objective carbonyl compound such as cyclopentanone in the presence of a base such as lithium diisopropyl amide in a solvent such as toluene, dichloromethane and tetrahydrofuran, or a mixed solvent thereof and reacting −80 to 30° C., preferably −80 to 0° C. for 0.1 to 24 hours, preferably 0.1 to 12 hours.

Step 2

Compound m can be prepared by reacting Compound 1 in the presence of an acid such as hydrochloric acid, hydrobromic acid, sulfuric acid or trifluoroacetic acid in a solvent such as dioxane, methanol and dichloromethane, or a mixed solvent thereof at 0 to 80° C., preferably 0 to 30° C. for 0.5 to 48 hours, preferably 1 to 24 hours.

Step 3

Compound (Id) can be prepared by adding isocyanate having a protective group such as benzoyl isocyanate which is commercially available or prepared by the known methods to Compound m, reacting at −30 to 50° C., preferably −10 to 25° C. for 0.1 to 12 hours, preferably 0.1 to 3 hours in a solvent such as dioxane, tetrahydrofuran, toluene and acetone, or a mixed solvent thereof, and subsequently, adding concentrated sulfuric acid or concentrated nitric acid, followed by a reaction at 0 to 100° C., preferably 0 to 60° C., for 0.5 to 24 hours, preferably 1 to 12 hours.

Compound (Id) wherein a dashed line means the absence of a bond can be prepared by preparing Compound (Id) wherein any one of a dashed line means the presence of a bond, followed by hydrogen addition under the usual conditions.

5) Synthesis of Compound (Ie)

[Chemical Formula 43]

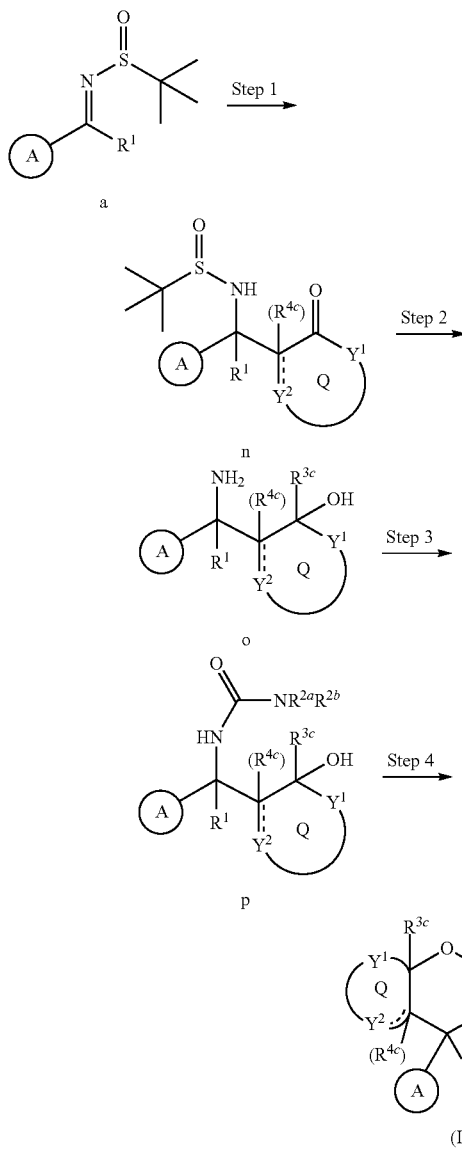

wherein each symbol is the same as defined above.

Step 1

Compound n can be prepared by adding Compound a which can be prepared by the known methods to enolate which is prepared by reacting an objective carbonyl compound such as cyclopentanone in the presence of a base such as lithium diisopropyl amide in a solvent such as toluene, dichloromethane and tetrahydrofuran, or a mixed solvent thereof and reacting at −80 to 30° C., preferably −80 to 0° C. for 0.1 to 24 hours, preferably 0.1 to 12 hours Step 2

Compound o can be prepared by adding a Grignard reagent such as methylmagnesium bromide which is commercially available or can be prepared by the known methods to Compound n in a solvent such as dioxane, tetrahydrofuran, ether and toluene, or a mixed solvent thereof, and reacting at −80 to 80° C., preferably −20 to 30° C. for 0.5 to 48 hours, preferably 1 to 12 hours, followed by reacting in the presence of an acid such as hydrochloric acid, hydrobromic acid, sulfuric acid or trifluoroacetic acid at 0 to 80° C., preferably 0 to 30° C. for 0.5 to 48 hours, preferably 1 to 24 hours.

Step 3

Compound p can be prepared by adding isocyanate having a protective group such as benzoyl isocyanate which is commercially available or prepared by the known methods to Compound o, reacting at −30 to 50° C., preferably −10 to 25° C., for 0.1 to 12 hours, preferably 0.1 to 3 hours in a solvent such as dioxane, tetrahydrofuran, toluene and acetone, or a mixed solvent thereof, and subsequently, adding concentrated sulfuric acid or concentrated nitric acid, followed by reacting at 0° C. to 100° C., preferably 0° C. to 60° C., for 0.5 to 24 hours, preferably 1 to 12 hours.

Step 4

Compound (Ie) can be prepared by adding oxalyl chloride, thionyl chloride or the like and a catalytic amount of N,N-dimethylformamide, or by adding a chlorinating reagent such as 1-chloro-2-trimethylpropenylamine to a Compound p in a solvent such as dichloromethane, tetrahydrofuran and toluene and reacting at 0 to 100° C., preferably 10 to 50° C. for 0.5 to 72 hours, preferably 0.5 to 6 hours.

6) Synthesis of Compound (If)

[Chemical Formula 44]

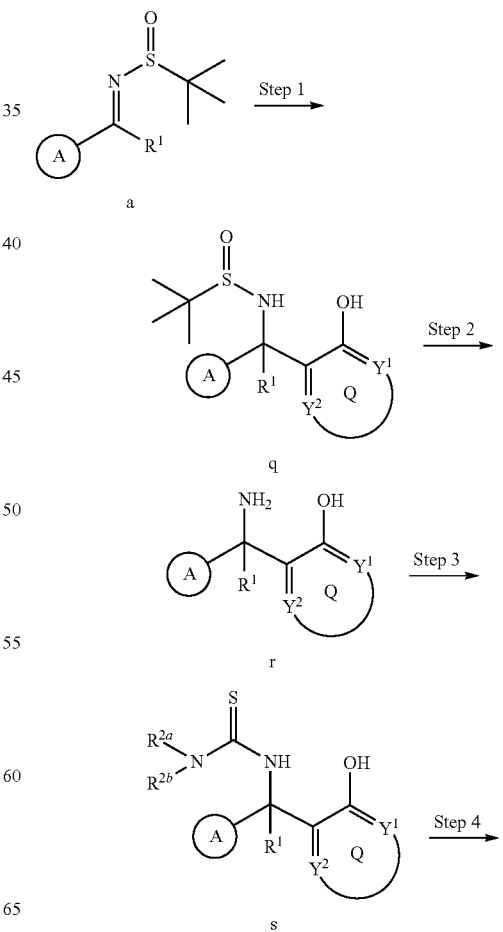

-continued

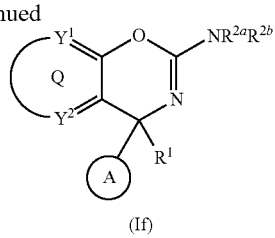

(If)

wherein each symbol is the same as defined above.

Step 1

Compound q can be prepared by adding Compound a which can be prepared by the known methods to a Grignard reagent such as phenylmagnesium bromide having an optionally protected hydroxy group at ortho position or a lithium reagent such as pyridyl lithium having an optionally protected hydroxy group at ortho position and reacting them in a solvent such as toluene, diethyl ether and tetrahydrofuran, or a mixed solvent thereof at −80 to 30° C., preferably −80 to 0° C. for 0.1 to 24 hours, preferably 0.1 to 12 hours, followed by removing a protective group of the hydroxy group by the known methods.

Step 2

Compound r can be prepared by reacting Compound q in the presence of an acid such as hydrochloric acid, hydrobromic acid, sulfuric acid or trifluoroacetic acid in a solvent such as dioxane, methanol and dichloromethane, or a mixed solvent thereof at 0° C. to 80° C., preferably 0° C. to 30° C. for 0.5 to 48 hours, preferably 1 to 24 hours.

Step 3

Compound s can be prepared by adding isothiocyanate having a protective group which is commercially available or prepared by the known methods such as benzoyl isothiocyanate and reacting them in a solvent such as dioxane, tetrahydrofuran, toluene and acetone, or a mixed solvent thereof at −30° C. to 50° C., preferably −10° C. to 25° C. for 0.1 to 12 hours, preferably 0.1 to 3 hours.

Step 4

Compound (If) can be prepared by reacting Compound s with an alkylating agent such as methyl iodide, diethyl sulfate and benzyl bromide in the presence or absence of a base such as diisopropyl ethyl amine, triethylamine, pyridine, sodium hydroxide in a solvent such as methanol, ethanol, dimethylformamide and tetrahydrofuran at 0° C. to 200° C., preferably 40° C. to 150° C. for 1 to 48 hours, preferably 0.5 to 24 hours.

In the above all steps, an order of steps to be implemented may be appropriately changed, and each intermediate may be isolated, and used in a next step.

7) Conversion of a Substituent

Above-mentioned Compounds (Ia) to (If) and compounds wherein ring A is substituted with various substituent, for example, ring B—Z— group or the like, can be prepared according to the method mentioned above or the known methods such as methods described in Patent Document 2, Patent Document 3, Patent Document 4 and the like.

Moreover, the optically active isomer of the compound (I) can be prepared by using an optically active compound as a starting material, performing an asymmetric synthesis in the suitable step to prepare an optically active intermediate, or optical resolution of the racemate of the intermediate or the objective compound in the appropriate step. The method of optical resolution include the separation of optical isomer using an optically active column, the kinetics optical resolution using enzyme reactions or the like, the crystallization and separation of diastereomers by the salt formation using chiral acids or chiral bases, the preferential crystallization or the like.

Specific embodiments of the present invention are illustrated below. Each symbol is as defined above.

(A)

In the formula (I), the followings are exemplified.

[Chemical Formula 45]

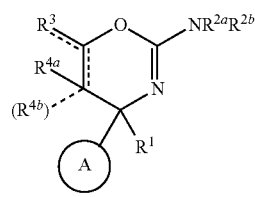

(I)

Ring A includes substituted carbocycle or substituted or unsubstituted heterocycle.

Ring A includes

[Chemical Formula 46]

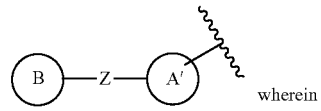

wherein

[Chemical Formula 47]

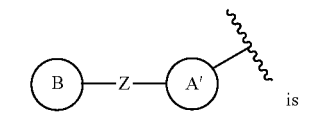

is

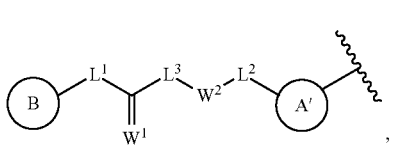

(i)

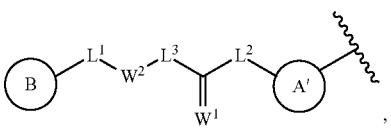

(ii)

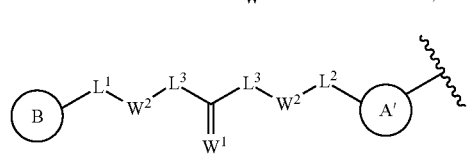

(iii)

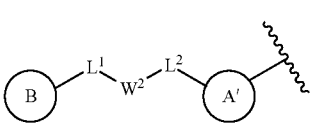

(iv)

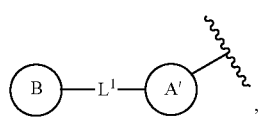

(v)

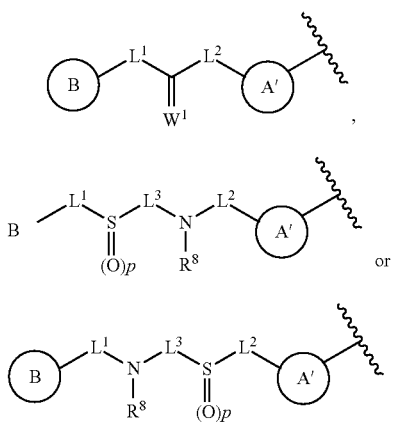

Ring A' and ring B are each independently substituted or unsubstituted carbocycle or substituted or unsubstituted heterocycle, $L^1$, $L^2$, and $L^3$ are each independently a bond, substituted or unsubstituted alkynylene, substituted or unsubstituted alkenylene or substituted or unsubstituted alkynylene, $=W^1$ is $=O$, $=S$, or $=NR^9$, $W^2$ is O, S, or $N(R^8)$, $R^8$ is hydrogen, substituted or unsubstituted alkyl, substituted or unsubstituted alkenyl, substituted or unsubstituted alkynyl or substituted or unsubstituted acyl, $R^9$ is hydrogen, hydroxy, substituted or unsubstituted alkyl, substituted or unsubstituted alkenyl, substituted or unsubstituted alkynyl or substituted or unsubstituted acyl, when ring A is (i), then the constituent carbon atom of $L^1$ and the constituent carbon atom of $L^2$, or the constituent carbon atom of $L^1$ and the nitrogen atom of $W^2$ may be connected with substituted or unsubstituted alkylene to form a ring, when ring A is (ii), then the constituent carbon atom of $L^1$ and the constituent carbon atom of $L^2$, or the nitrogen atom of $W^2$ and the constituent carbon atom of $L^2$ may be connected with substituted or unsubstituted alkylene to form a ring when ring A is (iii), then two nitrogen atoms of $W^2$ may be connected with substituted or unsubstituted alkylene to form a ring, when ring A is (vi), then the constituent carbon atom of $L^1$ and the constituent carbon atom of $L^2$ may be connected with substituted or unsubstituted alkylene to form a ring, p is 1 or 2, and when multiple $L^3$, multiple $W^2$, or multiple $R^9$ are present, each of them may be independently different.

Ring A includes

[Chemical Formula 48]

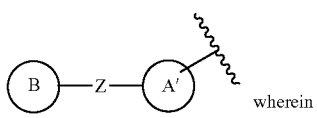 wherein

[Chemical Formula 49]

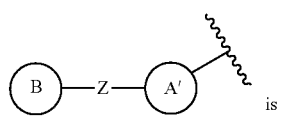 is

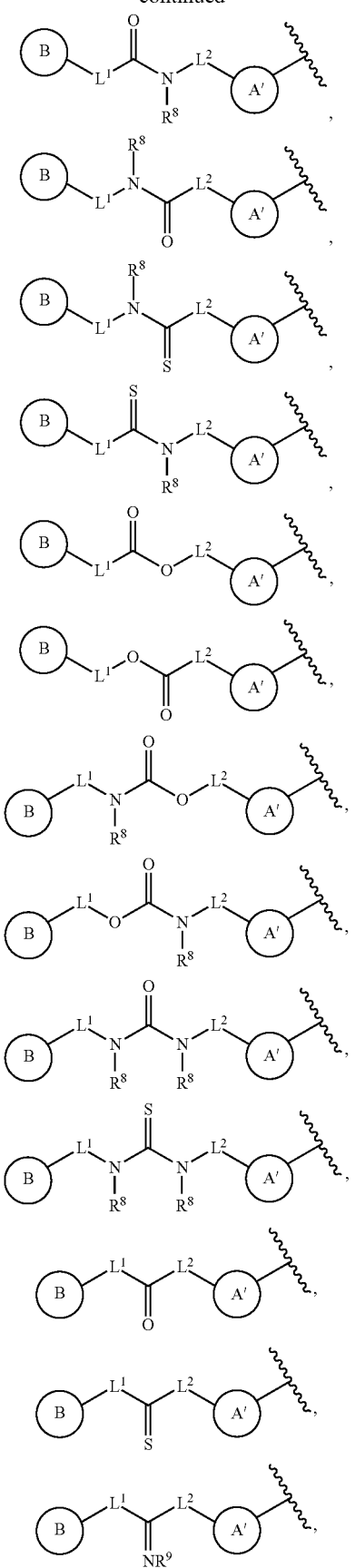

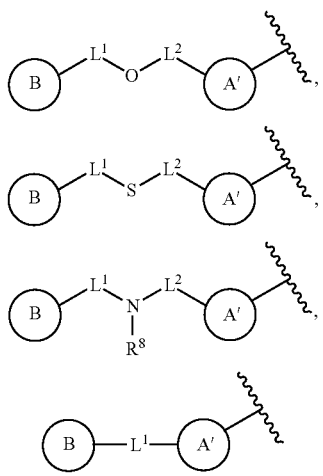

[Chemical Formula 50]

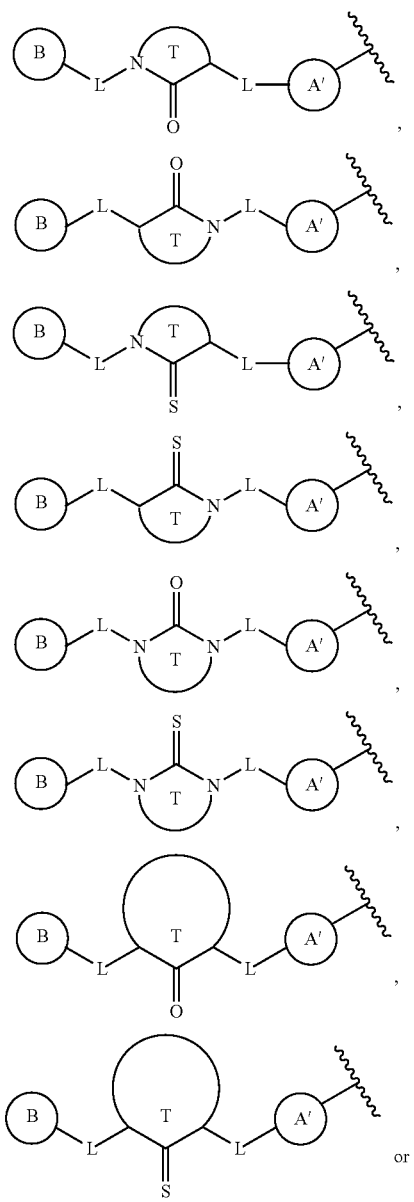

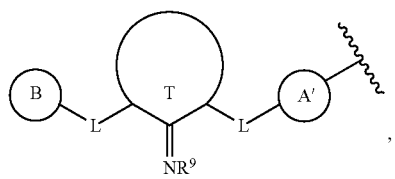

wherein L is each independently a bond, substituted or unsubstituted alkylene, substituted or unsubstituted alkenylene, substituted or unsubstituted alkynylene, ring T is a ring which may be substituted with a group(s) selected from the substituent group α, and other each symbol is the same as defined above.

Ring A includes

[Chemical Formula 51]

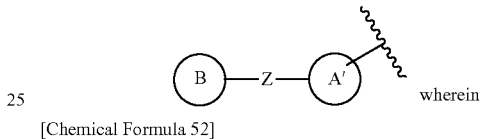 wherein

[Chemical Formula 52]

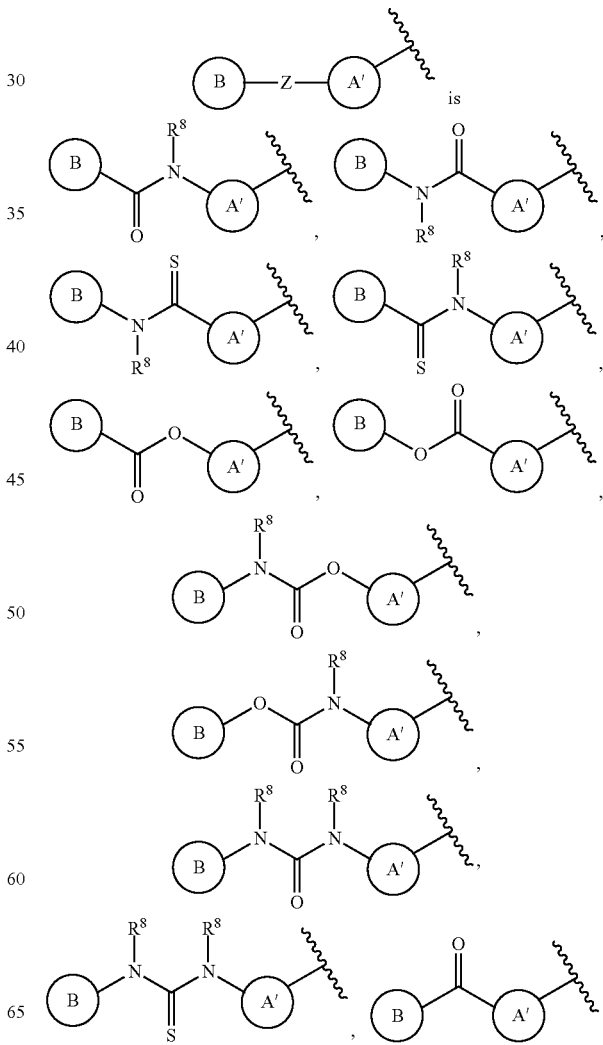

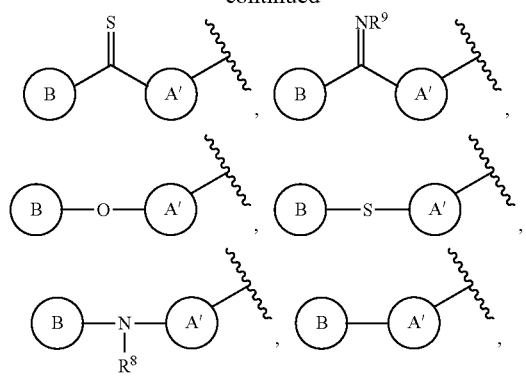
[Chemical Formula 53]
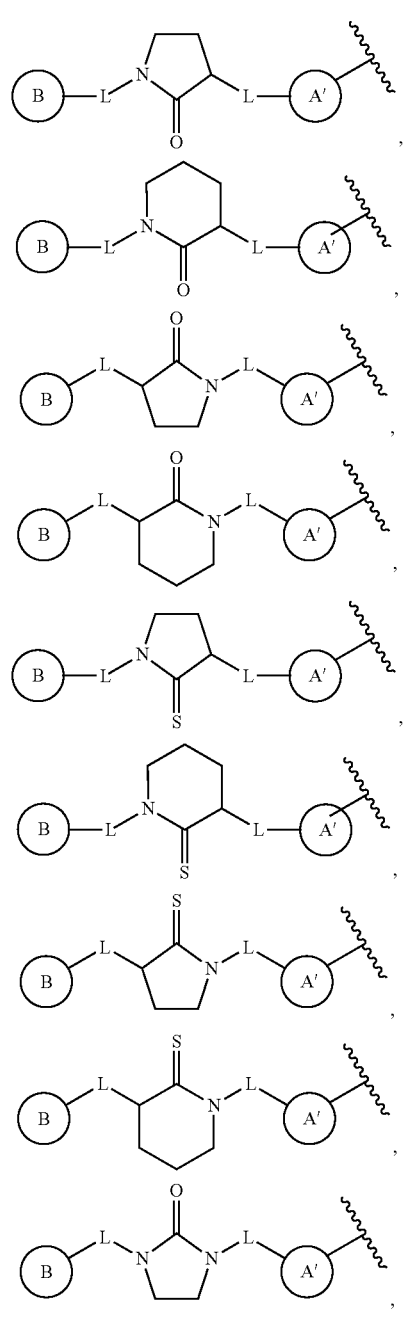
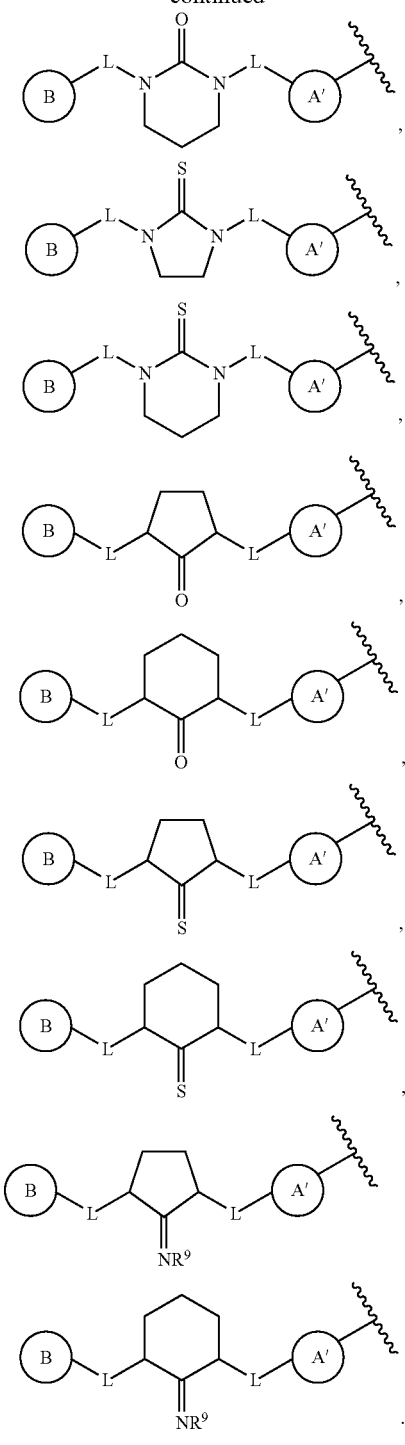
Ring A includes
[Chemical Formula 54]
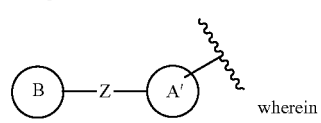
wherein -continued

[Chemical Formula 55]

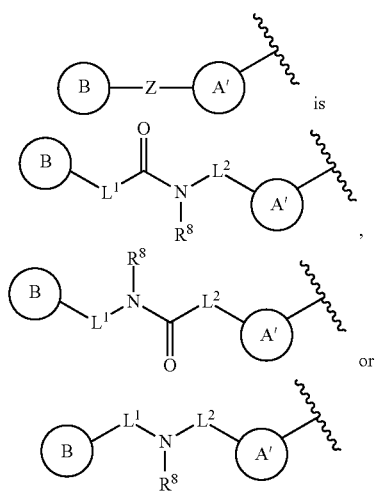

L¹ and L² include each independently a bond, substituted or unsubstituted alkylene, substituted or unsubstituted alkenylene or substituted or unsubstituted alkynylene, and R⁸ includes hydrogen, substituted or unsubstituted alkyl, substituted or unsubstituted alkenyl, substituted or unsubstituted alkynyl or substituted or unsubstituted acyl.

R⁸ includes hydrogen.

Ring A includes

[Chemical Formula 56]

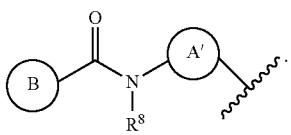

Ring A' and ring B include each independently substituted or unsubstituted carbocycle or substituted or unsubstituted heterocycle.

Ring A' is, for example, substituted or unsubstituted benzene and ring B is substituted or unsubstituted pyridine, substituted or unsubstituted pyrimidine or substituted or unsubstituted pyrazine.

R¹ includes substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, a substituted or unsubstituted carbocyclic group or a substituted or unsubstituted heterocyclic group.

R¹ includes substituted or unsubstituted alkyl, substituted or unsubstituted alkenyl, substituted or unsubstituted alkynyl, cyano, a substituted or unsubstituted carbocyclic group or a substituted or unsubstituted heterocyclic group.

R¹ is, for example, C1 to C3 unsubstituted alkyl.

R²ᵃ and R²ᵇ are each independently hydrogen, substituted or unsubstituted alkyl, substituted or unsubstituted acyl, substituted or unsubstituted alkoxycarbonyl or substituted or unsubstituted carbamoyl.

R²ᵃ and R²ᵇ are, for example, both hydrogen.

[Chemical Formula 57]

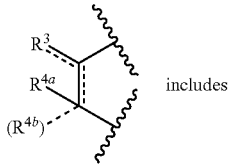 includes (r-a)

(r-b)

(r-c)

(r-d)

As one aspect in substituent (r-a), R^{za} and R^{zb} each independently include hydrogen, halogen, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, a substituted or unsubstituted carbocyclic group, substituted or unsubstituted carbocyclyloxy, substituted or unsubstituted carbocyclylthio, substituted or unsubstituted carbocyclyloxycarbonyl, a substituted or unsubstituted heterocyclic group, substituted or unsubstituted heterocyclyloxy, substituted or unsubstituted heterocyclylthio, or substituted or unsubstituted heterocyclyloxycarbonyl, or $R^{za}$ and $R^{zb}$ together with the carbon atom to which they are attached may form a substituted or unsubstituted carbocycle or a substituted or unsubstituted heterocycle.

As one aspect in substituent (r-a), examples of $R^{za}$ and $R^{zb}$ are each independently hydrogen, halogen and substituted or unsubstituted alkyl, or $R^{za}$ and $R^{zb}$ together with the carbon atom to which they are attached may form a substituted or unsubstituted carbocycle.

As one aspect in substituent (r-a), examples of $R^{za}$ and $R^{zb}$ are each independently, hydrogen, halogen and substituted or unsubstituted alkyl.

As one aspect in substituent (r-b), the dashed a means, for example, the presence of a bond.

As one aspect in substituent (r-b), the dashed line a means, for example, the absence of a bond.

As one aspect in substituent (r-b), $R^{3a}$ and $R^{3b}$ are each independently, hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl, or $R^{3a}$ and $R^{3b}$ together with the carbon atom to which they are attached may form a substituted or unsubstituted carbocycle or a substituted or unsubstituted heterocycle, and when dashed line a means the presence of a bond, then $R^{3b}$ is absent.

As one aspect in substituent (r-b), examples of $R^{3a}$ and $R^{3b}$ are each independently, hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkylthio, substituted or unsubstituted alkenylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl, and when the dashed line a means the presence of a bond, then $R^{3b}$ is absent.

As one aspect in substituent (r-b), $R^{3a}$ is, for example, alkyl, $R^{3b}$ is, for example, hydrogen, and the dashed line a means the absence of a bond.

As one aspect in substituent (r-b), both of $R^{3a}$ and $R^{3b}$ are hydrogen, and the dashed line a means the absence of a bond.

As one aspect in substituent (r-b), $R^{3a}$ is, for example, hydrogen and the dashed line a means the presence of a bond.

As one aspect in substituent (r-b), $R^{3a}$ is, for example, alkyl, and the dashed line a means the presence of a bond.

As one aspect in substituent (r-c), examples of $R^{3c}$ are hydrogen, halogen, substituted or unsubstituted alkyl, substituted or unsubstituted alkenyl, substituted or unsubstituted alkynyl, substituted or unsubstituted amino, substituted or unsubstituted carbamoyl, substituted or unsubstituted thiocarbamoyl, carboxy, substituted or unsubstituted alkoxycarbonyl, substituted or unsubstituted alkenyloxycarbonyl, a substituted or unsubstituted carbocyclic group, substituted or unsubstituted carbocyclyloxycarbonyl, a substituted or unsubstituted heterocyclic group, substituted or unsubstituted heterocyclyloxycarbonyl, and when the dashed line b means the presence of a bond, then $R^{3c}$ is absent.

As one aspect in substituent (r-c), $R^{3c}$ is, for example, hydrogen and the dashed line b means the absence of a bond.

As one aspect in substituent (r-c), $R^{3c}$ is, for example, absent and the dashed line b means the presence of a bond.

As one aspect in substituent (r-a), (r-b) and/or (r-c), $R^{4a}$, $R^{4b}$ and $R^{4c}$ are each independently, hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl, $R^{4a}$ and $R^{4b}$ together with the carbon atom to which they are attached may form a substituted or unsubstituted carbocycle or a substituted or unsubstituted heterocycle, and when the dashed line a means the presence of a bond, then $R^{4b}$ is absent and when the dashed line c means the presence of a bond, then $R^{4c}$ is absent.

As one aspect in substituent (r-a), (r-b), or (r-c), $R^{4a}$, $R^{4b}$, and $R^{4c}$ are each independently, for example, hydrogen, halogen, hydroxy, substituted or unsubstituted alkyl, substituted or unsubstituted alkenyl or substituted or unsubstituted alkynyl and when the dashed line a means the presence of a bond, then $R^{4b}$ is absent, and when the dashed line c means the presence of a bond, then $R^{4c}$ is absent.

As one aspect in substituent (r-a), for example, both of $R^{4a}$ and $R^{4b}$ are hydrogen.

As one aspect in substituent (r-b), for example, both of $R^{4a}$ and $R^{4b}$ are hydrogen and the dashed line a means the absence of a bond.

As one aspect in substituent (r-b), $R^{4a}$ is, for example, hydrogen and the dashed line a means the presence of a bond.

As one aspect in substituent (r-c), $R^{4c}$ is, for example, hydrogen and the dashed line c means the absence of a bond.

As one aspect in substituent (r-c), $R^{4c}$ is, for example, absent and the dashed line c means the presence of a bond.

As one aspect in substituent (r-c) or (r-d), ring Q is, for example, substituted or unsubstituted carbocycle or substituted or unsubstituted heterocycle.

As one aspect in substituent (r-c), $Y^1$ and $Y^2$ are each independently —C($R^5$)($R^6$)—, —C($R^5$)=, —N($R^7$)—, —S—, —SO—, —SO$_2$—, or —O—.

As one aspect in substituent (r-c), $Y^1$ and $Y^2$ are, for example, each independently —C($R^5$)($R^6$)— or —C($R^5$)=.

As one aspect in substituent (r-d), $Y^3$ and $Y^4$ are each independently —C($R^5$)($R^6$)—, —N($R^7$)—, —S—, —SO—, —SO$_2$—, or —O—.

As one aspect in substituent (r-d), $Y^3$ and $Y^4$ are, for example, each independently —C($R^5$)($R^6$)—.

As one aspect in substituent (r-c) or (r-d), $R^5$ and $R^6$ are, for example, each independently, hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl.

As one aspect in substituent (r-c) or (r-d), $R^5$ and $R^6$ are, for example, each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkylthio, substituted or unsubstituted alkenylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted carbocyclic group, substituted or unsubstituted carbocyclyloxy, substituted or unsubstituted carbocyclylthio, substituted or unsubstituted carbocyclyloxycarbonyl, substituted or unsubstituted carbocyclylsulfinyl, substituted or unsubstituted carbocyclylsulfonyl, substituted or unsubstituted heterocyclic group, substituted or unsubstituted heterocyclyloxy, substituted or unsubstituted heterocyclylthio, substituted or unsubstituted heterocyclyloxycarbonyl, substituted or unsubstituted heterocyclylsulfinyl or substituted or unsubstituted heterocyclylsulfonyl.

As one aspect in substituent (r-c) or (r-d), $R^5$ and $R^6$ are, for example, each independently, hydrogen, halogen, hydroxy, substituted or unsubstituted alkyl, substituted or unsubstituted alkoxy, substituted or unsubstituted acyl, cyano, nitro, carboxy, substituted or unsubstituted alkoxycarbonyl, substituted or unsubstituted amino or substituted or unsubstituted carbamoyl.

As one aspect in substituent (r-c) or (r-d), $R^7$ is hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted thiocarbamoyl, substituted or unsubstituted sulfamoyl, substituted or unsubstituted amino, substituted or unsubstituted carbocyclic group, substituted or unsubstituted carbocyclyloxy, substituted or unsubstituted carbocyclyloxycarbonyl, substituted or unsubstituted carbocyclylsulfinyl, substituted or unsubstituted carbocyclylsulfonyl, substituted or unsubstituted heterocyclic group, substituted or unsubstituted heterocyclyloxy, substituted or unsubstituted heterocyclyloxycarbonyl, substituted or unsubstituted heterocyclylsulfinyl or substituted or unsubstituted heterocyclylsulfonyl.

As one aspect in substituent (r-c) or (r-d), $R^7$ is, for example, hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted acyl, cyano, nitro, carboxy, substituted or unsubstituted alkoxycarbonyl, substituted or unsubstituted alkenyloxycarbonyl, substituted or unsubstituted alkylsulfinyl, substituted or unsubstituted alkenylsulfinyl, substituted or unsubstituted alkylsulfonyl, substituted or unsubstituted alkenylsulfonyl, substituted or unsubstituted carbamoyl, substituted or unsubstituted thiocarbamoyl, substituted or unsubstituted amino, substituted or unsubstituted carbocyclic group, substituted or unsubstituted carbocyclyloxy, substituted or unsubstituted carbocyclyloxycarbonyl, substituted or unsubstituted carbocyclylsulfinyl, substituted or unsubstituted carbocyclylsulfonyl, substituted or unsubstituted heterocyclic group, substituted or unsubstituted heterocyclyloxy, substituted or unsubstituted heterocyclyloxycarbonyl, substituted or unsubstituted heterocyclylsulfinyl or substituted or unsubstituted heterocyclylsulfonyl.

As one aspect in substituent (r-c) or (r-d), $R^7$ is, for example, hydrogen, halogen, hydroxy, substituted or unsubstituted alkyl, substituted or unsubstituted acyl, cyano, carboxy, substituted or unsubstituted alkoxycarbonyl, or substituted or unsubstituted carbamoyl.

[Chemical Formula 58]

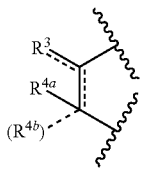

is, for example,

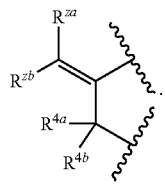

[Chemical Formula 59]

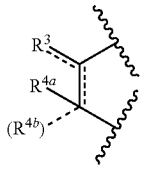

is, for example,

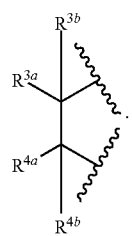

[Chemical Formula 60]

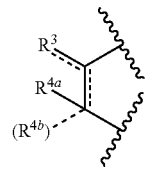

is, for example,

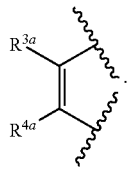

[Chemical Formula 61]

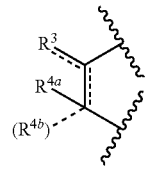

is, for example,

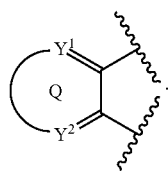

[Chemical Formula 62]

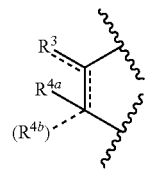

is, for example,

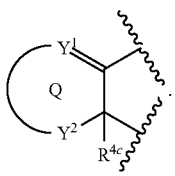

[Chemical Formula 63]

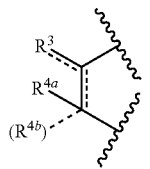

is, for example,

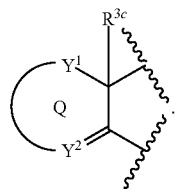

[Chemical Formula 64]

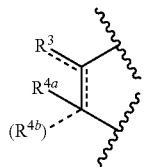

is, for example,

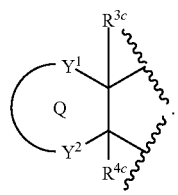

[Chemical Formula 65]

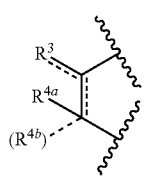

is, for example,

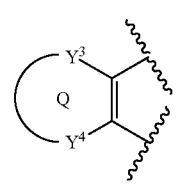

[Chemical Formula 66]

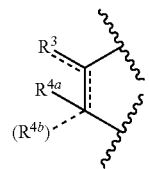

is, for example,

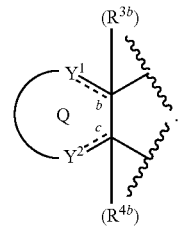

and more specifically,

[Chemical Formula 67]

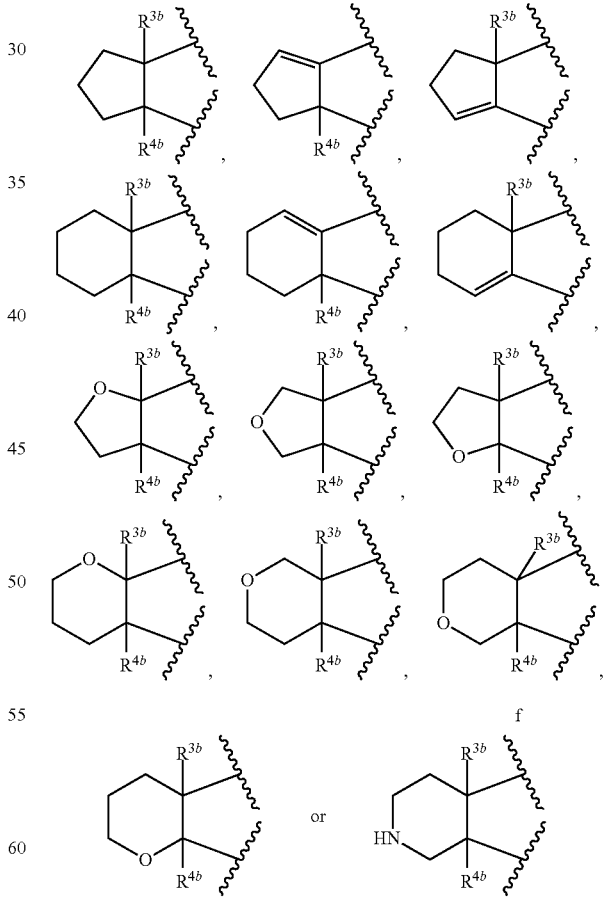

Any available position in these groups may be substituted with one or more substituents selected from substituent group α, unsubstituted alkyl and alkyl substituted with one or more substituents selected from the substituent group α.

[Chemical Formula 68]

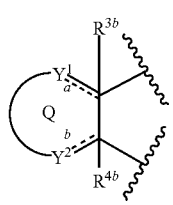

is, for example,

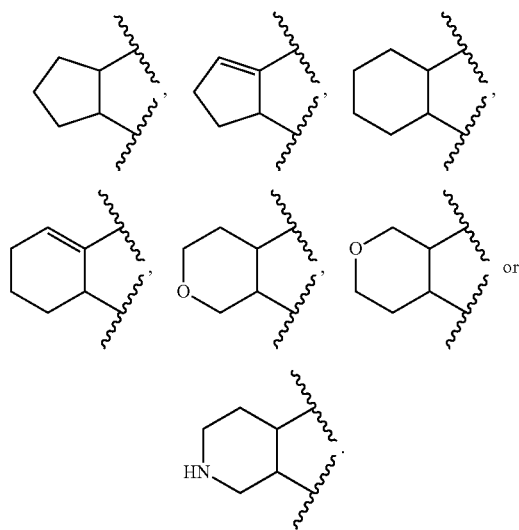

Any available position in these groups may be substituted with one or more substituents selected from substituent group α, unsubstituted alkyl and alkyl substituted with one or more substituents selected from the substituent group α.

[Chemical Formula 69]

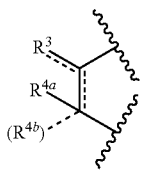

is, for example,

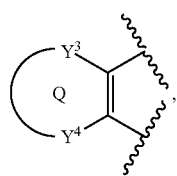

and more specifically,

[Chemical Formula 70]

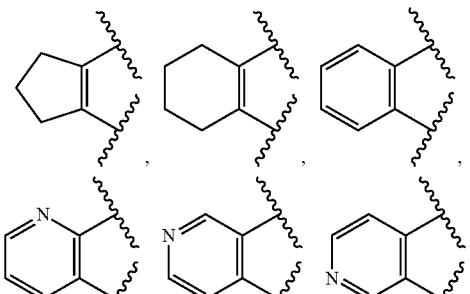

,

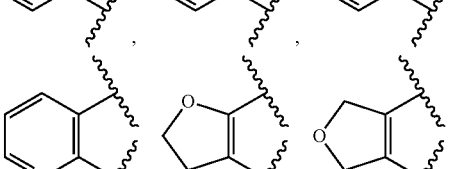

,

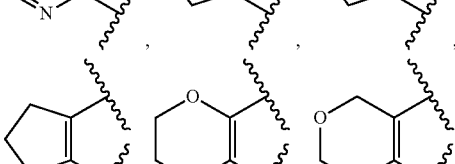

,

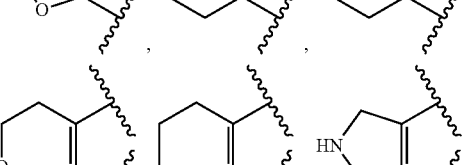

,

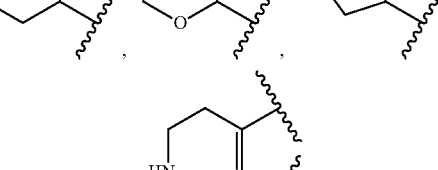

or

Any available position in these groups may be substituted with one or more substituents selected from substituent group α, unsubstituted alkyl and alkyl substituted with one or more substituents selected from the substituent group α.

As one aspect in the compound (I), the following compound is exemplified:

[Chemical Formula 71]

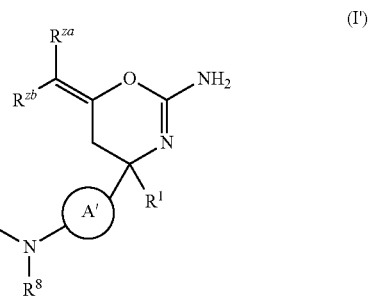

(I')

wherein ring A' is substituted or unsubstituted carbocycle wherein the substituent is, for example, halogen, ring B is substituted or unsubstituted pyridine, substituted or unsubstituted pyrimidine or substituted or unsubstituted pyrazine wherein the substituent is, for example, halogen, hydroxy, alkoxy, amino or cyano,
$R^1$ is substituted or unsubstituted alkyl, more specifically, $R^1$ is unsubstituted alkyl,
$R^8$ is hydrogen, substituted or unsubstituted alkyl or substituted or unsubstituted acyl, more specifically, $R^8$ is hydrogen,
$R^{z\,a}$ and $R^{z\,b}$ are each independently hydrogen or substituted or unsubstituted alkyl, more specifically, both of $R^{z\,a}$ and $R^{z\,b}$ are hydrogen.

As another aspect, the following compound is exemplified:

[Chemical Formula 72]

(I'')

wherein ring A' is substituted or unsubstituted carbocycle wherein the substituent is, for example, halogen; or substituted or unsubstituted thiophen wherein the substituent is, for example, halogen,
ring B is substituted or unsubstituted pyridine, substituted or unsubstituted pyrimidine or substituted or unsubstituted pyrazine wherein the substituent is, for example, halogen, hydroxy, alkyl, halogeno alkyl, alkynyl, alkoxy, halogenoalkoxy, amino or cyano,
$R^1$ is substituted or unsubstituted alkyl, more specifically, $R^1$ is unsubstituted alkyl,
$R^8$ is hydrogen, substituted or unsubstituted alkyl or substituted or unsubstituted acyl, more specifically, $R^8$ is hydrogen.

As other embodiment, the following compound is exemplified:

[Chemical Formula 73]

(I''')

wherein ring A' is substituted or unsubstituted carbocycle wherein the substituent is, for example, halogen,
ring B is substituted or unsubstituted pyridine, substituted or unsubstituted pyrimidine or substituted or unsubstituted pyrazine wherein the substituent is, for example, halogen, hydroxy, alkyl, halogeno alkyl, alkoxy, halogenoalkoxy, amino or cyano,
$R^1$ is substituted or unsubstituted alkyl, more specifically, $R^1$ is unsubstituted alkyl,
$R^3$ is hydrogen or substituted or unsubstituted alkyl, more specifically, $R^3$ is unsubstituted alkyl,
$R^8$ is hydrogen, substituted or unsubstituted alkyl or substituted or unsubstituted acyl, more specifically, $R^8$ is hydrogen.

As another aspect, the compound of the formula (I) wherein

[Chemical Formula 74]

is r1, r2, r3, r4, r5, r6, r7 or

-continued

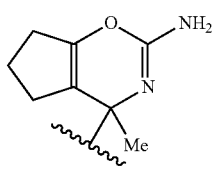

wherein Me is methyl;

the compound of the formula (I) wherein ring A is

[Chemical Formula 75]

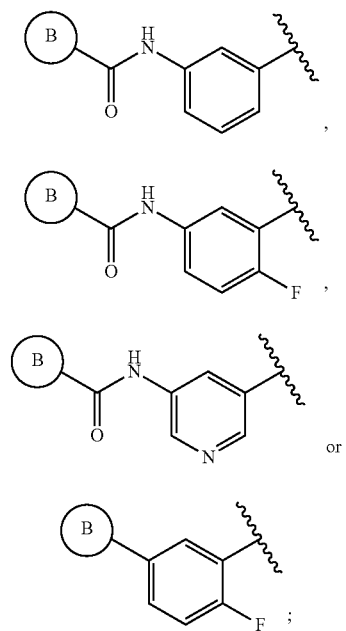

the compound of the formula (I) wherein ring B is

[Chemical Formula 76]

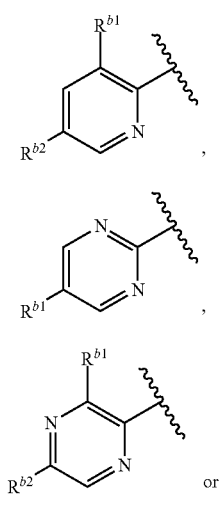

-continued

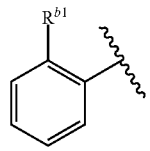

wherein $R^{b1}$ and $R^{b2}$ are each independently hydrogen, chloro, fluoro, methoxy, butynyloxy, cyano, amino, or carbamoyl;

the compound of the formula (I) wherein the combination of ring B, $R^{b1}$, and $R^{b2}$ (B, $R^{b1}$, $R^{b2}$) is as follows:

(B1, hydrogen, hydrogen) (hereinafter referred to as ring B is b1)
(B1, hydrogen, chloro) (hereinafter referred to as ring B is b2)
(B1, hydrogen, fluoro)(hereinafter referred to as ring B is b3),
(B1, hydrogen, methoxy)(hereinafter referred to as ring B is b4),
(B1, hydrogen, butynyloxy)(hereinafter referred to as ring B is b5),
(B1, hydrogen, cyano)(hereinafter referred to as ring B is b6),
(B1, hydrogen, amino)(hereinafter referred to as ring B is b7),
(B1, hydrogen, carbamoyl)(hereinafter referred to as ring B is b8),
(B1, chloro, hydrogen)(hereinafter referred to as ring B is b9),
(B1, chloro, chloro)(hereinafter referred to as ring B is b10),
(B1, chloro, fluoro)(hereinafter referred to as ring B is b11),
(B1, chloro, methoxy)(hereinafter referred to as ring B is b12),
(B1, chloro, butynyloxy)(hereinafter referred to as ring B is b13),
(B1, chloro, cyano)(hereinafter referred to as ring B is b14),
(B1, chloro, amino)(hereinafter referred to as ring B is b15),
(B1, chloro, carbamoyl)(hereinafter referred to as ring B is b16),
(B1, fluoro, hydrogen)(hereinafter referred to as ring B is b17),
(B1, fluoro, chloro)(hereinafter referred to as ring B is b18),
(B1, fluoro, fluoro)(hereinafter referred to as ring B is b19),
(B1, fluoro, methoxy)(hereinafter referred to as ring B is b20),
(B1, fluoro, butynyloxy)(hereinafter referred to as ring B is b21),
(B1, fluoro, cyano)(hereinafter referred to as ring B is b22),
(B1, fluoro, amino)(hereinafter referred to as ring B is b23),
(B1, fluoro, carbamoyl)(hereinafter referred to as ring B is b24),
(B1, methoxy, hydrogen)(hereinafter referred to as ring B is b25),
(B1, methoxy, chloro)(hereinafter referred to as ring B is b26),
(B1, methoxy, fluoro)(hereinafter referred to as ring B is b27),
(B1, methoxy, methoxy)(hereinafter referred to as ring B is b28),
(B1, methoxy, butynyloxy)(hereinafter referred to as ring B is b29),
(B1, methoxy, cyano)(hereinafter referred to as ring B is b30),
(B1, methoxy, amino)(hereinafter referred to as ring B is b31),
(B1, methoxy, carbamoyl)(hereinafter referred to as ring B is b32),
(B1, butynyloxy, hydrogen)(hereinafter referred to as ring B is b33),
(B1, butynyloxy, chloro)(hereinafter referred to as ring B is b34), (B1, butynyloxy, fluoro)(hereinafter referred to as ring B is b35),
(B1, butynyloxy, methoxy)(hereinafter referred to as ring B is b36),
(B1, butynyloxy, cyano)(hereinafter referred to as ring B is b37),
(B1, butynyloxy, amino)(hereinafter referred to as ring B is b38),
(B1, butynyloxy, carbamoyl)(hereinafter referred to as ring B is b39),
(B1, cyano, hydrogen)(hereinafter referred to as ring B is b40),
(B1, cyano, chloro)(hereinafter referred to as ring B is b41),
(B1, cyano, fluoro)(hereinafter referred to as ring B is b42),
(B1, cyano, methoxy)(hereinafter referred to as ring B is b43),
(B1, cyano, butynyloxy)(hereinafter referred to as ring B is b44),
(B1, cyano, cyano)(hereinafter referred to as ring B is b45),
(B1, cyano, amino)(hereinafter referred to as ring B is b46),
(B1, cyano, carbamoyl)(hereinafter referred to as ring B is b47),
(B1, amino, hydrogen)(hereinafter referred to as ring B is b48),
(B1, amino, chloro)(hereinafter referred to as ring B is b49),
(B1, amino, fluoro)(hereinafter referred to as ring B is b50),
(B1, amino, methoxy)(hereinafter referred to as ring B is b51),
(B1, amino, butynyloxy)(hereinafter referred to as ring B is b52),
(B1, amino, cyano)(hereinafter referred to as ring B is b53),
(B1, carbamoyl, hydrogen)(hereinafter referred to as ring B is b54),
(B1, carbamoyl, chloro)(hereinafter referred to as ring B is b55),
(B1, carbamoyl, fluoro)(hereinafter referred to as ring B is b56),
(B1, carbamoyl, methoxy)(hereinafter referred to as ring B is b57),
(B1, carbamoyl, butynyloxy)(hereinafter referred to as ring B is b58),
(B1, carbamoyl, cyano)(hereinafter referred to as ring B is b59),
(B3, hydrogen, hydrogen)(hereinafter referred to as ring B is b60),
(B3, hydrogen, chloro)(hereinafter referred to as ring B is b61),
(B3, hydrogen, fluoro)(hereinafter referred to as ring B is b62),
(B3, hydrogen, methoxy)(hereinafter referred to as ring B is b63),
(B3, hydrogen, butynyloxy)(hereinafter referred to as ring B is b64),
(B3, hydrogen, cyano)(hereinafter referred to as ring B is b65),
(B3, hydrogen, amino)(hereinafter referred to as ring B is b66),
(B3, hydrogen, carbamoyl)(hereinafter referred to as ring B is b67),
(B3, chloro, hydrogen)(hereinafter referred to as ring B is b68),
(B3, chloro, chloro)(hereinafter referred to as ring B is b69),
(B3, chloro, fluoro)(hereinafter referred to as ring B is b70),
(B3, chloro, methoxy)(hereinafter referred to as ring B is b71),
(B3, chloro, butynyloxy)(hereinafter referred to as ring B is b72),
(B3, chloro, cyano)(hereinafter referred to as ring B is b73),
(B3, chloro, amino)(hereinafter referred to as ring B is b74),
(B3, chloro, carbamoyl)(hereinafter referred to as ring B is b75),
(B3, fluoro, hydrogen)(hereinafter referred to as ring B is b76),
(B3, fluoro, chloro)(hereinafter referred to as ring B is b77),
(B3, fluoro, fluoro)(hereinafter referred to as ring B is b78),
(B3, fluoro, methoxy)(hereinafter referred to as ring B is b79),
(B3, fluoro, butynyloxy)(hereinafter referred to as ring B is b80),
(B3, fluoro, cyano)(hereinafter referred to as ring B is b81),
(B3, fluoro, amino)(hereinafter referred to as ring B is b82),
(B3, fluoro, carbamoyl)(hereinafter referred to as ring B is b83),
(B3, methoxy, hydrogen)(hereinafter referred to as ring B is b84),
(B3, methoxy, chloro)(hereinafter referred to as ring B is b85),
(B3, methoxy, fluoro)(hereinafter referred to as ring B is b86),
(B3, methoxy, methoxy)(hereinafter referred to as ring B is b87),
(B3, methoxy, butynyloxy)(hereinafter referred to as ring B is b88),
(B3, methoxy, cyano)(hereinafter referred to as ring B is b89),
(B3, methoxy, amino)(hereinafter referred to as ring B is b90),
(B3, methoxy, carbamoyl)(hereinafter referred to as ring B is b91),
(B3, butynyloxy, hydrogen)(hereinafter referred to as ring B is b92),
(B3, butynyloxy, chloro)(hereinafter referred to as ring B is b93),
(B3, butynyloxy, fluoro)(hereinafter referred to as ring B is b94),
(B3, butynyloxy, methoxy)(hereinafter referred to as ring B is b95),
(B3, butynyloxy, cyano)(hereinafter referred to as ring B is b96),
(B3, butynyloxy, amino)(hereinafter referred to as ring B is b97),
(B3, butynyloxy, carbamoyl)(hereinafter referred to as ring B is b98),
(B3, cyano, hydrogen)(hereinafter referred to as ring B is b99),
(B3, cyano, chloro)(hereinafter referred to as ring B is b100),
(B3, cyano, fluoro)(hereinafter referred to as ring B is b101),
(B3, cyano, methoxy)(hereinafter referred to as ring B is b102),
(B3, cyano, butynyloxy)(hereinafter referred to as ring B is b103),
(B3, cyano, cyano)(hereinafter referred to as ring B is b104),
(B3, cyano, amino)(hereinafter referred to as ring B is b105),
(B3, cyano, carbamoyl)(hereinafter referred to as ring B is b106),
(B3, amino, hydrogen)(hereinafter referred to as ring B is b107),
(B3, amino, chloro)(hereinafter referred to as ring B is b108),
(B3, amino, fluoro)(hereinafter referred to as ring B is b109),
(B3, amino, methoxy)(hereinafter referred to as ring B is b110),
(B3, amino, butynyloxy)(hereinafter referred to as ring B is bill),
(B3, amino, cyano)(hereinafter referred to as ring B is b112),
(B3, carbamoyl, hydrogen)(hereinafter referred to as ring B is b113), (B3, carbamoyl, chloro)(hereinafter referred to as ring B is b114),
(B3, carbamoyl, fluoro)(hereinafter referred to as ring B is b115),
(B3, carbamoyl, methoxy)(hereinafter referred to as ring B is b116),
(B3, carbamoyl, butynyloxy)(hereinafter referred to as ring B is b117), or
(B3, carbamoyl, cyano)(hereinafter referred to as ring B is b118),
the compound of the formula (I) wherein the combination of rings B and $R^{b1}$ (B, $R^{b1}$) is as follows:
(B2, hydrogen)(hereinafter referred to as Ring B is b119),
(B2, chloro)(hereinafter referred to as Ring B is b120),
(B2, fluoro)(hereinafter referred to as Ring B is b121),
(B2, methoxy)(hereinafter referred to as Ring B is b122),
(B2, butynyloxy)(hereinafter referred to as Ring B is b123),
(B2, cyano)(hereinafter referred to as Ring B is b124),
(B2, amino)(hereinafter referred to as Ring B is b125),
(B2, carbamoyl)(hereinafter referred to as Ring B is b126),
(B4, hydrogen)(hereinafter referred to as Ring B is b127),
(B4, chloro)(hereinafter referred to as Ring B is b128),
(B4, fluoro)(hereinafter referred to as Ring B is b129),
(B4, methoxy)(hereinafter referred to as Ring B is b130),
(B4, butynyloxy)(hereinafter referred to as Ring B is b131),
(B4, cyano)(hereinafter referred to as Ring B is b132),
(B4, amino)(hereinafter referred to as Ring B is b133) or
(B4, carbamoyl)(hereinafter referred to as Ring B is b134).

In the formula (I), the combination of

[Chemical Formula 77]

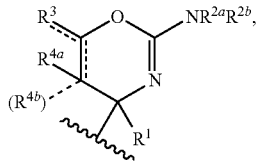

ring A and ring B (r, A, b) is as follows:
(r1,A1,b1),(r1,A1,b2),(r1,A1,b3),(r1,A1,b4),(r1,A1,b5),(r1,A1,b6),(r1,A1,b7),(r1,A1,b8),(r1,A1,b9),(r1,A1,b10),(r1,A1,b11),(r1,A1,b12),(r1,A1,b13),(r1,A1,b14),(r1,A1,b15),(r1,A1,b16),(r1,A1,b17),(r1,A1,b18),(r1,A1,b19),(r1,A1,b20),(r1,A1,b21),(r1,A1,b22),(r1,A1,b23), 1,A1,b24),(r1,A1,b25),(r1,A1,b26),(r1,A1,b27),(r1,A1,b28),(r1,A1,b29),(r1,A1,b30),(r1,A1,b31),(r1,A1,b32),(r1,A1,b33),(r1,A1,b34),(r1,A1,b35),(r1,A1,b36),(r1,A1,b37),(r1,A1,b38),(r1,A1,b39),(r1,A1,b40),(r1,A1,b41),(r1,A1,b42),(r1,A1,b43),(r1,A1,b44),(r1,A1,b45),(r1,A1,b46),(r1,A1,b47),(r1,A1,b48),(r1,A1,b49),(r1,A1,b50),(r1,A1,b51),(r1,A1,b52),(r1,A1,b53),(r1,A1,b54),(r1,A1,b55),(r1,A1,b56),(r1,A1,b57),(r1,A1,b58),(r1,A1,b59),(r1,A1,b60),(r1,A1,b61),(r1,A1,b62),(r1,A1,b63),(r1,A1,b64),(r1,A1,b65),(r1,A1,b66),(r1,A1,b67),(r1,A1,b68),(r1,A1,b69),(r1,A1,b70),(r1,A1,b71),(r1,A1,b72),(r1,A1,b73),(r1,A1,b74),(r1,A1,b75),(r1,A1,b76),(r1,A1,b77),(r1,A1,b78),(r1,A1,b79),(r1,A1,b80),(r1,A1,b81),(r1,A1,b82),(r1,A1,b83),(r1,A1,b84),(r1,A1,b85),(r1,A1,b86),(r1,A1,b87),(r1,A1,b88),(r1,A1,b89),(r1,A1,b90),(r1,A1,b91),(r1,A1,b92),(r1,A1,b93),(r1,A1,b94),(r1,A1,b95),(r1,A1,b96),(r1,A1,b97),(171,A1,b98),(r1,A1,b99),(r1,A1,b100),(r1,A1,b101),(r1,A1,b102),(r1,A1,b103),(r1,A1,b104),(r1,A1,b105),(r1,A1,b106),(r1,A1,b107),(r1,A1,b108),(r1,A1,b109),(r1,A1,b110),(r1,A1,b111),(r1,A1,b112),(r1,A1,b113),(r1,A1,b114),(r1,A1,b115),(r1,A1,b116),(r1,A1,b117),(r1,A1,b118),(r1,A1,b119),(r1,A1,b120),(r1,A1,b121),(r1,A1,b122),(r1,A1,b123),(r1,A1,b124),(r1,A1,b125),(r1,A1,b126),(r1,A1,b127),(r1,A1,b128),(r1,A1,b129),(r1,A1,b130),(r1,A1,b131),(r1,A1,b132),(r1,A1,b133),(r1,A1,b134),(r1,A2,b1),(r1,A2,b2),(r1,A2,b3),(r1,A2,b4),(r1,A2,b5),(r1,A2,b6),(r1,A2,b7),(r1,A2,b8),(r1,A2,b9),(r1,A2,b10),(r1,A2,b11),(r1,A2,b12),(r1,A2,b13),(r1,A2,b14),(r1,A2,b15),(r1,A2,b16),(r1,A2,b17),(r1,A2,b18),(r1,A2,b19),(r1,A2,b20),(r1,A2,b21),(r1,A2,b22),(r1,A2,b23),(r1,A2,b24),(r1,A2,b25),(r1,A2,b26),(r1,A2,b27),(r1,A2,b28),(r1,A2,b29),(r1,A2,b30),(r1,A2,b31), 1,A2,b32),(r1,A2,b33),(r1,A2,b34),(r1,A2,b35),(r1,A2,b36),(r1,A2,b37),(r1,A2,b38),(r1,A2,b39),(r1,A2,b40),(r1,A2,b41),(r1,A2,b42),(r1,A2,b43),(r1,A2,b44),(r1,A2,b45),(r1,A2, b46),(r1,A2,b47),(r1,A2,b48),(r1,A2,b49),(r1,A2,b50),(r1,A2,b51),(r1,A2,b52),(r1,A2,b53),(r1,A2,b54),(r1,A2,b55),(r1,A2,b56),(r1,A2,b57),(r1,A2,b58),(r1,A2,b59),(r1,A2,b60),(r1,A2,b61),(r1,A2,b62),(r1,A2,b63),(r1,A2,b64),(r1,A2,b65),(r1,A2,b66),(r1,A2,b67),(r1,A2,b68),(r1,A2,b69),(r1,A2,b70),(r1,A2,b71),(r1,A2,b72),(r1,A2,b73),(r1,A2,b74),(r1,A2,b75),(r1,A2,b76),(r1,A2,b77),(r1,A2,b78),(r1,A2,b79),(r1,A2,b80),(r1,A2,b81),(r1,A2,b82),(r1,A2,b83),(r1,A2,b84),(r1,A2,b85),(r1,A2,b86),(r1,A2,b87),(r1,A2,b88),(r1,A2,b89),(r1,A2,b90),(r1,A2,b91),(r1,A2,b92),(r1,A2,b93),(r1,A2,b94),(r1,A2,b95),(r1,A2,b96),(r1,A2,b97),(r1,A2,b98),(r1,A2,b99),(r1,A2,b100),(r1,A2,b101),(r1,A2,b102),(r1,A2,b103),(r1,A2,b104),(r1,A2,b105),(r1,A2,b106),(r1,A2,b107),(r1,A2,b108),(r1,A2,b109),(r1,A2,b110),(r1,A2,b111),(r1,A2,b112),(r1,A2,b113),(r1,A2,b114),(r1,A2,b115),(r1,A2,b116),(r1,A2,b117),(r1,A2,b118),(r1,A2,b119),(r1,A2,b120),(r1,A2,b121),(r1,A2,b122),(r1,A2,b123),(r1,A2,b124),(r1,A2,b125),(r1,A2,b126),(r1,A2,b127),(r1,A2,b128),(r1,A2,b129),(r1,A2,b130),(r1,A2,b131),(r1,A2,b132),(r1,A2,b133),(r1,A2,b134),(r1,A3,b1),(r1,A3,b2),(r1,A3,b3),(r1,A3,b4),(r1,A3,b5),(r1,A3,b6),(r1,A3,b7),(r1,A3,b8),(r1,A3,b9),(r1,A3,b10), 1,A3,b11),(r1,A3,b12),(r1,A3,b13),(r1,A3,b14),(r1,A3,b15),(r1,A3,b16),(r1,A3,b17),(r1,A3,b18),(r1,A3,b19),(r1,A3,b20),(r1,A3,b21),(r1,A3,b22),(r1,A3,b23),(r1,A3,b24),(r1,A3,b25),(r1,A3,b26),(r1,A3,b27),(r1,A3,b28),(r1,A3,b29),(r1,A3,b30),(r1,A3,b31),(r1,A3,b32),(r1,A3,b33),(r1,A3,b34),(r1,A3,b35),(r1,A3,b36),(r1,A3,b37),(r1,A3,b38),(r1,A3,b39),(r1,A3,b40),(r1,A3,b41),(r1,A3,b42),(r1,A3,b43),(r1,A3,b44),(r1,A3,b45),(r1,A3,b46),(r1,A3,b47),(r1,A3,b48),(r1,A3,b49),(r1,A3,b50),(r1,A3,b51),(r1,A3,b52),(r1,A3,b53),(r1,A3,b54),(r1,A3,b55),(r1,A3,b56),(r1,A3,b57),(r1,A3,b58), 1,A3,b59),(r1,A3,b60),(r1,A3,b61),(r1,A3,b62),(r1,A3,b63),(r1,A3,b64),(r1,A3,b65),(r1,A3,b66),(r1,A3,b67),(r1,A3,b68),(r1,A3,b69),(r1,A3,b70),(r1,A3,b71),(r1,A3,b72),(r1,A3,b73),(r1,A3,b74),(r1,A3,b75),(r1,A3,b76),(r1,A3,b77),(r1,A3,b78),(r1,A3,b79),(r1,A3,b80),(r1,A3,b81),(r1,A3,b82),(r1,A3,b83),(r1,A3,b84),(r1,A3,b85),(r1,A3,b86),(r1,A3,b87),(r1,A3,b88),(r1,A3,b89),(r1,A3,b90),(r1,A3,b91),(r1,A3,b92),(r1,A3,b93),(r1,A3,b94),(r1,A3,b95),(r1,A3,b96),(r1,A3,b97),(r1,A3,b98),(r1,A3,b99),(r1,A3,b100),(r1,A3,b101),(r1,A3,b102),(r1,A3,b103),(r1,A3,b104),(r1,A3,b105),(r1,A3,b106),(r1,A3,b107),(r1,A3,b108),(r1,A3,b109),(r1,A3,b110),(r1,A3,b111),(r1,A3,b112),(r1,A3,b113),(r1,A3,b114),(r1,A3,b115),(r1,A3,b116),(r1,A3,b117),(r1,A3,b118),(r1,A3,b119),(r1,A3,b120),(r1,A3,b121),(r1,A3,b122),(r1,A3,b123),(r1,A3,b124),(r1,A3,b125),(r1,A3,b126),(r1,A3,b127),(r1,A3,b128),(r1,A3,b129),(r1,A3,b130),(r1,A3,b131),(r1,A3,b132),(r1,A3,b133),(r1,A3,b134),(r1,A4,b1),(r1,A4,b2),(r1,A4,b3),(r1,A4,b4),(r1,A4,b5),(r1,A4,b6),(r1,A4,b7),(r1,A4,b8), 1,A4,b9),(r1,A4,b10),(r1,A4,b11),(r1,A4,b12),(r1,A4,b13),(r1,A4,b14),(r1,A4,b15),(r1,A4,b16),(r1,A4,b17),(r1,A4,b18),(r1,A4,b19),(r1,A4,b20),(r1,A4, b21),(r1,A4,b22),(r1,A4,b23),(r1,A4,b24),(r1,A4,b25),(r1,A4,b26),(r1,A4,b27),(r1,A4,b28),(r1,A4,b29),(r1,A4,b30),(r1,A4,b31),(r1,A4,b32),(r1,A4,b33),(r1,A4,b34),(r1,A4,b35),(r1,A4,b36),(r1,A4,b37),(r1,A4,b38),(r1,A4,b39),(r1,A4,b40),(r1,A4,b41),(r1,A4,b42),(r1,A4,b43),(r1,A4,b44),(r1,A4,b45),(r1,A4,b46),(r1,A4,b47),(r1,A4,b48),(r1,A4,b49),(r1,A4,b50),(r1,A4,b51),(r1,A4,b52),(r1,A4,b53),(r1,A4,b54),(r1,A4,b55),(r1,A4,b56),(r1,A4,b57),(r1,A4,b58),(r1,A4,b59),(r1,A4,b60),(r1,A4,b61),(r1,A4,b62),(r1,A4,b63),(r1,A4,b64),(r1,A4,b65),(r1,A4,b66),(r1,A4,b67),(r1,A4,b68),(r1,A4,b69),(r1,A4,b70),(r1,A4,b71),(r1,A4,b72),(r1,A4,b73),(r1,A4,b74),(r1,A4,b75),(r1,A4,b76),(r1,A4,b77),(r1,A4,b78),(r1,A4,b79),(r1,A4,b80),(r1,A4,b81),(r1,A4,b82),(r1,A4,b83),(r1,A4,b84),(r1,A4,b85),(r1,A4,b86),(r1,A4,b87),(r1,A4,b88),(r1,A4,b89),(r1,A4,b90),(r1,A4,b91),(r1,A4,b92),(r1,A4,b93),(r1,A4,b94),(r1,A4,b95),(r1,A4,b96),(r1,A4,b97), 1,A4,b98),(r1,A4,b99),(r1,A4,b100),(r1,A4,b101),(r1,A4,b102),(r1,A4,b103),(r1,A4,b104),(r1,A4,b105),(r1,A4,b106),(r1,A4,b107),(r1,A4,b108),(r1,A4,b109),(r1,A4,b110),(r1,A4,b111),(r1,A4,b112),(r1,A4,b113),(r1,A4,b114),(r1,A4,b115),(r1,A4,b116),(r1,A4,b117),(r1,A4,b118),(r1,A4,b119),(r1,A4,b120),(r1,A4,b121),(r1,A4,b122),(r1,A4,b123),(r1,A4,b124),(r1,A4,b125),(r1,A4,b126),(r1,A4,b127),(r1,A4,b128),(r1,A4,b129),(r1,A4,b130),(r1,A4,b131),(r1,A4,b132),(r1,A4,b133),(r1,A4,b134),
(r2,A1,b1),(r2,A1,b2),(r2,A1,b3),(r2,A1,b4),(r2,A1,b5),(r2,A1,b6),(r2,A1,b7),(r2,A1,b8),(r2,A1,b9),(r2,A1,b10),(r2,A1,b11),(r2,A1,b12),(r2,A1,b13),(r2,A1,b14),(r2,A1,b15),(r2,A1,b16),(r2,A1,b17),(r2,A1,b18),(r2,A1,b19),(r2,A1,b20),(r2,A1,b21),(r2,A1,b22),(r2,A1,b23),(r2,A1,b24),(r2,A1,b25),(r2,A1,b26),(r2,A1,b27),(r2,A1,b28),(r2,A1,b29),(r2,A1,b30),(r2,A1,b31),(r2,A1,b32),(r2,A1,b33),(r2,A1,b34),(r2,A1,b35),(r2,A1,b36),(r2,A1,b37),(r2,A1,b38),(r2,A1,b39),(r2,A1,b40),(r2,A1,b41),(r2,A1,b42),(r2,A1,b43),(r2,A1,b44),(r2,A1,b45),(r2, A1,b46),(r2,A1,b47),(r2,A1,b48),(r2,A1,b49),(r2,A1,b50),(r2,A1,b51),(r2,A1,b52),(r2,A1,b53),(r2,A1,b54),(r2,A1,b55),(r2,A1,b56),(r2,A1,b57),(r2,A1,b58),(r2,A1,b59),(r2,A1,b60),(r2,A1,b61),(r2,A1,b62),(r2,A1,b63),(r2,A1,b64),(r2,A1,b65),(r2,A1,b66),(r2,A1,b67),(r2,A1,b68),(r2,A1,b69),(r2,A1,b70),(r2,A1,b71),(r2,A1,b72),(r2,A1,b73),(r2,A1,b74),(r2,A1,b75),(r2,A1,b76),(r2,A1,b77),(r2,A1,b78),(r2,A1,b79),(r2,A1,b80),(r2,A1,b81),(r2,A1,b82),(r2,A1,b83),(r2,A1,b84),(r2,A1,b85),(r2,A1,b86),(r2,A1,b87),(r2,A1,b88),(r2,A1,b89),(r2,A1,b90),(r2,A1,b91),(r2,A1,b92),(r2,A1,b93),(r2,A1,b94),(r2,A1,b95),(r2,A1,b96),(r2,A1,b97),(r2,A1,b98),(r2,A1,b99),(r2,A1,b100),(r2,A1,b101),(r2,A1,b102),(r2,A1,b103),(r2,A1,b104),(r2,A1,b105),(r2,A1,b106),(r2,A1,b107),(r2,A1,b108),(r2,A1,b109),(r2,A1,b110),(r2,A1, b111),(r2,A1,b112),(r2,A1,b113),(r2,A1,b114),(r2,A1,b115),(r2,A1,b116),(r2,A1,b117),(r2, A1,b118),(r2,A1,b119),(r2,A1,b120),(r2,A1,b121),(r2,A1,b122),(r2,A1,b123),(r2,A1,b124),(r2,A1,b125),(r2,A1,b126),(r2,A1,b127),(r2,A1,b128),(r2,A1,b129),(r2,A1,b130),(r2,A1,b131),(r2,A1,b132),(r2,A1,b133),(r2,A1,b134),(r2,A2,b1),(r2,A2,b2),(r2,A2,b3),(r2,A2,b4), 2,A2,b5),(r2,A2,b6),(r2,A2,b7),(r2,A2,b8),(r2,A2,b9),(r2,A2,b10),(r2,A2,b11),(r2,A2,b12),(r2,A2,b13),(r2,A2,b14),(r2,A2,b15),(r2,A2,b16),(r2,A2,b17),(r2,A2,b18),(r2,A2,b19),(r2,A2,b20),(r2,A2,b21),(r2,A2,b22),(r2,A2,b23),(r2,A2,b24),(r2,A2,b25),(r2,A2,b26),(r2,A2,b27),(r2,A2,b28),(r2,A2,b29),(r2,A2,b30),(r2,A2,b31),(r2,A2,b32),(r2,A2,b33),(r2,A2,b34),(r2,A2,b35),(r2,A2,b36),(r2,A2,b37),(r2,A2,b38),(r2,A2,b39),(r2,A2,b40),(r2,A2,b41),(r2,A2,b42),(r2,A2,b43),(r2,A2,b44),(r2,A2,b45),(r2,A2,b46),(r2,A2,b47),(r2,A2,b48),(r2,A2,b49),(r2,A2,b50),(r2,A2,b51),(r2,A2,b52),(r2,A2,b53),(r2,A2,b54),(r2,A2,b55),(r2,A2,b56),(r2,A2,b57),(r2,A2,b58),(r2,A2,b59),(r2,A2,b60),(r2,A2,b61),(r2,A2,b62),(r2,A2,b63),(r2,A2,b64),(r2,A2,b65),(r2,A2,b66),(r2,A2,b67),(r2,A2,b68),(r2,A2,b69),(r2,A2,b70),(r2,A2,b71),(r2,A2,b72),(r2,A2,b73),(r2,A2,b74),(r2,A2,b75),(r2,A2, b76),(r2,A2,b77),(r2,A2,b78),(r2,A2,b79),(r2,A2,b80),(r2,A2,b81),(r2,A2,b82),(r2,A2,b83),(r2,A2,b84),(r2,A2,b85),(r2,A2,b86),(r2,A2,b87),(r2,A2,b88),(r2,A2,b89),(r2,A2,b90),(r2,A2,b91),(r2,A2,b92),(r2,A2,b93),(r2,A2,b94),(r2,A2,b95),(r2,A2,b96),(r2,A2,b97),(r2,A2,b98),(r2,A2,b99),(r2,A2,b100),(r2,A2,b101),(r2,A2,b102),(r2,A2,b103),(r2,A2,b104),(r2,A2,b105),(r2,A2,b106),(r2,A2,b107),(r2,A2,b108),(r2,A2,b109),(r2,A2,b110),(r2,A2,b111),(r2,A2,b112),(r2,A2,b113),(r2,A2,b114),(r2,A2,b115),(r2,A2,b116),(r2,A2,b117),(r2,A2,b118),(r2,A2,b119),(r2,A2,b120),(r2,A2,b121),(r2,A2,b122),(r2,A2,b123),(r2,A2,b124),(r2,A2,b125),(r2,A2,b126),(r2,A2,b127),(r2,A2,b128),(r2,A2,b129),(r2,A2,b130),(r2,A2,b131),(r2,A2,b132),(r2,A2,b133),(r2,A2,b134),(r2,A3,b1),(r2,A3,b2),(r2,A3,b3),(r2,A3,b4),(r2,A3,b5),(r2,A3,b6),(r2,A3,b7),(r2,A3,b8),(r2,A3,b9),(r2,A3,b10),(r2,A3,b11),(r2,A3,b12),(r2,A3,b13),(r2,A3,b14),(r2,A3,b15),(r2,A3,b16),(r2,A3,b17),(r2,A3,b18),(r2,A3,b19),(r2,A3,b20),(r2,A3,b21),(r2,A3,b22),(r2,A3,b23),(r2,A3,b24),(r2,A3,b25),(r2,A3,b26),(r2,A3,b27),(r2,A3,b28),(r2,A3,b29),(r2,A3,b30),(r2,A3,b31),(r2,A3,b32),(r2,A3,b33),(r2,A3,b34),(r2,A3,b35),(r2,A3,b36),(r2,A3,b37),(r2,A3,b38),(r2,A3, b39),(r2,A3,b40),(r2,A3,b41),(r2,A3,b42),(r2,A3,b43),(r2,A3,b44),(r2,A3,b45),(r2,A3,b46),(r2,A3,b47),(r2,A3,b48),(r2,A3,b49),(r2,A3,b50),(r2,A3,b51),(r2,A3,b52),(r2,A3,b53),(r2,A3,b54),(r2,A3,b55),(r2,A3,b56),(r2,A3,b57),(r2,A3,b58),(r2,A3,b59),(r2,A3,b60),(r2,A3,b61),(r2,A3, b62),(r2,A3,b63),(r2,A3,b64),(r2,A3,b65),(r2,A3,b66),(r2,A3,b67),(r2,A3,b68),(r2,A3,b69),(r2,A3,b70),(r2,A3,b71),(r2,A3,b72),(r2,A3,b73),(r2,A3,b74),(r2,A3,b75),(r2,A3,b76),(r2,A3,b77),(r2,A3,b78),(r2,A3,b79),(r2,A3,b80),(r2,A3,b81),(r2,A3,b82),(r2,A3,b83),(r2,A3,b84),(r2,A3,b85),(r2,A3,b86),(r2,A3,b87),(r2,A3,b88),(r2,A3,b89),(r2,A3,b90),(r2,A3,b91),(r2,A3,b92),(r2,A3,b93),(r2,A3,b94),(r2,A3,b95),(r2,A3,b96),(r2,A3,b97),(r2,A3,b98),(r2,A3,b99),(r2,A3,b100),(r2,A3,b101),(r2,A3,b102),(r2,A3,b103),(r2,A3,b104),(r2,A3,b105),(r2,A3,b106),(r2,A3,b107),(r2,A3,b108),(r2,A3,b109),(r2,A3,b110),(r2,A3,b111),(r2,A3,b112),(r2,A3,b113),(r2,A3,b114),(r2,A3,b115),(r2,A3,b116),(r2,A3,b117),(r2,A3,b118),(r2,A3,b119),(r2,A3,b120),(r2,A3,b121),(r2,A3,b122),(r2,A3,b123),(r2,A3,b124),(r2,A3,b125),(r2,A3,b126),(r2,A3,b127),(r2,A3,b128),(r2,A3,b129),(r2,A3,b130),(r2,A3,b131),(r2,A3,b132),(r2,A3,b133),(r2,A3,b134),(r2,A4,b1),(r2,A4,b2),(r2,A4,b3),(r2,A4,b4),(r2,A4,b5),(r2,A4,b6),(r2,A4,b7),(r2,A4,b8),(r2,A4,b9),(r2,A4,b10),(r2,A4,b11),(r2,A4,b12),(r2,A4,b13),(r2,A4,b14),(r2,A4,b15),(r2,A4,b16),(r2,A4,b17),(r2,A4,b18),(r2,A4,b19),(r2,A4,b20),(r2,A4,b21),(r2,A4,b22),(r2,A4,b23),(r2,A4,b24),(r2,A4,b25),(r2,A4,b26),(r2,A4,b27),(r2,A4,b28),(r2,A4,b29),(r2,A4,b30),(r2,A4,b31),(r2,A4,b32),(r2,A4,b33),(r2,A4,b34),(r2,A4,b35),(r2,A4,b36),(r2,A4,b37),(r2,A4,b38),(r2,A4,b39),(r2,A4,b40),(r2,A4,b41),(r2,A4,b42),(r2,A4,b43),(r2,A4,b44),(r2,A4,b45),(r2,A4,b46),(r2,A4,b47),(r2,A4,b48),(r2,A4,b49),(r2,A4,b50),(r2,A4,b51),(r2,A4,b52),(r2,A4, b53),(r2,A4,b54),(r2,A4,b55),(r2,A4,b56),(r2,A4,b57),(r2,A4,b58),(r2,A4,b59),(r2,A4,b60),(r2,A4,b61),(r2,A4,b62),(r2,A4,b63),(r2,A4,b64),(r2,A4,b65),(r2,A4,b66),(r2,A4,b67),(r2,A4,b68),(r2,A4,b69),(r2,A4,b70),(r2,A4,b71),(r2,A4,b72),(r2,A4,b73),(r2,A4,b74),(r2,A4,b75),(r2,A4,b76),(r2,A4,b77),(r2,A4,b78),(r2,A4,b79),(r2,A4,b80),(r2,A4,b81),(r2,A4,b82),(r2,A4,b83),(r2,A4,b84),(r2,A4,b85),(r2,A4,b86),(r2,A4,b87),(r2,A4,b88),(r2,A4,b89),(r2,A4,b90),(r2,A4, b91),(r2,A4,b92),(r2,A4,b93),(r2,A4,b94),(r2,A4,b95),(r2,A4,b96),(r2,A4,b97),(r2,A4,b98),(r2,A4,b99),(r2,A4,b100),(r2,A4,b101),(r2,A4,b102),(r2,A4,b103),(r2,A4,b104),(r2,A4,b105),(r2,A4,b106),(r2,A4,b107),(r2,A4,b108),(r2,A4,b109),(r2,A4,b110),(r2,A4,b111),(r2,A4,b112),(r2,A4,b113),(r2,A4,b114),(r2,A4,b115),(r2,A4,b116),(r2,A4,b117),(r2,A4,b118),(r2,A4,b119),(r2,A4,b120),(r2,A4,b121),(r2,A4,b122),(r2,A4,b123),(r2,A4,b124),(r2,A4,b125),(r2,A4,b126),(r2,A4,b127),(r2,A4,b128),(r2,A4,b129),(r2,A4,b130),(r2,A4,b131),(r2,A4,b132),(r2,A4,b133),(r2,A4,b134),
(r3,A1,b1),(r3,A1,b2),(r3,A1,b3),(r3,A1,b4),(r3,A1,b5),(r3,A1,b6),(r3,A1,b7),(r3,A1,b8),(r3,A1,b9),(r3,A1,b10),(r3,A1,b11),(r3,A1,b12),(r3,A1,b13),(r3,A1,b14),(r3,A1,b15),(r3,A1,b16),(r3,A1,b17),(r3,A1,b18),(r3,A1,b19),(r3,A1,b20),(r3,A1,b21),(r3,A1,b22),(r3,A1,b23),(r3,A1,b24),(r3,A1,b25),(r3,A1,b26),(r3,A1,b27),(r3,A1,b28),(r3,A1,b29),(r3,A1,b30),(r3,A1,b31),(r3,A1,b32),(r3,A1,b33),(r3,A1,b34),(r3,A1,b35),(r3,A1,b36),(r3,A1,b37),(r3,A1,b38),(r3,A1,b39),(r3,A1,b40),(r3,A1,b41),(r3,A1,b42),(r3,A1,b43),(r3,A1,b44),(r3,A1,b45),(r3,A1,b46),(r3,A1,b47),(r3,A1,b48),(r3,A1,b49),(r3,A1,b50),(r3,A1,b51),(r3,A1,b52),(r3,A1,b53),(r3,A1,b54),(r3,A1,b55),(r3,A1,b56),(r3,A1,b57),(r3,A1,b58),(r3,A1,b59),(r3,A1,b60),(r3,A1,b61),(r3,A1,b62),(r3,A1,b63),(r3,A1,b64),(r3,A1,b65),(r3,A1,b66),(r3,A1,b67),(r3,A1,b68),(r3,A1,b69),(r3,A1,b70),(r3,A1,b71),(r3,A1,b72),(r3,A1,b73),(r3,A1,b74),(r3,A1,b75),(r3,A1,b76),(r3,A1,b77),(r3,A1,b78),(r3,A1,b79),(r3,A1,b80),(r3,A1,b81),(r3,A1,b82),(r3,A1,b83),(r3,A1,b84),(r3,A1,b85),(r3,A1,b86),(r3,A1,b87),(r3,A1,b88),(r3,A1,b89),(r3,A1,b90),(r3,A1,b91),(r3,A1,b92),(r3,A1,b93),(r3,A1,b94),(r3,A1,b95),(r3,A1,b96),(r3,A1,b97),(r3,A1,b98),(r3,A1,b99),(r3,A1,b100),(r3,A1,b101),(r3,A1,b102),(r3,A1,b103),(r3,A1,b104),(r3,A1,b105),(r3,A1,b106),(r3,A1,b107),(r3,A1,b108),(r3,A1,b109),(r3,A1,b110),(r3,A1,b111),(r3,A1,b112),(r3,A1,b113),(r3,A1,b114),(r3,A1,b115),(r3,A1,b116),(r3,A1,b117),(r3,A1,b118),(r3,A1,b119),(r3,A1,b120),(r3,A1,b121),(r3,A1,b122),(r3,A1,b123),(r3,A1,b124),(r3,A1,b125),(r3,A1,b126),(r3,A1,b127),(r3,A1,b128),(r3,A1,b129),(r3,A1,b130),(r3,A1,b131),(r3,A1,b132),(r3,A1,b133),(r3,A1,b134),(r3,A2,b1),(r3,A2,b2),(r3,A2,b3),(r3,A2,b4),(r3,A2,b5),(r3,A2,b6),(r3,A2,b7),(r3,A2,b8),(r3,A2,b9),(r3,A2,b10),(r3,A2,b11),(r3,A2,b12),(r3,A2,b13),(r3,A2,b14),(r3,A2,b15),(r3,A2,b16),(r3,A2,b17),(r3,A2,b18),(r3,A2,b19),(r3,A2,b20),(r3,A2,b21),(r3,A2,b22),(r3,A2,b23),(r3,A2,b24),(r3,A2,b25),(r3,A2,b26),(r3,A2,b27),(r3,A2,b28),(r3,A2,b29),(r3,A2,b30),(r3,A2,b31),(r3,A2,b32),(r3,A2,b33),(r3,A2,b34),(r3,A2,b35),(r3,A2,b36),(r3,A2,b37),(r3,A2,b38),(r3,A2,b39),(r3,A2,b40),(r3,A2,b41),(r3,A2,b42),(r3,A2,b43),(r3,A2,b44),(r3,A2,b45),(r3,A2,b46),(r3,A2,b47),(r3,A2,b48),(r3,A2,b49),(r3,A2,b50),(r3,A2,b51),(r3,A2,b52),(r3,A2,b53),(r3,A2,b54),(r3,A2,b55),(r3,A2,b56),(r3,A2,b57),(r3,A2,b58),(r3,A2,b59),(r3,A2,b60),(r3,A2,b61),(r3,A2,b62),(r3,A2,b63),(r3,A2,b64),(r3,A2,b65),(r3,A2,b66),(r3,A2,b67),(r3,A2,b68),(r3,A2,b69),(r3,A2,b70),(r3,A2,b71),(r3,A2,b72),(r3,A2,b73),(r3,A2,b74),(r3,A2,b75),(r3,A2,b76),(r3,A2,b77),(r3,A2,b78),(r3,A2,b79),(r3,A2,b80),(r3,A2,b81),(r3,A2,b82),(r3,A2,b83),(r3,A2,b84),(r3,A2,b85),(r3,A2,b86),(r3,A2,b87),(r3,A2,b88),(r3,A2,b89),(r3,A2,b90),(r3,A2,b91),(r3,A2,b92),(r3,A2,b93),(r3,A2,b94),(r3,A2,b95),(r3,A2,b96),(r3,A2,b97),(r3,A2,b98),(r3,A2,b99),(r3,A2,b100),(r3,A2,b101),(r3,A2,b102),(r3,A2,b103),(r3,A2,b104),(r3,A2,b105),(r3,A2,b106),(r3,A2,b107),(r3,A2,b108),(r3,A2,b109),(r3,A2,b110),(r3,A2,b111),(r3,A2,b112),(r3,A2,b113),(r3,A2,b114),(r3,A2,b115),(r3,A2,b116),(r3,A2,b117),(r3,A2,b118),(r3,A2,b119),(r3,A2,b120),(r3,A2,b121),(r3,A2,b122),(r3,A2,b123),(r3,A2,b124),(r3,A2,b125),(r3,A2,b126),(r3,A2,b127),(r3,A2,b128),(r3,A2,b129),(r3,A2,b130),(r3,A2,b131),(r3,A2,b132),(r3,A2,b133),(r3,A2,b134),(r3,A3,b1),(r3,A3,b2),(r3,A3,b3),(r3,A3,b4),(r3,A3,b5),(r3,A3,b6),(r3,A3,b7),(r3,A3,b8),(r3,A3,b9),(r3,A3,b10),(r3,A3,b11),(r3,A3,b12),(r3,A3,b13),(r3,A3,b14),(r3,A3,b15),(r3,A3,b16),(r3,A3,b17),(r3,A3,b18),(r3,A3,b19),(r3,A3,b20),(r3,A3,b21),(r3,A3,b22),(r3,A3,b23),(r3,A3,b24),(r3,A3,b25),(r3,A3,b26),(r3,A3,b27),(r3,A3,b28),(r3,A3,b29),(r3,A3,b30),(r3,A3,b31),(r3,A3,b32),(r3,A3,b33),(r3,A3,b34),(r3,A3,b35),(r3,A3,b36),(r3,A3,b37),(r3,A3,b38),(r3,A3,b39),(r3,A3,b40),(r3,A3,b41),(r3,A3,b42),(r3,A3,b43),(r3,A3,b44),(r3,A3,b45),(r3,A3,b46),(r3,A3,b47),(r3,A3,b48),(r3,A3,b49),(r3,A3,b50),(r3,A3,b51),(r3,A3,b52),(r3,A3,b53),(r3,A3,b54),(r3,A3,b55),(r3,A3,b56),(r3,A3,b57),(r3,A3,b58),(r3,A3,b59),(r3,A3,b60),(r3,A3,b61),(r3,A3,b62),(r3,A3,b63),(r3,A3,b64),(r3,A3,b65),(r3,A3,b66),(r3,A3,b67),(r3,A3,b68),(r3,A3,b69),(r3,A3,b70),(r3,A3,b71),(r3,A3,b72),(r3,A3,b73),(r3,A3,b74),(r3,A3,b75),(r3,A3,b76),(r3,A3,b77),(r3,A3,b78),(r3,A3,b79),(r3,A3,b80),(r3,A3,b81),(r3,A3,b82),(r3,A3,b83),(r3,A3,b84),(r3,A3,b85),(r3,A3,b86),(r3,A3,b87),(r3,A3,b88),(r3,A3,b89),(r3,A3,b90),(r3,A3,b91),(r3,A3,b92),(r3,A3,b93),(r3,A3,b94),(r3,A3,b95),(r3,A3,b96),(r3,A3,b97),(r3,A3,b98),(r3,A3,b99),(r3,A3,b100),(r3,A3,b101),(r3,A3,b102),(r3,A3,b103),(r3,A3,b104),(r3,A3,b105),(r3,A3,b106),(r3,A3,b107),(r3,A3,b108),(r3,A3,b109),(r3,A3,b110),(r3,A3,b111),(r3,A3,b112),(r3,A3,b113),(r3,A3,b114),(r3,A3,b115),(r3,A3,b116),(r3,A3,b117),(r3,A3,b118),(r3,A3,b119),(r3,A3,b120),(r3,A3,b121),(r3,A3,b122),(r3,A3,b123),(r3,A3,b124),(r3,A3,b125),(r3,A3,b126),(r3,A3,b127),(r3,A3,b128),(r3,A3,b129),(r3,A3,b130),(r3,A3,b131),(r3,A3,b132),(r3,A3,b133),(r3,A3,b134),(r3,A4,b1),(r3,A4,b2),(r3,A4,b3),(r3,A4,b4),(r3,A4,b5),(r3,A4,b6),(r3,A4,b7),(r3,A4,b8),(r3,A4,b9),(r3,A4,b10),(r3,A4,b11),(r3,A4,b12),(r3,A4,b13),(r3,A4,b14),(r3,A4,b15),(r3,A4,b16),(r3,A4,b17),(r3,A4,b18),(r3,A4,b19),(r3,A4,b20),(r3,A4,b21),(r3,A4,b22),(r3,A4,b23),(r3,A4,b24),(r3,A4,b25),(r3,A4,b26),(r3,A4,b27),(r3,A4,b28),(r3,A4,b29),(r3,A4,b30),(r3,A4,b31),(r3,A4,b32),(r3,A4,b33),(r3,A4,b34),(r3,A4,b35),(r3,A4,b36),(r3,A4,b37),(r3,A4,b38),(r3,A4,b39),(r3,A4,b40),(r3,A4,b41),(r3,A4,b42),(r3,A4,b43),(r3,A4,b44),(r3,A4,b45),(r3,A4,b46),(r3,A4,b47),(r3,A4,b48),(r3,A4,b49),(r3,A4,b50),(r3,A4,b51),(r3,A4,b52),(r3,A4,b53),(r3,A4,b54),(r3,A4,b55),(r3,A4,b56),(r3,A4,b57),(r3,A4,b58),(r3,A4,b59),(r3,A4,b60),(r3,A4,b61),(r3,A4,b62),(r3,A4,b63),(r3,A4,b64),(r3,A4,b65),(r3,A4,b66),(r3,A4,b67),(r3,A4,b68),(r3,A4,b69),(r3,A4,b70),(r3,A4,b71),(r3,A4,b72),(r3,A4,b73),(r3,A4,b74),(r3,A4,b75),(r3,A4,b76),(r3,A4,b77),(r3,A4,b78),(r3,A4,b79),(r3,A4,b80),(r3,A4,b81),(r3,A4,b82),(r3,A4,b83),(r3,A4,b84),(r3,A4,b85),(r3,A4,b86),(r3,A4,b87),(r3,A4,b88),(r3,A4,b89),(r3,A4,b90),(r3,A4,b91),(r3,A4,b92),(r3,A4,b93),(r3,A4,b94),(r3,A4,b95),(r3,A4,b96),(r3,A4,b97),(r3,A4,b98),(r3,A4,b99),(r3,A4,b100),(r3,A4,b101),(r3,A4,b102),(r3,A4,b103),(r3,A4,b104),(r3,A4,b105),(r3,A4,b106),(r3,A4,b107),(r3,A4,b108),(r3,A4,b109),(r3,A4,b110),(r3,A4,b111),(r3,A4,b112),(r3,A4,b113),(r3,A4,b114),(r3,A4,b115),(r3,A4,b116),(r3,A4,b117),(r3,A4,b118),(r3,A4,b119),(r3,A4,b120),(r3,A4,b121),(r3,A4,b122),(r3,A4,b123),(r3,A4,b124),(r3,A4,b125),(r3,A4,b126),(r3,A4,b127),(r3,A4,b128),(r3,A4,b129),(r3,A4,b130),(r3,A4,b131),(r3,A4,b132),(r3,A4,b133),(r3,A4,b134),
(r4,A1,b1),(r4,A1,b2),(r4,A1,b3),(r4,A1,b4),(r4,A1,b5),(r4,A1,b6),(r4,A1,b7),(r4,A1,b8),(r4,A1,b9),(r4,A1,b10),(r4,A1,b11),(r4,A1,b12),(r4,A1,b13),(r4,A1,b14),(r4,A1,b15),(r4,A1,b16),(r4,A1,b17),(r4,A1,b18),(r4,A1,b19),(r4,A1, b20),(r4,A1,b21),(r4,A1,b22),(r4,A1,b23),(r4,A1,b24),(r4,A1,b25),(r4,A1,b26),(r4,A1,b27),(r4,A1,b28),(r4,A1,b29),(r4,A1,b30),(r4,A1,b31),(r4,A1,b32),(r4,A1,b33),(r4,A1,b34),(r4,A1,b35),(r4,A1,b36),(r4,A1,b37),(r4,A1,b38),(r4,A1,b39),(r4,A1,b40),(r4,A1,b41),(r4,A1,b42),(r4,A1,b43),(r4,A1,b44),(r4,A1,b45),(r4,A1,b46),(r4,A1,b47),(r4,A1,b48),(r4,A1,b49),(r4,A1,b50),(r4,A1,b51),(r4,A1,b52),(r4,A1,b53),(r4,A1,b54),(r4,A1,b55),(r4,A1,b56),(r4,A1,b57),(r4,A1,b58),(r4,A1,b59),(r4,A1,b60),(r4,A1,b61),(r4,A1,b62),(r4,A1,b63),(r4,A1,b64),(r4,A1,b65),(r4,A1,b66),(r4,A1,b67),(r4,A1,b68),(r4,A1,b69),(r4,A1,b70),(r4,A1,b71),(r4,A1,b72),(r4,A1,b73),(r4,A1,b74),(r4,A1,b75),(r4,A1,b76),(r4,A1,b77),(r4,A1,b78),(r4,A1,b79),(r4,A1,b80),(r4,A1,b81),(r4,A1,b82),(r4,A1,b83),(r4,A1,b84),(r4,A1,b85),(r4,A1,b86),(r4,A1,b87),(r4,A1,b88),(r4,A1,b89),(r4,A1,b90),(r4,A1,b91),(r4,A1,b92),(r4,A1,b93),(r4,A1,b94),(r4,A1,b95),(r4,A1,b96),(r4,A1,b97),(r4,A1,b98),(r4,A1,b99),(r4,A1,b100),(r4,A1,b101),(r4,A1,b102),(r4,A1,b103),(r4,A1,b104),(r4,A1,b105),(r4,A1,b106),(r4,A1,b107),(r4,A1,b108),(r4,A1,b109),(r4,A1,b110),(r4,A1,b111),(r4,A1,b112),(r4,A1,b113),(r4,A1,b114),(r4,A1,b115),(r4,A1,b116),(r4,A1,b117),(r4,A1,b118),(r4,A1,b119),(r4,A1,b120),(r4,A1,b121),(r4,A1,b122),(r4,A1,b123),(r4,A1,b124),(r4,A1,b125),(r4,A1,b126),(r4,A1,b127),(r4,A1,b128),(r4,A1,b129),(r4,A1,b130),(r4,A1,b131),(r4,A1,b132),(r4,A1,b133),(r4,A1,b134),(r4,A2,b1),(r4,A2,b2),(r4,A2,b3),(r4,A2,b4),(r4,A2,b5),(r4,A2,b6),(r4,A2,b7),(r4,A2,b8),(r4,A2,b9),(r4,A2,b10),(r4,A2,b11),(r4,A2,b12),(r4,A2,b13),(r4,A2,b14),(r4,A2,b15),(r4,A2,b16),(r4,A2,b17),(r4,A2,b18),(r4,A2,b19),(r4,A2,b20),(r4,A2,b21),(r4,A2,b22),(r4,A2,b23),(r4,A2,b24),(r4,A2,b25),(r4,A2,b26),(r4,A2,b27),(r4,A2,b28),(r4,A2,b29),(r4,A2,b30),(r4,A2,b31),(r4,A2,b32),(r4,A2,b33),(r4,A2,b34),(r4,A2,b35),(r4,A2,b36),(r4,A2,b37),(r4,A2,b38),(r4,A2,b39),(r4,A2,b40),(r4,A2,b41),(r4,A2,b42),(r4,A2,b43),(r4,A2,b44),(r4,A2,b45),(r4,A2,b46),(r4,A2,b47),(r4,A2,b48),(r4,A2,b49),(r4,A2,b50),(r4,A2,b51),(r4,A2,b52),(r4,A2,b53),(r4,A2,b54),(r4,A2,b55),(r4,A2,b56),(r4,A2,b57),(r4,A2,b58),(r4,A2,b59),(r4,A2,b60),(r4,A2,b61),(r4,A2,b62),(r4,A2,b63),(r4,A2,b64),(r4,A2,b65),(r4,A2,b66),(r4,A2,b67),(r4,A2,b68),(r4,A2,b69),(r4,A2,b70),(r4,A2,b71),(r4,A2,b72),(r4,A2,b73),(r4,A2,b74),(r4,A2,b75),(r4,A2,b76),(r4,A2,b77),(r4,A2,b78),(r4,A2,b79),(r4,A2,b80),(r4,A2,b81),(r4,A2,b82),(r4,A2,b83),(r4,A2,b84),(r4,A2,b85),(r4,A2,b86),(r4,A2,b87),(r4,A2,b88),(r4,A2,b89),(r4,A2,b90),(r4,A2,b91),(r4,A2,b92),(r4,A2,b93),(r4,A2,b94),(r4,A2,b95),(r4,A2,b96),(r4,A2,b97),(r4,A2,b98),(r4,A2,b99),(r4,A2,b100),(r4,A2,b101),(r4,A2,b102),(r4,A2,b103),(r4,A2,b104),(r4,A2,b105),(r4,A2,b106),(r4,A2,b107),(r4,A2,b108),(r4,A2,b109),(r4,A2,b110),(r4,A2,b111),(r4,A2,b112),(r4,A2,b113),(r4,A2,b114),(r4,A2,b115),(r4,A2,b116),(r4,A2,b117),(r4,A2,b118),(r4,A2,b119),(r4,A2,b120),(r4,A2,b121),(r4,A2,b122),(r4,A2,b123),(r4,A2,b124),(r4,A2,b125),(r4,A2,b126),(r4,A2,b127),(r4,A2,b128),(r4,A2,b129),(r4,A2,b130),(r4,A2,b131),(r4,A2,b132),(r4,A2,b133),(r4,A2,b134),(r4,A3,b1),(r4,A3,b2),(r4,A3,b3),(r4,A3,b4),(r4,A3,b5),(r4,A3,b6),(r4,A3,b7),(r4,A3,b8),(r4,A3,b9),(r4,A3,b10),(r4,A3,b11),(r4,A3,b12),(r4,A3,b13),(r4,A3,b14),(r4,A3,b15),(r4,A3,b16),(r4,A3,b17),(r4,A3,b18),(r4,A3,b19),(r4,A3,b20),(r4,A3,b21),(r4,A3,b22),(r4,A3,b23),(r4,A3,b24),(r4,A3,b25),(r4,A3,b26),(r4,A3,b27),(r4,A3,b28),(r4,A3,b29),(r4,A3,b30),(r4,A3,b31),(r4,A3,b32),(r4,A3,b33),(r4,A3,b34),(r4,A3,b35),(r4,A3,b36),(r4,A3,b37),(r4,A3,b38),(r4,A3,b39),(r4,A3,b40),(r4,A3,b41),(r4,A3,b42),(r4,A3,b43),(r4,A3,b44),(r4,A3,b45),(r4,A3,b46),(r4,A3,b47),(r4,A3,b48),(r4,A3,b49),(r4,A3,b50),(r4,A3,b51),(r4,A3,b52),(r4,A3,b53),(r4,A3,b54),(r4,A3,b55),(r4,A3,b56),(r4,A3,b57),(r4,A3,b58),(r4,A3,b59),(r4,A3,b60),(r4,A3,b61),(r4,A3,b62),(r4,A3,b63),(r4,A3,b64),(r4,A3,b65),(r4,A3,b66),(r4,A3,b67),(r4,A3,b68),(r4,A3,b69),(r4,A3,b70),(r4,A3,b71),(r4,A3,b72),(r4,A3,b73),(r4,A3,b74),(r4,A3,b75),(r4,A3,b76),(r4,A3,b77),(r4,A3,b78),(r4,A3,b79),(r4,A3,b80),(r4,A3,b81),(r4,A3,b82),(r4,A3,b83),(r4,A3,b84),(r4,A3,b85),(r4,A3,b86),(r4,A3,b87),(r4,A3,b88),(r4,A3,b89),(r4,A3,b90),(r4,A3,b91),(r4,A3,b92),(r4,A3,b93),(r4,A3,b94),(r4,A3,b95),(r4,A3,b96),(r4,A3,b97),(r4,A3,b98),(r4,A3,b99),(r4,A3,b100),(r4,A3,b101),(r4,A3,b102),(r4,A3,b103),(r4,A3,b104),(r4,A3,b105),(r4,A3,b106),(r4,A3,b107),(r4,A3,b108),(r4,A3,b109),(r4,A3,b110),(r4,A3,b111),(r4,A3,b112),(r4,A3,b113),(r4,A3,b114),(r4,A3,b115),(r4,A3,b116),(r4,A3,b117),(r4,A3,b118),(r4,A3,b119),(r4,A3,b120),(r4,A3,b121),(r4,A3,b122),(r4,A3,b123),(r4,A3,b124),(r4,A3,b125),(r4,A3,b126),(r4,A3,b127),(r4,A3,b128),(r4,A3,b129),(r4,A3,b130),(r4,A3,b131),(r4,A3,b132),(r4,A3,b133),(r4,A3,b134),(r4,A4,b1),(r4,A4,b2),(r4,A4,b3),(r4,A4,b4),(r4,A4,b5),(r4,A4,b6),(r4,A4,b7),(r4,A4,b8),(r4,A4,b9),(r4,A4,b10),(r4,A4,b11),(r4,A4,b12),(r4,A4,b13),(r4,A4,b14),(r4,A4,b15),(r4,A4,b16),(r4,A4,b17),(r4,A4,b18),(r4,A4,b19),(r4,A4,b20),(r4,A4,b21),(r4,A4,b22),(r4,A4,b23),(r4,A4,b24),(r4,A4,b25),(r4,A4,b26),(r4,A4,b27),(r4,A4,b28),(r4,A4,b29),(r4,A4,b30),(r4,A4,b31),(r4,A4,b32),(r4,A4,b33),(r4,A4,b34),(r4,A4,b35),(r4,A4,b36),(r4,A4,b37),(r4,A4,b38),(r4,A4,b39),(r4,A4,b40),(r4,A4,b41),(r4,A4,b42),(r4,A4,b43),(r4,A4,b44),(r4,A4,b45),(r4,A4,b46),(r4,A4,b47),(r4,A4,b48),(r4,A4,b49),(r4,A4,b50),(r4,A4,b51),(r4,A4,b52),(r4,A4,b53),(r4,A4,b54),(r4,A4,b55),(r4,A4,b56),(r4,A4,b57),(r4,A4,b58),(r4,A4,b59),(r4,A4,b60),(r4,A4,b61),(r4,A4,b62),(r4,A4,b63),(r4,A4,b64),(r4,A4,b65),(r4,A4,b66),(r4,A4,b67),(r4,A4,b68),(r4,A4,b69),(r4,A4,b70),(r4,A4,b71),(r4,A4,b72),(r4,A4,b73),(r4,A4,b74),(r4,A4,b75),(r4,A4,b76),(r4,A4,b77),(r4,A4,b78),(r4,A4,b79),(r4,A4,b80),(r4,A4,b81),(r4,A4,b82),(r4,A4,b83),(r4,A4,b84),(r4,A4,b85),(r4,A4,b86),(r4,A4,b87),(r4,A4,b88),(r4,A4,b89),(r4,A4,b90),(r4,A4,b91),(r4,A4,b92),(r4,A4,b93),(r4,A4,b94),(r4,A4,b95),(r4,A4,b96),(r4,A4,b97),(r4,A4,b98),(r4,A4,b99),(r4,A4,b100),(r4,A4,b101),(r4,A4,b102),(r4,A4,b103),(r4,A4,b104),(r4,A4,b105),(r4,A4,b106),(r4,A4,b107),(r4,A4,b108),(r4,A4,b109),(r4,A4,b110),(r4,A4,b111),(r4,A4,b112),(r4,A4,b113),(r4,A4,b114),(r4,A4,b115),(r4,A4,b116),(r4,A4,b117),(r4,A4,b118),(r4,A4,b119),(r4,A4,b120),(r4,A4,b121),(r4,A4,b122),(r4,A4,b123),(r4,A4,b124),(r4,A4,b125),(r4,A4,b126),(r4,A4,b127),(r4,A4,b128),(r4,A4,b129),(r4,A4,b130),(r4,A4,b131),(r4,A4,b132),(r4,A4,b133),(r4,A4,b134),(r5,A1,b1),(r5,A1,b2),(r5,A1,b3),(r5,A1,b4),(r5,A1,b5),(r5,A1,b6),(r5,A1,b7),(r5,A1,b8),(r5,A1,b9),(r5,A1,b10),(r5,A1,b11),(r5,A1,b12),(r5,A1,b13),(r5,A1,b14),(r5,A1,b15),(r5,A1,b16),(r5,A1,b17),(r5,A1,b18),(r5,A1,b19),(r5,A1,b20),(r5,A1,b21),(r5,A1,b22),(r5,A1,b23),(r5,A1,b24),(r5,A1,b25),(r5,A1,b26),(r5,A1,b27),(r5,A1,b28),(r5,A1,b29),(r5,A1,b30),(r5,A1,b31),(r5,A1,b32),(r5,A1,b33),(r5,A1,b34),(r5,A1,b35),(r5,A1,b36),(r5,A1,b37),(r5,A1,b38),(r5,A1,b39),(r5,A1,b40),(r5,A1,b41),(r5,A1,b42),(r5,A1,b43),(r5,A1,b44),(r5,A1,b45),(r5,A1,b46),(r5,A1,b47),(r5,A1,b48),(r5,A1,b49),(r5,A1,b50),(r5,A1,b51),(r5,A1,b52),(r5,A1,b53),(r5,A1,b54),(r5,A1,b55),(r5,A1,b56),(r5,A1,b57),(r5,A1,b58),(r5,A1,b59),(r5,A1,b60),(r5,A1,b61),(r5,A1,b62),(r5,A1,b63),(r5,A1,b64),(r5,A1,b65),(r5,A1,b66),(r5,A1,b67),(r5,A1,b68),(r5,A1,b69),(r5,A1,b70),(r5,A1,b71),(r5,A1,b72),(r5,A1,b73),(r5,A1,b74),(r5,A1,b75),(r5,A1,b76),(r5,A1,b77),(r5,A1,b78),(r5,A1,b79),(r5,A1,b80),(r5,A1,b81),(r5,A1,b82),(r5,A1,b83),(r5,A1,b84),(r5,A1,b85),(r5,A1,b86),(r5,A1,b87),(r5,A1,b88),(r5,A1,b89),(r5,A1, b90),(r5,A1,b91),(r5,A1,b92),(r5,A1,b93),(r5,A1,b94),(r5,A1,b95),(r5,A1,b96),(r5,A1,b97),(r5,A1,b98),(r5,A1,b99),(r5,A1,b100),(r5,A1,b101),(r5,A1,b102),(r5,A1,b103),(r5,A1,b104),(r5,A1,b105),(r5,A1,b106),(r5,A1,b107),(r5,A1,b108),(r5,A1,b109),(r5,A1,b110),(r5,A1,b111),(r5,A1,b112),(r5,A1,b113),(r5,A1,b114),(r5,A1,b115),(r5,A1,b116),(r5,A1,b117),(r5,A1,b118),(r5,A1,b119),(r5,A1,b120),(r5,A1,b121),(r5,A1,b122),(r5,A1,b123),(r5,A1,b124),(r5,A1,b125),(r5,A1,b126),(r5,A1,b127),(r5,A1,b128),(r5,A1,b129),(r5,A1,b130),(r5,A1,b131),(r5,A1,b132),(r5,A1,b133),(r5,A1,b134),(r5,A2,b1),(r5,A2,b2),(r5,A2,b3),(r5,A2,b4),(r5,A2,b5),(r5,A2,b6),(r5,A2,b7),(r5,A2,b8),(r5,A2,b9),(r5,A2,b10),(r5,A2,b11),(r5,A2,b12),(r5,A2,b13),(r5,A2,b14),(r5,A2,b15),(r5,A2,b16),(r5,A2,b17),(r5,A2,b18),(r5,A2,b19),(r5,A2,b20),(r5,A2,b21),(r5,A2,b22),(r5,A2,b23),(r5,A2,b24),(r5,A2,b25),(r5,A2,b26),(r5,A2,b27),(r5,A2,b28),(r5,A2,b29),(r5,A2,b30),(r5,A2,b31),(r5,A2,b32),(r5,A2,b33),(r5,A2,b34),(r5,A2,b35),(r5,A2,b36),(r5,A2,b37),(r5,A2,b38),(r5,A2,b39),(r5,A2,b40),(r5,A2,b41),(r5,A2,b42),(r5,A2,b43),(r5,A2,b44),(r5,A2,b45),(r5,A2,b46),(r5,A2,b47),(r5,A2,b48),(r5,A2,b49),(r5,A2,b50),(r5,A2,b51),(r5,A2,b52),(r5,A2,b53),(r5,A2,b54),(r5,A2,b55),(r5,A2,b56),(r5,A2,b57),(r5,A2,b58),(r5,A2,b59),(r5,A2,b60),(r5,A2,b61),(r5,A2,b62),(r5,A2,b63),(r5,A2,b64),(r5,A2,b65),(r5,A2,b66),(r5,A2,b67),(r5,A2,b68),(r5,A2,b69),(r5,A2,b70),(r5,A2,b71),(r5,A2,b72),(r5,A2,b73),(r5,A2,b74),(r5,A2,b75),(r5,A2,b (r5,A2,b77),(r5,A2,b78),(r5,A2,b79),(r5,A2,b80),(r5,A2,b81),(r5,A2,b82),(r5,A2,b83),(r5,A2,b84),(r5,A2,b85),(r5,A2,b86),(r5,A2,b87),(r5,A2,b88),(r5,A2,b89),(r5,A2,b90),(r5,A2,b91),(r5,A2,b92),(r5,A2,b93),(r5,A2,b94),(r5,A2,b95),(r5,A2,b96),(r5,A2,b97),(r5,A2,b98),(r5,A2,b99),(r5,A2,b100),(r5,A 2,b101),(r5,A2,b102),(r5,A2,b103),(r5,A2,b104),(r5,A2,b105),(r5,A2,b106),(r5,A2,b107),(r5,A2,b108),(r5,A2,b109),(r5,A2,b110),(r5,A2,b111),(r5,A2,b112),(r5,A2,b113),(r5,A2,b114),(r5,A2,b115),(r5,A2,b116),(r5,A2,b117),(r5,A2,b118),(r5,A2,b119),(r5,A2,b120),(r5,A2,b121),(r5,A2,b122),(r5,A2,b123),(r5,A2,b124),(r5,A2,b125),(r5,A2,b126),(r5,A2,b127),(r5,A2,b128),(r5,A2,b129),(r5,A2,b130),(r5,A2,b131),(r5,A2,b132),(r5,A2,b133),(r5,A2,b134),(r5,A3,b1),(r5,A3,b2),(r5,A3,b3),(r5,A3,b4),(r5,A3,b5),(r5,A3,b6),(r5,A3,b7),(r5,A3,b8),(r5,A3,b9),(r5,A3,b10),(r5,A3,b11),(r5,A3,b12),(r5,A3,b13),(r5,A3,b14),(r5,A3,b15),(r5,A3,b16),(r5,A3,b17),(r5,A3,b18),(r5,A3,b19),(r5,A3,b20),(r5,A3,b21),(r5,A3,b22),(r5,A3,b23),(r5,A3,b24),(r5,A3,b25),(r5,A3,b26),(r5,A3,b27),(r5,A3,b28),(r5,A3,b29),(r5,A3,b30),(r5,A3,b31),(r5,A3,b32),(r5,A3,b33),(r5,A3,b34),(r5,A3,b35),(r5,A3,b36),(r5,A3,b37),(r5,A3,b38),(r5,A3,b39),(r5,A3,b40),(r5,A3,b41),(r5,A3,b42),(r5,A3,b43),(r5,A3, b44),(r5,A3,b45),(r5,A3,b46),(r5,A3,b47),(r5,A3,b48),(r5,A3,b49),(r5,A3,b50),(r5,A3,b51),(r5,A3,b52),(r5,A3,b53),(r5,A3,b54),(r5,A3,b55),(r5,A3,b56),(r5,A3,b57),(r5,A3,b58),(r5,A3,b59),(r5,A3,b60),(r5,A3,b61),(r5,A3,b62),(r5,A3,b63),(r5,A3,b64),(r5,A3,b65),(r5,A3,b66),(r5,A3,b67),(r5,A3,b68),(r5,A3,b69),(r5,A3,b70),(r5,A3,b71),(r5,A3,b72),(r5,A3,b73),(r5,A3,b74),(r5,A3,b75),(r5,A3,b76),(r5,A3,b77),(r5,A3,b78),(r5,A3,b79),(r5,A3,b80),(r5,A3,b81),(r5,A3,b82),(r5,A3,b83),(r5,A3,b84),(r5,A3,b85),(r5,A3,b86),(r5,A3,b87),(r5,A3,b88),(r5,A3,b89),(r5,A3,b90),(r5,A3,b91),(r5,A3,b92),(r5,A3,b93),(r5,A3,b94),(r5,A3,b95),(r5,A3,b96),(r5,A3,b97),(r5,A3,b98),(r5,A3,b99),(r5,A3,b100),(r5,A3,b101),(r5,A3,b102),(r5,A3,b103),(r5,A3,b104),(r5,A3,b105),(r5,A3,b106),(r5,A3,b107),(r5,A3,b108),(r5,A3,b109),(r5,A3,b110),(r5,A3,b111),(r5,A3,b112),(r5,A3,b113),(r5,A3,b114),(r5,A3,b115),(r5,A3,b116),(r5,A3,b117),(r5,A3,b118),(r5,A3,b119),(r5,A3,b120),(r5,A3,b121),(r5,A3,b122),(r5,A3,b123),(r5,A3,b124),(r5,A3,b125),(r5,A3,b126),(r5,A3,b127),(r5,A3,b128),(r5,A3,b129),(r5,A3,b130),(r5,A3,b131),(r5,A3,b132),(r5,A3,b133),(r5,A3,b134),(r5,A4,b1),(r5,A4,b2),(r5,A4,b3),(r5,A4,b4),(r5,A4,b5),(r5,A4,b6),(r5,A4,b7),(r5,A4,b8),(r5,A4,b9),(r5,A4,b10),(r5,A4,b11),(r5,A4,b12),(r5,A4,b13),(r5,A4,b14),(r5,A4,b15),(r5,A4,b16),(r5,A4,b17),(r5,A4,b18),(r5,A4,b19),(r5,A4,b20),(r5,A4,b21),(r5,A4,b22),(r5,A4,b23),(r5,A4,b24),(r5,A4,b25),(r5,A4,b26),(r5,A4,b27),(r5,A4,b28),(r5,A4,b29),(r5,A4,b30),(r5,A4,b31),(r5,A4,b32),(r5,A4, b33),(r5,A4,b34),(r5,A4,b35),(r5,A4,b36),(r5,A4,b37),(r5,A4,b38),(r5,A4,b39),(r5,A4, b40),(r5,A4,b41),(r5,A4,b42),(r5,A4,b43),(r5,A4,b44),(r5,A4,b45),(r5,A4,b46),(r5,A4,b47),(r5,A4,b48),(r5,A4,b49),(r5,A4,b50),(r5,A4,b51),(r5,A4,b52),(r5,A4,b53),(r5,A4,b54),(r5,A4,b55),(r5,A4,b56),(r5,A4,b57),(r5,A4,b58),(r5,A4,b59),(r5,A4,b60),(r5,A4,b61),(r5,A4,b62),(r5,A4,b63),(r5,A4,b64),(r5,A4,b65),(r5,A4,b66),(r5,A4,b67),(r5,A4,b68),(r5,A4,b69),(r5,A4,b70),(r5,A4,b71),(r5,A4,b72),(r5,A4,b73),(r5,A4,b74),(r5,A4,b75),(r5,A4,b76),(r5,A4,b77),(r5,A4,b78),(r5,A4,b79),(r5,A4,b80),(r5,A4,b81),(r5,A4,b82),(r5,A4,b83),(r5,A4,b84),(r5,A4,b85),(r5,A4,b86),(r5,A4,b87),(r5,A4,b88),(r5,A4,b89),(r5,A4,b90),(r5,A4,b91),(r5,A4,b92),(r5,A4,b93),(r5,A4,b94),(r5,A4,b95),(r5,A4,b96),(r5,A4,b97),(r5,A4,b98),(r5,A4,b99),(r5,A4,b100),(r5,A4,b101),(r5,A4,b102),(r5,A4,b103),(r5,A4,b104),(r5,A4,b105),(r5,A4,b106),(r5,A4,b107),(r5,A4,b108),(r5,A4,b109),(r5,A4,b110),(r5,A4,b111),(r5,A4,b112),(r5,A4,b113),(r5,A4,b114),(r5,A4,b115),(r5,A4,b116),(r5,A4,b117),(r5,A4,b118),(r5,A4,b119),(r5,A4,b120),(r5,A4,b121),(r5,A4,b122),(r5,A4,b123),(r5,A4,b124),(r5,A4,b125),(r5,A4,b126),(r5,A4,b127),(r5,A4,b128),(r5,A4,b129),(r5,A4,b130),(r5,A4,b131),(r5,A4,b132),(r5,A4,b133),(r5,A4,b134), (r6,A1,b1),(r6,A1,b2),(r6,A1,b3),(r6,A1,b4),(r6,A1,b5),(r6,A1,b6),(r6,A1,b7),(r6,A1,b8),(r6,A1,b9),(r6,A1,b10),(r6,A1,b11),(r6,A1,b12),(r6,A1,b13),(r6,A1,b14),(r6,A1,b15),(r6,A1,b16),(r6,A1,b17),(r6,A1,b18),(r6,A1,b19),(r6,A1,b20),(r6,A1,b21),(r6,A1,b22),(r6,A1,b23),(r6,A1,b24),(r6,A1,b25),(r6,A1,b26),(r6,A1,b27),(r6,A1,b28),(r6,A1,b29),(r6,A1,b30),(r6,A1,b31),(r6,A1,b32),(r6,A1,b33),(r6,A1,b34),(r6,A1,b35),(r6,A1,b36),(r6,A1,b37),(r6,A1,b38),(r6,A1,b39),(r6,A1,b40),(r6,A1,b41),(r6,A1,b42),(r6,A1,b43),(r6,A1,b44),(r6,A1,b45),(r6, A1,b46),(r6,A1,b47),(r6,A1,b48),(r6,A1,b49),(r6,A1,b50),(r6,A1,b51),(r6,A1,b52),(r6,A1,b53),(r6,A1,b54),(r6,A1,b55),(r6,A1,b56),(r6,A1,b57),(r6,A1,b58),(r6,A1,b59),(r6,A1,b60),(r6,A1,b61),(r6,A1,b62),(r6,A1,b63),(r6,A1,b64),(r6,A1,b65),(r6,A1,b66),(r6,A1,b67),(r6,A1,b68),(r6,A1,b69),(r6,A1,b70),(r6,A1,b71),(r6,A1,b72),(r6,A1,b73),(r6,A1,b74),(r6,A1,b75),(r6,A1,b76),(r6,A1,b77),(r6,A1,b78),(r6,A1,b79),(r6,A1,b80),(r6,A1,b81),(r6,A1,b82),(r6,A1,b83),(r6,A1,b84),(r6,A1,b85),(r6,A1,b86),(r6,A1,b87),(r6,A1,b88),(r6,A1,b89),(r6,A1,b90),(r6,A1,b91),(r6,A1,b92),(r6,A1,b93),(r6,A1,b94),(r6,A1,b95),(r6,A1,b96),(r6,A1,b97),(r6,A1,b98),(r6,A1,b99),(r6,A1,b100),(r6,A1,b101),(r6,A1,b102),(r6,A1,b103),(r6,A1,b104),(r6,A1,b105),(r6,A1,b106),(r6,A1,b107),(r6,A1,b108),(r6,A1,b109),(r6,A1,b110),(r6,A1, b111),(r6,A1,b112),(r6,A1,b113),(r6,A1,b114),(r6,A1,b115),(r6,A1,b116),(r6,A1,b117),(r6, A1,b118),(r6,A1,b119),(r6,A1,b120),(r6,A1,b121),(r6,A1,b122),(r6,A1,b123),(r6,A1,b124),(r6,A1,b125),(r6,A1,b126),(r6,A1,b127),(r6,A1,b128),(r6,A1,b129),(r6,A1,b130),(r6,A1,b131),(r6,A1,b132),(r6,A1,b133),(r6,A1,b134),(r6,A2,b1),(r6,A2,b2),(r6,A2,b3),(r6,A2,b4),(r6,A2,b5),(r6,A2,b6),(r6,A2, b7),(r6,A2,b8),(r6,A2,b9),(r6,A2,b10),(r6,A2,b11),(r6,A2,b12),(r6,A2,b13),(r6,A2,b14),(r6,A2,b15),(r6,A2,b16),(r6,A2,b17),(r6,A2,b18),(r6,A2,b19),(r6,A2,b20),(r6,A2,b21),(r6,A2,b22), (r6,A2,b23),(r6,A2,b24),(r6,A2,b25),(r6,A2,b26),(r6,A2,b27),(r6,A2,b28),(r6,A2,b29),(r6,A2,b30),(r6,A2,b31),(r6,A2,b32),(r6,A2,b33),(r6,A2,b34),(r6,A2,b35),(r6,A2,b36),(r6,A2,b37),(r6,A2,b38),(r6,A2,b39),(r6,A2,b40),(r6,A2,b41),(r6,A2,b42),(r6,A2,b43),(r6,A2,b44),(r6,A2,b45),(r6,A2,b46),(r6,A2,b47),(r6,A2,b48),(r6,A2,b49),(r6,A2,b50),(r6,A2,b51),(r6,A2,b52),(r6,A2,b53),(r6,A2,b54),(r6,A2,b55),(r6,A2,b56),(r6,A2,b57),(r6,A2,b58),(r6,A2,b59),(r6,A2,b60),(r6,A2,b61),(r6,A2,b62),(r6,A2,b63),(r6,A2,b64),(r6,A2,b65),(r6,A2,b66),(r6,A2,b67),(r6,A2,b68),(r6,A2,b69),(r6,A2,b70),(r6,A2,b71),(r6,A2,b72),(r6,A2,b73),(r6,A2,b74),(r6,A2,b75),(r6,A2,b76),(r6,A2,b77),(r6,A2,b78),(r6,A2,b79),(r6,A2,b80),(r6,A2,b81),(r6,A2,b82),(r6,A2,b83),(r6,A2,b84),(r6,A2,b85),(r6,A2,b86),(r6,A2,b87),(r6,A2,b88),(r6,A2,b89),(r6,A2,b90),(r6,A2,b91),(r6,A2,b92),(r6,A2,b93),(r6,A2,b94),(r6,A2,b95),(r6,A2,b96),(r6,A2,b97),(r6,A2,b98),(r6,A2,b99),(r6,A2,b100),(r6,A2,b101),(r6,A2,b102),(r6,A2,b103),(r6,A2,b104),(r6,A2,b105),(r6,A2,b106),(r6,A2,b107),(r6,A2,b108),(r6,A2,b109),(r6,A2,b110),(r6,A2,b111),(r6,A2,b112),(r6,A2,b113),(r6,A2,b1.14),(r6,A2,b115),(r6,A2,b116),(r6,A2,b117),(r6,A2,b118),(r6,A2,b119),(r6,A2,b120),(r6,A2,b121),(r6,A2,b122),(r6,A2,b123),(r6,A2,b124),(r6,A2,b125),(r6,A2,b126),(r6,A2,b127),(r6,A2,b128),(r6,A2,b129),(r6,A2,b130),(r6,A2,b131),(r6,A2,b132),(r6,A2,b133),(r6,A2,b134),(r6,A3,b1),(r6,A3,b2),(r6,A3,b3),(r6,A3,b4),(r6,A3,b5),(r6,A3,b6),(r6,A3,b7),(r6,A3,b8),(r6,A3,b9),(r6,A3,b10),(r6,A3,b11),(r6,A3,b12),(r6,A3,b13),(r6,A3,b14),(r6,A3,b15),(r6,A3,b16),(r6,A3,b17),(r6,A3,b18),(r6,A3,b19),(r6,A3,b20),(r6,A3,b21),(r6,A3,b22),(r6,A3,b23),(r6,A3,b24),(r6,A3,b25),(r6,A3,b26),(r6,A3,b27),(r6,A3,b28),(r6,A3,b29),(r6,A3,b30),(r6,A3,b31),(r6,A3,b32),(r6,A3,b33),(r6,A3,b34),(r6,A3,b35),(r6,A3,b36),(r6,A3,b37),(r6,A3,b38),(r6,A3,b39),(r6,A3,b40),(r6,A3,b41),(r6,A3,b42),(r6,A3,b43),(r6,A3,b44),(r6,A3,b45),(r6,A3,b46),(r6,A3,b47),(r6,A3,b48),(r6,A3,b49),(r6,A3,b50),(r6,A3,b51),(r6,A3,b52),(r6,A3,b53),(r6,A3,b54),(r6,A3,b55),(r6,A3,b56),(r6,A3,b57),(r6,A3,b58),(r6,A3,b59),(r6,A3,b60),(r6,A3,b61),(r6,A3,b62),(r6,A3,b63),(r6,A3,b64),(r6,A3,b65),(r6,A3,b66),(r6,A3,b67),(r6,A3,b68),(r6,A3,b69),(r6,A3,b70),(r6,A3,b71),(r6,A3,b72),(r6,A3,b73),(r6,A3,b74),(r6,A3,b75),(r6,A3,b76),(r6,A3,b77),(r6,A3,b78),(r6,A3,b79),(r6,A3,b80),(r6,A3,b81),(r6,A3,b82),(r6,A3,b83),(r6,A3,b84),(r6,A3,b85),(r6,A3,b86),(r6,A3,b87),(r6,A3,b88),(r6,A3,b89),(r6,A3,b90),(r6,A3,b91),(r6,A3,b92),(r6,A3,b93),(r6,A3,b94),(r6,A3,b95),(r6,A3,b96),(r6,A3,b97),(r6,A3,b98),(r6,A3,b99),(r6,A3,b100),(r6,A3,b101),(r6,A3,b102),(r6,A3,b103),(r6,A3,b104),(r6,A3,b105),(r6,A3,b106),(r6,A3,b107),(r6,A3,b108),(r6,A3,b109),(r6,A3,b110),(r6,A3,b111),(r6,A3,b112),(r6,A3,b113),(r6,A3,b114),(r6,A3,b115),(r6,A3,b116),(r6,A3,b117),(r6,A3,b118),(r6,A3,b119),(r6,A3,b120),(r6,A3,b121),(r6,A3,b122),(r6,A3,b123),(r6,A3,b124),(r6,A3,b125),(r6,A3,b126),(r6,A3,b127),(r6,A3,b128),(r6,A3,b129),(r6,A3,b130),(r6,A3,b131),(r6,A3,b132),(r6,A3,b133),(r6,A3,b134),(r6,A4,b1),(r6,A4,b2),(r6,A4,b3),(r6,A4,b4),(r6,A4,b5),(r6,A4,b6),(r6,A4,b7),(r6,A4,b8),(r6,A4,b9),(r6,A4,b10),(r6,A4,b11),(r6,A4,b12),(r6,A4,b13),(r6,A4,b14),(r6,A4,b15),(r6,A4,b16),(r6,A4,b17),(r6,A4,b18),(r6,A4,b19),(r6,A4,b20),(r6,A4,b21),(r6,A4,b22),(r6,A4,b23),(r6,A4,b24),(r6,A4,b25),(r6,A4,b26),(r6,A4,b27),(r6,A4,b28),(r6,A4,b29),(r6,A4,b30),(r6,A4,b31),(r6,A4,b32),(r6,A4,b33),(r6,A4,b34),(r6,A4,b35),(r6,A4,b36),(r6,A4,b37),(r6,A4,b38),(r6,A4,b39),(r6,A4,b40),(r6,A4,b41),(r6,A4,b42),(r6,A4,b43),(r6,A4,b44),(r6,A4,b45),(r6,A4,b46),(r6,A4,b47),(r6,A4,b48),(r6,A4,b49),(r6,A4,b50),(r6,A4,b51),(r6,A4,b52),(r6,A4,b53),(r6,A4,b54),(r6,A4,b55),(r6,A4,b56),(r6,A4,b57),(r6,A4,b58),(r6,A4,b59),(r6,A4,b60),(r6,A4,b61),(r6,A4,b62),(r6,A4,b63),(r6,A4,b64),(r6,A4,b65),(r6,A4,b66),(r6,A4,b67),(r6,A4,b68),(r6,A4,b69),(r6,A4,b70),(r6,A4,b71),(r6,A4,b72),(r6,A4,b73),(r6,A4,b74),(r6,A4,b75),(r6,A4,b76),(r6,A4,b77),(r6,A4,b78),(r6,A4,b79),(r6,A4,b80),(r6,A4,b81),(r6,A4,b82),(r6,A4,b83),(r6,A4,b84),(r6,A4,b85),(r6,A4,b86),(r6,A4,b87),(r6,A4,b88),(r6,A4,b89),(r6,A4,b90),(r6,A4,b91),(r6,A4,b92),(r6,A4,b93),(r6,A4,b94),(r6,A4,b95),(r6,A4,b96),(r6,A4,b97),(r6,A4,b98),(r6,A4,b99),(r6,A4,b100),(r6,A4,b101),(r6,A4,b102),(r6,A4,b103),(r6,A4,b104),(r6,A4,b105),(r6,A4,b106),(r6,A4,b107),(r6,A4,b108),(r6,A4,b109),(r6,A4,b110),(r6,A4,b111),(r6,A4,b112),(r6,A4,b113),(r6,A4,b114),(r6,A4,b115),(r6,A4,b116),(r6,A4,b117),(r6,A4,b118),(r6,A4,b119),(r6,A4,b120),(r6,A4,b121),(r6,A4,b122),(r6,A4,b123),(r6,A4,b124),(r6,A4,b125),(r6,A4,b126),(r6,A4,b127),(r6,A4,b128),(r6,A4,b129),(r6,A4,b130),(r6,A4,b131),(r6,A4,b132),(r6,A4,b133),(r6,A4,b134),
(r7,A1,b1),(r7,A1,b2),(r7,A1,b3),(r7,A1,b4),(r7,A1,b5),(r7,A1,b6),(r7,A1,b7),(r7,A1,b8),(r7,A1,b9),(r7,A1,b10),(r7,A1,b11),(r7,A1,b12),(r7,A1,b13),(r7,A1,b14),(r7,A1,b15),(r7,A1,b16),(r7,A1,b17),(r7,A1,b18),(r7,A1,b19),(r7,A1,b20),(r7,A1,b21),(r7,A1,b22),(r7,A1,b23),(r7,A1,b24),(r7,A1,b25),(r7,A1,b26),(r7,A1,b27),(r7,A1,b28),(r7,A1,b29),(r7,A1,b30),(r7,A1,b31),(r7,A1,b32),(r7,A1,b33),(r7,A1,b34),(r7,A1,b35),(r7,A1,b36),(r7,A1,b37),(r7,A1,b38),(r7,A1,b39),(r7,A1,b40),(r7,A1,b41),(r7,A1,b42),(r7,A1,b43),(r7,A1,b44),(r7,A1,b45),(r7,A1,b46),(r7,A1,b47),(r7,A1,b48),(r7,A1,b49),(r7,A1,b50),(r7,A1,b51),(r7,A1,b52),(r7,A1,b53),(r7,A1,b54),(r7,A1,b55),(r7,A1,b56),(r7,A1,b57),(r7,A1,b58),(r7,A1,b59),(r7,A1,b60),(r7,A1,b61),(r7,A1,b62),(r7,A1,b63),(r7,A1,b64),(r7,A1,b65),(r7,A1,b66),(r7,A1,b67),(r7,A1,b68),(r7,A1,b69),(r7,A1,b70),(r7,A1,b71),(r7,A1,b72),(r7,A1,b73),(r7,A1,b74),(r7,A1,b75),(r7,A1,b76),(r7,A1,b77),(r7,A1,b78),(r7,A1,b79),(r7,A1,b80),(r7,A1,b81),(r7,A1,b82),(r7,A1,b83),(r7,A1,b84),(r7,A1,b85),(r7,A1,b86),(r7,A1,b87),(r7,A1,b88),(r7,A1,b89),(r7,A1,b90),(r7,A1,b91),(r7,A1,b92),(r7,A1,b93),(r7,A1,b94),(r7,A1,b95),(r7,A1,b96),(r7,A1,b97),(r7,A1,b98),(r7,A1,b99),(r7,A1,b100),(r7,A1,b101),(r7,A1,b102),(r7,A1,b103),(r7,A1,b104),(r7,A1,b105),(r7,A1,b106),(r7,A1,b107),(r7,A1,b108),(r7,A1,b109),(r7,A1,b110),(r7,A1,b111),(r7,A1,b112),(r7,A1,b113),(r7,A1,b114),(r7,A1,b115),(r7,A1,b116),(r7,A1,b117),(r7,A1,b118),(r7,A1,b119),(r7,A1,b120),(r7,A1,b121),(r7,A1,b122),(r7,A1,b123),(r7,A1,b124),(r7,A1,b125),(r7,A1,b126),(r7,A1,b127),(r7,A1,b128),(r7,A1,b129),(r7,A1,b130),(r7,A1,b131),(r7,A1,b132),(r7,A1,b133),(r7,A1,b134),(r7,A2,b1),(r7,A2,b2),(r7,A2,b3),(r7,A2,b4),(r7,A2,b5),(r7,A2,b6),(r7,A2,b7),(r7,A2,b8),(r7,A2,b9),(r7,A2,b10),(r7,A2,b11),(r7,A2,b12),(r7,A2,b13),(r7,A2,b14),(r7,A2,b15),(r7,A2,b16),(r7,A2,b17),(r7,A2,b18),(r7,A2,b19),(r7,A2,b20),(r7,A2,b21),(r7,A2,b22),(r7,A2,b23),(r7,A2,b24),(r7,A2,b25),(r7,A2,b26),(r7,A2,b27),(r7,A2,b28),(r7,A2,b29),(r7,A2,b30),(r7,A2,b31),(r7,A2,b32),(r7,A2,b33),(r7,A2,b34),(r7,A2,b35),(r7,A2,b36),(r7,A2,b37),(r7,A2,b38),(r7,A2,b39),(r7,A2,b40),(r7,A2,b41),(r7,A2,b42),(r7,A2,b43),(r7,A2,b44),(r7,A2,b45),(r7,A2,b46),(r7,A2,b47),(r7,A2,b48),(r7,A2,b49),(r7,A2,b50),(r7,A2,b51),(r7,A2,b52),(r7,A2,b53),(r7,A2,b54),(r7,A2,b55),(r7,A2,b56),(r7,A2,b57),(r7,A2,b58),(r7,A2,b59),(r7,A2,b60),(r7,A2,b61),(r7,A2,b62),(r7,A2,b83),(r7,A2,b64),(r7,A2,b85),(r7,A2,b86),(r7,A2,b67),(r7,A2,b68),(r7,A2,b89),(r7,A2,b70),(r7,A2,b71),(r7,A2,b72),(r7,A2,b73),(r7,A2,b74),(r7,A2,b75),(r7,A2,b76),(r7,A2,b77),(r7,A2,b78),(r7,A2,b79),(r7,A2,b80),(r7,A2,b81),(r7,A2,b82),(r7,A2,b83),(r7,A2,b84),(r7,A2,b85),(r7,A2,b86),(r7,A2,b87),(r7,A2,b88),(r7,A2,b89),(r7,A2,b90),(r7,A2,b91),(r7,A2,b92), (r7,A2,b93),(r7,A2,b94),(r7,A2,b95),(r7,A2,b98),(r7,A2,b97),(r7,A2,b98),(r7,A2,b99),(r7,A2,b100),(r7,A2,b101),(r7,A2,b102),(r7,A2,b103),(r7,A2,b104),(r7,A2,b105),(r7,A2,b108),(r7,A2,b107),(r7,A2,b108),(r7,A2,b109),(r7,A2,b110),(r7,A2,b111),(r7,A2,b112),(r7,A2,b113),(r7,A2,b114),(r7,A2,b115),(r7,A2,b116),(r7,A2,b117),(r7,A2,b118),(r7,A2,b119),(r7,A2,b120),(r7,A2,b121),(r7,A2,b122),(r7,A2,b123),(r7,A2,b124),(r7,A2,b125),(r7,A2,b128),(r7,A2,b127),(r7,A2,b128),(r7,A2,b129),(r7,A2,b130),(r7,A2,b131),(r7,A2,b132),(r7,A2,b133),(r7,A2,b134),(r7,A3,b1),(r7,A3,b2),(r7,A3,b3),(r7,A3,b4),(r7,A3,b5),(r7,A3,b6),(r7,A3,b7),(r7,A3,b8),(r7,A3,b9),(r7,A3,b10),(r7,A3,b11),(r7,A3,b12),(r7,A3,b13),(r7,A3,b14),(r7,A3,b15),(r7,A3,b18),(r7,A3,b17),(r7,A3,b18),(r7,A3,b19),(r7,A3,b20),(r7,A3,b21),(r7,A3,b22),(r7,A3,b23),(r7,A3,b24),(r7,A3,b25),(r7,A3,b26),(r7,A3,b27),(r7,A3,b28),(r7,A3,b29),(r7,A3,b30),(r7,A3,b31),(r7,A3,b32),(r7,A3,b33),(r7,A3,b34),(r7,A3,b35),(r7,A3,b36),(r7,A3,b37),(r7,A3,b38),(r7,A3,b39),(r7,A3,b40),(r7,A3,b41),(r7,A3,b42),(r7,A3,b43),(r7,A3,b44),(r7,A3,b45),(r7,A3,b46),(r7,A3,b47),(r7,A3,b48),(r7,A3,b49),(r7,A3,b50),(r7,A3,b51),(r7,A3,b52),(r7,A3,b53),(r7,A3,b54),(r7,A3,b55),(r7,A3,b56),(r7,A3,b57),(r7,A3,b58),(r7,A3,b59),(r7,A3,b80),(r7,A3,b61),(r7,A3,b82),(r7,A3,b63),(r7,A3,b84),(r7,A3,b65),(r7,A3,b86),(r7,A3,b67),(r7,A3,b68),(r7,A3,b89),(r7,A3,b70),(r7,A3,b71),(r7,A3,b72),(r7,A3,b73),(r7,A3,b74),(r7,A3,b75),(r7,A3,b76),(r7,A3,b77),(r7,A3,b78),(r7,A3,b79),(r7,A3,b80),(r7,A3,b81),(r7,A3,b82),(r7,A3,b83),(r7,A3,b84),(r7,A3,b85),(r7,A3,b86),(r7,A3,b87),(r7,A3,b88),(r7,A3,b89),(r7,A3,b90),(r7,A3,b91),(r7,A3,b92),(r7,A3,b93),(r7,A3,b94),(r7,A3,b95),(r7,A3,b96),(r7,A3,b97),(r7,A3,b98),(r7,A3,b99),(r7,A3,b100),(r7,A3,b101),(r7,A3,b102),(r7,A3,b103),(r7,A3,b104),(r7,A3,b105),(r7,A3,b106),(r7,A3,b107),(r7,A3,b108),(r7,A3,b109),(r7,A3,b110),(r7,A3,b111),(r7,A3,b112),(r7,A3,b113),(r7,A3,b114),(r7,A3,b115),(r7,A3,b116),(r7,A3,b117),(r7,A3,b118),(r7,A3,b119),(r7,A3,b120),(r7,A3,b121),(r7,A3,b122),(r7,A3,b123),(r7,A3,b124),(r7,A3,b125),(r7,A3,b126),(r7,A3,b127),(r7,A3,b128),(r7,A3,b129),(r7,A3,b130),(r7,A3,b131),(r7,A3,b132),(r7,A3,b133),(r7,A3,b134),(r7,A4,b1),(r7,A4,b2),(r7,A4,b3),(r7,A4,b4),(r7,A4,b5),(r7,A4,b6),(r7,A4,b7),(r7,A4,b8),(r7,A4,b9),(r7,A4,b10),(r7,A4,b11),(r7,A4,b12),(r7,A4,b13),(r7,A4,b14),(r7,A4,b15),(r7,A4,b16),(r7,A4,b17),(r7,A4,b18),(r7,A4,b19),(r7,A4,b20),(r7,A4,b21),(r7,A4,b22),(r7,A4,b23),(r7,A4,b24),(r7,A4,b25),(r7,A4,b28),(r7,A4,b27),(r7,A4,b28),(r7,A4,b29),(r7,A4,b30),(r7,A4,b31),(r7,A4,b32),(r7,A4,b33),(r7,A4,b34),(r7,A4,b35),(r7,A4,b36),(r7,A4,b37),(r7,A4,b38),(r7,A4,b39),(r7,A4,b40),(r7,A4,b41),(r7,A4,b42),(r7,A4,b43),(r7,A4,b44),(r7,A4,b45),(r7,A4,b48),(r7,A4,b47),(r7,A4,b48),(r7,A4,b49),(r7,A4,b50),(r7,A4,b51),(r7,A4,b52),(r7,A4,b53),(r7,A4,b54),(r7,A4,b55),(r7,A4,b56),(r7,A4,b57),(r7,A4,b58),(r7,A4,b59),(r7,A4,b60),(r7,A4,b61),(r7,A4,b62),(r7,A4,b63),(r7,A4,b64),(r7,A4,b65),(r7,A4,b66),(r7,A4,b67),(r7,A4,b68),(r7,A4,b69),(r7,A4,b70),(r7,A4,b71),(r7,A4,b72),(r7,A4,b73),(r7,A4,b74),(r7,A4,b75),(r7,A4,b76),(r7,A4,b77),(r7,A4,b78),(r7,A4,b79),(r7,A4,b80),(r7,A4,b81),(r7,A4,b82),(r7,A4,b83),(r7,A4,b84),(r7,A4,b85),(r7,A4,b86),(r7,A4,b87),(r7,A4,b88),(r7,A4,b89),(r7,A4,b90),(r7,A4,b91),(r7,A4,b92),(r7,A4,b93),(r7,A4,b94),(r7,A4,b95),(r7,A4,b96),(r7,A4,b97),(r7,A4,b98),(r7,A4,b99),(r7,A4,b100),(r7,A4,b101),(r7,A4,b102),(r7,A4,b103),(r7,A4,b104),(r7,A4,b105),(r7,A4,b106),(r7,A4,b107),(r7,A4,b108),(r7,A4,b109),(r7,A4,b110),(r7,A4,b111),(r7,A4,b112),(r7,A4,b113),(r7,A4,b114),(r7,A4,b115),(r7,A4,b116),(r7,A4,b117),(r7,A4,b118),(r7,A4,b119),(r7,A4,b120),(r7,A4,b121),(r7,A4,b122),(r7,A4,b123),(r7,A4,b124),(r7,A4,b125),(r7,A4,b126),(r7,A4,b127),(r7,A4,b128),(r7,A4,b129),(r7,A4,b130),(r7,A4,b131),(r7,A4,b132),(r7,A4,b133),(r7,A4,b134),(r8,A1,b1),(r8,A1,b2),(r8,A1,b3),(r8,A1,b4),(r8,A1,b5),(r8,A1,b6),(r8,A1,b7),(r8,A1,b8),(r8,A1,b9),(r8,A1,b10),(r8,A1,b11),(r8,A1,b12),(r8,A1,b13),(r8,A1,b14),(r8,A1,b15),(r8,A1,b16),(r8,A1,b17),(r8,A1,b18),(r8,A1,b19),(r8,A1,b20),(r8,A1,b21),(r8,A1,b22),(r8,A1,b23),(r8,A1,b24),(r8,A1,b25),(r8,A1,b26),(r8,A1,b27),(r8,A1,b28),(r8,A1,b29),(r8,A1,b30),(r8,A1,b31),(r8,A1,b32),(r8,A1,b33),(r8,A1,b34),(r8,A1,b35),(r8,A1,b36),(r8,A1,b37),(r8,A1,b38),(r8,A1,b39),(r8,A1,b40),(r8,A1,b41),(r8,A1,b42),(r8,A1,b43),(r8,A1,b44),(r8,A1,b45),(r8,A1,b46),(r8,A1,b47),(r8,A1,b48),(r8,A1,b49),(r8,A1,b50),(r8,A1,b51),(r8,A1,b52),(r8,A1,b53),(r8,A1,b54),(r8,A1,b55),(r8,A1,b56),(r8,A1,b57),(r8,A1,b58),(r8,A1,b59),(r8,A1,b60),(r8,A1,b61),(r8,A1,b62),(r8,A1,b63),(r8,A1,b64),(r8,A1,b65),(r8,A1,b66),(r8,A1,b67),(r8,A1,b68),(r8,A1,b69),(r8,A1,b70),(r8,A1,b71),(r8,A1,b72),(r8,A1,b73),(r8,A1,b74),(r8,A1,b75),(r8,A1,b76),(r8,A1,b77),(r8,A1,b78),(r8,A1,b79),(r8,A1,b80),(r8,A1,b81),(r8,A1,b82),(8,A1,b83),(r8,A1,b84),(r8,A1,b85),(r8,A1,b86),(r8,A1,b87),(r8,A1,b88),(r8,A1,b89),(r8,A1,b90),(r8,A1,b91),(r8,A1,b92),(r8,A1,b93),(r8,A1,b94),(r8,A1,b95),(r8,A1,b96),(r8,A1,b97),(r8,A1,b98),(r8,A1,b99),(r8,A1,b100),(r8,A1,b101),(r8,A1,b102),(r8,A1,b103),(r8,A1,b104),(r8,A1,b105),(r8,A1,b106),(r8,A1,b107),(r8,A1,b108),(r8,A1,b109),(r8,A1,b110),(r8,A1,b111),(r8,A1,b112),(r8,A1,b113),(r8,A1,b114),(r8,A1,b115),(r8,A1,b116),(r8,A1,b117),(r8,A1,b118),(r8,A1,b119),(r8,A1,b120),(r8,A1,b121),(r8,A1,b122),(r8,A1,b123),(r8,A1,b124),(r8,A1,b125),(r8,A1,b126),(r8,A1,b127),(r8,A1,b128),(r8,A1,b129),(r8,A1,b130),(r8,A1,b131),(r8,A1,b132),(r8,A1,b133),(r8,A1,b134),(r8,A2,b1),(r8,A2,b2),(r8,A2,b3),(r8,A2,b4),(r8,A2,b5),(r8,A2,b6),(r8,A2,b7),(r8,A2,b8),(r8,A2,b9),(r8,A2,b10),(r8,A2,b11),(r8,A2,b12),(r8,A2,b13),(r8,A2,b14),(r8,A2,b15),(r8,A2,b16),(r8,A2,b17),(r8,A2,b18),(r8,A2,b19),(r8,A2,b20),(r8,A2,b21),(r8,A2,b22),(r8,A2,b23),(r8,A2,b24),(r8,A2,b25),(r8,A2,b26),(r8,A2,b27),(r8,A2,b28),(r8,A2,b29),(r8,A2,b30),(r8,A2,b31),(r8,A2,b32),(r8,A2,b33),(r8,A2,b34),(r 8,A2,b35),(r8,A2,b36),(r8,A2,b37),(r8,A2,b38),(r8,A2,b39),(r8,A2,b40),(r8,A2,b41),(r8,A2,b42),(r8,A2,b43),(r8,A2,b44),(r8,A2,b45),(r8,A2,b46),(r8,A2,b47),(r8,A2,b48),(r8,A2,b49),(r8,A2,b50),(r8,A2,b51),(r8,A2,b52),(r8,A2,b53),(r8,A2,b54),(r8,A2,b55),(r8,A2,b56),(r8,A2,b57),(r8,A2,b58),(r8,A2,b59),(r8,A2,b60),(r8,A2,b61),(r8,A2,b62),(r8,A2,b63),(r8,A2,b64),(r8,A2,b65),(r8,A2,b66),(r8,A2,b67),(r8,A2,b68),(r8,A2,b69),(r8,A2,b70),(r8,A2,b71),(r8,A2,b72),(r8,A2,b73),(r8,A2,b74),(r8,A2,b75),(r8,A2,b76),(r8,A2,b77),(r8,A2,b78),(r8,A2,b79),(r8,A2,b80),(r8,A2,b81),(r8,A2,b82),(r8,A2,b83),(r8,A2,b84),(r8,A2,b85),(r8,A2,b86),(r8,A2,b87),(r8,A2,b88),(r8,A2,b89),(r8,A2,b90),(r8,A2,b91),(r8,A2,b92),(r8,A2,b93),(r8,A2,b94),(r8,A2,b95),(r8,A2,b96),(r8,A2,b97),(r8,A2,b98),(r8,A2,b99),(r8,A2,b100),(r8,A2,b101),(r8,A2,b102),(r8,A2,b103),(r8,A2,b104),(r8,A2,b105),(r8,A2,b106),(r8,A2,b107),(r8,A2,b108),(r8,A2,b109),(r8,A2,b110),(r8,A2,b111),(r8,A2,b112),(r8,A2,b113),(r8,A2,b114),(r8,A2,b115),(r8,A2,b116),(r8,A2,b117),(r8,A2,b118),(r8,A2,b119),(r8,A2,b120),(r8,A2,b121),(r8,A2,b122),(r8,A2,b123),(r8,A2,b124),(r8,A2,b125),(r8,A2,b126),(r8,A2,b127),(r8,A2,b128),(r8,A2,b129),(r8,A2,b130),(r8,A2,b131),(r8,A2,b132),(r8,A2,b133),(r8,A2,b134),(r8,A3,b1),(r8,A3,b2),(r8,A3,b3),(r8,A3,b4),(r8,A3,b5),(r8,A3,b6),(r8,A3,b7),(r8,A3,b8),(r8,A3,b9),(r8,A3,b10),(r8,A3,b11),(r8,A3,b12),(r8,A3,b13),(r8,A3,b14),(r8,A3,b15),(r8,A3,b16),(r8,A3,b17),(r8,A3,b18),(r8,A3,b19),(r8,A3,b20),(r8,A3,b21),(r8,A3,b22),(r8,A3,b23),(r8,A3, b24),(r8,A3,b25),(r8,A3,b26),(r8,A3,b27),(r8,A3,b28),(r8,
A3,b29),(r8,A3,b30),(r8,A3,b31),(r8,A3,b32),(r8,A3,b33),
(r8,A3,b34),(r8,A3,b35),(r8,A3,b36),(r8,A3,b37),(r8,A3,
b38),(r8,A3,b39),(r8,A3,b40),(r8,A3,b41),(r8,A3,b42),(r8,
A3,b43),(r8,A3,b44),(r8,A3,b45),(r8,A3,b46),(r8,A3,b47),
(r8,A3,b48),(r8,A3,b49),(r8,A3,b50),(r8,A3,b51),(r8,A3,
b52),(r8,A3,b53),(r8,A3,b54),(r8,A3,b55),(r8,A3,b56),(r8,
A3,b57),(r8,A3,b58),(r8,A3,b59),(r8,A3,b60),(r8,A3,b61),
(r8,A3,b62),(r8,A3,b63),(r8,A3,b64),(r8,A3,b65),(r8,A3,
b66),(r8,A3,b67),(r8,A3,b68),(r8,A3,b69),(r8,A3,b70),(r8,
A3,b71),(r8,A3,b72),(r8,A3,b73),(r8,A3,b74),(r8,A3,b75),
(r8,A3,b76),(r8,A3,b77),(r8,A3,b78),(r8,A3,b79),(r8,A3,
b80),(r8,A3,b81),(r8,A3,b82),(r8,A3,b83),(r8,A3,b84),(r8,
A3,b85),(r8,A3,b86),(r8,A3,b87),(r8,A3,b88),(r8,A3,b89),
(r8,A3,b90),(r8,A3,b91),(r8,A3,b92),(r8,A3,b93),(r8,A3,
b94),(r8,A3,b95),(r8,A3,b96),(r8,A3,b97),(r8,A3,b98),(r8,
A3,b99),(r8,A3,b100),(r8,A3,b101),(r8,A3,b102),(r8,A3,
b103),(r8,A3,b104),(r8,A3,b105),(r8,A3,b106),(r8,A3,
b107),(r8,A3,b108),(r8,A3,b109),(r8,A3,b110),(r8,A3,
b111),(r8,A3,b112),(r8,A3,b113),(r8,A3,b114),(r8,A3,
b115),(r8,A3,b116),(r8,A3,b117),(r8,A3,b118),(r8,A3,
b119),(r8,A3,b120),(r8,A3,b121),(r8,A3,b122),(r8,A3,
b123),(r8,A3,b124),(r8,A3,b125),(r8,A3,b126),(r8,A3,
b127),(r8,A3,b128),(r8,A3,b129),(r8,A3,b130),(r8,A3,
b131),(r8,A3,b132),(r8,A3,b133),(r8,A3,b134),(r8,A4,b1),
(r8,A4,b2),(r8,A4,b3),(r8,A4,b4),(r8,A4,b5),(r8,A4,b6),(r8,
A4,b7),(r8,A4,b8),(r8,A4,b9),(r8,A4,b10),(r8,A4,b11),(r8,
A4,b12),(r8,A4,b13),(r8,A4,b14),(r8,A4,b15),(r8,A4,b16),
(r8,A4,b17),(r8,A4,b18),(r8,A4,b19),(r8,A4,b20),(r8,A4,
b21),(r8,A4,b22),(r8,A4,b23),(r8,A4,b24),(r8,A4,b25),(r8,
A4,b26),(r8,A4,b27),(r8,A4, b28),(r8,A4, b29),(r8,A4, b30),
(r8,A4, b31),(r8,A4,b32),(r8,A4, b33),(r8,A4, b34),(r8,A4,
b35),(r8,A4, b36),(r8,A4,b37),(r8,A4, b38),(r8,A4, b39),(r8,
A4, b40),(r8,A4, b41),(r8,A4,b42),(r8,A4, b43),(r8,A4,b44),
(r8,A4,b45),(r8,A4, b46),(r8,A4,b47),(r8,A4, b48),(r8,A4,
b49),(r8,A4,b50),(r8,A4, b51),(r8,A4, b52),(r8,A4,b53),(r8,
A4, b54),(r8,A4,b55),(r8,A4,b56),(r8,A4, b57),(r8,A4, b58),
(r8,A4, b59),(r8,A4,b60),(r8,A4,b61),(r8,A4, b62),(r8,A4,
b63),(r8,A4,b64),(r8,A4,b65),(r8,A4,b66),(r8,A4,b67) (r8,
A4,b68),(r8,A4,b69),(r8,A4,b70),(r8,A4,b71),(r8,A4, b72),
(r8,A4,b73),(r8,A4, b74),(r8,A4, b75),(r8,A4, b76),(r8,A4,
b77),(r8,A4,b78),(r8,A4,b79),(r8,A4, b80),(r8,A4, b81),(r8,
A4, b82),(r8,A4,b83),(r8,A4,b84),(r8,A4,b85),(r8,A4, b86),
(r8,A4,b87),(r8,A4,b88),(r8,A4,b89),(r8,A4,b90),(r8,A4,
b91),(r8,A4,b92),(r8,A4,b93),(r8,A4, b94),(r8,A4, b95),(r8,
A4, b96),(r8,A4,b97),(r8,A4,b98),(r8,A4, b99),(r8,A4,
b100),(r8,A4,b101),(r8,A4,b102),(r8,A4,b103),(r8,A4,
b104),(r8,A4,b105),(r8,A4,b106),(r8,A4,b107),(r8,A4,
b108),(r8,A4,b109),(r8,A4,b110),(r8,A4,b111),(r8,A4,
b112),(r8,A4,b113),(r8,A4,b114),(r8,A4,b115),(r8,A4,
b116),(r8,A4,b117),(r8,A4,b118),(r8,A4,b119),(r8,A4,
b120),(r8,A4,b121),(r8,A4,b122),(r8,A4,b123),(r8,A4,
b124),(r8,A4,b125),(r8,A4,b126),(r8,A4,b127),(r8,A4,
b128),(r8,A4,b129),(r8,A4,b130),(r8,A4,b131),(r8,A4,
b132),(r8,A4,b133) or (r8,A4,b134).

The present compounds are useful in disease induced by the production, secretion or deposition of-amyloid β protein, and are effective in treatment and/or prevention, and symptom improvement of such as dementia of the Alzheimer's type (Alzheimer's disease, senile dementia of Alzheimer type), Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia with Alzheimer's and vascular type, dementia with Parkinson's Disease, dementia with progressive supranuclear palsy, dementia with Cortico-basal degeneration, Alzheimer's disease with diffuse Lewy body disease, age-related macular degeneration, Parkinson's Disease, amyloid angiopathy and so on.

In the present invention, "treating Alzheimer's disease" includes prevention of aggravation of MCI and prevention of onset of familial Alzheimer's disease. In the present invention, "a pharmaceutical composition for treating Alzheimer's disease" includes a pharmaceutical composition for prevention of aggravation of MCI and prevention of onset of familial Alzheimer's disease.

Since the present compound has high inhibitory activity on BACE1, and/or has high selectivity on other enzymes, it can be a medicament with reduced side effect. Further, since the compound has high effect of reducing amyloid β production in a cell system, particularly, has high effect of reducing amyloid β production in brain, it can be an excellent medicament. In addition, by converting the compound into an optically active compound having suitable stereochemistry, the compound can be a medicament having a larger safety margin on the side effect. In addition, the present compound also has advantages that metabolism stability is high, solubility is high, oral absorbability is high, good bioavailability is exhibited, clearance is good, brain transference is high, a half life is high, non-protein binding rate is high, hERG channel inhibition is low, CYP inhibition is low, CYP MBI (irreversible inhibition (mechanism-based inhibition)) is low and/or an Ames test is negative.

The present compounds can be administrated in combination with other pharmaceutical agents such as other therapeutic drugs for Alzheimer's disease, e.g., acetylcholinesterase and the like. The present compounds can be treated with concomitantly with the anti-dementia agents such as Donepezil Hydrochloride, Tacrine, Galantamine, Rivastigmine, Zanapezil, Memantine, and Vinpocetine.

When the present compound is administered to a human, it can be administered orally as powders, granules, tablets, capsules, pills, solutions, or the like, or parenterally as injectables, suppositories, transdermal absorbable agents, inhalations, or the like. In addition, the present compound can be formulated into pharmaceutical preparations by adding pharmaceutical additives such as excipients, binders, wetting agents, disintegrating agents, lubricants and the like, which are suitable for formulations and an effective amount of the present compound.

A dose is different depending on state of disease, an administration route, and an age and a weight of a patient, and is usually 0.1 μg to 1 g/day, preferably 0.01 to 200 mg/day when orally administered to an adult, and is usually 1 μg to 10 g/day, preferably 0.1 to 2 g/day when parenterally administered.

EXAMPLE

Following examples and test examples illustrate the present invention in more detail, but the present invention is not limited by these examples.

$^1$H-NMR was measured in deuterium chloroform (CDCl$_3$) using tetramethylsilane as an internal standard, or measured in dimethylsulfoxide-D6 (DMSO-d$_6$). δ values were shown as ppm. Binding constants (J) were shown as Hz. In the data, s, d, t, m, br or brs means singlet, doublet, triplet, multiplet, broad or broad singlet, respectively.

In examples, the meaning of each abbreviation is as follows:
Me methyl
Bu butyl
Bz benzoyl
Boc tert-butoxycarbonyl THF tetrahydrofuran
DMF N, N-dimethylformamide
EDC 1-ethyl-3-(3-dimethylamino propyl)carbodiimide
DIBAL diisobutylaluminium hydride
MCPBA meta-chloroperbenzoic acid LC/MS data of Compounds (I–1) to (1-54) were measured under the condition A, Compound (1-55) to (1-67) were measured under the condition B, and a retention time and [M+H]$^+$ are shown.

Condition A
Column: Shim-pack XR-ODS (2.2 μm, i.d. 50×3 0 mm) (Shimadzu)
Flow rate: 1.6 mL/min
Column oven: 50° C.
UV detection wavelength: 254 nm
Mobile phase: [A] 0.1% formic acid-containing aqueous solution; [B] 0.1% formic acid-containing acetonitrile solution
Gradient: performing linear gradient of 10% to 100% solvent [B] for 3 minutes, and keeping 100% solvent [B] for 1 minute Condition B
Column: XBridge (Registered trademark) C18 (5 μm, i.d. 4.6×50 mm) (Waters)
Flow rate: 3 mL/min
UV detection wavelength: 254 nm
Mobile phase: [A] is 0.1% formic acid-containing aqueous solution, [B] is 0.1% formic acid-containing acetonitrile solution
Gradient: Linear gradient of 10% to 100% solvent [B] for 3 minutes was performed, and 100% solvent [B] was maintained for 1 minutes.

Example 1

Synthesis of Compound (I-12) and (I-13)

[Chemical Formula 78]

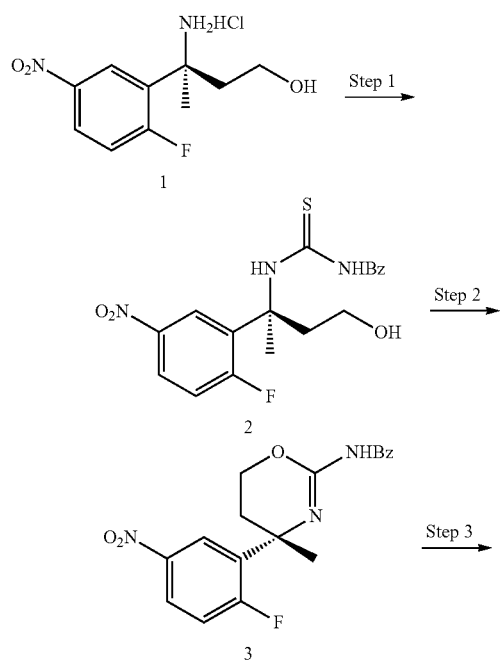

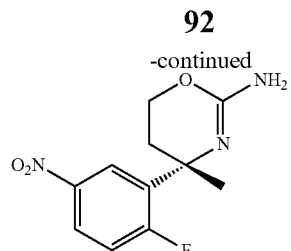

I-12

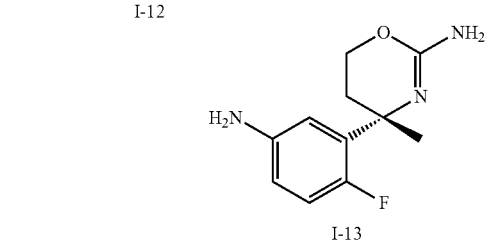

I-13

Step 1

To a solution of Compound 1 (1.20 g) in acetone (70 ml)-water (40 ml) was added a solution of benzoyl isothiocyanate (0.82 g) in acetone at 0° C. and the mixture was stirred for 2 hours at room temperature. The solvent was evaporated under reduced pressure, the residue was purified by column chromatography to give Compound 2 (1.35 g).

$^1$H-NMR (CDCl$_3$) δ: 1.69 (1H, t, J=4.7 Hz), 2.14 (3H, s) 2.21-2.31 (1H, m), 2.73-2.83 (1H, m), 3.78-3.98 (2H, m), 7.15 (1H, dd, J=11.1, 9.1 Hz) 7.48-7.55 (2H, m), 7.60-7.67 (1H, m), 7.85 (2H, d, 7.2 Hz), 8.14-8.20 (1H, m), 8.30-8.34 (1H, m), 8.81 (1H, s), 11.56 (1H, s).

Step 2

To a solution of Compound 2 (1.26 g) obtained in Step 1 in acetonitrile (5 ml) were added methyl iodide (0.30 ml) and diisopropylethylamine (0.84 ml). The mixture was stirred at room temperature for 2 hours and at 40° C. for 2 hours. To the reaction mixture was added water and the mixture was extracted with ethyl acetate. The organic layer was washed successively with water and brine, and dried over anhydrous magnesium sulfate. The solvent was evaporated under reduced pressure and the residue was purified by column chromatography to give Compound 3 (1.11 g).

$^1$H-NMR (CDCl$_3$) δ: 1.88 (3H, s), 2.30-2.40 (1H, m), 2.66-2.74 (1H, m), 4.01-4.10 (1H, m), 4.42-4.49 (1H, m), 7.25-7.32 (1H, m), 8.37 (1H, dd, J=7.1, 2.9 Hz) 7.39-7.54 (3H, m), 8.21-8.29 (3H, m), 11.90 (1H, br).

Step 3

To Compound 3 (1.10 g) obtained in Step 2 was added concentrated sulfuric acid (3.28 ml) and the mixture was stirred at 80° C. for 1.5 hours. The reaction mixture was added to a saturated aqueous sodium bicarbonate solution and the mixture was extracted with ethyl acetate. The organic layer was successively washed with water and brine, and dried over anhydrous magnesium sulfate. The solvent was evaporated under reduced pressure and the residue was purified by column chromatography to give Compound (I-12) (0.615 g).

$^1$H-NMR (CDCl$_3$) δ: 1.58 (3H, s), 2.22 (2H, t, J=5.4 Hz), 3.86-3.94 (1H, m), 4.15-4.25 (3H, m), 7.14 (1H, dd, J=10.7, 8.9 Hz), 8.09-8.15 (1H, m), 8.62 (1H, dd, J=7.0, 3.0 Hz).

Step 4

To a solution of Compound (I-12) (614 mg) obtained in Step 3 in THF (5 ml) was added 10% palladium-carbon (120 mg) and the mixture was stirred for 20 hours under hydrogen atmosphere. The reaction solution was filtered through Celite and the filtrate was concentrated under reduced pressure. The obtained residue was purified by column chromatography and recrystallized from ethyl acetate-hexane to give Compound (I-13) (400 mg).

$^1$H-NMR (CDCl$_3$) δ: 1.54 (3H, s), 1.97-2.07 (1H, m), 2.30-2.38 (1H, m), 3.54 (2H, brs), 3.83 (1H, dt, J=3.2, 10.6 Hz), 4.10 (1H, ddd, 10.6, 4.7, 4.2 Hz), 6.48 (1H, ddd, 8.4, 3.7, 3.2 Hz), 6.78 (1H, dd, J=11.8, 8.4 Hz), 6.86 (1H, dd, J=6.9, 3.0 Hz).

Example 2

Synthesis of Compounds (I-14) and (I-15)

[Chemical Formula 79]

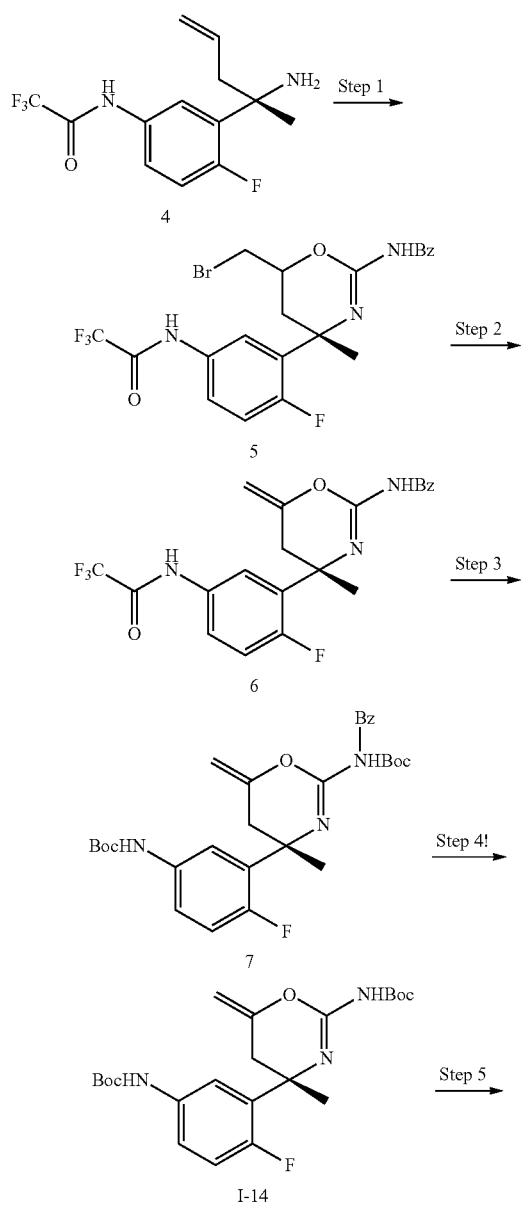

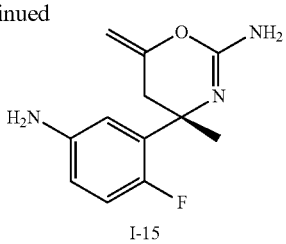

Step 1

To a solution of Compound 4 (1.1 g) obtained by Reference Example mentioned below in tetrahydrofuran (10 ml) was added benzoyl isocyanate (854 μl) at 0° C. and the mixture was stirred at room temperature for 30 minutes. To the mixture was added N-bromosuccinimide (675 mg) and the mixture was stirred at room temperature for 30 minutes. To the mixture was added ethyl acetate and the mixture was successively washed with water and brine and dried over anhydrous magnesium sulfate. The solvent was evaporated under reduced pressure to give Compound (5) (2.4 g) as a crude product.

Step 2

To a solution of Compound (5) (2.4 g) obtained in Step 1 in tetrahydrofuran (12 ml) and dimethylsulfide (12 ml) was added sodium tert-butoxide and the mixture was stirred at room temperature for 2 hours. The reaction solution was poured into 1 mol/L hydrochloric acid and extracted with ethyl acetate. The organic layer was washed successively with 1 mol/L aqueous hydrochloric acid solution, water and brine and dried over magnesium sulfate. The solvent was evaporated under reduced pressure to give Compound (6) (2.1 g) as a crude product.

Step 3

To a solution of Compound (6) (2.1 g) obtained in Step 2 in tetrahydrofuran (16 ml) were added di-tert-butyl dicarbonate (1.8 ml) and N,N-dimethyl-4-aminopyridine (9.2 mg). The mixture was stirred at room temperature for 30 minutes. To the mixture was added triethylamine (522 μl), and the mixture was stirred for 30 minutes. To the mixture were added N,N-dimethyl-4-aminopyridine (460 mg) and di-tert-butyl dicarbonate (0.9 ml), and the mixture was stirred at room temperature for 20 minutes. To the mixture was added 2 mol/L aqueous solution of potassium carbonate and the mixture was extracted with ethyl acetate. The organic layer was washed with 1 mol/L aqueous solution of citric acid and brine and dried over magnesium sulfate. The solvent was evaporated under reduced pressure and the obtained residue was subject to column chromatography to give Compound (7) (0.99 g).

$^1$H-NMR (CDCl$_3$) δ: 1.40 (3H, s), 1.47 (9H, s), 1.53 (9H, s), 2.51 (1H, d, J=14.0 Hz), 2.88 (1H, d, J=14.0 Hz), 4.38 (1H, s), 4.75 (1H, s), 6.30 (1H, s), 6.87 (1H, br), 6.93 (1H, dd, J=11.7, 9.0 Hz), 7.42-7.65 (4H, m), 7.80-7.83 (2H, m).

Step 4

To a solution of Compound (7) (914 mg) obtained in Step 3 in methanol (3 ml) and tetrahydrofuran (5 ml) was added 1 mol/L aqueous solution of sodium hydroxide (1.7 ml) at 0° C. and the mixture was stirred for 80 minutes. The reaction mixture was extracted with ethyl acetate, washed with brine and dried over magnesium sulfate. The solvent was evaporated under reduced pressure and the obtained residue was subjected to column chromatography to give Compound (I-14) (695 mg).

$^1$H-NMR (CDCl$_3$) δ: 1.52 (9H, s) and 1.54 (9H, s) 1.75 (3H, s) 2.70 (1H, d, J=14.0 Hz), 3.20 (1H, d, J=14.0 Hz) 4.25

(1H, s), 4.66 (1H, s), 6.48 (1H, s), 6.96 (1H, br), 7.02 (1H, dd, J=11.4, 9.0 Hz), 7.51 (1H, m), 10.0 (1H, s).

Step 5

To a solution of Compound (I-14) obtained in Step 4 in methylene chloride (2 ml) was added trifluoroacetate (2 ml) at 0° C. and the mixture was stirred at room temperature for 80 minutes. The solvent was evaporated under reduced pressure and were added ethyl acetate and a saturated aqueous sodium bicarbonate solution. The mixture was stirred vigorously. The mixture was extracted with ethyl acetate, washed with brine and dried over magnesium sulfate. The solvent was evaporated under reduces pressure to give Compound (I-15) (427 mg) as a crude product.

$^1$H-NMR (CDCl$_3$) δ: 1.63 (3H, s), 2.69 (1H, d, J=14.1 Hz), 3.02 (1H, d, J=14.1 Hz), 3.58 (2H, s), 4.28 (1H, s), 4.60 (1H, s), 6.51 (1H, ddd, J=8.8, 3.2, 2.8 Hz), 6.72 (1H, dd, J=6.9, 2.8 Hz), 6.81 (1H, dd, J=11.7, 8.8 Hz).

Reference Example

[Chemical Formula 80]

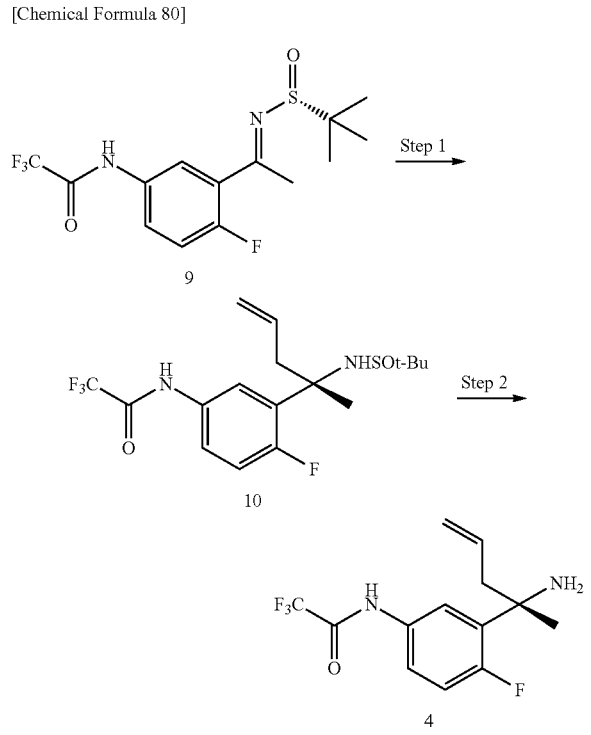

Step 1

Compound (9) (12 g) was dissolved in tetrahydrofuran (240 ml). To the solution was dropwisely added 1 mol/L allylmagnesium bromide/ether solution during 1 hour at −78° C. The mixture was stirred at −78° C. for 1 hour and poured into a saturated aqueous solution of ammonium chloride. The mixture was extracted with ethyl acetate and the organic layer was dried over anhydrous sodium sulfate. After removing an inorganic material by filtration, the solvent was evaporated under reduced pressure. The residue was subjected to column chromatography to give Compound (10) (9.7 g).

$^1$H-NMR (CDCl$_3$) δ: 1.21 (9H, s), 1.68 (3H, s), 2.79 (1H, dd, J=13.4, 7.3 Hz), 2.92 (1H, dd, J=13.4, 6.8 Hz), 4.16 (1H, s), 5.10 (1H, d, J=9.6 Hz), 5.13 (1H, d, J=17.2 Hz) 5.52-5.66 (1H, m), 6.95 (1H, dd, J=10.6, 10.1 Hz), 7.55-7.62 (1H, m), 7.67-7.72 (1H, m), 9.96 (1H, s).

Step 2

Compound (10) (3.99 g) was dissolved in ethanol (20 ml). To the solution was added a solution of 1 mol/L hydrochloric acid-ethanol with stirring at room temperature and the mixture was stirred for 1 hour at room temperature. The solvent was evaporated under reduced pressure. The residue was diluted with ethyl acetate and the solution was extracted with 2 mol/L hydrochloric acid. The obtained aqueous layer was made alkalinized with potassium carbonate (pH 8 to 9), and extracted with ethyl acetate. The organic layer was dried over anhydrous sodium sulfate. After removing an inorganic material by filtration, the solvent was evaporated under reduced pressure to give Compound (4).

$^1$H-NMR (CDCl$_3$) δ: 1.51 (3H, s), 1.75-1.89 (2H, br), 2.47 (1H, dd, J=13.1, 8.1 Hz) 2.76 (1H, dd, J=13.1, 7.1 Hz), 5.03-5.11 (2H, m), 5.46-5.58 (1H, m), 7.01-7.08 (1H, m), 7.52-7.60 (2H, m), 8.25-8.36 (1H, br).

Example 3

Synthesis of Compound (1-54)

[Chemical Formula 81]

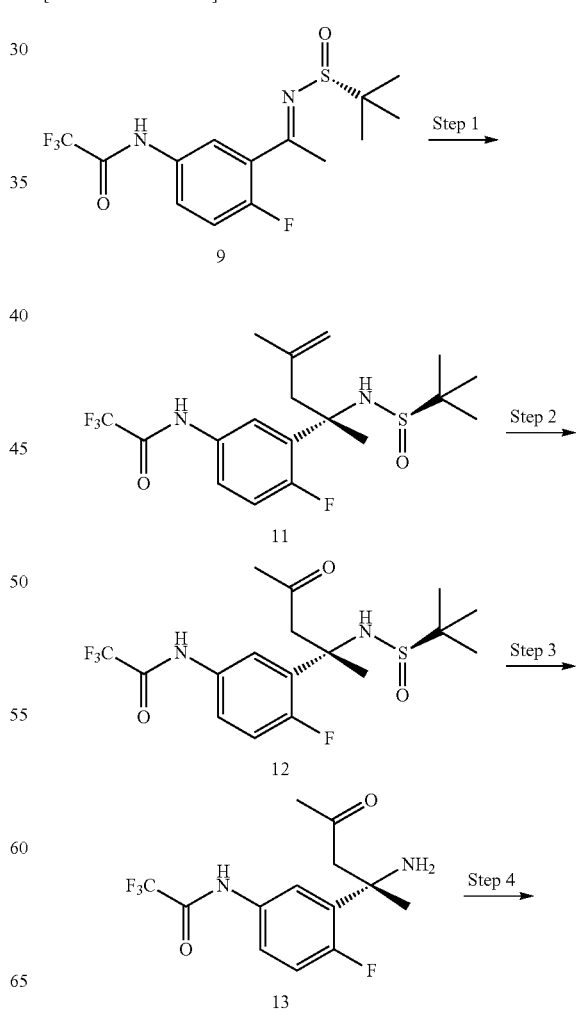

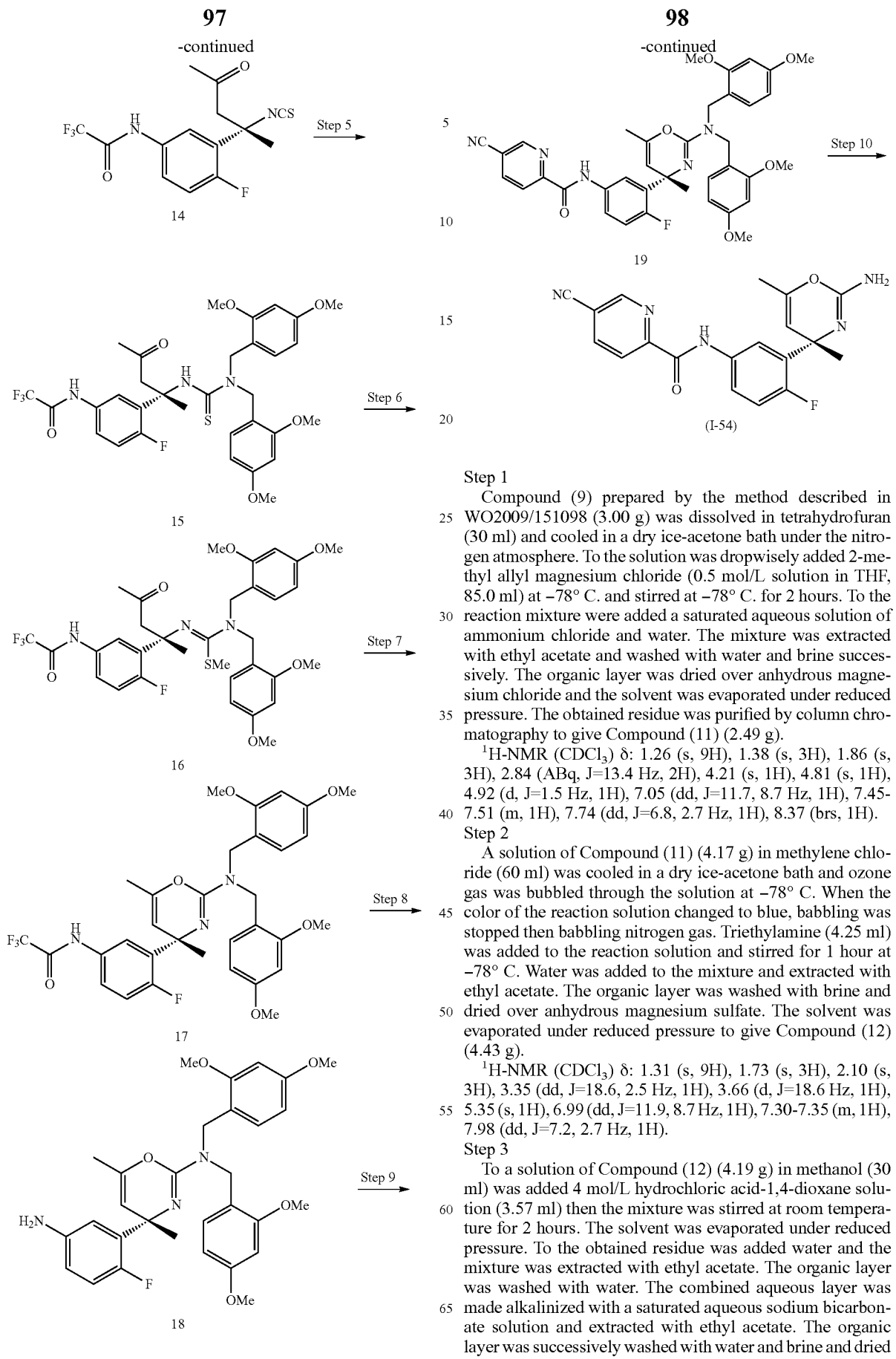

Step 1

Compound (9) prepared by the method described in WO2009/151098 (3.00 g) was dissolved in tetrahydrofuran (30 ml) and cooled in a dry ice-acetone bath under the nitrogen atmosphere. To the solution was dropwisely added 2-methyl allyl magnesium chloride (0.5 mol/L solution in THF, 85.0 ml) at −78° C. and stirred at −78° C. for 2 hours. To the reaction mixture were added a saturated aqueous solution of ammonium chloride and water. The mixture was extracted with ethyl acetate and washed with water and brine successively. The organic layer was dried over anhydrous magnesium chloride and the solvent was evaporated under reduced pressure. The obtained residue was purified by column chromatography to give Compound (11) (2.49 g).

$^1$H-NMR (CDCl$_3$) δ: 1.26 (s, 9H), 1.38 (s, 3H), 1.86 (s, 3H), 2.84 (ABq, J=13.4 Hz, 2H), 4.21 (s, 1H), 4.81 (s, 1H), 4.92 (d, J=1.5 Hz, 1H), 7.05 (dd, J=11.7, 8.7 Hz, 1H), 7.45-7.51 (m, 1H), 7.74 (dd, J=6.8, 2.7 Hz, 1H), 8.37 (brs, 1H).

Step 2

A solution of Compound (11) (4.17 g) in methylene chloride (60 ml) was cooled in a dry ice-acetone bath and ozone gas was bubbled through the solution at −78° C. When the color of the reaction solution changed to blue, babbling was stopped then babbling nitrogen gas. Triethylamine (4.25 ml) was added to the reaction solution and stirred for 1 hour at −78° C. Water was added to the mixture and extracted with ethyl acetate. The organic layer was washed with brine and dried over anhydrous magnesium sulfate. The solvent was evaporated under reduced pressure to give Compound (12) (4.43 g).

$^1$H-NMR (CDCl$_3$) δ: 1.31 (s, 9H), 1.73 (s, 3H), 2.10 (s, 3H), 3.35 (dd, J=18.6, 2.5 Hz, 1H), 3.66 (d, J=18.6 Hz, 1H), 5.35 (s, 1H), 6.99 (dd, J=11.9, 8.7 Hz, 1H), 7.30-7.35 (m, 1H), 7.98 (dd, J=7.2, 2.7 Hz, 1H).

Step 3

To a solution of Compound (12) (4.19 g) in methanol (30 ml) was added 4 mol/L hydrochloric acid-1,4-dioxane solution (3.57 ml) then the mixture was stirred at room temperature for 2 hours. The solvent was evaporated under reduced pressure. To the obtained residue was added water and the mixture was extracted with ethyl acetate. The organic layer was washed with water. The combined aqueous layer was made alkalinized with a saturated aqueous sodium bicarbonate solution and extracted with ethyl acetate. The organic layer was successively washed with water and brine and dried over anhydrous magnesium sulfate. The solvent was evaporated under reduced pressure to give Compound (13) (3.00 g).

$^1$H-NMR (CDCl$_3$) δ: 1.48 (s, 3H), 2.06 (s, 3H), 2.18 (br, 2H), 2.86 (d, J=17.8 Hz, 1H), 3.44 (d, J=17.8 Hz, 1H), 7.01 (dd, J=11.7, 8.7 Hz, 1H), 7.60-7.70 (m, 2H), 8.17 (br, 1H).

Step 4

To a solution of Compound (13) (2.48 g) in ethyl acetate (25 ml)-toluene (15 ml) were added potassium carbonate (2.24 g) and water (20 ml) then the mixture was cooled in an ice bath. To the mixture was added a solution of thiophosgene (1.40 g) in toluene (10 ml) and stirred for 1 hour at 0° C. Water was added to the reaction solution and and the mixture was extracted with ethyl acetate. The organic layer was washed with water and brine, successively. The organic layer was dried over anhydrous magnesium sulfate and the solvent was evaporated under reduced pressure to give Compound (14) (2.82 g).

$^1$H-NMR (CDCl$_3$) δ: 1.90 (s, 3H), 2.15 (s, 3H), 3.34 (ABq, J=17.1 Hz, 2H), 7.07 (dd, J=11.4, 8.9 Hz, 1H), 7.57 (dd, J=6.9, 2.9 Hz, 1H), 7.79-7.85 (m, 1H), 8.13 (br, 1H).

Step 5

To a solution of Compound (14) (2.82 g) in THF (40 ml) was added bis(2,4-dimethoxybenzyl)amine (3.08 g) then the mixture was stirred for 16 hours at room temperature. The solvent was evaporated under reduced pressure. Water and 2 mol/L hydrochloric acid were added to the residue and was extracted with ethyl acetate. The organic layer was washed with water, a saturated aqueous sodium bicarbonate solution, water and brine, successively and dried over anhydrous magnesium sulfate. The solvent was evaporated under reduced pressure and the obtained residue was purified by column chromatography to give Compound (15) (4.61 g).

$^1$H-NMR (CDCl$_3$) δ: 1.81 (s, 3H), 2.15 (s, 3H), 3.11 (d, J=16.8 Hz, 1H), 3.79 (s, 6H), 3.80 (s, 6H), 4.46 (d, J=16.8 Hz, 1H), 4.77 (br, 2H), 5.03 (br, 2H), 6.45-6.52 (m, 4H), 6.86 (brs, 1H), 7.00 (dd, J=11.3, 8.7 Hz, 1H), 7.11-7.20 (m, 3H), 7.52-7.57 (m, 1H), 7.93 (br, 1H).

Step 6

To a solution of Compound (15) (4.61 g) in acetonitrile (20 ml) were added N,N-diisopropylethyl amine (2.42 ml) and methyl iodide (1.97 g) then the mixture was stirred at room temperature for 24 hours. The solvent was evaporated under reduced pressure. Water was added to the residue and the mixture was extracted with ethyl acetate. The organic layer was successively washed with 1 mol/L hydrochloric acid, water, a saturated aqueous solution of sodium bicarbonate, water and brine, and dried over anhydrous magnesium sulfate. The solvent was evaporated under reduced pressure to give Compound (16) (4.36 g).

$^1$H-NMR (CDCl$_3$) δ: 1.80 (s, 3H), 1.96 (s, 3H), 2.06 (s, 3H), 3.14 (s, 2H), 3.74 (s, 6H), 3.80 (s, 6H), 4.52 (s, 4H), 6.40-6.49 (m, 4H), 7.00 (dd, J=11.4, 8.9 Hz, 1H), 7.09-7.14 (m, 3H), 7.71-7.80 (m, 2H).

Step 7

To a solution of Compound (16) (4.36 g) in acetonitrile (20 ml) was added N,N-diisopropylethyl amine (3.36 ml) then the mixture was heated under reflux for 48 hours. Water was added to the reaction solution and the mixture was extracted with ethyl acetate. The organic layer was successively washed with water and brine, and dried over anhydrous magnesium sulfate. The solvent was evaporated under reduced pressure and the obtained residue was purified by column chromatography to give Compound (17) (820 mg).

$^1$H-NMR (CDCl$_3$) δ: 1.54 (s, 3H), 1.76 (s, 3H), 3.76 (s, 6H), 3.79 (s, 6H), 4.29 (d, J=16.2 Hz, 2H), 4.81 (d, J=16.2 Hz, 2H), 5.30 (d, J=2.5 Hz, 1H), 6.43-6.47 (m, 4H), 6.98 (dd, J=11.1, 8.7 Hz, 1H), 7.14-7.18 (m, 3H), 7.40-7.44 (m, 1H), 7.80-7.86 (m, 1H).

Step 8

To a solution of Compound (17) (34 mg) in methanol (1.5 ml) were added potassium carbonate (22.3 mg), THF (0.5 ml) and water (0.5 ml) then the mixture was stirred for 20 hours at 40° C. To the reaction solution were added a saturated aqueous sodium bicarbonate solution and water and the mixture was extracted with ethyl acetate. The organic layer was successively washed with water and brine, and dried over anhydrous magnesium sulfate. The solvent was evaporated under reduced pressure and the obtained residue was purified by column chromatography to give Compound (18) (20.7 mg).

$^1$H-NMR (CDCl$_3$) δ: 1.52 (s, 3H), 1.73 (s, 3H), 3.19 (br, 2H), 3.76 (s, 6H), 3.80 (s, 6H), 4.31 (d, J=16.3 Hz, 2H), 4.81 (d, J=16.3 Hz, 2H), 5.27 (d, J=2.2 Hz, 1H), 6.34-6.39 (m, 1H), 6.44-6.50 (m, 4H), 6.60 (dd, J=6.7, 3.0 Hz, 1H), 6.71 (dd, J=11.6, 8.6 Hz, 1H), 7.19 (d, J=7.9 Hz, 2H).

Step 9

To a solution of Compound (18) (86.3 mg) in DMF (1 ml) were added 5-cyano picolinic acid hydrate and EDC hydrochloride (40.2 mg) then the mixture was stirred at room temperature for 20 hours. To the mixture were added 5-cyano picolinic acid hydrate (53.5 mg) and EDC hydrochloride (61.8 mg) and the mixture was stirred at room temperature for 3 hours. To the reaction solution were added a saturated aqueous sodium bicarbonate solution and water and the mixture was extracted with ethyl acetate. The organic layer was successively washed with water and brine and dried over anhydrous magnesium sulfate. The solvent was evaporated under reduced pressure and the obtained residue was purified by column chromatography to give Compound (19) (98.5 mg).

$^1$H-NMR (CDCl$_3$) δ: 1.58 (s, 3H), 1.76 (s, 3H), 3.71 (s, 6H), 3.77 (s, 6H), 4.36 (d, J=16.1 Hz, 2H), 4.78 (d, J=16.1 Hz, 2H), 5.33 (d, J=3.4 Hz, 1H), 6.42-6.46 (m, 4H), 7.02 (dd, J=11.2, 8.7 Hz, 1H), 7.19-7.25 (m, 2H), 7.41 (dd, J=6.7, 2.9 Hz, 1H), 8.05-8.11 (m, 1H), 8.18 (dd, J=8.2, 2.0 Hz, 1H), 8.39 (d, J=8.2 Hz, 1H), 8.90 (d, J=2.0 Hz, 1H), 9.50 (brs, 1H).

Step 10

To Compound (19) (98.5 mg) were added anisole (0.11 ml) and trifluoroacetic acid (10 ml) and the mixture was stirred at 80° C. for 15 hours. The solvent was evaporated under reduced pressure. To the residue were added a saturated aqueous sodium bicarbonate solution and water and the mixture was extracted with chloroform. The organic layer was dried over anhydrous magnesium sulfate and the solvent was evaporated under reduced pressure. The obtained residue was purified by column chromatography to give Compound (1-54) (25.9 mg).

$^1$H-NMR (CDCl$_3$) δ: 1.61 (s, 3H), 1.80 (s, 3H), 4.38 (br, 2H), 5.27 (dd, J=2.8, 1.3 Hz, 1H), 7.03 (dd, J=11.4, 8.9 Hz, 1H), 7.67 (dd, J=6.9, 2.9 Hz, 1H), 7.86-7.92 (m, 1H), 8.17 (dd, J=8.1, 2.0 Hz, 1H), 8.39 (d, J=8.1 Hz, 1H), 8.82 (d, J=2.0 Hz, 1H), 9.81 (brs, 1H).

101

Example 4

Synthesis of Compound (I-55)

[Chemical Formula 82]

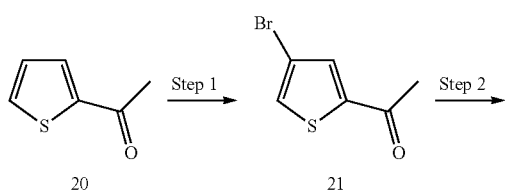

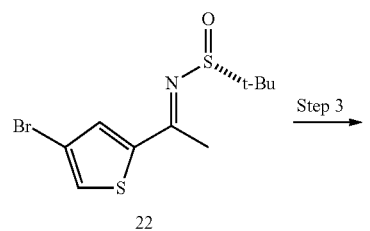

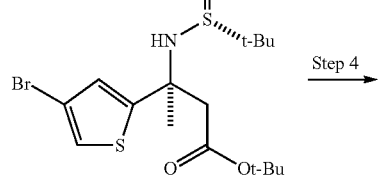

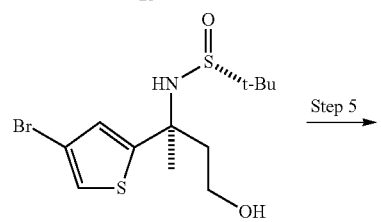

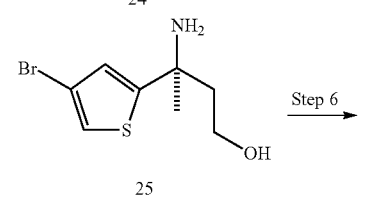

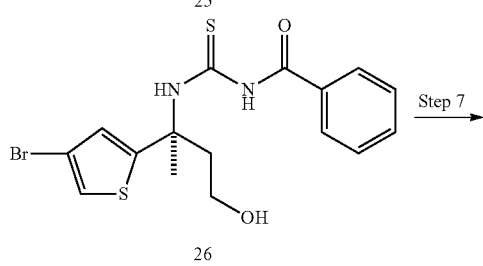

102

-continued

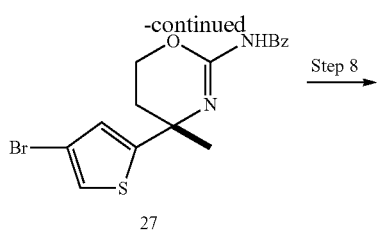

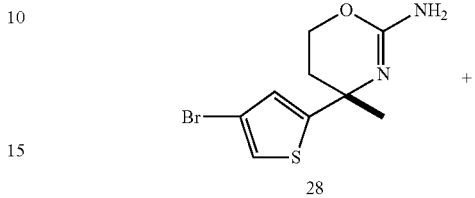

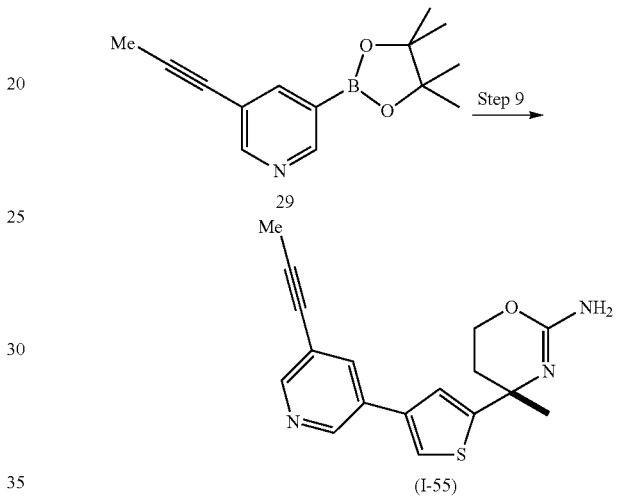

Step 1

Compound (20) (30 g) was dissolved in chloroform (60 ml). To the solution were added triethyl aluminium (33.3 g) and bromide (12.9 ml) at 0° C. and the mixture was stirred at room temperature for 1 hour. The reaction mixture was warmed to 50° C. and stirred for 2 hours. To the reaction mixture was added trimethyl aluminium (16.0 g) and the mixture was stirred for 1 hour. After the the reaction solution was allowed to cool to room temperature, sodium acetate was added and the mixture was filtered through Celite. The filtrate was extracted with chloroform and dried over sodium sulfate. The solvent was evaporated under reduced pressure and the obtained residue was purified by chromatography to give Compound (21) (40 g).

$^1$H-NMR (CDCl$_3$) δ: 2.56 (s, 3H), 7.53 (d, J=1.4 Hz, 1H), 7.58 (d, J=1.4 Hz, 1H).

Step 2

Compound (21) (27 g) was dissolved in tetrahydrofuran (150 ml). To the solution were added (R)-2-methyl propane-2-sulfinamide (20 g) and titanium tetraethoxide (38.6 ml) and the mixture was stirred at 70° C. for 3.5 hours, followed by stirring for 6 hours at 90° C. To the reaction mixture was added brine and filtered through Celite. The filtrate was extracted with ethyl acetate and dried over sodium sulfate. The solvent was evaporated under reduced pressure and the obtained residue was purified by chromatography to give Compound (22) (30.1 g).

$^1$H-NMR (CDCl$_3$) δ: 1.30 (s, 9H), 2.71 (s, 3H), 7.39 (d, J=1.4 Hz, 1H), 7.41 (d, J=1.4 Hz, 1H).

Step 3

To tetrahydrofuran (70 ml) in a eggplant flask were added lithium diisopropyl amide (100 ml, 2 M), t-butyl acetate (26.4 ml) and triisopropoxy titanium (Iv) chloride (98 ml) at −70 to −60° C. and the mixture was stirred for 1 hour. To the reaction mixture were added Compound (22) (30.1 g) and tetrahydrofuran (98 ml) and the mixture was stirred at −60 to −50° C. for 1.5 hours. A saturated aqueous solution of ammonium chloride was added to the reaction mixture. The mixture was filtered through Celite and the filtrate was dried over sodium sulfate. The solvent was evaporated under reduced pressure and the obtained residue was purified by chromatography to give Compound (23) (13.4 g).

$^1$H-NMR (CDCl$_3$) δ: 1.29 (s, 9H), 1.37 (s, 9H), 1.79 (s, 3H), 2.89 (d, J=15.8 Hz, 1H), 2.99 (d, J=15.8 Hz, 1H), 5.74 (s, 1H), 6.81 (d, J=1.4 Hz, 1H), 7.09 (d, J=1.4 Hz, 1H).

Step 4

Compound (23) (13.4 g) was dissolved in toluene (50 ml) and was added DIBAL (58 ml, 1M in hexane) at −78° C. After the mixture was stirred at 0° C. for 2 hours, ethyl acetate and an aqueous solution of Rochelle salt were added and the mixture was extracted. The oil layer was washed with water and dried over sodium sulfate. The solvent was evaporated under reduced pressure and the obtained residue was purified by chromatography and recrystallized to give Compound (24) (2.62 g).

$^1$H-NMR (CDCl$_3$) δ: 1.27 (s, 9H), 1.78 (s, 3H), 2.17 (ddd, J=15.1, 6.1, 3.4 Hz, 1H), 2.30 (brddd, J=15.1, 8.5, 3.4 Hz, 1H), 3.15 (brdd, J=7.5, 3.4 Hz, 1H), 3.74 (dddd, J=11.8, 8.5, 7.5, 3.4 Hz, 1H), 3.95 (dddd, J=11.8, 6.1, 3.4, 3.4 Hz, 1H), 5.20 (brs, 1H), 6.77 (d, J=1.4 Hz, 1H), 7.11 (d, J=1.4 Hz, 1H).

Step 5

Compound (24) (1.0 g) was dissolved in methanol (10 ml). To the solution was added concentrated hydrochloric acid (2 ml) at 0° C. The mixture was stirred for 1 hour at 0° C. followed by stirring at room temperature for 2 hours. To the reaction solution were added a saturated aqueous sodium bicarbonate solution and ethyl acetate and the mixture was extracted and dried over sodium sulfate. The solvent was evaporated under reduced pressure and the obtained residue was purified by chromatography to give Compound (25) (617 mg).

$^1$H-NMR (CDCl$_3$) δ: 1.60 (s, 3H), 1.94 (ddd, J=14.4, 6.5, 4.4 Hz, 1H), 1.97 (ddd, J=14.4, 6.8, 4.4 Hz, 1H), 2.47 (brs, 2H), 3.67 (ddd, J=11.5, 6.5, 4.4 Hz, 1H), 3.82 (ddd, J=11.5, 6.8, 4.4 Hz, 1H), 6.83 (d, J=1.4 Hz, 1H), 7.09 (d, J=1.4 Hz, 1H).

Step 6

Compound (25) (200 mg) was dissolved in tetrahydrofuran (2 ml). To the solution was added benzoyl isothiocyanate (121 μl) and the mixture was stirred for 30 minutes. The solvent was evaporated under reduced pressure to give Compound (26) (280 mg, quant).

$^1$H-NMR (CDCl$_3$) δ: 2.07 (s, 3H), 2.33 (dt, J=13.5, 6.3 Hz, 1H), 2.71 (dt, J=13.5, 6.3 Hz, 1H), 3.82 (dt, J=11.2, 6.3 Hz, 1H), 3.84 (dt, J=11.2, 6.3 Hz, 1H), 6.90 (brs, 1H), 7.13 (brs, 1H), 7.51 (m, 2H), 7.63 (m, 1H), 7.84 (m, 2H), 8.84 (s, 1H), 11.46 (s, 1H).

Step 7

Compound (26) (280 mg) was dissolved in dichloromethane (4 ml). To the solution was added mCPBA (514 mg) at room temperature and the mixture was stirred at room temperature for 1 hour. To the mixture were added a saturated aqueous sodium bicarbonate solution and ethyl acetate and the mixture was extracted and dried over sodium sulfate. The insoluble solid in dichloromethane was removed by filtration and the solvent was evaporated under reduced pressure to give Compound (27) (340 mg, quant).

$^1$H-NMR (CDCl$_3$) δ: 1.83 (s, 3H), 2.32 (dd, J=5.8, 4.0 Hz, 1H), 2.33 (dd, J=8.1, 4.0 Hz, 1H), 4.28 (ddd, J=11.8, 8.1, 5.8 Hz, 1H), 4.45 (ddd, J=11.8, 4.0, 4.0 Hz, 1H), 6.92 (d, J=1.4 Hz, 1H), 7.18 (d, J=1.4 Hz, 1H), 7.42 (m, 2H), 7.50 (m, 1H), 8.22 (m, 2H).

Step 8

Compound (27) (340 mg) was dissolved in ethanol (4 ml). To the solution was added sodium hydroxide (320 mg) and stirred at 90° C. for 2.5 hours. The reaction mixture was made acidified with 2 mol/L aqueous solution of hydrochloric acid. The solution was back-extracted with ethyl acetate to remove an impure material. The aqueous layer was alkalinized with sodium carbonate and extracted with ethyl acetate. The organic layer was dried over sodium sulfate and the solvent was evaporated under reduced pressure to give Compound (28) (141 mg).

$^1$H-NMR (CDCl$_3$) δ: 1.54 (s, 3H), 2.04 (ddd, J=13.9, 8.9, 4.6 Hz, 1H), 2.07 (ddd, J=13.9, 4.6, 4.2 Hz, 1H), 4.01 (ddd, J=10.9, 8.9, 4.2 Hz, 1H), 4.16 (ddd, J=10.9, 4.6, 4.6 Hz, 1H), 6.74 (d, J=1.4 Hz, 1H), 7.05 (d, J=1.4 Hz, 1H).

Step 9

Compound (28) (141 mg), Compound (29) (149 mg), palladium (0) tetrakis triphenylphosphine complex (118 mg) and sodium carbonate (217 mg) was added in a eggplant flask. After nitrogen gas replacement was carried out, dioxane (5 ml) and water (0.2 ml) were added and the mixture was stirred at 110° C. for 7 hours. After the reaction mixture was allowed to cool to room temperature, the mixture was acidified with water and 2 mol/L aqueous solution of hydrochloric acid. The solution was back-extracted with ethyl acetate to remove an impure material. The aqueous layer was alkalinized with potassium carbonate and extracted with ethyl acetate. The organic layer was filtered through Celite and dried over sodium sulfate. The solvent was evaporated under reduced pressure and the obtained residue was purified by chromatography and recrystallized to give Compound (1-55) (11.5 mg).

The following compounds are prepared in a similar manner to the above. In the tables, RT means retention time (minute) and D means deuterium.

TABLE 1-1

| No. | Structure | NMR (solvent: shift value ascending order) | MS [M + 1] | LC/MS RT |
|---|---|---|---|---|
| I-1 | 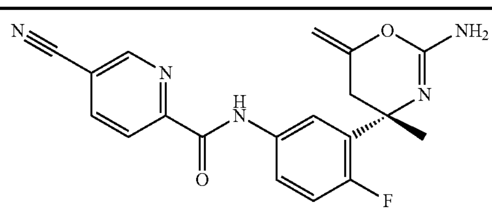 | 1H-NMR (DMSO-d6) δ: 1.55 (3H, s), 2.72 (1H, d, 14.4 Hz), 2.81 (1H, d, 14.4 Hz), 4.14 (2H, br), 4.20 (1H, s), 4.53 (1H, s), 7.06 (1H, dd, J = 11.5, 9.0 Hz), 7.71 (1H, dd, J = 6.9, 3.0 Hz), 7.96 (1H, ddd, J = 9.0, 4.2, 3.0 Hz), 8.19 (1H, dd, J = 8.1, 1.8 Hz), 8.42 (1H, d, J = 8.1 Hz), 8.88 (1H, d, J = 1.8 Hz), 9.85 (1H, s) | | |

TABLE 1-1-continued

| No. | Structure | NMR (solvent: shift value ascending order) | MS [M + 1] | LC/MS RT |
|---|---|---|---|---|
| I-2 | (5-chloropyridine-2-carboxamide derivative) | 1H-NMR (CDCl3) δ: 1.54 (3H, s), 2.71 (1H, d, J = 14.4 Hz), 2.80 (1H, d, J = 14.4 Hz), 4.15 (2H, br), 4.19 (1H, d, J = 0.9 Hz), 4.52 (1H, d, J = 0.9 Hz), 7.04 (1H, dd, J = 11.7, 8.8 Hz), 7.65 (1H, dd, J = 6.9, 2.9 Hz), 7.87 (1H, dd, J = 8.4, 2.4 Hz), 7.98 (1H, ddd, J = 8.8, 4.2, 2.9 Hz), 8.23 (1H, d, J = 8.4, 0.6 Hz), 8.55 (1H, d, J = 2.4, 0.6 Hz), 9.82 (1H, s) | 375, 377 | 1.27 |
| I-3 | (5-methoxypyrazine-2-carboxamide derivative) | 1H-NMR (CDCl3) δ: 1.54 (3H, s), 2.71 (1H, d, J = 14.2 Hz), 2.80 (1H, d, J = 14.2 Hz), 4.06 (3H, s), 4.16 (2H, br), 4.19 (1H, d, J = 0.9 Hz), 4.52 (1H, d, J = 0.9 Hz), 7.03 (1H, dd, J = 11.6, 8.8 Hz), 7.62 (1H, dd, J = 7.0, 2.8 Hz), 7.97 (1H, ddd, J = 8.8, 4.0, 2.8 Hz), 8.13 (1H, d, J = 1.4 Hz), 9.00 (1H, d, J = 1.4 Hz), 9.49 (1H, s) | 372 | 1.13 |
| I-4 | (3,5-dichloropyridine-2-carboxamide derivative) | 1H-NMR (CDCl3) δ: 1.53 (3H, s), 2.71 (1H, d, J = 14.1 Hz), 2.81 (1H, d, J = 14.1 Hz), 4.18 (2H, br), 4.20 (1H, s), 4.53 (1H, s), 7.03 (1H, dd, J = 11.6, 8.8 Hz), 7.56 (1H, dd, J = 6.9, 2.6 Hz), 7.89 (1H, J = 2.1 Hz), 8.03 (1H, ddd, J = 8.8, 4.0, 2.6 Hz), 8.44 (1H, d, J = 2.1 Hz), 9.72 (1H, s) | 409, 411 | 1.26 |
| I-5 | (3,5-difluoropyridine-2-carboxamide derivative) | 1H-NMR (CDCl3) δ: 1.54 (3H, d, J = 0.9 Hz), 2.71 (1H, d, J = 14.4 Hz), 2.80 (1H, d, J = 14.4 Hz), 4.15 (2H, br), 4.20 (1H, d, J = 1.5 Hz), 4.52 (1H, d, J = 1.5 Hz), 7.03 (1H, dd, J = 11.6, 8.8 Hz), 7.38 (1H, ddd, J = 10.2, 8.4, 2.1 Hz), 7.59 (1H, dd, J = 6.9, 2.8 Hz), 8.00 (1H, ddd, J = 8.8, 4.0, 2.8 Hz), 8.34 (1H, d, J = 2.1 Hz), 9.59 (1H, s) | 377 | 1.12 |
| I-6 | (5-cyanopyridine-2-carboxamide derivative) | 1H-NMR (CDCl3) δ: 1.59 (3H, d, J = 1.2 Hz), 2.14 (1H, ddd, J = 13.8, 9.6, 4.0 Hz), 2.38 (1H, ddd, J = 13.8, 5.4, 3.3 Hz), 3.89 (1H, ddd, J = 10.9, 9.6, 3.3 Hz), 4.19 (1H, ddd, J = 10.9, 5.4, 4.0 Hz), 7.06 (1H, dd, J = 11.5, 8.8 Hz), 7.56 (1H, dd, J = 7.0, 2.8 Hz), 8.03 (1H, ddd, J = 8.8, 4.0, 2.8 Hz), 8.19 (1H, dd, J = 8.2, 2.0 Hz), 8.42 (1H, dd, J = 8.2, 0.8 Hz), 8.89 (1H, dd, J = 2.0, 0.8 Hz), 9.86 (1H, s) | | |

TABLE 1-2

| No. | Structure | NMR (solvent: shift value ascending order) | MS [M + 1] | LC/MS RT |
|---|---|---|---|---|
| I-7 | (5-cyanopyridine-2-carboxamide derivative with Cl) | 1H-NMR (CDCl3) δ: 1.70 (3H, s), 2.14 (1H, ddd, J = 13.8, 9.6, 4.0 Hz), 2.68 (1H, ddd, J = 14.2, 6.0, 3.4 Hz), 3.84 (1H, ddd, J = 11.6, 8.3, 2.5 Hz), 4.15 (1H, ddd, J = 10.9, 6.1, 4.0 Hz), 7.38 (1H, d, J = 8.6 Hz), 7.77 (1H, d, J = 2.7 Hz), 8.01 (1H, dd, J = 8.6, 2.7 Hz), 8.19 (1H, dd, J = 8.1, 2.0 Hz), 8.42 (1H, dd, J = 8.1, 0.8 Hz), 8.89 (1H, dd, J = 2.0, 0.8 Hz), 9.89 (1H, s) | | |
| I-8 | (5-chloropyridine-2-carboxamide derivative) | 1H-NMR (CDCl3) δ: 1.59 (3H, d, J = 1.1 Hz), 2.12 (1H, ddd, J = 13.8, 9.6, 3.9 Hz), 2.36 (1H, ddd, J = 13.8, 5.4, 3.3 Hz), 3.87 (1H, ddd, J = 10.9, 9.6, 3.3 Hz), 4.17 (1H, ddd, J = 10.9, 5.4, 3.9 Hz), 7.04 (1H, dd, J = 11.6, 8.7 Hz), 7.52 (1H, dd, J = 6.9, 2.9 Hz), 7.87 (1H, dd, J = 8.4, 2.4 Hz), 8.03 (1H, ddd, J = 8.7, 4.1, 2.9 Hz), 8.23 (1H, d, J = 8.4, 0.8 Hz), 8.55 (1H, d, J = 2.4, 0.8 Hz), 9.82 (1H, s) | 363, 365 | 1.15 |

TABLE 1-2-continued

| No. | Structure | NMR (solvent: shift value ascending order) | MS [M + 1] | LC/MS RT |
|---|---|---|---|---|
| I-9 | 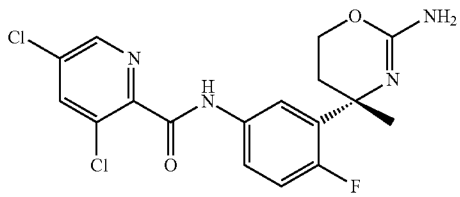 [SMILES: C[C@@]1(c2cc(NC(=O)c3ncc(Cl)cc3Cl)ccc2F)CCOC(N)=N1] | 1H-NMR (CDCl3) δ: 1.58 (3H, d, J = 1.1 Hz), 2.12 (1H, ddd, J = 14.4, 9.6, 3.9 Hz), 2.35 (1H, ddd, J = 14.4, 5.4, 3.3 Hz), 3.87 (1H, ddd, J = 11.1, 9.6, 3.3 Hz), 4.15 (1H, ddd, J = 11.1, 5.4, 3.9 Hz), 7.03 (1H, dd, J = 11.4, 8.9 Hz), 7.40 (1H, dd, J = 6.9, 2.9 Hz), 7.89 (1H, d, J = 2.1 Hz), 8.10 (1H, ddd, J = 8.9, 4.1, 2.9 Hz), 8.47 (1H, d, J = 2.1 Hz), 9.72 (1H, s) | 397, 399 | 1.19 |
| I-10 | 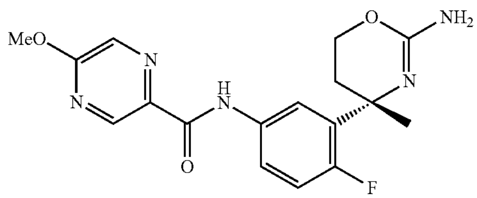 [SMILES: COc1cnc(C(=O)Nc2ccc(F)c([C@]3(C)CCOC(N)=N3)c2)cn1] | 1H-NMR (CDCl3) δ: 1.60 (3H, d, J = 1.2 Hz), 2.12 (1H, ddd, J = 13.8, 9.6, 3.9 Hz), 2.36 (1H, ddd, J = 13.8, 5.4, 3.3 Hz), 3.87 (1H, ddd, J = 10.8, 9.6, 3.3 Hz), 4.06 (3H, s), 4.17 (1H, ddd, J = 10.8, 5.4, 3.9 Hz), 7.04 (1H, dd, J = 11.7, 8.9 Hz), 7.48 (1H, dd, J = 7.2, 2.8 Hz), 8.03 (1H, ddd, J = 8.9, 4.2, 2.8 Hz), 8.15 (1H, d, J = 1.3 Hz), 9.00 (1H, d, J = 1.3 Hz), 9.50 (1H, s) | 360 | 1.06 |
| I-11 | 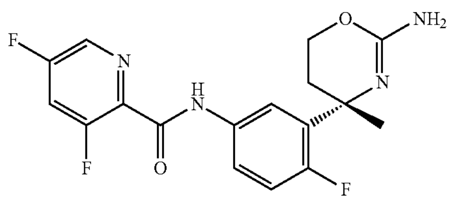 [SMILES: C[C@@]1(c2cc(NC(=O)c3ncc(F)cc3F)ccc2F)CCOC(N)=N1] | 1H-NMR (CDCl3) δ: 1.62 (3H, d, J = 1.2 Hz), 2.14 (1H, ddd, J = 14.1, 9.9, 4.2 Hz), 2.39 (1H, ddd, J = 14.1, 5.4, 3.0 Hz), 3.90 (1H, ddd, J = 11.1, 9.9, 3.0 Hz), 4.19 (1H, ddd, J = 11.1, 5.4, 4.2 Hz), 7.05 (1H, dd, J = 11.6, 8.7 Hz), 7.38 (1H, dd, J = 10.2, 8.4, 2.1 Hz), 7.45 (1H, dd, J = 7.0, 2.8 Hz), 8.07 (1H, ddd, J = 8.7, 4.1, 2.8 Hz), 8.36 (1H, d, J = 2.1 Hz), 9.61 (1H, s) | 365 | 1.00 |

TABLE 1-3

| No. | Structure | NMR (solvent: shift value ascending order) |
|---|---|---|
| I-12 | 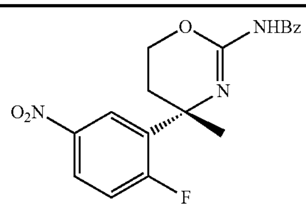 | $^1$H-NMR (CDCl$_3$) δ: 1.58 (3H, s), 2.22 (2H, t, J = 5.4 Hz), 3.86-3.94 (1H, m), 4.15-4.25 (3H, m), 7.14 (1H, dd, J = 10.7, 8.9 Hz), 8.09-8.15 (1H, m), 8.62 (1H, dd, J = 7.0, 3.0 Hz). |
| I-13 | 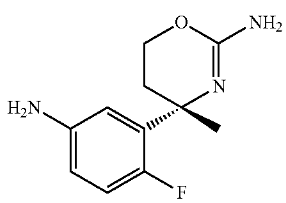 [SMILES: C[C@@]1(c2cc(N)ccc2F)CCOC(N)=N1] | $^1$H-NMR (CDCl$_3$) δ: 1.54 (3H, s), 1.97-2.07 (1H, m), 2.30-2.38 (1H, m), 3.54 (2H, brs), 3.83 (1H, dt, J = 3.2, 10.6 Hz), 4.10 (1H, ddd, 10.6, 4.7, 4.2 Hz), 6.48 (1H, ddd, 8.4, 3.7, 3.2 Hz), 6.78 (1H, dd, J = 11.8, 8.4 Hz), 6.86 (1H, dd, J = 6.9, 3.0 Hz). |
| I-14 | 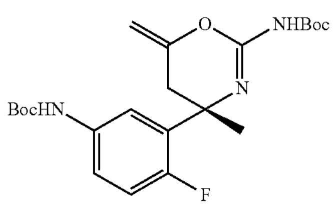 [SMILES: C=C1C[C@@](C)(c2cc(NC(=O)OC(C)(C)C)ccc2F)N=C(NC(=O)OC(C)(C)C)O1] | $^1$H-NMR (CDCl$_3$) δ: 1.52 (9H, s), 1.54 (9H, s), 1.75 (3H, s), 2.70 (1H, d, J = 14.0 Hz), 3.20 (1H, d, J = 14.0 Hz), 4.25 (1H, s), 4.66 (1H, s), 6.48 (1H, s), 6.96 (1H, br), 7.02 (1H, dd, J = 11.4, 9.0 Hz), 7.51 (1H, m), 10.0 (1H, s). |
| I-15 | 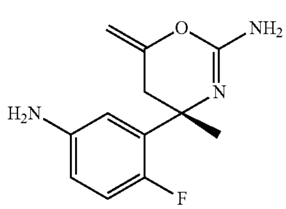 [SMILES: C=C1C[C@@](C)(c2cc(N)ccc2F)N=C(N)O1] | $^1$H-NMR (CDCl$_3$) δ: 1.63 (3H, s), 2.69 (1H, d, J = 14.1 Hz), 3.02 (1H, d, J = 14.1 Hz), 3.58 (2H, s), 4.28 (1H, s), 4.60 (1H, s), 6.51 (1H, ddd, J = 8.8, 3.2, 2.8 Hz), 6.72 (1H, dd, J = 6.9, 2.8 Hz), 6.81 (1H, dd, J = 11.7, 8.8 Hz). |

TABLE 1-3-continued

| No. | Structure | NMR (solvent: shift value ascending order) |
|---|---|---|
| I-16 | 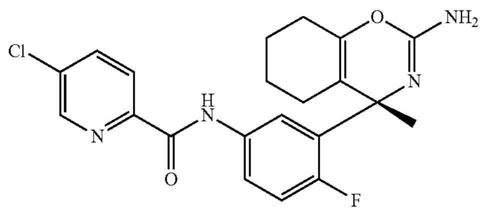 | |
| I-17 | 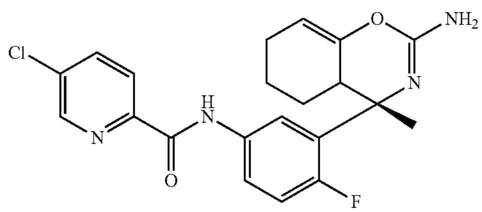 | |
| I-18 | 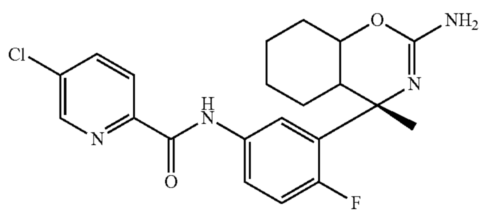 [SMILES: C[C@]1(c2cc(NC(=O)c3ccc(Cl)cn3)ccc2F)N=C(N)OC2CCCCC21] | |
| I-19 | 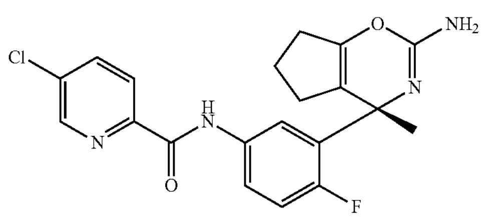 [SMILES: C[C@]1(c2cc(NC(=O)c3ccc(Cl)cn3)ccc2F)N=C(N)OC2=C1CCC2] | |

TABLE 1-4

| No. | Structure |
|---|---|
| I-20 | 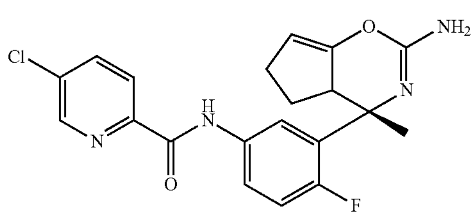 |
| I-21 | 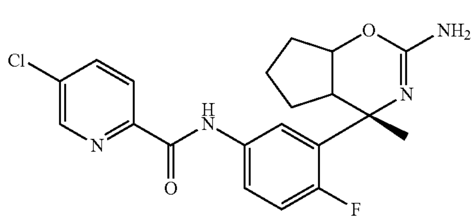 |
| I-22 | |
| I-23 | |

TABLE 1-4-continued
| No. | Structure |
|---|---|
| I-24 | 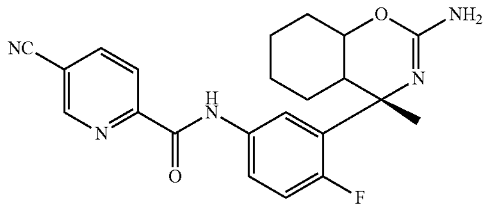 [SMILES: C[C@]1(c2cc(NC(=O)c3ccc(C#N)cn3)ccc2F)N=C(N)OC2CCCCC21] |
| I-25 | 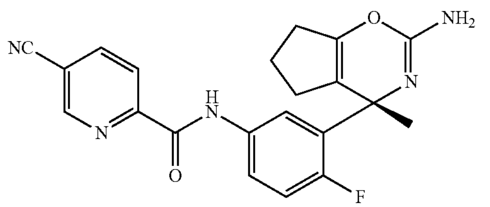 [SMILES: C[C@]1(c2cc(NC(=O)c3ccc(C#N)cn3)ccc2F)N=C(N)OC2=C1CCC2] |
| I-26 | 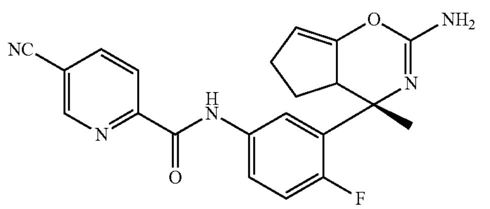 |
| I-27 | 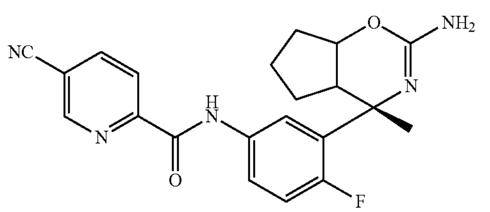 [SMILES: C[C@]1(c2cc(NC(=O)c3ccc(C#N)cn3)ccc2F)N=C(N)OC2CCCC21] |
| I-28 | 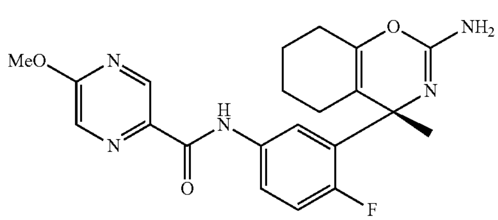 [SMILES: COc1cnc(C(=O)Nc2ccc(F)c([C@@]3(C)N=C(N)OC4=C3CCCC4)c2)cn1] |
| I-29 | 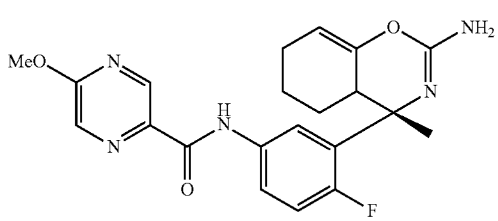 [SMILES: COc1cnc(C(=O)Nc2ccc(F)c([C@@]3(C)N=C(N)OC4=CCCCC43)c2)cn1] |
| I-30 | 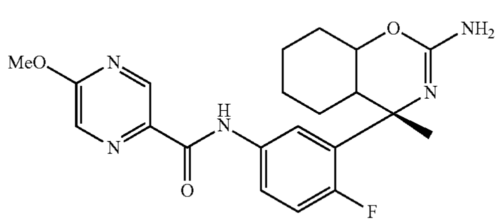 [SMILES: COc1cnc(C(=O)Nc2ccc(F)c([C@@]3(C)N=C(N)OC4CCCCC43)c2)cn1] |
TABLE 1-4-continued
| No. | Structure |
|---|---|
| I-31 |  |
| I-32 | |
| I-33 | |
| I-34 | |
| I-35 | |
TABLE 1-5
| No. | Structure |
|---|---|
| I-36 | 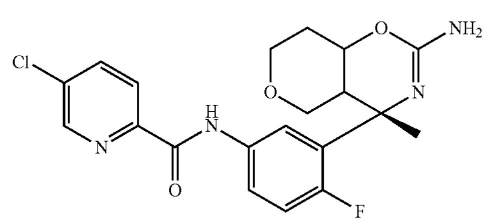 [SMILES: C[C@]1(c2cc(NC(=O)c3ccc(Cl)cn3)ccc2F)N=C(N)OC2CCOCC21] |

TABLE 1-5-continued

| No. | Structure |
|---|---|
| I-37 | 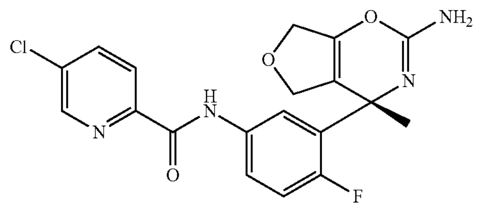 [SMILES: C[C@]1(c2cc(NC(=O)c3ccc(Cl)cn3)ccc2F)N=C(N)OC2=C1COC2] |
| I-38 | 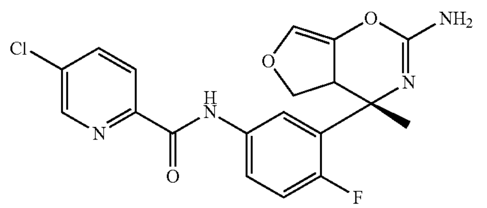 |
| I-39 | 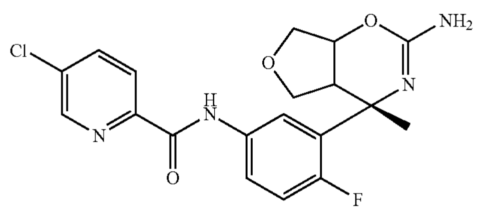 [SMILES: C[C@]1(c2cc(NC(=O)c3ccc(Cl)cn3)ccc2F)N=C(N)OC2COCC21] |
| I-40 | 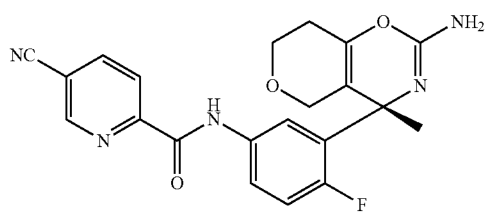 |
| I-41 | 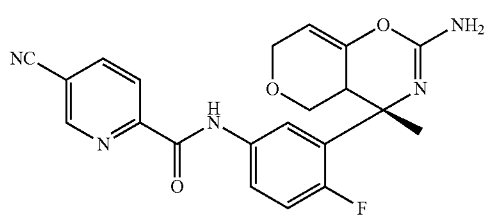 [SMILES: C[C@]1(c2cc(NC(=O)c3ccc(C#N)cn3)ccc2F)N=C(N)OC2=CCOCC21] |
| I-42 | 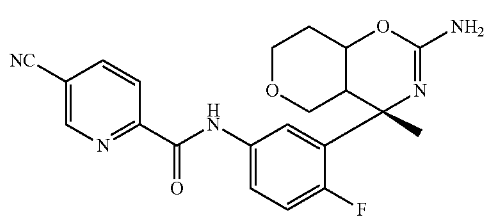 [SMILES: C[C@]1(c2cc(NC(=O)c3ccc(C#N)cn3)ccc2F)N=C(N)OC2CCOCC21] |
| I-43 | 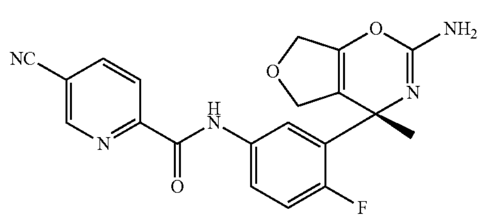 [SMILES: C[C@]1(c2cc(NC(=O)c3ccc(C#N)cn3)ccc2F)N=C(N)OC2=C1COC2] |

TABLE 1-5-continued

| No. | Structure |
|---|---|
| I-44 | 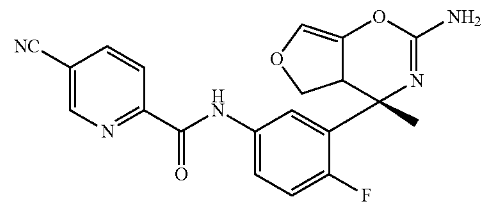 [SMILES: C[C@]1(c2cc(NC(=O)c3ccc(C#N)cn3)ccc2F)N=C(N)OC2=COCC21] |
| I-45 | 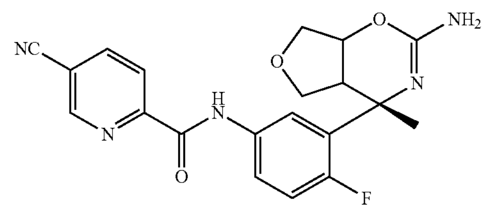 [SMILES: C[C@]1(c2cc(NC(=O)c3ccc(C#N)cn3)ccc2F)N=C(N)OC2COCC21] |
| I-46 | 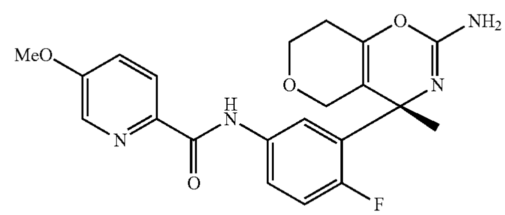 [SMILES: COc1ccc(C(=O)Nc2ccc(F)c([C@@]3(C)N=C(N)OC4=C3COCC4)c2)nc1] |
| I-47 | 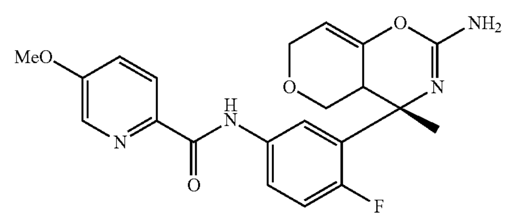 [SMILES: COc1ccc(C(=O)Nc2ccc(F)c([C@@]3(C)N=C(N)OC4=CCOCC43)c2)nc1] |
| I-48 | 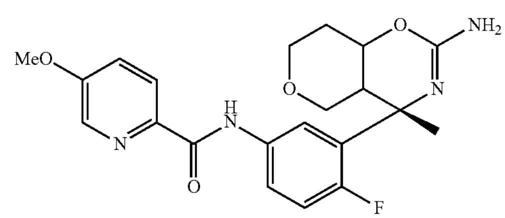 [SMILES: COc1ccc(C(=O)Nc2ccc(F)c([C@@]3(C)N=C(N)OC4CCOCC43)c2)nc1] |
| I-49 | 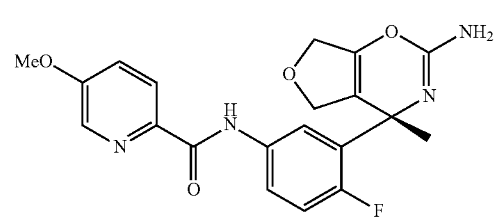 [SMILES: COc1ccc(C(=O)Nc2ccc(F)c([C@@]3(C)N=C(N)OC4=C3COC4)c2)nc1] |

TABLE 1-5-continued

| No. | Structure |
|---|---|
| I-50 | (structure) |
| I-51 | (structure) |

TABLE 1-6

| No. | Structure | NMR (solvent: shift value ascending order) | MS [M + 1] | LC/MS RT |
|---|---|---|---|---|
| I-52 | (structure) | 1H-NMR (CDCl3) δ: 2.37-2.46 (2H, m). 3.91 (1H, td, J = 9.9, 3.9 Hz), 4.21-4.31 (3H, m), 6.06 (1H, t, J = 56.1 Hz), 7.12 (1H, dd, J = 11.4, 8.9 Hz), 7.70 (1H, J = 6.9, 2.8 Hz), 8.13 (1H, ddd, J = 8.9, 4.2, 2.8 Hz), 8.20 (1H, dd, J = 8.1, 2.1 Hz), 8.42 (1H, dd, J = 8.14, 0.9 Hz), 8.89 (1H, dd, J = 2.1, 0.9 Hz), 9.89 (1H, s) | 390 | 0.96 |
| I-53 | (structure) | 1H-NMR (CDCl3) δ: 2.33-2.46 (2H, m). 3.91 (1H, td, J = 10.5, 4.2 Hz), 4.21-4.30 (3H, m), 6.06 (1H, t, J = 56.1 Hz), 7.11 (1H, dd, J = 11.4, 8.9 Hz), 7.70 (1H, J = 6.9, 2.7 Hz), 8.12 (1H, ddd, J = 8.9, 3.9, 2.7 Hz), 8.20 (1H, dd, J = 8.1, 1.8 Hz), 8.42 (1H, d, J = 8.1 Hz), 8.89 (1H, d, J = 1.8 Hz), 9.89 (1H, s) | | |
| I-54 | (structure) | 1H-NMR (CDCl3) δ: 1.61 (s, 3H), 1.80 (s, 3H), 4.38 (br, 2H), 5.27 (dd, J = 2.8, 1.3 Hz, 1H), 7.03 (dd, J = 11.4, 8.9 Hz, 1H), 7.67 (dd, J = 6.9, 2.9 Hz, 1H), 7.86-7.92 (m, 1H), 8.17 (dd, J = 8.1, 2.0 Hz, 1H), 8.39 (d, J = 8.1 Hz, 1H), 8.82 (d, J = 2.0 Hz, 1H), 9.81 (brs, 1H). | 366 | 0.99 |
| I-55 | (structure) | 1H-NMR (CDCl3) δ: 1.63 (s, 3H), 2.09 (s, 3H), 2.11 (ddd, J = 13.8, 9.7, 4.5 Hz, 1H), 2.17 (ddd, J = 13.8, 4.5, 3.7 Hz, 1H), 4.08 (ddd, J = 10.6, 9.7, 3.7 Hz, 1H), 4.21 (ddd, J = 10.6, 4.5, 4.5 Hz, 1H), 7.10 (d, J = 1.4 Hz, 1H), 7.34 (d, J = 1.4 Hz, 1H), 7.82 (dd, J = 2.1, 1.8 Hz, 1H), 8.49 (d, J = 1.8 Hz, 1H), 8.69 (d, J = 2.1 Hz, 1H). | 311 | 1.01 |
| I-56 | (structure) | 1H-NMR (CDCl3) δ: 1.60 (3H, d, J = 0.9 Hz), 1.79 (3H, d, J = 0.9 Hz), 5.24-5.25 (1H, m), 7.02 (1H, dd, J = 11.4, 8.8 Hz), 7.37 (1H, ddd, J = 10.5, 8.1, 2.1 Hz), 7.53 (1H, dd, J = 6.9, 2.9 Hz), 7.93 (1H, ddd, J = 8.8, 4.2, 2.9 Hz), 8.33 (1H, d, J = 2.1 Hz), 9.57 (1H, s). | 377 | 1.09 |

TABLE 1-6-continued

| No. | Structure | NMR (solvent: shift value ascending order) | MS [M + 1] | LC/MS RT |
|---|---|---|---|---|
| I-57 | 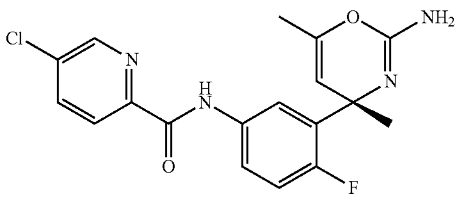 [SMILES: CC1=C[C@@](C)(c2cc(NC(=O)c3ccc(Cl)cn3)ccc2F)N=C(N)O1] | 1H-NMR (CDCl3) δ: 1.61 (3H, d, J = 0.9 Hz), 1.80 (3H, d, J = 0.9 Hz), 4.16 (2H, br s), 5.24-5.26 (1H, m), 7.03 (1H, dd, J = 11.3, 8.7 Hz), 7.61 (1H, dd, J = 7.0, 2.7 Hz), 7.84-7.92 (2H, m), 8.23 (1H, d, J = 8.4 Hz), 8.54 (1H, d, J = 2.1 Hz), 9.80 (1H, s). | 375 | 1.2 |

TABLE 1-7

| No. | Structure | NMR (solvent: shift value ascending order) | MS [M + 1] | LC/MS RT |
|---|---|---|---|---|
| I-58 | 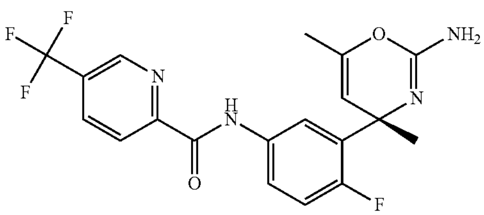 [SMILES: CC1=C[C@@](C)(c2cc(NC(=O)c3ccc(C(F)(F)F)cn3)ccc2F)N=C(N)O1] | 1H-NMR (CDCl3) δ: 1.62 (3H, d, J = 1.2 Hz), 1.80 (3H, d, J = 1.1 Hz), 5.26-5.28 (1H, m), 7.03 (1H, dd, J = 11.4, 8.8 Hz), 7.64 (1H, dd, J = 6.9, 2.8 Hz), 7.91 (1H, ddd, J = 8.8, 4.1, 2.8 Hz), 8.14 (1H, dd, J = 8.2, 1.6 Hz), 8.40 (1H, d, J = 8.2 Hz), 8.84-8.85 (1H, m), 9.90 (1H, s). | 409 | 1.32 |
| I-59 | 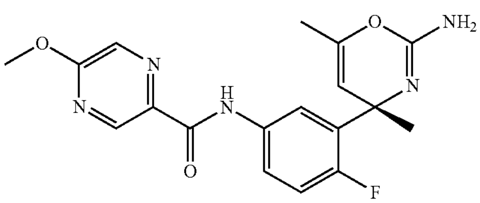 [SMILES: COc1cnc(C(=O)Nc2ccc(F)c([C@]3(C)C=C(C)OC(N)=N3)c2)cn1] | 1H-NMR (CDCl3) δ: 1.60 (3H, d, J = 0.9 Hz), 1.79 (3H, d, J = 1.1 Hz), 4.06 (3H, s), 5.24-5.25 (1H, m), 7.02 (1H, dd, J = 11.4, 8.8 Hz), 7.57 (1H, dd, J = 6.9, 2.9 Hz), 7.89 (1H, ddd, J = 8.8, 4.1, 2.9 Hz), 8.12 (1H, d, J = 1.2 Hz), 8.99 (1H, d, J = 1.2 Hz), 9.47 (1H, s). | 372 | 1.07 |
| I-60 | 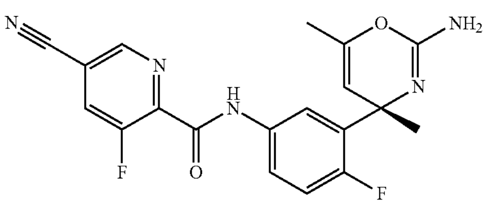 [SMILES: CC1=C[C@@](C)(c2cc(NC(=O)c3ncc(C#N)cc3F)ccc2F)N=C(N)O1] | 1H-NMR (CDCl3) δ: 1.61 (3H, s), 1.80 (3H, s), 5.26 (1H, d, J = 1.1 Hz), 7.04 (1H, dd, J = 11.2, 8.8 Hz), 7.55 (1H, dd, J = 6.8, 2.8 Hz), 7.87-7.95 (2H, m), 8.68-8.68 (1H, m), 9.62 (1H, s). | 384 | 1.07 |
| I-61 | 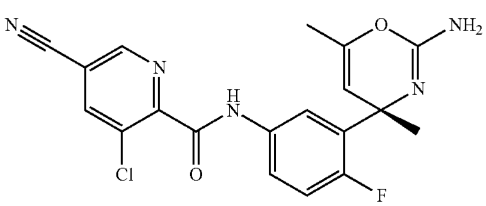 | 1H-NMR (CDCl3) δ: 1.61 (3H, s), 1.80 (3H, s), 5.26-5.27 (1H, m), 7.03 (1H, dd, J = 11.2, 8.8 Hz), 7.53 (1H, dd, J = 6.7, 2.4 Hz), 7.94 (1H, ddd, J = 8.8, 3.6, 2.4 Hz), 8.14-8.15 (1H, m), 8.73 (1H, d, J = 1.7 Hz), 9.68 (1H, br s). | 400 | 1.15 |
| I-62 | 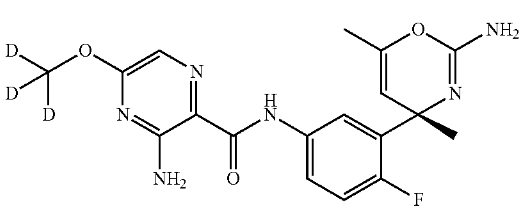 [SMILES: [2H]C([2H])([2H])Oc1cnc(C(=O)Nc2ccc(F)c([C@]3(C)C=C(C)OC(N)=N3)c2)c(N)n1] | 1H-NMR (CDCl3) δ: 1.67 (3H, s), 1.82 (3H, s), 5.27-5.28 (1H, m), 5.68 (2H, br s), 7.00 (1H, dd, J = 11.3, 8.8 Hz), 7.44 (1H, d, J = 0.9 Hz), 7.52 (1H, dd, J = 7.0, 2.6 Hz), 7.77 (1H, ddd, J = 8.8, 3.6, 2.6 Hz), 9.50 (1H, s). | 390 | 1.25 |

TABLE 1-7-continued

| No. | Structure | NMR (solvent: shift value ascending order) | MS [M + 1] | LC/MS RT |
|---|---|---|---|---|
| I-63 | 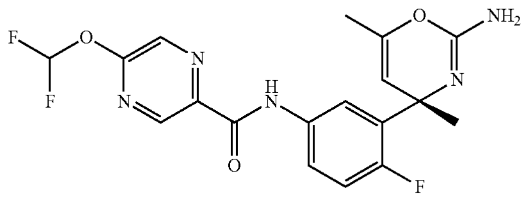 [SMILES: CC1=C[C@@](C)(c2cc(NC(=O)c3cnc(OC(F)F)cn3)ccc2F)N=C(N)O1] | 1H-NMR (CDCl3) δ: 1.60 (3H, s), 1.79 (3H, s), 5.25 (1H, d, J = 1.1 Hz), 7.03 (1H, dd, J = 11.3, 8.8 Hz), 7.50 (0H, t, J = 71.0 Hz), 7.59 (1H, dd, J = 6.8, 2.9 Hz), 7.87 (1H, ddd, J = 8.8, 3.9, 2.9 Hz), 8.30 (1H, d, J = 1.1 Hz), 9.04 (1H, d, J = 0.9 Hz), 9.44 (1H, s). | 407 | 1.27 |

TABLE 1-8

| No. | Structure | NMR (solvent: shift value ascending order) | MS [M + 1] | LC/MS RT |
|---|---|---|---|---|
| I-64 | 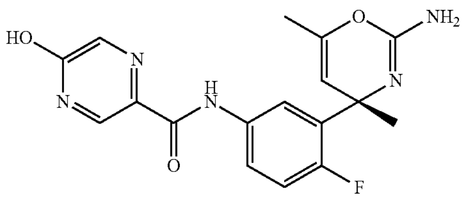 [SMILES: CC1=C[C@@](C)(c2cc(NC(=O)c3cnc(O)cn3)ccc2F)N=C(N)O1] | 1H-NMR (DMSO-d6) δ: 1.46 (3H, s), 1.75 (3H, s), 5.14 (1H, d, J = 1.5 Hz), 5.70-5.75 (2H, m), 7.04 (1H, dd, J = 11.7, 9.1 Hz), 7.62-7.70 (2H, m), 7.79 (1H, d, J = 7.6 Hz), 8.24 (1H, s), 9.85 (1H, s). | 358 | 0.84 |
| I-65 | 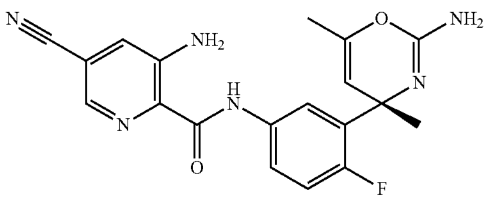 [SMILES: CC1=C[C@@](C)(c2cc(NC(=O)c3ncc(C#N)cc3N)ccc2F)N=C(N)O1] | 1H-NMR (CDCl3) δ: 1.63 (3H, d, J = 0.9 Hz), 1.81 (3H, d, J = 1.1 Hz), 5.28-5.29 (1H, m), 6.54 (2H, br s), 7.01 (1H, dd, J = 11.3, 9.3 Hz), 7.29 (1H, d, J = 1.7 Hz), 7.65-7.69 (2H, m), 8.03 (1H, d, J = 1.7 Hz), 9.89 (1H, s). | 381 | 1.24 |
| I-66 | 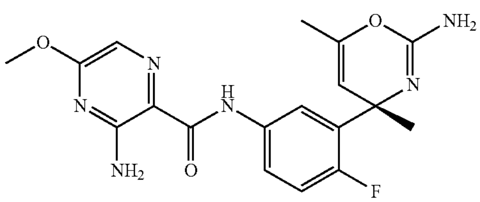 [SMILES: COc1cnc(C(=O)Nc2ccc(F)c([C@]3(C)C=C(C)OC(N)=N3)c2)c(N)n1] | 1H-NMR (CDCl3) δ: 1.68 (3H, s), 1.83 (3H, s), 3.93 (3H, s), 4.64 (2H, br s), 5.29 (1H, d, J = 4.3 Hz), 7.00 (1H, dd, J = 11.4, 8.8 Hz), 7.51 (1H, dd, J = 7.0, 3.0 Hz), 7.78 (1H, ddd, J = 8.8, 4.0, 3.0 Hz), 9.50 (1H, s). | 387 | 1.22 |
| I-67 | 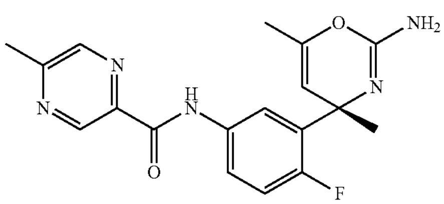 [SMILES: CC1=C[C@@](C)(c2cc(NC(=O)c3cnc(C)cn3)ccc2F)N=C(N)O1] | 1H-NMR (CDCl3) δ: 1.61 (3H, d, J = 1.2 Hz), 1.79 (3H, d, J = 1.1 Hz), 2.68 (3H, s), 5.25 (1H, dd, J = 2.7, 1.1 Hz), 7.03 (1H, dd, J = 11.3, 8.8 Hz), 7.60 (1H, dd, J = 6.9, 2.8 Hz), 7.90 (1H, ddd, J = 8.8, 4.1, 2.8 Hz), 8.41 (1H, d, J = 1.1 Hz), 9.34 (1H, d, J = 1.4 Hz), 9.60 (1H, s). | 356 | 0.96 |

The effect of the present compound is confirmed by the following test Examples.

Test Example 1

Assay of BACE1 Inhibiting Activity 48.5 μL of substrate peptide solution (Biotin-XSEVNLDAEFRHDSGC-Eu: X=ε-amino-n-capronic acid, Eu=Europium cryptate) was added to each well of 96-hole half-area plate (a black plate: Costar), and after addition of 0.5 μl of the test compound (dissolved in N,N'-dimethyl formaldehyde) and 1 μl of Recombinant human BACE1 (R&D Systems), the reaction mixture was incubated at 30° C. for 3 hours. The substrate peptide was synthesized by reacting Cryptate TBPCOOH mono SMP (CIS bio international) with Biotin-XSEVNLDAEFRHDSGC (Peptide Institute, Inc.). The final concentrations of the substrate peptide and Recombinant human BACE1 were adjusted to 18 nmol/L and 7.4 nmol/L, respectively, and the reaction was performed in sodium acetate buffer (50 mmol/L sodium acetate, pH 5.0, 0.008% Triton X-100).

After the incubation for reaction, 50 μl of 8.0 μg/ml Streptavidin-XL665 (CIS bio international) dissolved in phosphate buffer (150 mmol/L $K_2$ $HPO_4$.$KH_2PO_4$, pH 7.0, 0.008% Triton X-100, 0.8 mol/L KF) was added to each well and left stand at 30° C. for an hour. After then, fluorescence intensity was measured (excitation wavelength: 320 nm, measuring wavelength: 620 nm and 665 nm) using Wallac 1420 multilabel counter (Perkin Elmer life sciences). Enzymatic activity was determined from counting ratio of each wavelength (10,000×Count 665/Count 620) and 50% inhibitory concentration against the enzymatic activity was calculated.
Compound I-1: $IC_{50}$ 0.0473 μmol/L
Compound I-2: $IC_{50}$ 0.027 μmol/L
Compound I-6: $IC_{50}$ 0.054 μmol/L
Compound I-53: $IC_{50}$ 0.046 μmol/L
Compound I-54: $IC_{50}$ 0.097 μmol/L
Compounds I-3, 4 and 5, 7 to 11, 52 and 55 to 60 showed the $IC_{50}$ value of 30 μmol/L or less.

Test Example 2

Measurement of β-Amyloid (Aβ) Production Inhibitory Effect in Cell

Neuroblastoma SH-SY5Y cells (SH/APPwt) with human wild-type β-APP excessively expressed therein were prepared at 8×105 cells/mL, and 150 μl portions thereof were inoculated into each well of a 96-well culture plate (Falcon). The cells were cultured for 2 hours at 37° C. in a 5% gaseous carbon dioxide incubator. Then, a solution which had been preliminarily prepared by adding and suspending the test compound (DMSO (dimethyl sulfoxide) solution) so as to be 2 μl/50 μl medium was added to the cell sap. Namely, the final DMSO concentration was 1%, and the amount of the cell culture was 200 μl. After the incubation was performed for 24 hours from the addition of the test compound, 100 μl of the culture supernatant was collected from each fraction. The amount of the Aβ in each fraction was measured.

The Aβ amount was measured as follows. 10 μl of a homogeneous time resolved fluorescence (HTRF) measurement reagent (Amyloid β 1-40 peptide; IBA Molecular Holding, S.A.) and 10 μl of the culture supernatant were put into a 384-well half area microplate (black microplate, Costar) and mixed with each other, and then left standing overnight at 4° C. while the light was shielded. Then, the fluorescence intensity (excitation wavelength: 337 nm, measurement wavelength: 620 nm and 665 nm) was measured with a Wallac 1420 multilabel counter (Perkin Elmer life sciences). The Aβ amount was determined from the count rate at each measurement wavelength (10000×Count 665/Count 620), and the amount needed to inhibit Aβ production by 50% ($IC_{50}$) was calculated from at least six different dosages.
Compound I-1: $IC_{50}$ 0.0155 μmol/L Test Example 3

Lowering Effect on Brain 13 Amyloid in Rats

A test compound is suspended in 0.5% methylcellulose, the final concentration is adjusted to 2 mg/mL, and this is orally administered to male Crj:SD rat (7 to 9 weeks old) at 10 mg/kg. In a vehicle control group, only 0.5% methylcellulose is administered, and an administration test is performed at 3 to 8 animals per group. A brain is isolated 3 hours after administration, a cerebral hemisphere is isolated, a weight thereof is measured, the hemisphere is rapidly frozen in liquid nitrogen, and stored at −80° C. until extraction date. The frozen cerebral hemisphere is transferred to a homogenizer manufactured by Teflon (registered trade name) under ice cooling, a 5-fold volume of a weight of an extraction buffer (containing 1% CHAPS ({3-[(3-chloroamidopropyl)dimethylammonio]-1-propanesulfonate}), 20 mmol/L Tris-HCl (pH 8.0), 150 mmol/L NaCl, Complete (Roche) protease inhibitor) is added, up and down movement is repeated, and this is homogenized to solubilize for 2 minutes. The suspension is transferred to a centrifugation tube, allowed to stand on an ice for 3 hours or more and, thereafter centrifuged at 100,000×g, 4° C. for 20 minutes. After centrifugation, the supernatant is transferred to an ELISA plate (product No. 294-62501, Wako Junyaku Kogyo) for measuring 13 amyloid 40. ELISA measurement is performed according to the attached instruction. The lowering effect is calculated as a ratio compared to the brain β amyloid 40 level of vehicle control group of each test.

Test Example 4

CYP3A4 Fluorescent MBI Test

The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted by a substrate in a K-Pi buffer, NADPH as a co-factor was added to initiate a reaction as an index (without preincubation) and, after a predetermined time of a reaction, acetonitrile/0.5 mol/L Tris(trishydroxyaminomethane)=4/1 was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris(trishydroxyaminomethane) =4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving a drug to a reaction system was adopted as a control (100%), remaining activity (%) was calculated at each concentration of a test drug added as the solution, and $IC_{50}$ was calculated by reverse-presumption by a logistic model using a concentration and an inhibition rate. When a difference between $IC_{50}$ values is 5 μM or more, this was defined as (+), and, when the difference is 3 μM or less, this was defined as (−).
Compound I-52:

Test Example 5

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenytoin (CYP2C19), 5 µmol/L dextromethorphan (CYP2D6), 1 µmol/L terfenadine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, and a test drug in 50 mmol/L Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tolbutamide hydroxide (CYP2C9 metabolite), mephenytoin 4' hydroxide (CYP2C19 metabolite), dextrorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate. 1.53: five kinds >20 µM Test Example 6

FAT Test

Each 20 µL of freeze-stored *Salmonella typhimurium* (TA98 and TA100 strain) is inoculated in 10 mL of liquid nutrient medium (2.5% Oxoid nutrient broth No. 2), and the cultures are incubated at 37° C. under shaking for 10 hours. 9 mL of TA98 culture is centrifuged (2000×g, 10 minutes) to remove medium, and the bacteria is suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4 \cdot 7H_2O$: 0.1 g/L), and the suspension is added to 110 mL of Exposure medium (Micro F buffer containing Biotin: 8 µg/mL, histidine 0.2 µg/mL, glucose: 8 mg/mL) 3.16 mL of TA100 culture is added to 120 mL of Exposure medium to prepare the test bacterial solution. 588 µL of the test bacterial solution (or mixed solution of 498 µl of the test bacterial solution and 90 µL of the S9 mix in the case with metabolic activation system) are mixed with each 12 µL of the following solution: DMSO solution of the test substance (eight dose levels from maximum dose 50 mg/mL at 2-fold ratio); DMSO as negative control; 50 µg/mL of 4-nitroquinoline-1-oxide DMSO solution as positive control for TA98 without metabolic activation system; 0.25 µg/mL of 2-(2-furyl)-3-(5-nitro-2-furyl)acrylamide DMSO solution as positive control for TA100 without metabolic activation system; 40 µg/mL of 2-aminoanthracene DMSO solution as positive control for TA98 with metabolic activation system; or 20 µg/mL of 2-aminoanthracene DMSO solution as positive control for TA100 with metabolic activation system. 12 µL of the solution and 588 µL of the test bacterial solution (a mixed solution of 498 µl of the test bacterial solution and 90 µL of S9 mix with metabolic activation condition) were mixed and incubated at 37° C. under shaking for 90 minutes. 460 µL of the bacterial solution exposed to the test substance is mixed with 2300 µL of Indicator medium (Micro F buffer containing biotin: 8 µg/mL, histidine 0.2 µg/mL, glucose: 8 mg/mL, Bromo Cresol Purple: 37.5 µg/mL), each 50 µL is dispensed into 48 wells per dose in the microwell plates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. The mutagenicity was evaluated by counting the number of the yellow wells among the 48 total wells per dose and comparing with the negative control group. (−) means that mutagenicity is negative and (+) means positive.

Test Example 7

Solubility Test

The solubility of each compound is determined under 1% DMSO addition conditions. A 10 mM solution of the compound is prepared with DMSO, and 6 µL of the compound solution is added to 594 µL of an artificial intestinal juice (water and 118 mL of 0.2 mol/L NaOH reagent are added to 250 mL of 0.2 mol/L potassium dihydrogen phosphate reagent to reach 1000 mL) with a pH of 6.8. The mixture is left standing for 16 hours at 25° C., and the mixture is vacuum-filtered. The filtrate is two-fold diluted with methanol/water=1/1, and the compound concentration in the filtrate is measured with HPLC or LC/MS/MS by the absolute calibration method.

Test Example 8

Metabolism Stability Test

Using a commercially available pooled human hepatic microsomes, a test compound is reacted for a constant time, a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 pit of the reaction solution is added to 100 µL of a methanol/acetonitrile=1/1 (v/v), mixed and centrifuged at 3000 rpm for 15 minutes. The test compound in the supernatant is quantified by LC/MS/MS, and a remaining amount of the test compound after the reaction is calculated, letting a compound amount at 0 minute reaction time to be 100%. 1-53: 100%

Test Example 9 hERG Test

For the purpose of assessing risk of an electrocardiogram QT interval prolongation, effects on delayed rectifier K+ current ($I_{Kr}$), which plays an important role in the ventricular repolarization process of the compound of the present invention, is studied using HEK293 cells expressing human ether-a-go-go related gene (hERG) channel.

After a cell is retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds is recorded. After the generated current is stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the test compound has been dissolved at an objective concentration is applied to the cell under the room temperature condition for 10 minutes. From the recording $I_{Kr}$, an absolute value of the tail peak current is measured based on the current value at the resting membrane potential using an analysis software (DataXpress ver.1, Molecular Devices Corporation). Further, the % inhibition relative to the tail peak current before application of the test compound is calculated, and compared with the vehicle-applied group (0.1% dimethyl sulfoxide solution) to assess influence of the test compound on $I_{Kr}$.

The Example 10

Powder Solubility Test

Appropriate amounts of the test substances are put into appropriate containers. To the respective containers are added 200 μL of JP-1 fluid (sodium chloride 2.0 g, hydrochloric acid 7.0 mL and water to reach 1000 mL), 200 μL of JP-2 fluid (phosphate buffer (pH 6.8) 500 mL and water 500 mL), and 200 μL of 20 mmol/L TCA (sodium taurocholate)/JP-2 fluid (TCA 1.08 g and water to reach 100 mL) In the case that the test compound is dissolved after the addition of the test fluid, the bulk powder is added as appropriate. The containers are sealed, and shaken for 1 hour at 37° C. The mixtures are filtered, and 100 μL of methanol is added to each of the filtrate (100 μL) so that the filtrates are two-fold diluted. The dilution ratio may be changed if necessary. The dilutions are observed for bubbles and precipitates, and then the containers are sealed and shaken. Quantification is performed by HPLC with an absolute calibration method.

Test Example 11

BA Tests

Materials and methods for studies on oral absorption
(1) Animal: mice or rats
(2) Breeding conditions: mice or rats are allowed to freely take solid feed and sterilized tap water
(3) Dose and grouping: orally or intravenously administered at a predetermined dose; grouping is as follows (Dose depends on the compound)
Oral administration: 1 to 30 mg/kg (n=2 to 3)
Intravenous administration: 0.5 to 10 mg/kg (n=2 to 3)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe
(6) Evaluation items: blood is collected over time, and the plasma concentration of drug is measured by LC/MS/MS
(7) Statistical analysis: regarding the transition of the plasma concentration, the area under the plasma concentration-time curve (AUC) is calculated by non-linear least squares program WinNonlin (Registered trade name), and the bioavailability (BA) is calculated from the AUCs of the oral administration group and intravenous administration group Compound I-53:80.4%

Test Example 12

Brain Distribution Studies

Intravenous administration is carried out to a rat by 0.5 mg/mL/kg dosage of the compound. 30 minutes later, all blood is drawn from vena cava inferior under isoflurane anesthesia for death from exsanguination. Then, the brain is extracted and 20-25% of homogenate thereof is prepared with distilled water. On the other hand, the obtained blood is used as plasma after centrifuging. Then, to the brain sample is added the control plasma at 1:1. To the plasma samples is added the control brains at 1:1. Each sample is measured using LC/MS/MS. The obtained area ratio (a brain/plasma) is used for the brain Kp value.

Formulation Example 1

A granule containing the following ingredients is produced.

| Ingredient | Compound of the formula (I) | 10 mg |
|---|---|---|
| | Lactose | 700 mg |
| | Corn starch | 274 mg |
| | HPC-L | 16 mg |
| | | 1000 mg |

The compound of the formula (I), and lactose are passed through a 60 mesh sieve. Corn starch is passed through a 120 mesh sieve. These are mixed with a V-type mixer. To the mixed powder is added a HPC-L (low viscosity hydroxypropylcellulose) aqueous solution, this is kneaded, granulated (extrusion granulation, pore diameter 0.5 to 1 mm), and dried. The resulting dry granule is passed through a vibration sieve (12/60 mesh) to give a granule.

Formulation Example 2

A granule for filling a capsule containing the following ingredients is produced.

| Ingredient | Compound of the formula (I) | 15 mg |
|---|---|---|
| | Lactose | 90 mg |
| | Corn starch | 42 mg |
| | HPC-L | 3 mg |
| | | 150 mg |

The compound of the formula (I), and lactose are passed through a 60 mesh sieve. Corn starch is passed through a 120 mesh sieve. These are mixed, a HPC-L solution is added to the mixed powder, this is kneaded, granulated, and dried. The resulting dry granule is adjusted in a size, and 150 mg of it is filled into a No. 4 hard gelatin capsule.

Formulation Example 3

A tablet containing the following ingredients is produced.

| Ingredient | Compound of the formula (I) | 10 mg |
|---|---|---|
| | Lactose | 90 mg |
| | Microcrystalline cellulose | 30 mg |

-continued

| | |
|---|---|
| CMC-Na | 15 mg |
| Magnesium stearate | 5 mg |
| | 150 mg |

The compound of the formula (I), lactose, microcrystalline cellulose, and CMC-Na (carboxymethylcellulose sodium salt) are passed through a 60 mesh sieve, and mixed. Magnesium stearate is mixed into the mixed powder to give a mixed powder for tabletting. The present mixed powder is directly compressed to give a 150 mg of a tablet.

Formulation Example 4

The following ingredients are warmed, mixed, and sterilized to give an injectable.

| Ingredient | | |
|---|---|---|
| | Compound of the formula (I) | 3 mg |
| | Nonionic surfactant | 15 mg |
| | Purified water for injection | 1 ml |

INDUSTRIAL APPLICABILITY

The present compound can be a medicament useful as an agent for treating or preventing a disease induced by production, secretion and/or deposition of amyloid β protein.

The invention claimed is:
1. A compound of formula (I):

[Chemical Formula 1]

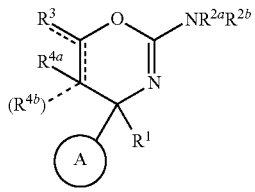

(I)

wherein
ring A is a substituted benzene, $R^1$ is substituted or unsubstituted alkyl, substituted or unsubstituted alkenyl, substituted or unsubstituted alkynyl, substituted or unsubstituted acyl, cyano, carboxy, substituted or unsubstituted alkoxycarbonyl, substituted or unsubstituted alkenyloxycarbonyl, substituted or unsubstituted alkynyloxycarbonyl, substituted or unsubstituted carbamoyl, substituted or unsubstituted thiocarbamoyl, a substituted or unsubstituted carbocyclic group or a substituted or unsubstituted heterocyclic group,
$R^{2a}$ and $R^{2b}$ are each independently hydrogen, substituted or unsubstituted alkyl, substituted or unsubstituted acyl, substituted or unsubstituted alkoxycarbonyl or substituted or unsubstituted carbamoyl,

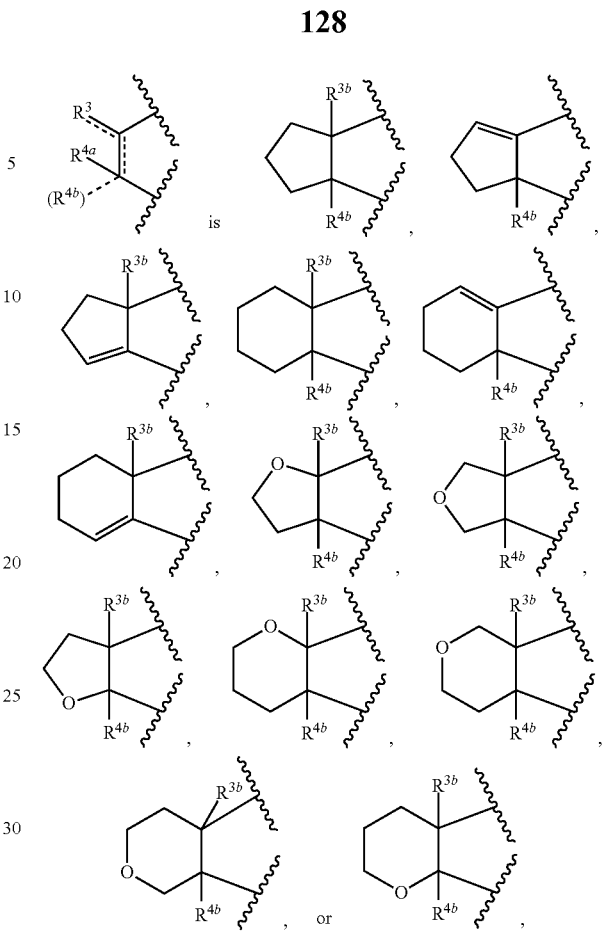

the above rings being optionally substituted at any available position with one or more substituents selected from the group consisting of alkyl substituted with one or more substituents selected from the substituent group α, unsubstituted alkyl and the substituent group α,
$R^{3b}$ and $R^{4b}$ are each independently hydrogen, halogen, hydroxy, substituted or unsubstituted alkyl, substituted or unsubstituted alkenyl, substituted or unsubstituted alkynyl, substituted or unsubstituted alkoxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted acyl, substituted or unsubstituted acyloxy, cyano, nitro, carboxy, substituted or unsubstituted alkoxycarbonyl, substituted or unsubstituted alkenyloxycarbonyl, substituted or unsubstituted alkynyloxycarbonyl, substituted or unsubstituted amino, substituted or unsubstituted carbamoyl, substituted or unsubstituted thiocarbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, a substituted or unsubstituted carbocyclic group, substituted or unsubstituted carbocyclyloxy, substituted or unsubstituted carbocyclylthio, substituted or unsubstituted carbocyclylalkyl, substituted or unsubstituted carbocyclylalkoxy, substituted or unsubstituted carbocyclyloxycarbonyl, substituted or unsubstituted carbocyclylsulfinyl, substituted or unsubstituted carbocyclylsulfonyl, a substituted or unsubstituted heterocyclic group, substituted or unsubstituted heterocyclyloxy, substituted or unsubstituted heterocyclylthio, substituted or unsubstituted heterocyclylalkyl, substituted or unsubstituted heterocyclylalkoxy, substituted or unsubstituted heterocyclyloxycarbonyl, substituted or unsubstituted heterocyclylsulfinyl or substituted or unsubstituted heterocyclylsulfonyl, wherein "acyl" includes formyl, alkylcarbonyl of a carbon number of 1 to 10, alkenylcarbonyl of a carbon number of 2 to 10, alkynylcarbonyl of a carbon number of 2 to 10, carbocyclylcarbonyl and heterocyclylcarbonyl, the substituents of "substituted benzene", "substituted or unsubstituted carbocycle", and "substituted or unsubstituted heterocycle" in ring A, ring A' and ring B are one or more substituents selected from (A) a group selected from the substituent group α wherein the substituent group α is a group consisting of halogen, hydroxy, alkoxy, halogenoalkoxy, hydroxyalkoxy, alkoxyalkoxy, acyl, acyloxy, carboxy, alkoxycarbonyl, amino, acylamino, alkylamino, imino, hydroxyimino, alkoxyimino, alkylthio, carbamoyl, alkylcarbamoyl, hydroxyalkylcarbamoyl, sulfamoyl, alkylsulfamoyl, alkylsulfinyl, alkylsulfonylamino, alkylsulfonylalkylamino, alkylsulfonylimino, alkylsulfinylamino, alkylsulfinylalkylamino, alkylsulfinylimino, cyano, nitro, a carbocyclic group and a heterocyclic group, each of which carbocycle and heterocycle is optionally substituted with one or more substituent selected from halogen, alkyl, hydroxy, and alkoxy;

(B) alkyl substituted with one or more groups selected from the substituent group α, hydroxyimino and alkoxyimino, or unsubstituted alkyl;

(C) aminoalkyl substituted with one or more groups selected from the substituent group α; alkenyl substituted with one or more substituents selected from the substituent group α, or unsubstituted alkenyl;

(D) alkynyl substituted with one or more substituents selected from the substituent group α, or unsubstituted alkynyl;

(E) alkoxy substituted with one or more substituents selected from the substituent group α;

(F) alkoxyalkoxy substituted with one or more substituents selected from the substituent group α;

(G) alkenyloxy substituted with one or more substituents selected from the substituent group α, or unsubstituted alkenyloxy;

(H) alkoxyalkenyloxy substituted with one or more substituents selected from the substituent group α;

(I) alkynyloxy substituted with one or more substituents selected from the substituent group α, unsubstituted alkynyloxy;

(J) alkoxyalkynyloxy substituted with one or more groups selected from the substituent group α;

(K) alkylthio substituted with one or more substituents selected from the substituent group α, or unsubstituted alkylthio;

(L) alkenylthio substituted with one or more substituents selected from the substituent group α, or unsubstituted alkenylthio;

(M) alkynylthio substituted with one or more substituents selected from the substituent group α, or unsubstituted alkynylthio;

(N) alkylamino substituted with one or more substituents selected from the substituent group α;

(O) alkenylamino substituted with one or more substituents selected from the substituent group α;

(P) alkynylamino substituted with one or more substituents selected from the substituent group α;

(Q) aminooxy substituted with one or more substituents selected from the substituent group α and alkylidene, or unsubstituted aminooxy;

(R) acyl substituted with one or more substituents selected from the substituent group α;

(S) alkylsulfonyl substituted with one or more substituents selected from the substituent group α, or unsubstituted alkylsulfonyl;

(T) alkylsulfinyl substituted with one or more substituents selected from the substituent group α, or unsubstituted alkylsulfinyl;

(U) alkylsulfamoyl substituted with one or more substituents selected from the substituent group α;

(V) a carbocyclic group substituted with one or more substituents selected from the substituent group α, azide, alkyl and halogenoalkyl;

(W) a heterocyclic group substituted with one or more substituents selected from the substituent group α, azide, alkyl and halogenoalkyl;

(X) carbocyclylalkyl substituted with one or more substituents selected from the substituent group α, azide, alkyl and halogenoalkyl, or unsubstituted carbocyclylalkyl;

(Y) heterocyclylalkyl substituted with one or more substituents selected from the substituent group α, azide, alkyl and halogenoalkyl, or unsubstituted heterocyclylalkyl;

(Z) carbocyclyloxy substituted with one or more substituents selected from the substituent group α, azide, alkyl and halogenoalkyl, or unsubstituted carbocyclyloxy;

(AA) heterocyclyloxy substituted with one or more substituents selected from the substituent group α, azide, alkyl and halogenoalkyl, or unsubstituted heterocyclyloxy;

(AB) carbocyclylalkoxy substituted with one or more substituents selected from the substituent group α, azide, alkyl and halogenoalkyl, or unsubstituted carbocyclylalkoxy;

(AC) heterocyclylalkoxy substituted with one or more substituents selected from the substituent group α, azide, alkyl and halogenoalkyl, or unsubstituted heterocyclylalkoxy;

(AD) carbocyclylalkoxycarbonyl substituted with one or more substituents selected from the substituent group α, azide, alkyl and halogenoalkyl, or unsubstituted carbocyclylalkoxycarbonyl;

(AE) heterocyclylalkoxycarbonyl substituted with one or more substituents selected from the substituent group α, azide, alkyl and halogenoalkyl, or unsubstituted heterocyclylalkoxycarbonyl;

(AF) carbocyclylthio such substituted with one or more substituents selected from the substituent group α, azide, alkyl and halogenoalkyl, or unsubstituted carbocyclylthio;

(AG) heterocyclylthio substituted with one or more substituents selected from the substituent group α, azide, alkyl and halogenoalkyl, or unsubstituted heterocyclylthio;

(AH) carbocyclylamino substituted with one or more substituents selected from the substituent group α, azide, alkyl and halogenoalkyl, or unsubstituted carbocyclylamino;

(AI) heterocyclylamino substituted with one or more substituents selected from the substituent group α, azide, alkyl and halogenoalkyl, or unsubstituted heterocyclylamino;
(AJ) carbocyclylalkylamino substituted with one or more substituents selected from the substituent group α, azide, alkyl and halogenoalkyl or unsubstituted carbocyclylalkylamino;
(AK) heterocyclylalkylamino substituted with one or more substituents selected from the substituent group α, azide, alkyl and halogenoalkyl, or unsubstituted heterocyclylalkylamino;
(AL) carbocyclylsulfamoyl substituted with one or more substituents selected from the substituent group α, azide, alkyl and halogenoalkyl, or unsubstituted carbocyclylsulfamoyl;
(AM) heterocyclylsulfamoyl substituted with one or more substituents selected from the substituent group α, azide, alkyl and halogenoalkyl, or unsubstituted heterocyclylsulfamoyl;
(AN) carbocyclylsulfonyl substituted with one or more substituents selected from the substituent group α, azide, alkyl and halogenoalkyl, or unsubstituted carbocyclylsulfonyl;
(AO) heterocyclylsulfonyl substituted with one or more substituents selected from the substituent group α, azide, alkyl and halogenoalkyl, or unsubstituted heterocyclylsulfonyl;
(AP) carbocyclylcarbamoyl substituted with one or more substituents selected from the substituent group α, azide, alkyl and halogenoalkyl, or unsubstituted carbocyclylcarbamoyl;
(AQ) heterocyclylcarbamoyl substituted with one or more substituents selected from the substituent group α, azide, alkyl and halogenoalkyl, or unsubstituted heterocyclylcarbamoyl;
(AR) carbocyclylalkylcarbamoyl substituted with one or more substituents selected from the substituent group α, azide, alkyl and halogenoalkyl, or unsubstituted carbocyclylalkylcarbamoyl;
(AS) heterocyclylalkylcarbamoyl substituted with one or more substituents selected from the substituent group α, azide, alkyl and halogenoalkyl, or unsubstituted heterocyclylalkylcarbamoyl;
(AT) carbocyclyloxycarbonyl substituted with one or more substituents selected from the substituent group α, azide, alkyl and halogenoalkyl, or unsubstituted carbocyclyloxycarbonyl;
(AU) heterocyclyloxycarbonyl substituted with one or more substituents selected from the substituent group α, azide, alkyl and halogenoalkyl, or unsubstituted heterocyclyloxycarbonyl;
(AV) alkylenedioxy substituted with halogen, or unsubstituted alkylenedioxy;
(AW) oxo; and
(AX) azide; and
ring A may be selected from the followings:

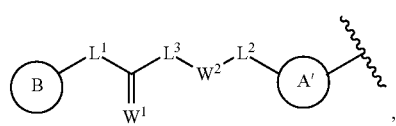

(i)

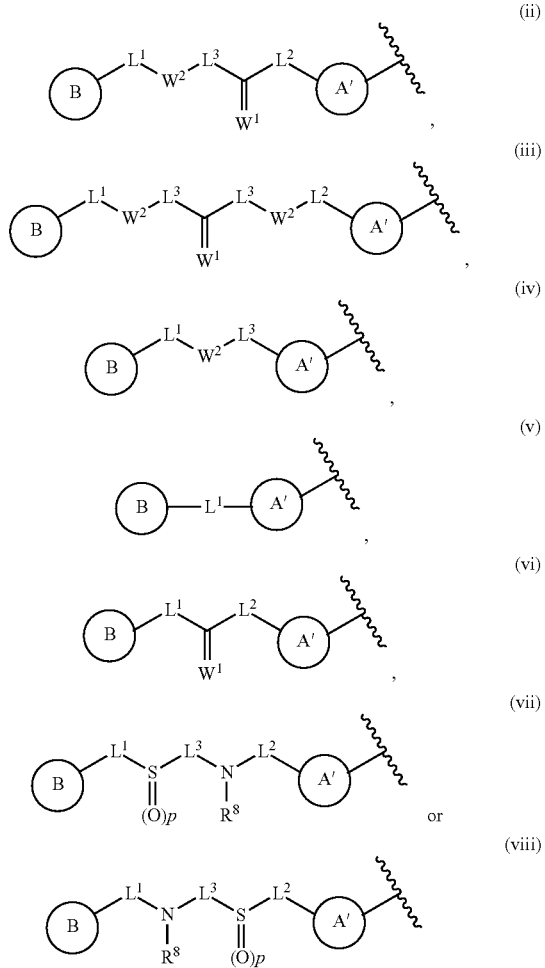

wherein ring A' is substituted or unsubstituted benzene, ring B is substituted or unsubstituted carbocycle or substituted or unsubstituted heterocycle wherein the substituents are defined above,
$L^1$, $L^2$, and $L^3$ are each independently a bond, substituted or unsubstituted alkylene, substituted or unsubstituted alkenylene or substituted or unsubstituted alkynylene,
=$W^1$ is =O, =S, or =$NR^9$,
$W^2$ is O, S, or N($R^8$),
$R^8$ is hydrogen, substituted or unsubstituted alkyl, substituted or unsubstituted alkenyl, substituted or unsubstituted alkynyl or substituted or unsubstituted acyl,
$R^9$ is hydrogen, hydroxy, substituted or unsubstituted alkyl, substituted or unsubstituted alkenyl, substituted or unsubstituted alkynyl or substituted or unsubstituted acyl, when ring A is (i), then the constituent carbon atom of $L^1$ and the constituent carbon atom of $L^2$, or the constituent carbon atom of $L^1$ and the nitrogen atom of $W^2$ may be connected with substituted or unsubstituted alkylene to form a ring,
when ring A is (ii), then the constituent carbon atom of $L^1$ and the constituent carbon atom of $L^2$, or the nitrogen atom of $W^2$ and the constituent carbon atom of $L^2$ may be connected with substituted or unsubstituted alkylene to form a ring,
when ring A is (iii), then two nitrogen atoms of $W^2$ may be connected with substituted or unsubstituted alkylene to form a ring, when ring A is (vi), then the constituent carbon atom of L¹ and the constituent carbon atom of L² may be connected by substituted or unsubstituted alkylene to form a ring, p is 1 or 2, and when multiple L³, multiple W², or multiple R⁹ are present, each of them may be independently different;

the substituents of "substituted or unsubstituted alkyl", "substituted or unsubstituted alkoxy", "substituted or unsubstituted alkoxycarbonyl", "substituted or unsubstituted alkylthio", "substituted or unsubstituted alkylsulfonyl", "substituted or unsubstituted alkylsulfinyl", "substituted or unsubstituted alkenyl", "substituted or unsubstituted alkenyloxy", "substituted or unsubstituted alkenyloxycarbonyl", "substituted or unsubstituted alkenylthio", "substituted or unsubstituted alkenylsulfinyl", "substituted or unsubstituted alkenylsulfonyl", "substituted or unsubstituted alkynyl", "substituted or unsubstituted alkynyloxy", "substituted or unsubstituted alkynylthio", "substituted or unsubstituted alkynyloxycarbonyl", "substituted or unsubstituted alkynylsulfinyl", "substituted or unsubstituted alkynylsulfonyl", "substituted or unsubstituted alkylene", "substituted or unsubstituted alkenylene", and "substituted or unsubstituted alkynylene" are one or more substituents selected from a substituent group α:

the substituents of "substituted or unsubstituted acyl" and "substituted or unsubstituted acyloxy" are one or more substituents selected from the substituent group α, and the ring portions of carbocyclylcarbonyl and heterocyclylcarbonyl may be substituted with one or more substituents selected from alkyl, substituent group α, and alkyl substituted with one or more substituents selected from substituent group α;

the substituent in "substituted or unsubstituted amino", "substituted or unsubstituted carbamoyl", "substituted or unsubstituted thiocarbamoyl" and "substituted or unsubstituted sulfamoyl" are one or two substituents selected from alkyl, acyl, hydroxy, alkoxy, alkoxycarbonyl, carbocyclic group and heterocyclic group;

the substituents of "substituted or unsubstituted carbocyclic group", "substituted or unsubstituted carbocyclylthio", "substituted or unsubstituted carbocyclyloxycarbonyl", "substituted or unsubstituted carbocyclyloxy", "substituted or unsubstituted carbocyclylsulfinyl", "substituted or unsubstituted carbocyclylsulfonyl", "substituted or unsubstituted carbocycle", "substituted or unsubstituted heterocyclic group", "substituted or unsubstituted heterocyclyloxy", "substituted or unsubstituted heterocyclylthio", "substituted or unsubstituted heterocyclyloxycarbonyl", "substituted or unsubstituted heterocycylsulfinyl", "substituted or unsubstituted heterocyclylsulfonyl", and "substituted or unsubstituted heterocycle" in other than the ring A and ring B are one or more substituents selected from the substituent group α, unsubstituted alkyl, and alkyl substituted with one or more substituents selected from the substituent group α;

its pharmaceutically acceptable salt or a solvate thereof.

2. The compound according to claim 1 wherein ring A is

[Chemical formula 5]

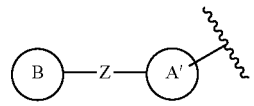

wherein ring A' and ring B are each independently a substituted or unsubstituted carbocycle or a substituted or unsubstituted heterocycle, Z is -L¹-C(=O)N(R⁸)-L²-, -L¹-N(R⁸)C(=O)-L²- or -L¹-N(R⁸)-L²-, L¹ and L² are each independently a bond, substituted or unsubstituted alkylene, substituted or unsubstituted alkenylene or substituted or unsubstituted alkynylene, R⁸ is hydrogen, substituted or unsubstituted alkyl, substituted or unsubstituted alkenyl, substituted or unsubstituted alkynyl or substituted or unsubstituted acyl, its pharmaceutically acceptable salt or a solvate thereof.

3. The compound according to claim 2 wherein —Z— is —C(=O)N(R⁸)—, its pharmaceutically acceptable salt or a solvate thereof.

4. The compound according to claim 2 wherein ring A' is substituted or unsubstituted benzene, and ring B is substituted or unsubstituted pyridine, substituted or unsubstituted pyrimidine or substituted or unsubstituted pyrazine, its pharmaceutically acceptable salt or a solvate thereof.

5. The compound according to claim 1 wherein R¹ is C1 to C3 unsubstituted alkyl, its pharmaceutically acceptable salt or a solvate thereof.

6. The compound according to claim 1 wherein R²ᵃ and R²ᵇ are both hydrogen, its pharmaceutically acceptable salt or a solvate thereof.

7. The compound according to claim 1 wherein R³ᶜ is hydrogen and R⁴ᶜ is hydrogen, its pharmaceutically acceptable salt or a solvate thereof.

8. The compound according to claim 1 wherein ring A is

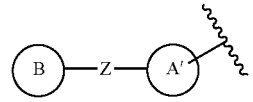

wherein ring A' and ring B are each independently a substituted or unsubstituted carbocycle or a substituted or unsubstituted heterocycle, —Z— is —C(=O)N(R⁸)—, R²ᵃ and R²ᵇ are both hydrogen, its pharmaceutically acceptable salt or a solvate thereof.

9. The compound according to claim 8 wherein R³ᵇ is hydrogen and R⁴ᵇ is hydrogen, its pharmaceutically acceptable salt or a solvate thereof.

10. A pharmaceutical composition comprising the compound according to claim 1, its pharmaceutically acceptable salt or a solvate thereof as an active ingredient.

11. A method for the treatment and/or symptom improvement of dementia of Alzheimer's disease, senile dementia of Alzheimer type, Down's syndrome, memory impairment, Creutzfeldt-Jakob disease, mild cognitive impairment (MCI), Dutch type of hereditary cerebral hemorrhage with amyloidosis, cerebral amyloid angiopathy, mixed dementia with Alzheimer's and vascular type, dementia with Parkinson's Disease, dementia with progressive supranuclear palsy, dementia with Cortico-basal degeneration, Alzheimer's disease with diffuse Lewy body disease, age-related macular degeneration, Parkinson's Disease, or amyloid angiopathy comprising administering the compound according to claim 1, its pharmaceutically acceptable salt or a solvate thereof.

12. The method according to claim 11, wherein the method is for the treatment and/or symptom improvement of dementia of the Alzheimer's type or mild cognitive impairment (MCI).

* * * * *